US012760003B2

(12) United States Patent
Sherman

(10) Patent No.: US 12,760,003 B2
(45) Date of Patent: Oct. 13, 2026

(54) MODULATORS OF BCL6 PROTEOLYSIS AND ASSOCIATED METHODS OF USE

(71) Applicant: Arvinas Operations, Inc., New Haven, CT (US)

(72) Inventor: Dan Sherman, Madison, CT (US)

(73) Assignee: Arvinas Operations, Inc., New Haven, CT (US)

( * ) Notice: Subject to any disclaimer, the term of this patent is extended or adjusted under 35 U.S.C. 154(b) by 298 days.

(21) Appl. No.: 18/490,704

(22) Filed: Oct. 19, 2023

(65) Prior Publication Data

US 2024/0190841 A1 Jun. 13, 2024

Related U.S. Application Data

(60) Provisional application No. 63/417,628, filed on Oct. 19, 2022, provisional application No. 63/417,657, filed on Oct. 19, 2022.

(51) Int. Cl.
*C07D 401/14* (2006.01)
*A61K 31/506* (2006.01)
*A61K 45/06* (2006.01)
*C07D 471/04* (2006.01)

(52) U.S. Cl.
CPC .......... *C07D 401/14* (2013.01); *A61K 31/506* (2013.01); *A61K 45/06* (2013.01); *C07D 471/04* (2013.01)

(58) Field of Classification Search
CPC .. C07D 401/14; C07D 471/04; A61K 31/506; A61K 45/06
USPC ..................................................... 514/252.18
See application file for complete search history.

(56) References Cited

U.S. PATENT DOCUMENTS 4,522,811 A 6/1985 Eppstein et al.
6,306,663 B1 10/2001 Kenten et al.
6,670,348 B1 12/2003 Rosen et al.
7,041,298 B2 5/2006 Deshaies et al.
7,208,157 B2 4/2007 Dashaies et al.
8,338,464 B2 12/2012 Melnick et al.
9,447,070 B2 9/2016 Muller et al.
9,500,653 B2 11/2016 Crews et al.
9,632,089 B2 4/2017 Crews et al.
10,647,698 B2 5/2020 Crew et al.
11,439,635 B2 9/2022 Barish et al.
11,505,539 B2 11/2022 Isaac et al.
11,512,095 B2 11/2022 Bellenie et al.
11,518,764 B2 12/2022 Al-Awar et al.
11,827,627 B2 11/2023 Beck et al.
11,883,393 B2 1/2024 Snyder et al.
11,986,532 B2 5/2024 Sherman
12,043,612 B2 7/2024 Allan et al.
12,310,975 B2 5/2025 Berlin et al.
2003/0096841 A1 5/2003 Robarge et al.
2008/0051432 A1 2/2008 Zhang
2008/0214501 A1 9/2008 Pan et al.
2012/0014979 A1 1/2012 Dent
2012/0270800 A1 10/2012 Verdine et al.
2014/0302523 A1 10/2014 Crews et al.
2014/0356322 A1 12/2014 Crews et al.
2015/0119435 A1 4/2015 Crews et al.
2015/0291562 A1 10/2015 Crew et al.
2015/0344473 A1 12/2015 Du et al.
2016/0022642 A1 1/2016 Crews et al.
2016/0045607 A1 2/2016 Crew et al.
2016/0058872 A1 3/2016 Crew et al.
2016/0136230 A1 5/2016 Campos et al.
2016/0214972 A1 7/2016 Jin et al.
2016/0243247 A1 8/2016 Bradner et al.
2016/0272639 A1 9/2016 Crew et al.
2016/0368911 A1 12/2016 Campos et al.
2017/0008904 A1 1/2017 Crew et al.
2017/0037004 A1 2/2017 Crew et al.
2017/0065719 A1 3/2017 Qian et al.
2017/0121321 A1 5/2017 Crews et al.
2017/0281784 A1 10/2017 Wang et al.
2017/0307614 A1 10/2017 Crews et al.
2017/0327469 A1 11/2017 Crew et al.
2018/0015087 A1 1/2018 Liu et al.
2018/0072711 A1 3/2018 Crew et al.
2018/0099940 A1 4/2018 Crew et al.
2018/0125821 A1 5/2018 Crew et al.
2018/0147202 A1 5/2018 Crew et al.
2018/0155322 A1 6/2018 Crew et al.
2018/0177750 A1 6/2018 Crew et al.
2018/0179183 A1 6/2018 Crew et al.
2018/0193470 A1 7/2018 Crew et al.
2018/0215731 A1 8/2018 Crew et al.

(Continued)

FOREIGN PATENT DOCUMENTS

CN 1844118 A 10/2006
CN 103688176 A 3/2014

(Continued)

OTHER PUBLICATIONS

Cerchietti, L. C., et al., "A peptomimetic inhibitor of BCL6 with potent antilymphoma effects in vitro and in vivo", Blood (Apr. 9, 2009); 113(15): 3397-3405. Epub Oct. 16, 2008.
Co-pending U.S. Appl. No. 18/407,150, inventors Sherman; Dan et al., filed Jan. 8, 2024.
Co-pending U.S. Appl. No. 18/610,001, inventor Berlin; Michael, filed Mar. 19, 2024.
Gough, S. M., et al., "Potent and Orally Bioavailable BCL6 Protac® Degraders Demonstrate Efficacy in Pre-Clinical Models of Diffuse Large B-Cell Lymphoma (DLBCL)", Arvinas Presentation, ASH 2021 Poster #2272 Atlanta GA, USA, Session 605. Molecular Pharmacology and Drug Resistance: Lymphoid Neoplasms: Poster II (Dec. 11, 2021) [online] https://www.arvinas.com/wp-content/uploads/2022/09/Arvinas-ASH-Presentation-2021.pdf; 11 pages.
Houston, J. G., "The Promise of Protac® Protein Degraders: What's Next for Arvinas' Pipeline & Platform", Arvinas Presentation (Oct. 14, 2020); 23 pages.

(Continued)

*Primary Examiner* — Kristin A Vajda
(74) *Attorney, Agent, or Firm* — McCarter & English, LLP

(57) ABSTRACT

This disclosure pertains to bifunctional compounds, the preparation thereof, and the use of these bifunctional compounds in the treatment of diseases or disorders that result from aggregation or accumulation of B-cell lymphoma 6 protein, in subjects in need thereof.

11 Claims, 1 Drawing Sheet

(56) References Cited

U.S. PATENT DOCUMENTS

| | | | |
|---|---|---|---|
| 2018/0228907 | A1 | 8/2018 | Crew et al. |
| 2018/0237418 | A1 | 8/2018 | Crew et al. |
| 2018/0256586 | A1 | 9/2018 | Crew et al. |
| 2022/0081416 | A1 | 3/2022 | Boulton et al. |
| 2022/0288074 | A1 | 9/2022 | Doerner Barbour et al. |
| 2022/0323457 | A1 | 10/2022 | Berlin et al. |
| 2022/0372016 | A1 | 11/2022 | Phillips et al. |
| 2022/0389034 | A1 | 12/2022 | Ammann et al. |
| 2022/0395576 | A1 | 12/2022 | Berlin et al. |
| 2023/0331600 | A1 | 10/2023 | Frail |
| 2023/0365594 | A1 | 11/2023 | Ammann et al. |
| 2024/0228482 | A1 | 7/2024 | Bi et al. |
| 2024/0246908 | A1 | 7/2024 | Ahlmark et al. |

FOREIGN PATENT DOCUMENTS

| | | | |
|---|---|---|---|
| EP | 2985285 | A1 | 2/2016 |
| JP | 2010502627 | A | 1/2010 |
| JP | 2024-052757 | A | 4/2024 |
| RU | 2008112221 | A | 10/2009 |
| RU | 2448101 | C2 | 4/2012 |
| RU | 2011121567 | A | 12/2012 |
| RU | 2012138709 | A | 3/2014 |
| WO | WO-9803502 | A1 | 1/1998 |
| WO | WO-0066119 | A1 | 11/2000 |
| WO | WO-02066512 | A1 | 8/2002 |
| WO | WO-2005016326 | A2 | 2/2005 |
| WO | WO-2006113942 | A2 | 10/2006 |
| WO | WO-2007106670 | A2 | 9/2007 |
| WO | WO-2008011392 | A2 | 1/2008 |
| WO | WO-2009015254 | A1 | 1/2009 |
| WO | WO-2010053732 | A1 | 5/2010 |
| WO | WO-2010141805 | A1 | 12/2010 |
| WO | WO-2012003281 | A2 | 1/2012 |
| WO | WO-2012040527 | A2 | 3/2012 |
| WO | WO-2012078559 | A2 | 6/2012 |
| WO | WO-2012090104 | A1 | 7/2012 |
| WO | WO-2012142498 | A2 | 10/2012 |
| WO | WO-2013106646 | A2 | 7/2013 |
| WO | WO-2013170147 | A1 | 11/2013 |
| WO | WO-2014108452 | A1 | 7/2014 |
| WO | WO-2014123418 | A1 | 8/2014 |
| WO | WO-2015000868 | A1 | 1/2015 |
| WO | WO-2015160845 | A2 | 10/2015 |
| WO | WO-2016105518 | A1 | 6/2016 |
| WO | WO-2016146985 | A1 | 9/2016 |
| WO | WO-2016149668 | A1 | 9/2016 |
| WO | WO-2016169989 | A1 | 10/2016 |
| WO | WO-2016172134 | A2 | 10/2016 |
| WO | WO-2016187723 | A1 | 12/2016 |
| WO | WO-2016197114 | A1 | 12/2016 |
| WO | WO-2017007612 | A1 | 1/2017 |
| WO | WO-2017011590 | A1 | 1/2017 |
| WO | WO-2017024317 | A2 | 2/2017 |
| WO | WO-2017024318 | A1 | 2/2017 |
| WO | WO-2017024319 | A1 | 2/2017 |
| WO | WO-2017030814 | A1 | 2/2017 |
| WO | WO-2017046036 | A1 | 3/2017 |
| WO | WO-2017079267 | A1 | 5/2017 |
| WO | WO-2017117473 | A1 | 7/2017 |
| WO | WO-2017117474 | A1 | 7/2017 |
| WO | WO-2017161119 | A1 | 9/2017 |
| WO | WO-2017176957 | A1 | 10/2017 |
| WO | WO-2017176958 | A1 | 10/2017 |
| WO | WO-2017185023 | A1 | 10/2017 |
| WO | WO-2017185031 | A1 | 10/2017 |
| WO | WO-2017185034 | A1 | 10/2017 |
| WO | WO-2017185036 | A1 | 10/2017 |
| WO | WO-2017197051 | A1 | 11/2017 |
| WO | WO-2017197055 | A1 | 11/2017 |
| WO | WO-2017197056 | A1 | 11/2017 |
| WO | WO-2017223415 | A1 | 12/2017 |
| WO | WO-2017223452 | A1 | 12/2017 |
| WO | WO-2018052945 | A1 | 3/2018 |
| WO | WO-2018052949 | A1 | 3/2018 |
| WO | WO-2018064589 | A1 | 4/2018 |
| WO | WO-2018089736 | A1 | 5/2018 |
| WO | WO-2018098275 | A1 | 5/2018 |
| WO | WO-2018098280 | A1 | 5/2018 |
| WO | WO-2018098288 | A1 | 5/2018 |
| WO | WO-2018102725 | A1 | 6/2018 |
| WO | WO-2018106870 | A1 | 6/2018 |
| WO | WO-2018108704 | A1 | 6/2018 |
| WO | WO-2018148440 | A1 | 8/2018 |
| WO | WO-2018215798 | A1 | 11/2018 |
| WO | WO-2018215801 | A1 | 11/2018 |
| WO | WO-2018237026 | A1 | 12/2018 |
| WO | WO-2019060693 | A1 | 3/2019 |
| WO | WO-2019060742 | A1 | 3/2019 |
| WO | WO-2019084026 | A1 | 5/2019 |
| WO | WO-2019084030 | A1 | 5/2019 |
| WO | WO-2019099926 | A1 | 5/2019 |
| WO | WO-2019099868 | A3 | 6/2019 |
| WO | WO-2019119138 | A1 | 6/2019 |
| WO | WO-2019195201 | A1 | 10/2019 |
| WO | WO-2021074620 | A1 | 4/2021 |
| WO | WO-2021077010 | A1 | 4/2021 |
| WO | WO-2022169780 | A1 | 8/2022 |
| WO | 2022/221673 | A1 | 10/2022 |
| WO | WO-2023015164 | A1 | 2/2023 |
| WO | WO-2023114460 | A1 | 6/2023 |
| WO | WO-2023212147 | A1 | 11/2023 |
| WO | WO-2023232133 | A1 | 12/2023 |
| WO | WO-2023240038 | A1 | 12/2023 |
| WO | WO-2023244917 | A1 | 12/2023 |
| WO | WO-2023244918 | A1 | 12/2023 |
| WO | WO-2024012449 | A1 | 1/2024 |
| WO | WO-2024015529 | A2 | 1/2024 |
| WO | WO-2024019995 | A1 | 1/2024 |
| WO | WO-2024035688 | A1 | 2/2024 |
| WO | WO-2024086094 | A1 | 4/2024 |
| WO | WO-2024086759 | A1 | 4/2024 |
| WO | 2024/151557 | A1 | 7/2024 |

OTHER PUBLICATIONS

Huckvale, R., et al., "Improved Binding Affinity and Pharmacokinetics Enable Sustained Degradation of BCL6 In Vivo", Journal of Medicinal Chemistry (2022); 65(12): 8191-8207. Epub Jun. 2, 2022.

Pearce, A. C., et al., "GSK137, a potent small-molecule BCL6 inhibitor with in vivo activity, suppresses antibody responses in mice", Journal of Biological Chemistry (2021); 297(2): 100928; 14 pages. Epub Jul. 15, 2021.

Sherman, D., "Pioneering the Future of Targeted Protein Degradation Therapeutics", Arvinas Presentation, Medicinal Chemistry (May 2021); 19 pages.

Arvinas et al., Pioneering Today with a different kind of medicine Transforming Tomorrow for patients who need US. Arvinas Presentation. 34 pages, Janaury 2024.

Caimi et al., EHA-3977: Trial in Progress: Phasel Study Of ARV-393, A Protac BCL6 Degrader, In Advanced Non-Hodgkin Lymphoma. Clinical. 2024;19:2 pages.

Caimi et al., Trial in Progress: Phase 1 Study of ARV-393, a Protac BCL6 Degrader, in Advanced Non-Hodgkin Lymphoma. Blood Cancer Discov. May 1, 2024;5(Suppl. 3):PO-010, 5 pages.

Cerchietti et al., A small molecule inhibitor of BCL6 kills DLBCL cells in vitro and in vivo. Cancer Cell. Apr. 13, 2010;17(4):400-411.

Garrido, Influence of external agents on the shape of crystals. Shape and Structures of Crystals, Exedra. Chapter 5. 204-225;34 pages, (1973).

Giron et al., Thermal analysis and calorimetric methods in the characterisation of polymorphs and solvates. Thermochimica Acta. 1995;248:1-59.

Gough et al., Oral ARV-393 Is A BCL6 Degrading Protac Efficacious As Monotherapy In B-cell Lymphoma Preclinical CDX And PDX Models. Lymphoma Biology & Translational Research. Abstract Submission for Poster Presentation. (2024); 2 pages.

Gu et al., B-cell Lymphoma 6 Inhibitors: Current Advances and Prospects of Drug Development for Diffuse Large B-cell Lymphomas. J Med Chem. Dec. 8, 2022;65(23):15559-15583.

(56) References Cited

OTHER PUBLICATIONS

Lien et al., Atomic and Molecular Structure and the States of Matter. Remington's Pharmaceutical Sciences, 16th Edition. pp. 160-181, (1980).
Nies et al., Principles of Therapeutics. Goodman & Gilman's the Pharmacological Basis Therapeutics. 9th Edition, Chapter 3. pp. 43-62, (1996).
Paolo et al., Abstract PO-101: Trial in Progress: Phase 1 Study of ARV-393, a Protac BCL6 Degrader, in Advanced Non-Hodgkin Lymphoma. Blood Cancer Discovery. American Association for Cancer Research. Blood Cancer Discovery. Jun. 19, 2024;5(3): 2 pages.
Paolo et al., Phase 1 ARV-393, a Protac BCL6 Degrader, in Advanced Non-Hodgkin Lymphoma. Blood. Nov. 5, 2024;144:6505.
Sherman et al., Abstract ND05: The discovery ARV-393, a potent, orally bioavailable BCL6 targeting Protac for the treatment of Non-Hodgkin's Lymphoma. Cancer Research. American Association for Cancer Research. Apr. 5, 2024;84(7):4 pages.
Sun et al., PROTACs: great opportunities for academia and industry. Signal Transduct Target Ther. Dec. 24, 2019;4:64, 33 pages.
International Search Report and Written Opinion for Application No. PCT/US2020/056145, dated Jan. 12, 2020, 10 pages.
International Preliminary Report on Patentability for Application No. PCT/US2020/056145, dated Apr. 19, 2022, 7 pages.
International Preliminary Report on Patentability for Application No. PCT/US2022/025041, dated Oct. 12, 2023, 9 pages.
International Preliminary Report on Patentability for Application No. PCT/US2023/077354, dated Mar. 1, 2024, 13 pages.
International Search Report and Written Opinion for Application No. PCT/US2022/025041, dated Jul. 20, 2022, 11 pages.
International Search Report and Written Opinion for Application No. PCT/US2023/077354, dated Mar. 25, 2024, 18 pages.
International Search Report and Written Opinion for Application No. PCT/US2024/010761, dated May 14, 2024, 7 pages.
International Search Report and Written Opinion for Application No. PCT/US2025/017973, dated Jun. 5, 2025, 11 pages.
International Search Report and Written Opinion for Application No. PCT/US2025/023271, dated Jul. 25, 2025, 9 pages.
Ahn, D., et al., "HIF-1α Peptide Derivatives with modifications at the hydroxyproline residue as activators of HIF-1α", Bioorganic & Medicinal Chemistry Letters (2009); 19(15): 4403-4405.
Alaggio, R., et al., "The 5th edition of the World Health Organization classification of haematolymphoid tumours: lymphoid neoplasms", Leukemia (2022); 36(7): 1720-1748.
[Author Unknown] "Cancer" Medline Plus Trusted Health Information for You [online] www.nlm.nih.gov/medlineplus/cancer.html (Jul. 6, 2007); 10 pages.
Bellenie, B. R., et al., "Achieving In Vivo Target Depletion through the Discovery and Optimization of Benzimidazolone BCL6 Degraders", Journal of Medicinal Chemistry (2020);63(8): 4047-4068.
Beveridge, R., et al, "Native Mass Spectrometry Can Effectively Predict Protac Efficacy", ACS Central Science (Jul. 6, 2020); 6: 1223-1230.
Bondeson, D. P., et al., "Catalytic in vivo protein knockdown by small-molecule Protacs", Nature Chemical Biology (2015); 11(8): 611-617.
Bondeson, D. P., et al., "Lessons in Protac design from selective degradation with a promiscuous warhead", Cell Chemical Biology (2018); 25(1): 78-87.
Bondeson, D. P., et al., "Targeted Protein Degradation by Small Molecules", Annual Review of Pharmacology and Toxicology (2017); 57:107-123.
Bouzide, A., et. al., "Silver(I) oxide-mediated facile and practical sulfonylation of alcohols", Tetrahedron Letters (Oct. 9, 2001); 42(50): 8781-8783.
Buckley, D. L., et al., "HaloPROTACS: use of small molecule Protacs to induce degradation of HaloTag fusion proteins", ACS Chemical Biology (2015); 10(8): 1831-1837.
Buckley, D. L., et al., "Small-molecule inhibitors of the interaction between the E3 ligase VHL and HIF1α", Angewandte Chemie (International Ed. in English) (2012); 51(46): 11463-11467.
Buckley, D. L., et al., "Targeting the von Hippel-Lindau E3 ubiquitin ligase using small molecules to disrupt the VHL/HIF-1α interaction", Journal of the American Chemical Society (2012); 134(10): 4465-4468.
Burslem, G. M., et al., "Small-Molecule Modulation of Protein Homeostasis", Chemical Reviews (2017); 117(17): 11269-11301.
Burslem, G. M., et al., "The Advantages of Targeted Protein Degradation Over Inhibition: An RTK Case Study", Cell Chemical Biology (2018); 25(1): 67-77.
Capitosti, S. M., et al., "Thalidomide analogues demonstrate dual inhibition of both angiogenesis and prostate cancer", Bioorganic & Medicinal Chemistry (2004); 12(2): 327-336.
Cardenas, M. G., et al., "Rationally designed BCL6 inhibitors target activated B cell diffuse large B cell lymphoma", Journal of Clinical Investigation (Sep. 1, 2016); 126(9): 3351-3362.
Carmony, K. C., et al., "Protac-induced proteolytic targeting", Methods in Molecular Biology (2012); 832: 627-638.
Cerchietti, L. C., et al., "A Small-Molecule Inhibitor of BCL6 Kills DLBCL Cells In Vitro and In Vivo", Cancer Cell (2010); 17(4): 400-411.
Chan, K., et al., "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (IBET726) BET Inhibitor Scaffolds", Journal of Medicinal Chemistry (Jun. 8, 2018) ; 61(2): 504-513.
Chen, J., et al., "A review on the latest progress of Chan-Lam coupling reaction", Advanced Synthesis and Catalysis (Jul. 14, 2020); 62(16): 3311-3331.
Churcher, I., "Protac-Induced Protein Degradation in Drug Discovery: Breaking the Rules or Just Making New Ones?", Journal of Medicinal Chemistry (2018); 61(2): 444-452.
Contino-Pepin, C., et al., "Preliminary biological evaluations of new thalidomide analogues for multiple sclerosis application", Bioorganic & Medicinal Chemistry Letters (2009); 19(3): 878-881.
Corson, T. W., et al., "Design and applications of bifunctional small molecules: why two heads are better than one", ACS Chemical Biology (2008); 3(11): 677-692.
Crew, A. P., et al., "Identification and Characterization of Von Hippel-Lindau-Recruiting Proteolysis Targeting Chimeras (PROTACs) of TANK-Binding Kinase 1", Journal of Medicinal Chemistry (2018); 61(2): 583-598.
Crews, C. M., "Targeting the undruggable proteome: the small molecules of my dreams", Chemistry & Biology (2010); 17(6): 551-555.
Cromm, P. M., et al., "Targeted protein degradation: from chemical biology to drug discovery", Cell chemical Biology (2017); 24(9): 1181-1190.
Cyrus, K., et al., "Impact of linker length on the activity of PROTACs", Molecular BioSystems (2011); 7(2): 359-364.
Cyrus, K., et al, "Jostling for position: Optimizing linker location in the design of estrogen receptor-targeting PROTACs", ChemMedChem (2010); 5(7): 979-985.
Cyrus, K., et al, "Two-Headed PROTAC: An Effective New Tool for Targeted Protein Degradation", Chembiochem (2010); 11(11): 1531-1534.
Database STN, CAS Registry No. 1004933-70-3, "2-Pyrrolidinecarboxamide, N-(4-bromo-2-fluorophenyl)-4-hydroxy-1-(2-naphthalenylsulfonyl)-, (2S,4R)-", Chemical Abstracts Service, American Chemical Society; entered Feb. 21, 2008; 1 page.
Database STN, CAS Registry No. 1542127-97-8, "4,7, 10,13-Tetraoxa-16-azaheneicosanamide, N-[4-[3-(4-amino-1,3-dihydro-1,3-dioxo-2H-isoindol-2-yl)-2,6-dioxo-3-piperidinyl]butyl]-21-[(3aS,4S,6aR)-hexahydro-2-oxo-1H-thieno[3,4-d]imidazol-4-yl]-17-oxo-", Chemical Abstracts Service, American Chemical Society; entered Feb. 11, 2014, 4 Pages.
Database STN, CAS Registry No. 871986-52-6, "2-Pyrrolidinecarboxamide, N-[(1S)-3-[(3aR,6aS)-5-(2,6-dimethylbenzoyl)hexahydropyrrolo[3,4-c]pyrrol-2(1H)-yl]-1-

(56) References Cited

OTHER PUBLICATIONS phenylpropyl]-1-(2-furanylcarbonyl)-4-hydroxy-", Chemical Abstracts Service, American Chemical Society; entered Jan. 16, 2006; 1 page.
Duplantier, A. J., et al., "Discovery, SAR, and Pharmacokinetics of a Novel 3- Hydroxyquinolin-2(1H)-one Series of Potent d-Amino Acid Oxidase (DAAO) Inhibitors", Journal of Medicinal Chemistry (May 13, 2009); 52(11): 3576-3585.
Fischer, E. S., et al., "Structure of the DDB1-CRBN E3 Ubiquitin ligase in complex with thalidomide", Nature (2014); 512(7512): 49-53.
Gadd, M. S., et al., "Structural basis of PROTAC cooperative recognition for selective protein degradation", Nature Chemical Biology (2017); 13(5): 514-521.
Galdeano, C., et al., "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities", Journal of Medicinal Chemistry (2014); 57(20): 8657-8663.
Golub, T. R., et al., "Molecular classification of cancer: class discovery and class prediction by gene expression monitoring", Science (1991); 286: 531-537.
Gosink, M., et al., "Redirecting the specificity of ubiquitination by modifying ubiquitin-conjugating enzymes", Proceedings of the National Academy of Sciences (1995); 92(20): 9117-9121.
Guo, W., et al., "Synthesis and Biological Evaluation of B-Cell Lymphoma 6 Inhibitors of N-Phenyl-4-pyrimidinamine Derivatives Bearing Potent Activities against Tumor Growth", Journal of Medicinal Chemistry (Jan. 23, 2020); 63(2): 676-695.
Han, X., et al., "Discovery of ARD-69 as a highly potent proteolysis targeting chimera (PROTAC) degrader of androgen receptor (AR) for the treatment of prostate cancer", Journal of Medicinal Chemistry (2019); 62(2): 941-964.
Hines, J., et al., "Posttranslational protein knockdown coupled to receptor tyrosine kinase activation with phosphoPROTACs", Proceedings of the National Academy of Sciences (2013); 110(22): 8942-8947.
Hon, W., et al., "Structural basis for the recognition of hydroxyproline in HIF-1$\alpha$ by pVHL", Nature (2002); 417(6892): 975-978.
Hu, J., et al., "Discovery of ERD-308 as a Highly Potent Proteolysis Targeting Chimera (PROTAC) Degrader of Estrogen Receptor (ER)", Journal of Medicinal Chemistry (2019); 62: 1420-1442.
Huang, H. T., et al., "A Chemoproteomic Approach to Query the Degradable Kinome Using a Multi-kinase Degrader", Cell Chemical Biology (2018); 25(1): 88-99.
Huang, X., et al., "Drugging the undruggables: exploring the ubiquitin system for drug development", Cell Research (2016); 26(4): 484-498.
Hughes, S. J., et al., "Molecular recognition of ternary complexes: a new dimension in the structure-guided design of chemical degraders", Essays in Biochemistry (2017); 61(5): 505-516.
Hurtz, C., et al., "Rationale for targeting BCL6 in MLL-rearranged acute lymphoblastic leukemia" Genes & Development (2019); 33(17-18): 1265-1279.
Itoh, Y., et al., "Development of target protein selective degradation inducer for protein knockdown," Bioorganic & Medicinal Chemistry (2011); 19(10): 3229-3241.
Itoh, Y., et al., "Protein knockdown using methyl bestatin-ligand hybrid molecules: design and synthesis of inducers of ubiquitination-mediated degradation of cellular retinoic acid-binding proteins", Journal of the American Chemical Society (2010); 132(16): 5820-5826.
Ivan, M., et al., "HIF$\alpha$ targeted for VHL-mediated destruction by proline hydroxylation: implications for $O_2$ sensing", Science (2001); 292(5516): 464-468.
Jang, E. R., et al., "Targeted Degradation of Proteins by PROTACs", Current Protocols in Chemical Biology (2010); 2(2): 71-87.
Kamada, Y., et al., "Discovery of a B-Cell Lymphoma 6 Protein-Protein Interaction Inhibitor by a Biophysics-Driven Fragment-Based Approach", Journal of Medicinal Chemistry (May 25, 2017); 60(10): 4358-4368.
Kerres, N., et al., "Chemically Induced Degradation of the Oncogenic Transcription Factor BCL6", Cell Reports (Sep. 19, 2017); 20(12): 2860-2875.
Khadra, A., et al., "Pd-PEPPSI-IPent$^{Cl}$ : A Useful Catalyst for the Coupling of 2-Aminopyridine Derivatives," Chemistry—A European Journal (2017); 23(13): 3206-3212.
Knott, E. B., "Compounds containing sulphur chromophores. Part I. The action of bases on heterocyclic sulphide quarternary salts", Journal of the Chemical Society (Resumed) (1955); 916-927.
Krönke, J., et al., "Lenalidomide causes selective degradation of IKZF1 and IKZF3 in multiple myeloma cells", Science (2014); 343(6168): 301-305.
Lai, A. C., et al., "Induced protein degradation: an emerging drug discovery paradigm", Nature Reviews Drug Discovery (2017); 16(2): 101-114.
Lai, A. C., et al., "Modular Protac design for the degradation of oncogenic BCR-ABL", Angewandte Chemie International Edition (2016); 55(2): 807-810.
Lala, P. K., et al., "Role of nitric oxide in tumor progression: lessons from experimental tumors", Cancer and Metastasis Reviews (1998); 17: 91-106.
Lebraud, H., et al., "Protein degradation by in-cell self-assembly of proteolysis targeting chimeras", ACS Central Science (2016); 2(12): 927-934.
Lee, H., et al., "Targeted degradation of the aryl hydrocarbon receptor by the PROTAC approach: a useful chemical genetic tool", Chembiochem (2007); 8(17): 2058-2062.
Levine, P. M., et al., "Targeting the androgen receptor with steroid conjugates: miniperspective", Journal of Medicinal Chemistry (2014); 57(20): 8224-8237.
Li, Y., et al., "Single polymer-drug conjugate carrying two drugs for fixed-dose co-delivery", Medicinal Chemistry (2014); 4(10): 676-683.
Liu, K., et al., "Design and biological characterization of hybrid compounds of curcumin and thalidomide for multiple myeloma", Organic & Biomolecular Chemistry (2013); 11(29): 4757-4763.
Lopez-Girona, A. E. A., et al., "Cereblon is a direct protein target for immunomodulatory and antiproliferative activities of lenalidomide and pomalidomide", Leukemia (2012); 26(11): 2326-2335.
Lu, G., et al., "The myeloma drug lenalidomide promotes the cereblon-dependent destruction of Ikaros proteins", Science (2014); 343(6168): 305-309.
Lu, J., et al., "Hijacking the E3 ubiquitin ligase cereblon to efficiently target BRD4", Chemistry & Biology (2015); 22(6): 755-763.
Maniaci, C., et al., "Homo-PROTACs: bivalent small-molecule dimerizers of the VHL E3 ubiquitin ligase to induce self-degradation", Nature Communications (2017); 8(1): 1-14.
Mccoull, W., et al., "Development of a Novel B-Cell Lymphoma 6 (BCL6) Protac To Provide Insight into Small Molecule Targeting of BCL6", ACS Chemical Biology (Nov. 16, 2018); 13(11): 3131-3141.
Mccoull, W., et al., "Discovery of Pyrazolo[1,5-a]pyrimidine B-Cell Lymphoma 6 (BCL6) Binders and Optimization to High Affinity Macrocyclic Inhibitors", Journal of Medicinal Chemistry (May 25, 2017); 60(10): 4386-4402.
Min, J., et al., "Structure of an HIF-1$\alpha$-pVHL complex: hydroxyproline recognition in signaling", Science (2002); 296(5574): 1886-1889.
Mullard, A., "First targeted protein degrader hits the clinic", Nature Reviews, Drug Discovery (Apr. 2019); 18: 237-239.
Muller, G. W., et al., "Amino-substituted thalidomide analogs: potent inhibitors of TNF-$\alpha$ production", Bioorganic & Medicinal Chemistry Letters (1999); 9(11): 1625-1630.
Neklesa, T. K., et al., "Greasy tags for protein removal", Nature (2012); 487(7407): 308-309.
Neklesa, T. K., et al., "Targeted protein degradation by PROTACs", Pharmacology & Therapeutics (2017); 174: 138-144.
Noguchi-Yachide, T., et al., "BET Bromodomain as a Target of Epigenetic Therapy", Chemical and Pharmaceutical Bulletin (Jun. 1, 2016); 64(6): 540-547.
Ohoka, N., et al., "Sniper (TACC3) induces cytoplasmic vacuolization and sensitizes cancer cells to Bortezomib", Cancer Science (2017); 108(5): 1032-1041.

(56) References Cited

OTHER PUBLICATIONS

Osher, E. L., et al., "A genetically selected cyclic peptide inhibitor of BCL6 homodimerization", Bioorganic & Medicinal Chemistry (Jul. 15, 2018); 26(11): 3034-3038.
Ottis, P., et al., "Assessing different E3 ligases for small molecule induced protein ubiquitination and degradation", ACS Chemical Biology (2017); 12(10): 2570-2578.
Ottis, P., et al., "Proteolysis-targeting chimeras: induced protein degradation as a therapeutic strategy", ACS Chemical Biology (2017); 12(4): 892-898.
Pfaff, P., et al., "Reversible Spatiotemporal Control of Induced Protein Degradation, by Bistable Photo Protacs", ACS Chemical Biology (2019); 5: 1682-1690.
Powell, C. E., et al., "Chemically Induced Degradation of Anaplastic Lymphoma Kinase (ALK)", Journal of Medicinal Chemistry (2018); 61: 4249-4255.
Pöstges, F., et al. "Solubility Enhanced Formulation Approaches to Overcome Oral Delivery Obstacles of PROTACs", Pharmaceutics (2023); 15(156): 1-14.
Puppala, D., et al., "Development of an aryl hydrocarbon receptor antagonist using the proteolysis-targeting chimeric molecules approach: a potential tool for chemoprevention", Molecular Pharmacology (2008); 73(4): 1064-1071.
Raina, K., et al., "Chemical Inducers of Targeted Protein Degradation", Journal of Biological Chemistry (2010); 285(15): 11057-11060.
Raina, K., et al., "Protac-induced BET protein degradation as a therapy for castration-resistant prostate cancer", Proceedings of the National Academy of Sciences (2016); 113(26): 7124-7129.
Raina, K., et al., "Targeted protein knockdown using small molecule degraders", Current Opinion in Chemical Biology (2017); 39: 46-53.
Remillard, D., et al., "Degradation of the BAF complex factor BRD9 by heterobifunctional ligands", Angewandte Chemie International Edition (2017); 56(21): 5738-5743.
Rodriguez-Gonzalez, A., et al., "Targeting steroid hormone receptors for ubiquitination and degradation in breast and prostate cancer", Oncogene (2008); 27(57): 7201-7211.
Rosania, G. R., et al., "Targeting hyperproliferative disorders with cyclin dependent kinase inhibitors", Expert Opinion on Therapeutic Patents (2000); 10(2): 215-230.
Rotili, D., et al., "Photoactivable peptides for identifying enzyme-substrate and protein-protein interactions", Chemical Communications (2011); 47(5): 1488-1490.
Ruchelman, A., et al., "Isosteric analogs of lenalidomide and pomalidomide: Synthesis and biological activity", Bioorganic & Medicinal Chemistry Letters (2013); 23(1): 360-365.
Sakamoto, K. M., et al., "Development of Protacs to target cancer-promoting proteins for ubiquitination and degradation", Molecular & Cellular Proteomics (2003); 2(12): 1350-1358.
Sakamoto, K. M., et al., "Protacs: Chimeric molecules that target proteins to the Skp1-Cullin-F box complex for ubiquitination and degradation", Proceedings of the National Academy of Sciences (2001); 98(15): 8554-8559.
Salami, J., et al., "Waste disposal—An attractive strategy for cancer therapy", Science (2017); 355(6330): 1163-1167.
Sameshima, T., et al., "Discovery of an Irreversible and Cell-Active BCL6 Inhibitor Selectively Targeting Cys53 Located at the Protein-Protein Interaction Interface", Biochemistry (Feb. 27, 2018); 57(8): 1369-1379.
Schiedel, M., et al., "Chemically induced degradation of sirtuin 2 (Sirt2) by a proteolysis targeting chimera (Protac) based on sirtuin rearranging ligands (SirReals)", Journal of Medicinal Chemistry (2018); 61(2): 482-491.
Schlager, S., et al., "Inducible knock-out of BCL6 in lymphoma cells results in tumor stasis", Oncotarget (Mar. 3, 2020); 11(9): 875-890.
Schneekloth, A. R., et al., "Targeted intracellular protein degradation induced by a small molecule: En route to chemical proteomics", Bioorganic & Medicinal Chemistry Letters (2008); 18(22): 5904-5908.
Schneekloth Jr, J. S., et al., "Chemical genetic control of protein levels: selective in vivo targeted degradation", Journal of the American Chemical Society (2004); 126(12): 3748-3754.
Scudellari, M., "The protein slayers", Nature (Mar. 21, 2019); 567: 298-300.
Stanton, B. Z., et al., "Chemically induced proximity in biology and medicine", Science (Mar. 9, 2018); 359(1117): 1-9.
Stewart, S. G., et al., "Efforts toward elucidating Thalidomide's molecular target: an expedient synthesis of the first Thalidomide biotin analogue", Organic & Biomolecular Chemistry (2010); 8(18): 4059-4062.
Stoppler, M. C., "Endometriosis definition and facts", MedicineNet.com [online] http://www.medicinenet.com/endometriosis/article.htm (Retrieved on Apr. 5, 2017); 7 pages.
Stoppler, M. C., "What about surgery for Endometriosis?", MedicineNet.com [online] http://www.medicinenet.com/endometriosis/article.htm (Retrieved on Apr. 5, 2017); 7 pages.
Sun, B., et al., "BET protein proteolysis targeting chimera (Protac) exerts potent lethal activity against mantle cell lymphoma cells", Leukemia (2018); 32: 343-352.
Teng, M., et al., "Rationally Designed Covalent BCL6 Inhibitor That Targets a Tyrosine Residue in the Homodimer Interface", ACS Medicinal Chemistry Letters (Apr. 3, 2020); 11(6): 1269-1273.
Thirumurugan, P., et al., "Click chemistry for drug development and diverse chemical-biology applications." Chemical Reviews (2013); 113(7): 4905-4979.
Toure, M., et al., "Small-molecule PROTACS: new approaches to protein degradation", Angewandte Chemie International Edition (2016); 55(6): 1966-1973.
Turk, B. E., et al., "Binding of thalidomide to alpha1-acid glycoprotein may be involved in its inhibition of tumor necrosis factor alpha production", Proceedings of the National Academy of Sciences (1996); 93(15): 7552-7556.
Van Molle, I., et al., "Dissecting fragment-based lead discovery at the von Hippel-Lindau protein: hypoxia inducible factor 1α protein-protein interface", Chemistry & Biology (2012); 19(10): 1300-1312.
Watson, I. D., et al., "Abstract 7: Discovery of OICR-10268: A potent and selective BCL6 inhibitor", Proceedings: AACR Annual Meeting 2019; Mar. 29-Apr. 3, 2019; Atlanta, GA; 1 page.
Winter, G. E., et al., "Phthalimide conjugation as a strategy for in vivo target protein degradation", Science (2015); 348(6241): 1376-1381.
Xie, H., et al., "The clinical advances of proteolysis targeting chimeras in oncology", Exploration of Targeted Anti-tumor Therapy (2021); 2(6): 511-521.
Yasui, T., et al., "Discovery of a novel B-cell lymphoma 6 (BCL6)-corepressor interaction inhibitor by utilizing structure based drug design", Bioorganic & Medicinal Chemistry (Sep. 1, 2017); 25(17): 4876-4886.
Yu, J., et al., "BCL6 induces EMT by promoting the ZEB1-mediated transcription repression of E-cadherin in breast cancer cells", Cancer Letters (2015); 365(2): 190-200.
Zengerle, M., et al., "Selective small molecule induced degradation of the BET bromodomain protein BRD4", Acs Chemical Biology (2015); 10(8): 1770-1777.
Zhang, D., et al., "Targeted Degradation of Proteins by Small Molecules: A Novel Tool for Functional Proteomics", Combinatorial Chemistry & High Throughput Screening (2004); 7(7): 689-697.
Zhou, B., et al., "Discovery of a Small-Molecule Degrader of Bromodomain and Extra-Terminal (BET) Proteins with Picomolar Cellular Potencies and Capable of Achieving Tumor Regression", Journal of Medicinal Chemistry (2018); 61(2): 462-481.

MODULATORS OF BCL6 PROTEOLYSIS AND ASSOCIATED METHODS OF USE

CROSS-REFERENCE TO RELATED APPLICATIONS

This application claims priority to, and the benefit of, U.S. Provisional Application No. 63/417,657, filed Oct. 19, 2022, and U.S. Provisional Application No. 63/417,628, filed Oct. 19, 2022, the contents of each of which are incorporated by reference in their entirety for all purposes.

TECHNICAL FIELD

The disclosure provides imide-based compounds, including bifunctional compounds comprising the same, and associated methods of use. The bifunctional compounds are useful as modulators of targeted ubiquitination, especially with respect to a variety of polypeptides and other proteins, which are degraded and/or otherwise inhibited by bifunctional compounds according to the present disclosure.

BACKGROUND OF THE DISCLOSURE

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination and are therefore attractive therapeutic targets. The development of ligands of E3 ligases has proven challenging, in part, due to the fact that they must disrupt protein-protein interactions. However, recent developments have provided specific ligands which bind to these ligases.

One E3 ubiquitin ligase with therapeutic potential is cereblon. Cereblon is a protein that in humans is encoded by the CRBN gene. Thalidomide and its analogs, e.g., pomalidomide and lenalidomide, are known to bind cereblon. These agents bind to cereblon, altering the specificity of the complex to induce the ubiquitination and degradation of transcription factors essential for multiple myeloma growth. Indeed, higher expression of cereblon has been linked to an increase in efficacy of imide drugs in the treatment of multiple myeloma.

However, non-specific effects, and the inability to target and modulate certain classes of proteins altogether, such as transcription factors, remain as obstacles to the development of effective anti-cancer agents. As such, small molecule therapeutic agents that leverage or potentiate cereblon's substrate specificity and, at the same time, are "tunable" such that a wide range of protein classes can be targeted and modulated with specificity would be very useful as a therapeutic.

SUMMARY

The present disclosure describes bifunctional compounds which function to recruit endogenous proteins to an E3 Ubiquitin Ligase for degradation, and methods of using the same. In particular, the present disclosure provides bifunctional or proteolysis targeting chimeric compounds, which find utility as modulators of targeted ubiquitination of a variety of polypeptides and other proteins, which are then degraded and/or otherwise inhibited by the bifunctional compounds as described herein. In addition, the description provides methods of using an effective amount of the compounds as described herein for the treatment or amelioration of a disease condition, such as breast cancer, ovarian cancer, leukemia, lymphoma, benign lymphoma, malignant lymphoma, Burkitt's lymphoma, non-Hodgkin's lymphoma, B-cell non-Hodgkin's lymphoma, sarcomas, Ewing's sarcoma, hemangiosarcoma, Kaposi's sarcoma, liposarcoma, myosarcomas, synovial sarcoma, meningeal sarcomas, carcinosarcoma, acute myeloid leukemia (AML), acute lymphoblastic leukemia (ALL), T-lineage acute lymphoblastic leukemia (T-ALL), T-lineage lymphoblastic lymphoma (T-LL), peripheral T-cell lymphoma, adult T-cell leukemia, pre-B acute lymphoblastic leukemia, pre-B lymphomas, B-cell lymphoma, large B-cell lymphoma, diffuse large B-cell lymphoma, B-cell acute lymphoblastic leukemia (ALL), Philadelphia chromosome positive acute lymphoblastic leukemia (ALL), Philadelphia chromosome positive chronic myeloid leukemia (CML), follicular lymphoma, intravascular large B-cell lymphoma, angioimmunoblastic T-cell lymphoma (AITL), T-cell lymphoma, B-cell leukemia, chronic myeloid leukemia, non-small cell lung cancer, systemic lupus erythematosus (SLE), brain tumors, or central nervous system cancers.

In one aspect, the disease or disorder is a cancer associated with aberrant BCL6 expression or activity.

In one aspect, the disease or disorder is associated with BCL6 accumulation and aggregation.

In one aspect, the disease or disorder is a cancer associated with BCL6 accumulation and aggregation.

In another aspect, the description provides methods for identifying the effects of the degradation of proteins of interest in a biological system using compounds according to the present disclosure.

In one aspect, this application pertains to a bifunctional compound of Formula (I):

Formula (I)

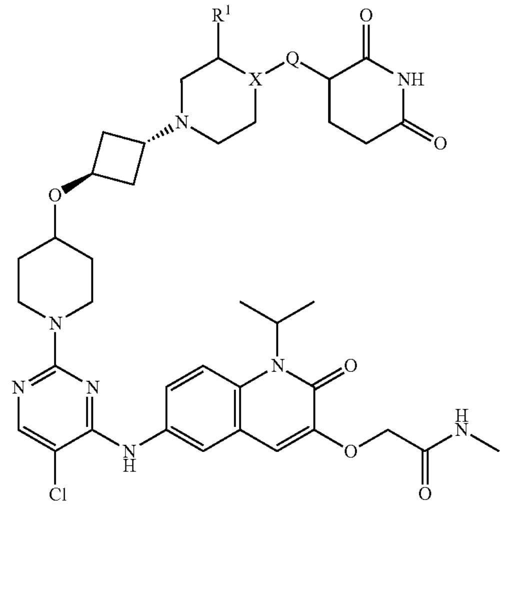

or a pharmaceutically acceptable salt, enantiomer, stereoisomer, or isotopic derivative thereof, wherein:

$R^1$ is H or $C_1$-$C_6$ alkyl;

Q is

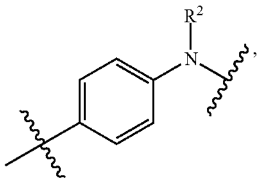

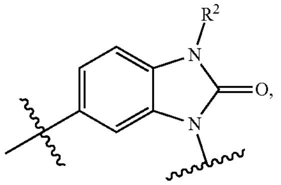

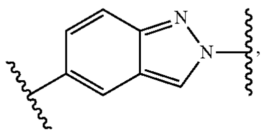

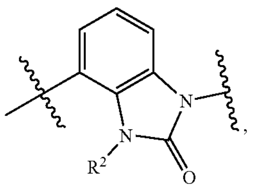

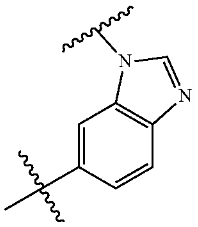

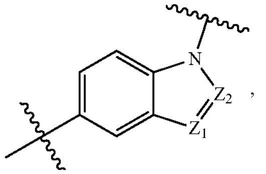

, or

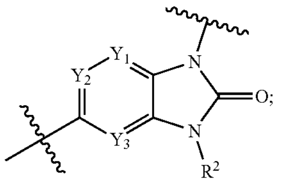

X is N or CH;

$Y_1$, $Y_2$, and $Y_3$ are each, independently, N or $CR^3$;

$Z_1$ and $Z_2$ are each, independently, N or CH;

$R^2$ is H or $C_1$-$C_6$ alkyl;

each $R^3$ is, independently, H, halogen, $C_1$-$C_6$ alkyl, $C_1$-$C_6$ haloalkyl, —O—$C_1$-$C_6$ alkyl), or —O—($C_1$-$C_6$ haloalkyl); and wherein ∿∿∿ of the Q indicates the point of attachment with the X or the glutaramide.

In one aspect, this application pertains to a bifunctional compound of Formula (II):

Formula (II)

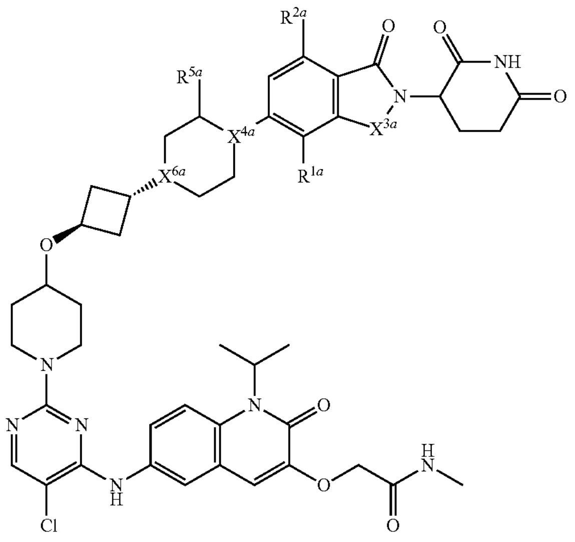

or a pharmaceutically acceptable salt, enantiomer, stereoisomer, or isotopic derivative thereof, wherein:

$R^{1a}$ is H or halogen;

$R^{2a}$ is H or $C_1$-$C_3$ alkyl;

$X^{3a}$ is $CHR^{3a}$ or C(O);

$R^{3a}$ is H or $C_1$-$C_3$ alkyl;

$X^{4a}$ and $X^{6a}$ are each independently CH or N; and $R^{5a}$ is H, $C_1$-$C_3$ alkyl or halogen.

In one aspect, this application pertains to a bifunctional compound of Formula (III):

Formula (III)

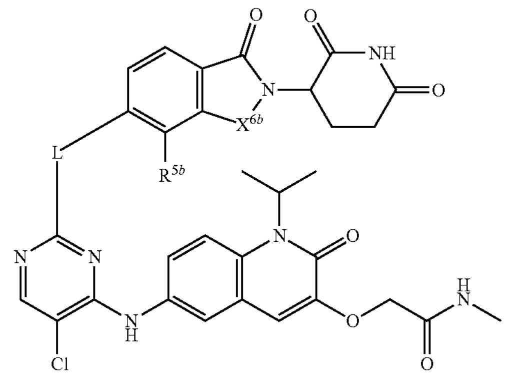

or a pharmaceutically acceptable salt, enantiomer, stereoisomer, or isotopic derivative thereof, wherein:

L is

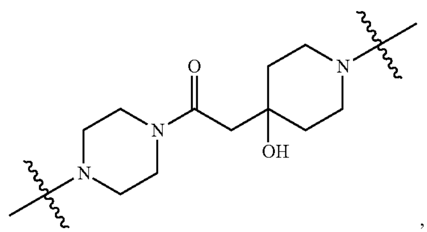

,

-continued

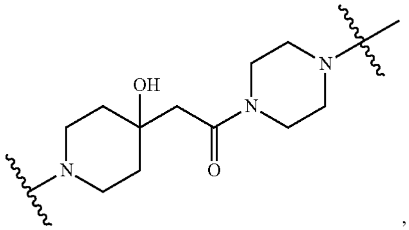

, or

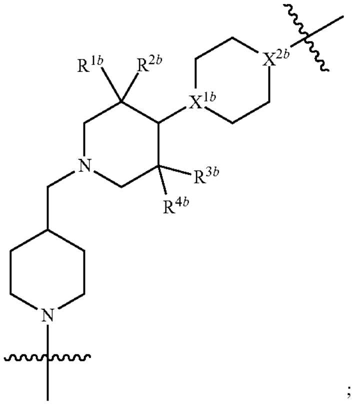

;

$X^{6b}$ is $CHR^{6b}$ or C(O);

$R^{6b}$ is H or $C_1$-$C_3$ alkyl;

$R^{1b}$, $R^{2b}$, $R^{3b}$, and $R^{4b}$ are each independently H or halogen, wherein at least one of $R^{1b}$, $R^{2b}$, $R^{3b}$, $R^{4b}$ is halogen;

$R^{5b}$ is H or halogen;

$R^{6b}$ is H or $C_1$-$C_3$ alkyl;

$X^{1b}$ and $X^{2b}$ are each independently CH or N, wherein at least one of $X^{1b}$ and $X^{2b}$ is N, and wherein each ∿∿∿ of L indicates a point of attachment.

In one aspect, this application pertains to a bifunctional compound of any of Formulas (I)-(III) or a pharmaceutically acceptable salt thereof.

In one aspect, this application pertains to a bifunctional compound of any of Formulas (I)-(III).

In one aspect, this application pertains to a bifunctional compound of any of Formulas (I)-(III), wherein the compound is as shown in Table 1, or a pharmaceutically acceptable salt, enantiomer, stereoisomer, or isotopic derivative thereof.

In one aspect, this application pertains to a bifunctional compound of any of Formulas (I)-(III), wherein the compound is as shown in Table 1, or a pharmaceutically acceptable salt thereof.

In one aspect, this application pertains to a bifunctional compound of any of Formulas (I)-(III), wherein the compound is as shown in Table 1.

In one embodiment, the application provides a pharmaceutical composition comprising a bifunctional compound described herein and one or more pharmaceutically acceptable excipients.

In one embodiment, the composition is formulated as a tablet, and comprises one or more of the following: emulsifier; surfactant; binder; disintegrant; glidant; and lubricant.

In one embodiment, the composition further comprises an effective amount of at least one additional anti-cancer agent.

In one embodiment, the application provides a method of treating cancer in a subject comprising administering to a subject in need thereof a therapeutically effective amount of a bifunctional compound described herein, or a therapeutically effective amount of a pharmaceutical composition described herein.

In one embodiment, the therapeutically effective amount of the bifunctional compound is administered orally to the subject.

In one embodiment, the therapeutically effective amount of the bifunctional compound is administered to the subject once a day, twice a day, three times a day, or four times a day.

In one embodiment, the therapeutically effective amount of the bifunctional compound is administered to the subject once a day.

In one embodiment, the therapeutically effective amount of the bifunctional compound is administered to the subject all at once or is administered in two, three, or four divided doses.

In one embodiment, the therapeutically effective amount of the bifunctional compound is about 1 mg to about 1000 mg.

In one embodiment, the therapeutically effective amount of the bifunctional compound is about 5 mg to about 750 mg.

In one embodiment, the therapeutically effective amount of the bifunctional compound is about 10 mg to about 500 mg.

In one embodiment, the therapeutically effective amount of the bifunctional compound is about 20 mg to about 250 mg.

In one embodiment, the subject is in a fed state at the time of administration.

In one embodiment, the subject is in a fasted state at the time of administration.

In one embodiment, the method further comprises administering an effective amount of at least one additional anti-cancer agent to the subject in need thereof.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which:

FIG. 1A represents exemplary proteolysis targeting chimeric compounds comprise a protein targeting moiety (PTM; rectangle), a cereblon ubiquitin ligase binding moiety (CLM; triangle), and a linker moiety (black line) coupling or tethering the PTM to the CLM. FIG. 1B illustrates the functional use of the proteolysis targeting chimeric compounds as described herein. Briefly, the CLM recognizes and binds to cereblon, an E3 Ubiquitin Ligase, and the PTM binds and recruits an intracellular target protein bringing it into close proximity to the cereblon E3 Ubiquitin Ligase. Typically, the cereblon E3 Ubiquitin Ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.

DETAILED DESCRIPTION

Definitions

Figure 1A:
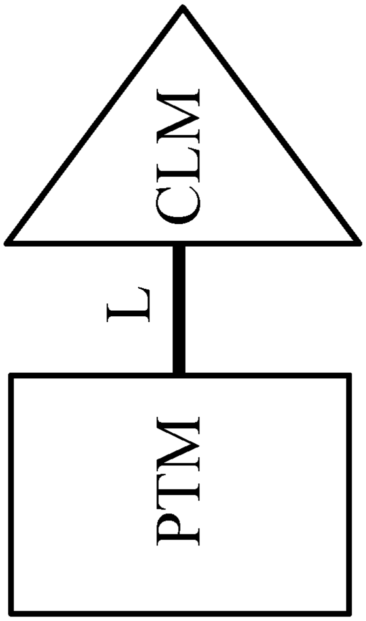
FIGS. 1A and 1B are illustrations of the general principle for the function of proteolysis targeting chimeric compounds.
Figure 1B:
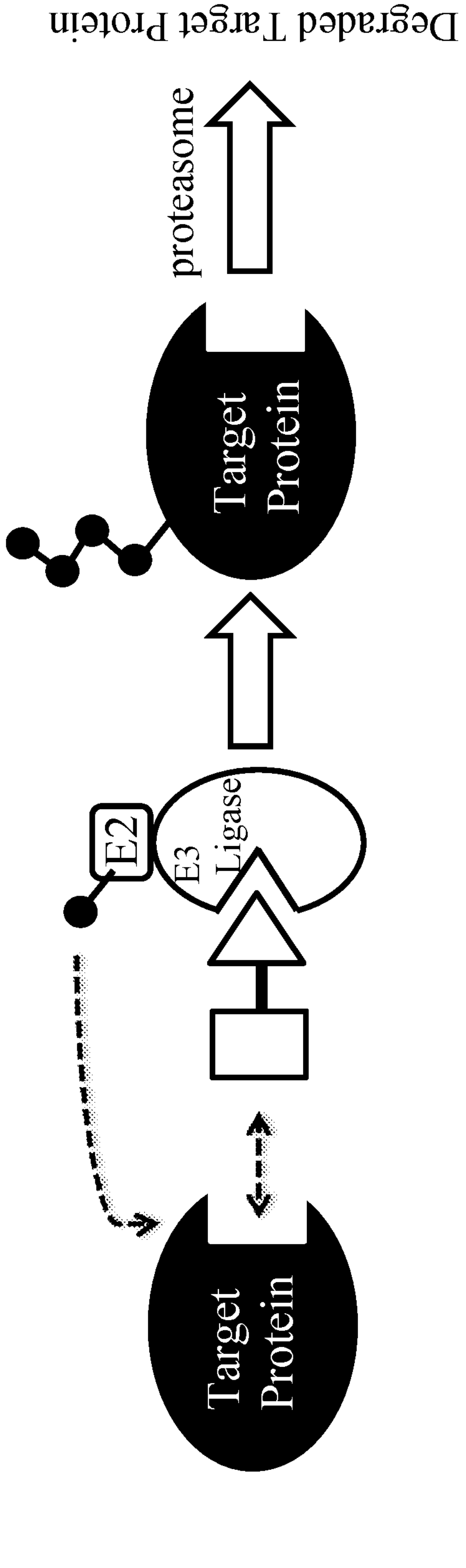

The term "Ubiquitin Ligase" refers to a family of proteins that facilitate the transfer of ubiquitin to a specific substrate protein, targeting the substrate protein for degradation. For example, cereblon is an E3 Ubiquitin Ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

As used herein, "Compound", "bifunctional compound", or "Compound of the Disclosure", as used herein, refers to the compounds disclosed by structure in the following tables and examples.

"Halogen" or "halo" refers to fluorine (F), chlorine (Cl), bromine (Br), or iodine (I).

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, neopentyl, and isohexyl.

"$C_1$-$C_6$ haloalkyl" refers to a straight or branched chain saturated hydrocarbon containing 1-6 carbon atoms that is substituted by one or more halogens. Examples of a $C_1$-$C_6$ haloalkyl group include, but are not limited to, trifluoromethyl, difluoromethyl, and fluoromethyl.

"Pharmaceutically acceptable salt", as used herein with respect to a compound of the disclosure, means a salt form of the compound of the disclosure as well as hydrates of the salt form with one or more water molecules present. Such salt and hydrated forms retain the biological activity of the compound of the disclosure and are not biologically or otherwise undesirable, i.e., exhibit minimal, if any, toxicological effects. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "isomer" refers to salts and/or compounds that have the same composition and molecular weight but differ in physical and/or chemical properties. The structural difference may be in constitution (geometric isomers) or in the ability to rotate the plane of polarized light (stereoisomers). With regard to stereoisomers, the salts of the compounds of the disclosure may have one or more asymmetric carbon atom and may occur as racemates, racemic mixtures and as individual enantiomers or diastereomers.

The compounds of the disclosure may exist in unsolvated as well as solvated forms such as, for example, hydrates.

"Solvate" means a solvent addition form that contains either a stoichiometric or non-stoichiometric amounts of solvent. Non-limiting examples of suitable solvates include ethanolate, methanolate, and the like. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of salts of the compounds of the disclosure.

"Isotopic derivative", as referred to herein, relates to a compound of the disclosure that is isotopically enriched or labelled (with respect to one or more atoms of the compound) with one or more stable isotopes. Thus, in this application, the compounds of the disclosure include, for example, compounds that are isotopically enriched or labelled with one or more atoms such as deuterium.

As used herein, "treating" describes the management and care of a subject for the purpose of combating a disease, condition, or disorder and includes decreasing or alleviating the symptoms or complications, or eliminating the disease, condition or disorder.

As used herein, "preventing" describes stopping the onset of the symptoms or complications of the disease, condition or disorder.

"Administration" refers to introducing an agent, such as a compound of the disclosure into a subject. The related terms "administering" and "administration of" (and grammatical equivalents) refer both to direct administration, which may be administration to a subject by a medical professional or by self-administration by the subject, and/or to indirect administration, which may be the act of prescribing a drug. For example, a physician who instructs a patient to self-administer a drug and/or provides a patient with a prescription for a drug is administering the drug to the patient.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an anti-cancer agent. In particularly preferred aspects, the co-administration of compounds results in synergistic activity and/or therapy, including anti-cancer activity.

"Therapeutically effective amount", as used herein means an amount of the free base of a compound of the disclosure that is sufficient to treat, ameliorate, or prevent a specified disease (e.g., lymphoma), disease symptom, disorder or condition, or to exhibit a detectable therapeutic or inhibitory effect. The effect can be detected by any assay method known in the art. The effective amount for a particular subject may depend upon the subject's body weight, size, and health; the nature and extent of the condition; and whether additional therapeutics are to be administered to the subject. Therapeutically effective amounts for a given situation can be determined by routine experimentation that is within the skill and judgment of the clinician.

"$C_{max}$", as used herein, refers to the observed maximum (peak) plasma concentration of a specified compound in the subject after administration of a dose of that compound to the subject.

"AUC", as used herein, refers to the total area under the plasma concentration-time curve, which is a measure of exposure to a compound of interest, and is the integral of the concentration-time curve after a single dose or at steady state. AUC is expressed in units of ng*H/mL (ng×H/mL), where "H" refers to hours.

"$AUC_{tau}$", as used herein, refers to the AUC from 0 hours to the end of a dosing interval.

"$AUC_{0-24}$" means the AUC from 0 hours to 24 hours after administration of a single dose.

"Controlled release" or "CR" as used herein with respect to an oral dosage form refers to where a compound of the disclosure is released from the dosage form according to a predetermined profile that may include when and where release occurs after oral administration and/or a specified rate of release over a specified time period "Controlled release agent" as used herein with respect to an oral dosage form of the disclosure refers to one or more substances or materials that modulate release of a compound of the disclosure from the dosage form. Controlled release agents may be materials which are organic or inorganic, naturally occurring, or synthetic, such as polymeric materials, triglycerides, derivatives of triglycerides, fatty acids and salts of fatty acids, talc, boric acid, colloidal silica, and combinations thereof.

"Enteric coating" as used herein with respect to a dosage form of the disclosure refers to a pH-dependent material that surrounds a core comprising a compound of the disclosure and which remains substantially intact in the acid environment of the stomach, but which dissolves in the pH environment of the intestines.

"Gastro-resistant" or "GR" as applied to a CR oral dosage form described herein means that release of a compound of the disclosure in the stomach of a subject shall not exceed 5%, 2.5%, 1% or 0.5% of the total amount of the compound of the disclosure in the dosage form.

"Oral dosage form" as used herein refers to a pharmaceutical drug product that contains a specified amount (dose) of a compound of the disclosure as the active ingredient, or a pharmaceutically acceptable salt and/or solvate thereof, and inactive components (excipients), formulated into a particular configuration that is suitable for oral administration, such as an oral tablet, liquid, or capsule. In one embodiment, the compositions are in the form of a tablet that can be scored.

The term "carrier", as used in this disclosure, encompasses pharmaceutically acceptable excipients and diluents, and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "about" as part of a quantitative expression such as "about X", includes any value that is 10% higher or lower than X, and also includes any numerical value that falls between X−10% and X+10%. Thus, for example, a weight of about 40 g includes a weight of between 36 to 44 g.

"Comprising" or "comprises" as applied to a particular dosage form, composition, use, method or process described or claimed herein means that the dosage form, composition, use, method, or process includes all of the recited elements in a specific description or claim, but does not exclude other elements. "Consists essentially of" and "consisting essentially of" means that the described or claimed composition, dosage form, method, use, or process does not exclude other materials or steps that do not materially affect the recited physical, pharmacological, pharmacokinetic properties or therapeutic effects of the composition, dosage form, method, use, or process. "Consists of" and "consisting of" means the exclusion of more than trace elements of other ingredients and substantial method or process steps.

"Fasted condition" or "fasted state" as used to describe a subject means the subject has not eaten for at least 4 hours before a time point of interest, such as the time of administering a compound of the disclosure. In an embodiment, a subject in the fasted state has not eaten for at least any of 6, 8, 10 or 12 hours prior to administration of a compound of the disclosure.

"Fed condition" or "fed state" as used to describe a subject herein means the subject has eaten less than 4 hours before a time point of interest, such as the time of administering a compound of the disclosure. In an embodiment, a subject in the fed state has eaten within at least any of 3, 2, 1 or 0.5 hours prior to administration of a compound of the disclosure.

As used herein, the term "anti-cancer agent" is used to describe an anti-cancer agent, or a therapeutic agent administered concurrently with an anti-cancer agent (e.g., palonosetron), with which may be co-administered and/or co-formulated with a compound of the disclosure to treat cancer, and the side effects associated with the cancer treatment. These agents include, for example, everolimus, venetoclax, palbociclib, tazemetostat, apelisib, olaparib, MK2206, ibrutinib, acalabrutinib, bendamustine, prednisone, cyclophosphamide, gemcitabine, polatuzumab, upadacitinib, abrocitinib, panobinostat, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR1 KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo [2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, and mixtures thereof.

In one embodiment, the anti-cancer agent is selected from the group consisting of temozolomide, capecitabine, irinotecan, tamoxifen, anastrazole, exemestane, letrozole, DES, Estradiol, estrogen, bevacizumab, goserelin acetate, leuprolide acetate, triptorelin pamoate, medroxyprogesterone acetate, hydroprogesterone caproate, raloxifene, megestrol acetate, carboplatin, cisplatin, dacarbazine, methotrexate, vinblastine, vinorelbine, topotecan, finasteride, arzoxifene, fulvestrant, prednisone, abiraterone, enzalutamide, apalutamide, darolutamide, sipuleucel-T, pembrolizumab, nivolumab, cemiplimab, atezolizumab (Tecentriq), avelumab (Bavencio), durvalumab (Imfinzi), docetaxel (Taxotere), cabazitaxel (Jevtana), mitoxantrone (Novantrone), estramustine (Emcyt), docetaxel, ketoconazole, histrelin, triptorelin, buserelin, cyproterone, flutamide, bicalutamide, nilutamide, pamidronate, and zolendronate.

The articles “a” and “an” are used in this disclosure to refer to one or more than one (i.e., to at least one) of the grammatical object of the article. By way of example, “an element” means one element or more than one element.

The term “and/or” is used in this disclosure to mean either “and” or “or” unless indicated otherwise.

The terms “patient” and “subject” are used interchangeably herein, and refer to a mammal, e.g., a human, mouse, rat, guinea pig, dog, cat, horse, cow, pig, or non-human primate, such as a monkey, chimpanzee, baboon or rhesus.

In one embodiment, the subject is a human.

In one embodiment, the subject is a human who has been diagnosed with multiple myeloma.

In one embodiment, the subject is a human who has been diagnosed with lymphoma.

In one embodiment, the subject is a human who has been diagnosed with B-cell non-Hodgkin lymphomas, large B-cell lymphoma, Burkitt’s lymphoma, follicular lymphoma, intravascular large B-cell lymphoma, B-cell leukemia, B-cell acute lymphoblastic leukemia, chronic myeloid leukemia, or non-small cell lung cancer.

Compounds of the Disclosure

In one aspect, the application pertains to a bifunctional or multifunctional compounds useful for regulating protein activity by inducing the degradation of a target protein. In some embodiments, the bifunctional compound comprises an E3 ubiquitin ligase binding moiety and a protein targeting moiety, preferably linked through a linker moiety, as otherwise described herein, wherein the E3 ubiquitin ligase binding moiety is coupled to the protein targeting moiety and wherein the E3 ubiquitin ligase binding moiety recognizes a ubiquitin pathway protein (e.g., an ubiquitin ligase, preferably an E3 ubiquitin ligase) and the protein targeting moiety recognizes the target protein such that degradation of the target protein will occur when the target protein is placed in proximity to the ubiquitin ligase, thus resulting in degradation/inhibition of the effects of the target protein and the control of protein levels. In certain embodiments, the bifunctional compound comprises a CLM coupled, e.g., linked covalently, directly, or indirectly, to a chemical linker L, and a PTM, which can be depicted as:

PTM-L-CLM

The CLM recognizes and binds to cereblon, an E3 Ubiquitin Ligase. The PTM is a small molecule protein binding moiety that binds and recruits an intracellular target protein or polypeptide bringing it into close proximity to the CLM to effect the degradation of the target protein, resulting in target protein ubiquitination. In certain embodiments, the PTM is a B-cell lymphoma 6 protein (BCL6) targeting moiety.

In one aspect, for the compounds described herein, the PTM comprises the following chemical structure:

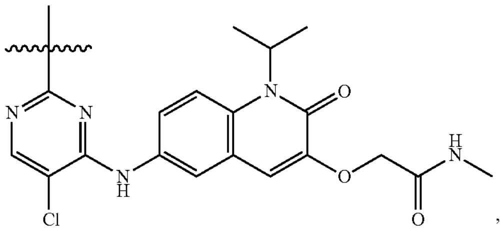 [SMILES: *c1ncc(Cl)c(Nc2ccc3c(c2)cc(OCC(=O)NC)c(=O)n3C(C)C)n1]
, wherein ∿∿∿ of the PTM indicates the point of attachment with the L.

In some embodiments for the compounds described herein, the L comprises the following chemical structures:

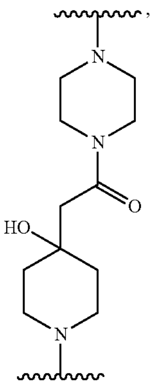
,
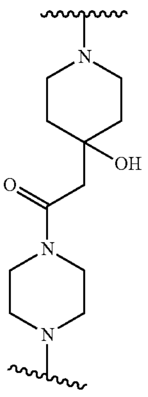
,

-continued

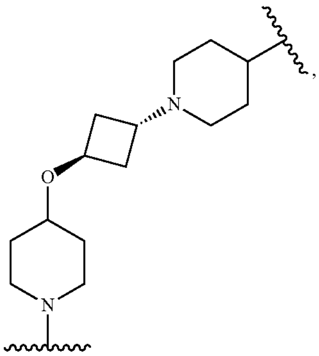
,
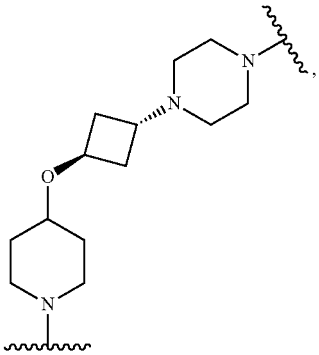
,
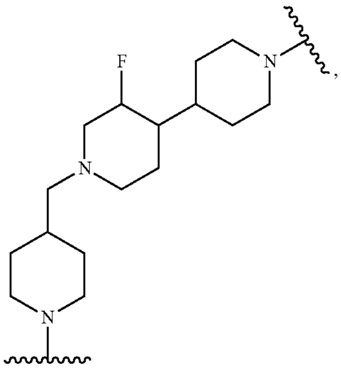
,
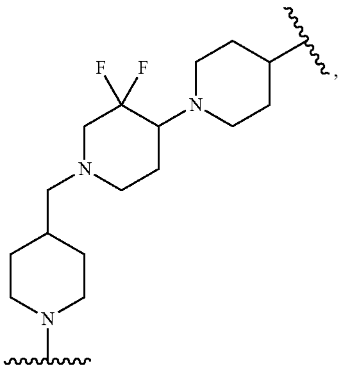
,

-continued
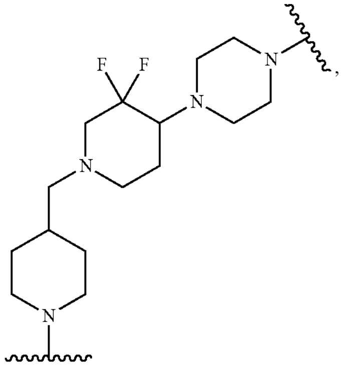
,
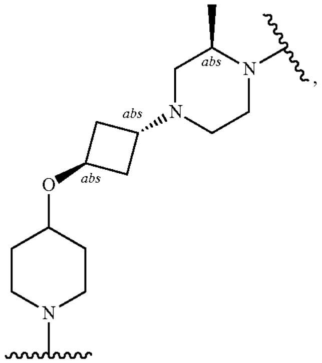
,
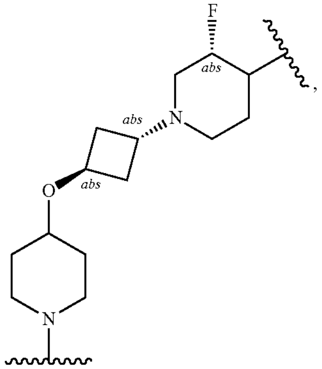
, and
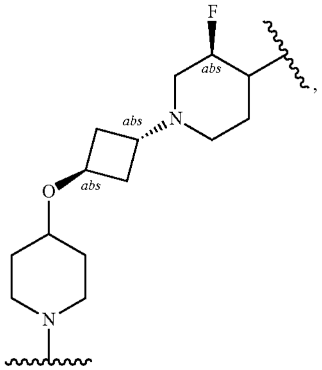 [SMILES: *C1CCN([C@H]2C[C@H](OC3CCN(*)CC3)C2)C[C@H]1F]
,
wherein ~~~ of the L indicates the point of attachment with the PTM or the CLM.
In some embodiments of the compounds described herein, the CLM comprises the following chemical structures:
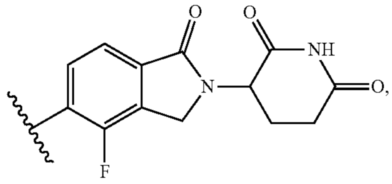
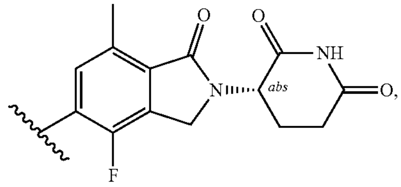
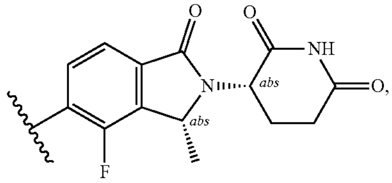
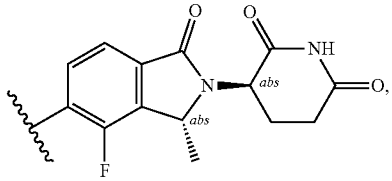
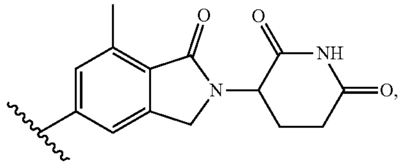
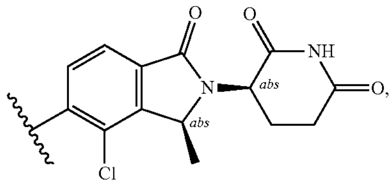
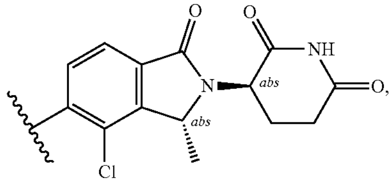
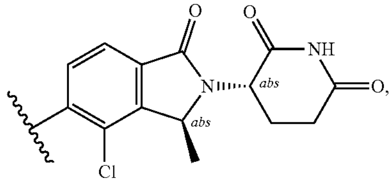
and
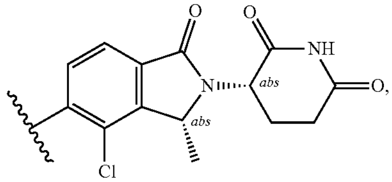 [SMILES: *c1ccc2c(c1Cl)[C@@H](C)N([C@H]1CCC(=O)NC1=O)C2=O]
wherein ~~~ of the CLM indicates the point of attachment with the L.

In one aspect, this application pertains to a bifunctional compound of Formula (I):

Formula (I)

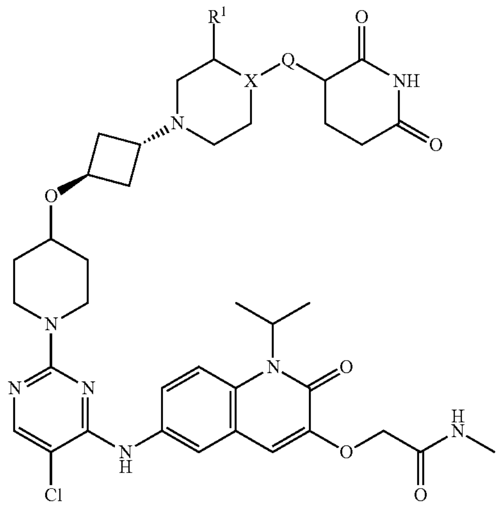

or a pharmaceutically acceptable salt, enantiomer, stereoisomer, or isotopic derivative thereof, wherein:

$R^1$ is H or $C_1$-$C_6$ alkyl;

Q is

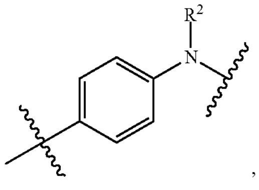

,

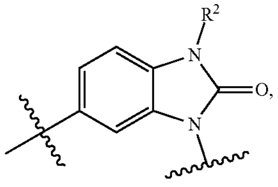

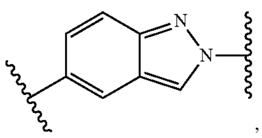

,

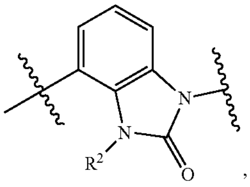

,

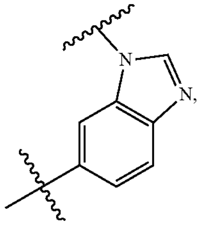

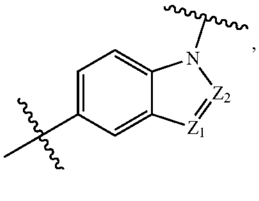

, or

-continued

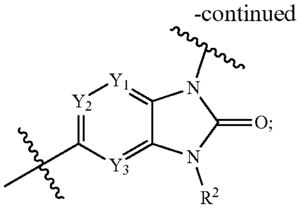

X is N or CH;

$Y_1$, $Y_2$, and $Y_3$ are each, independently, N or $CR^3$;

$Z_1$ and $Z_2$ are each, independently, N or CH;

$R^2$ is H or $C_1$-$C_6$ alkyl;

each $R^3$ is, independently, H, halogen, $C_1$-$C_6$ alkyl, $C_1$-$C_6$ haloalkyl, —O—($C_1$-$C_6$ alkyl), or —O—$C_1$-$C_6$ haloalkyl); and wherein ∿∿∿ of the Q indicates the point of attachment with the X or the glutaramide.

In one aspect, this application pertains to a bifunctional compound of Formula (I):

Formula (I)

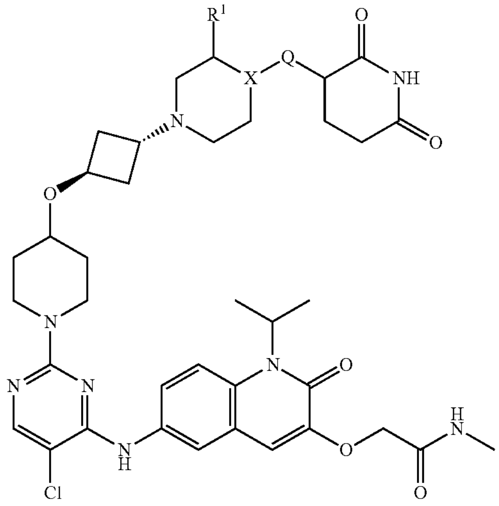

or a pharmaceutically acceptable salt thereof, wherein:

$R^1$ is H or $C_1$-$C_6$ alkyl;

Q is

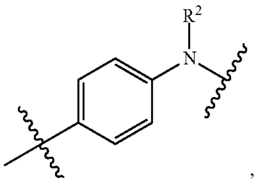

,

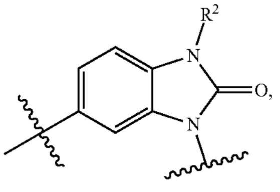

-continued

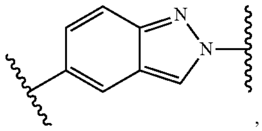

,

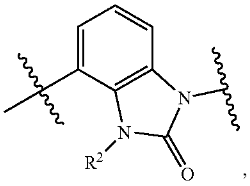

,

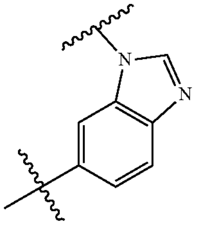

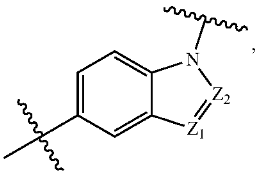

, or

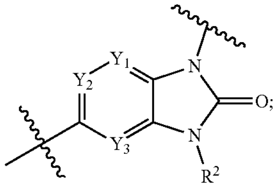

X is N or CH;

$Y_1$, $Y_2$, and $Y_3$ are each, independently, N or $CR^3$;

$Z_1$ and $Z_2$ are each, independently, N or CH;

$R^2$ is H or $C_1$-$C_6$ alkyl;

each $R^3$ is, independently, H, halogen, $C_1$-$C_6$ alkyl, $C_1$-$C_6$ haloalkyl, —O—($C_1$-$C_6$ alkyl), or —O—($C_1$-$C_6$ haloalkyl); and wherein ∿∿∿ of the Q indicates the point of attachment with the X or the glutaramide.

In one aspect, this application pertains to a bifunctional compound of Formula (I):

Formula (I)

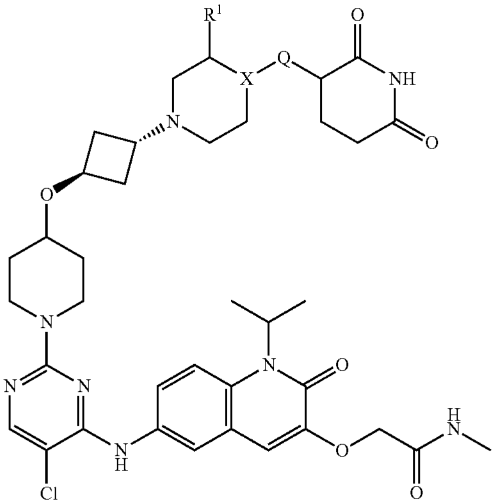

wherein:

$R^1$ is H or $C_1$-$C_6$ alkyl;

Q is

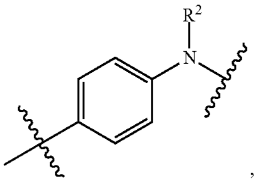

,

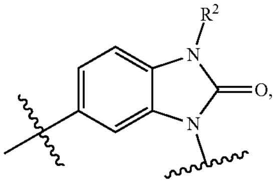

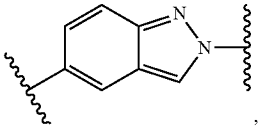

,

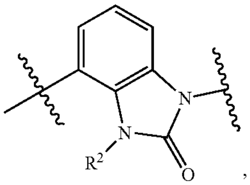

,

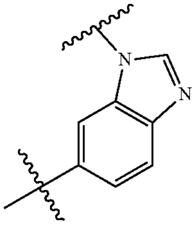

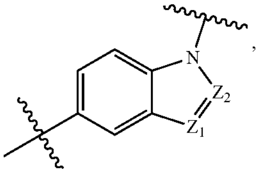

, or

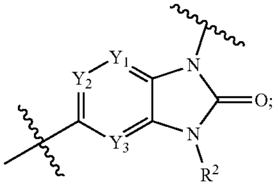

X is N or CH;

$Y_1$, $Y_2$, and $Y_3$ are each, independently, N or $CR^3$;

$Z_1$ and $Z_2$ are each, independently, N or CH;

$R^2$ is H or $C_1$-$C_6$ alkyl;

each $R^3$ is, independently, H, halogen, $C_1$-$C_6$ alkyl, $C_1$-$C_6$ haloalkyl, —O—($C_1$-$C_6$ alkyl), or —O—($C_1$-$C_6$ haloalkyl); and wherein ∿∿∿ of the Q indicates the point of attachment with the X or the glutaramide.

In some embodiments, $R^1$ is hydrogen. In some embodiments, $R^1$ is methyl.

In some embodiments, Q is

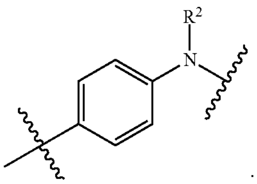

.

In some embodiments, Q is

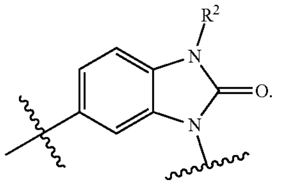

In some embodiments, Q is

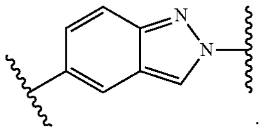 [SMILES: *c1ccc2nn(*)cc2c1]

In some embodiments, Q is

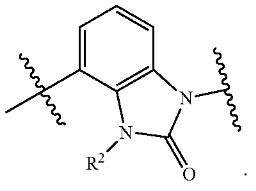

In some embodiments, Q is

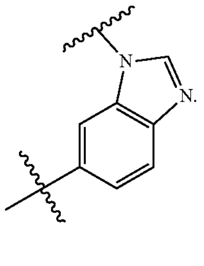 [SMILES: *c1ccc2ncn(*)c2c1]

In some embodiments, Q is

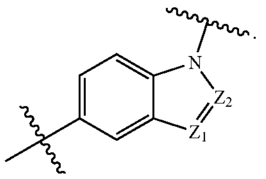

In some embodiments, Q is

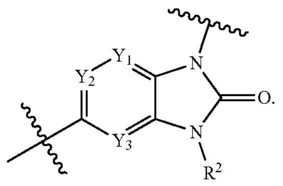

In some embodiments, each of $Y_1$, $Y_2$, and $Y_3$ is CH.

In some embodiments, one of $Y_1$, $Y_2$, and $Y_3$ is N, and the other two of $Y_1$, $Y_2$, or $Y_3$ are CH. In some embodiments, $Y_1$ is N, and $Y_2$ and $Y_3$ are CH. In some embodiments, $Y_2$ is N, and $Y_1$ and $Y_3$ are CH. In some embodiments, $Y_3$ is N, and $Y_1$ and $Y_2$ are CH.

In some embodiments, two of $Y_1$, $Y_2$, and $Y_3$ is N, and the other one of $Y_1$, $Y_2$, or $Y_3$ is CH. In some embodiments, $Y_1$ and $Y_2$ are N, and $Y_3$ is CH. In some embodiments, $Y_1$ and $Y_3$ are N, and $Y_2$ is CH. In some embodiments, $Y_2$ and $Y_3$ are N, and $Y_1$ is CH.

In some embodiments, $Z_1$ and $Z_2$ are each N.

In some embodiments, $Z_1$ and $Z_2$ are each CH.

In some embodiments, $Z_1$ is N and $Z_2$ is CH.

In some embodiments, $Z_1$ is CH and $Z_2$ is N.

In some embodiments, X is N. In some embodiments, X is CH.

In some embodiments, $R^2$ is H, methyl, ethyl, or isopropyl.

In some embodiments, $R^2$ is H.

In some embodiments, $R^2$ is methyl, ethyl, or isopropyl.

In some embodiments, $R^2$ is methyl.

In some embodiments, $R^2$ is ethyl.

In some embodiments, $R^2$ is isopropyl.

In some embodiments, each $R^3$ is, independently, hydrogen, methyl, fluoro, or methoxy.

In one aspect, this application pertains to a bifunctional compound of Formula (II):

Formula (II)

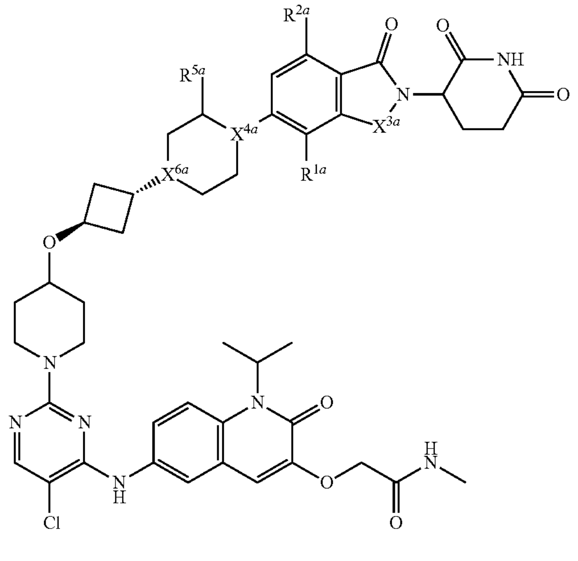

or a pharmaceutically acceptable salt, enantiomer, stereoisomer, or isotopic derivative thereof, wherein:

$R^{1a}$ is H or halogen; $R^{2a}$ is H or $C_1$-$C_3$ alkyl;

$X^{3a}$ is $CHR^{3a}$ or C(O);

$R^{3a}$ is H or $C_1$-$C_3$ alkyl;

$X^{4a}$ and $X^{6a}$ are each independently CH or N; and $R^{5a}$ is H, $C_1$-$C_3$ alkyl or halogen.

In one aspect, this application pertains to a bifunctional compound of Formula (II):

Formula (II)

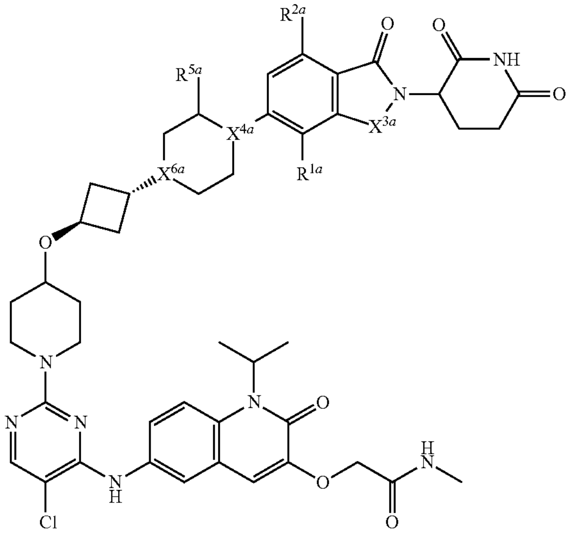

or a pharmaceutically acceptable salt thereof, wherein:

$R^{1a}$ is H or halogen;

$R^{2a}$ is H or $C_1$-$C_3$ alkyl;

$X^{3a}$ is $CHR^{3a}$ or C(O);

$R^{3a}$ is H or $C_1$-$C_3$ alkyl;

$X^{4a}$ and $X^{6a}$ are each independently CH or N; and $R^{5a}$ is H, $C_1$-$C_3$ alkyl or halogen.

In one aspect, this application pertains to a bifunctional compound of Formula (II):

Formula (II)

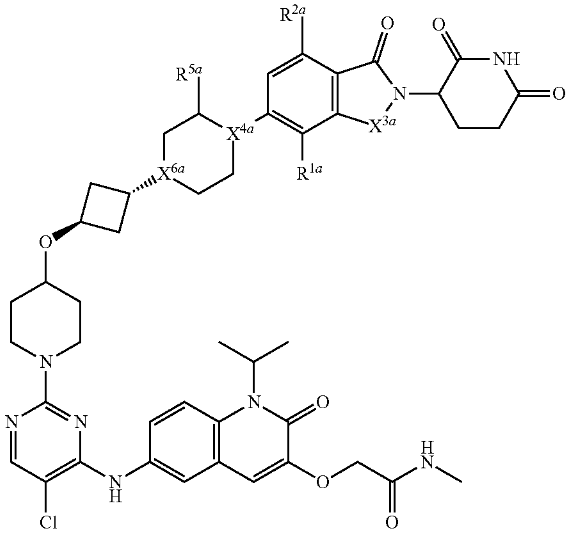

wherein:

$R^{1a}$ is H or halogen;

$R^{2a}$ is H or $C_1$-$C_3$ alkyl;

$X^{3a}$ is $CHR^{3a}$ or C(O);

$R^{3a}$ is H or $C_1$-$C_3$ alkyl;

$X^{4a}$ and $X^{6a}$ are each independently CH or N; and $R^{5a}$ is H, $C_1$-$C_3$ alkyl or halogen.

In some embodiments, the compound of Formula (II) is a compound of Formula (II-a):

Formula (II-a)

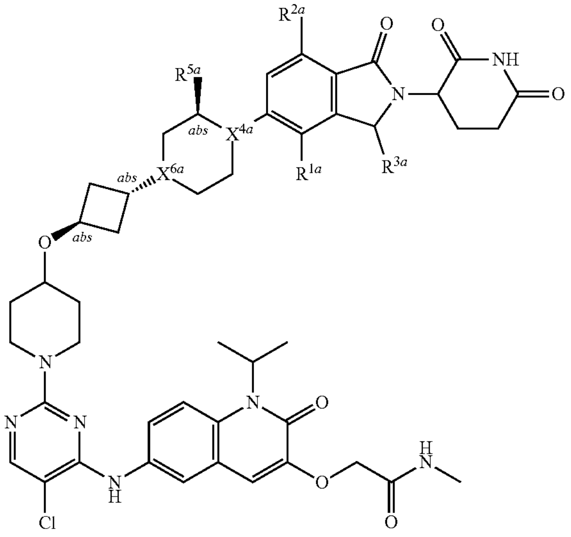

or a pharmaceutically acceptable salt thereof.

In some embodiments, the compound of Formula (II) is a compound of Formula (II-a).

In some embodiments, the compound of Formula (II) is a compound of Formula (II-b), Formula (II-c), Formula (II-d), Formula (II-e), Formula (II-f), Formula (II-g), Formula (II-h), Formula (II-i), or Formula (II-j):

Formula (II-b)

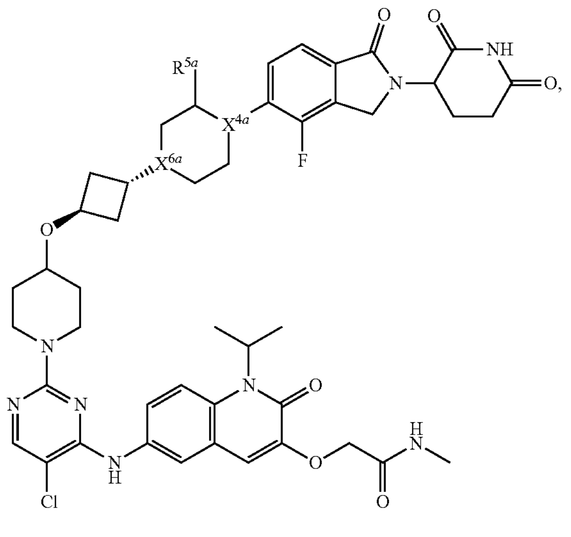

-continued
Formula (II-c)
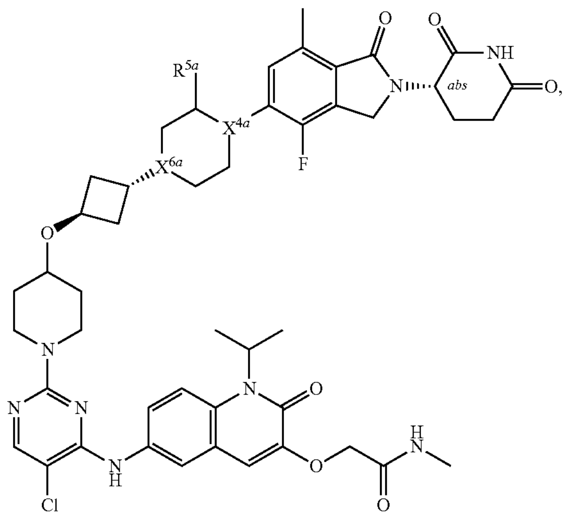
Formula (II-d)
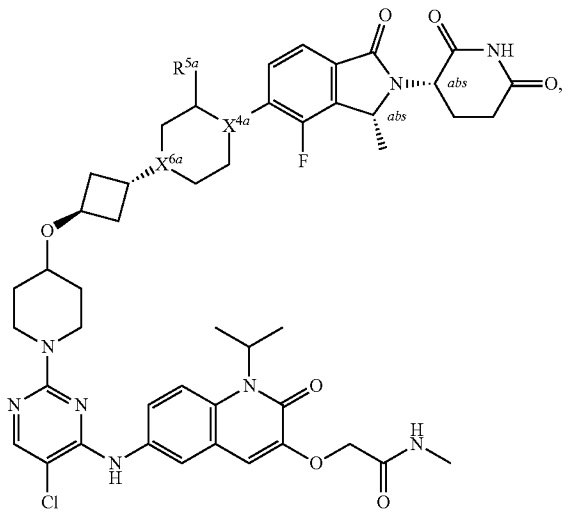
Formula (II-e)
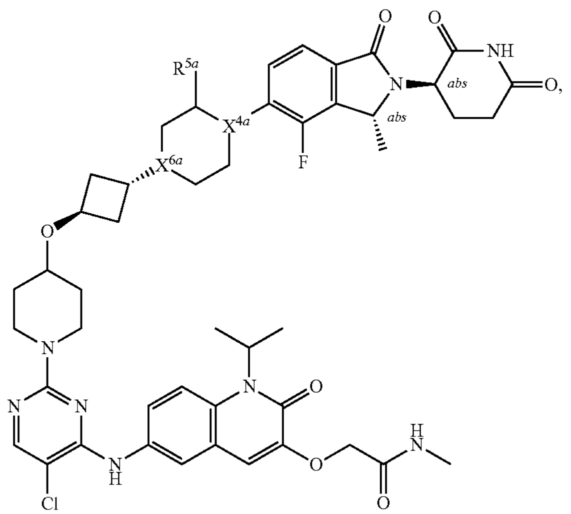
-continued
Formula (II-f)
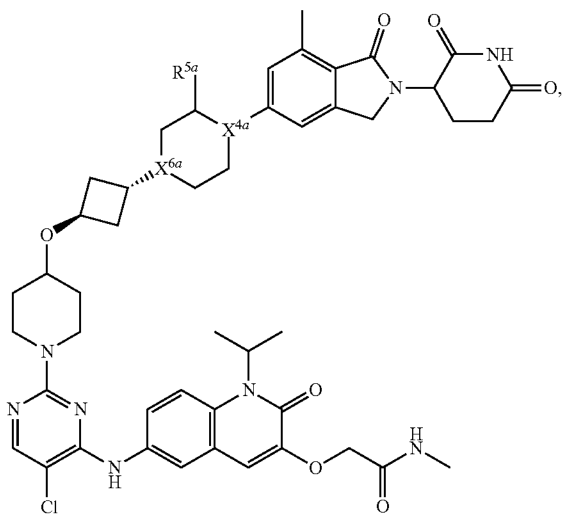
Formula (II-g)
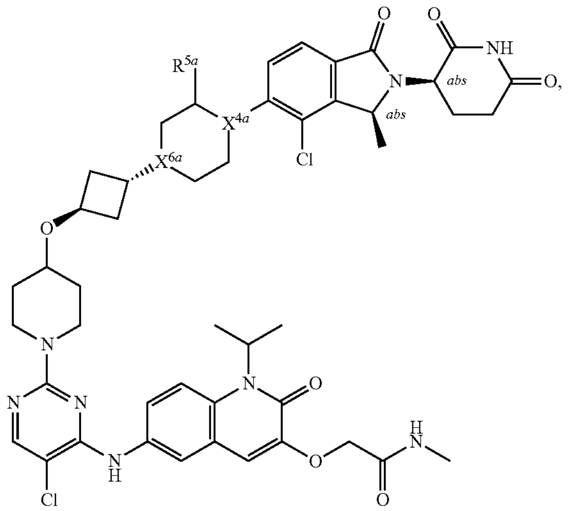
Formula (II-h)
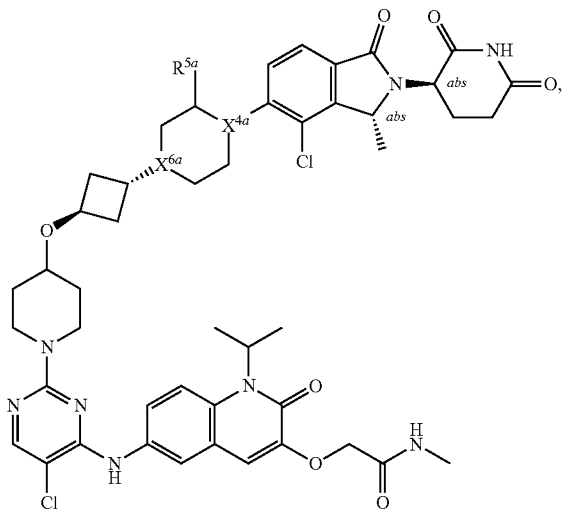

-continued

Formula (II-i)

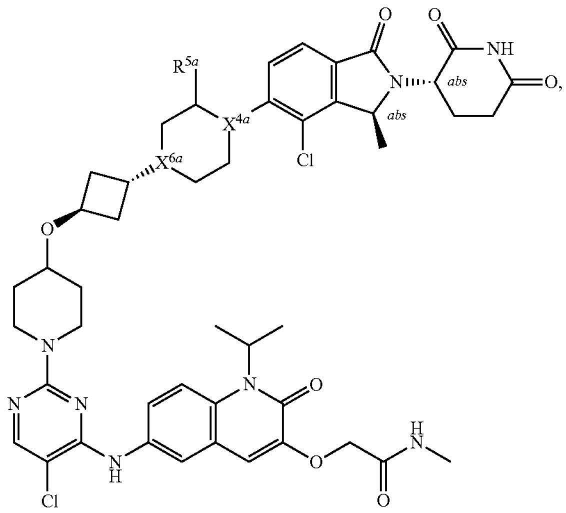

Formula (II-j)

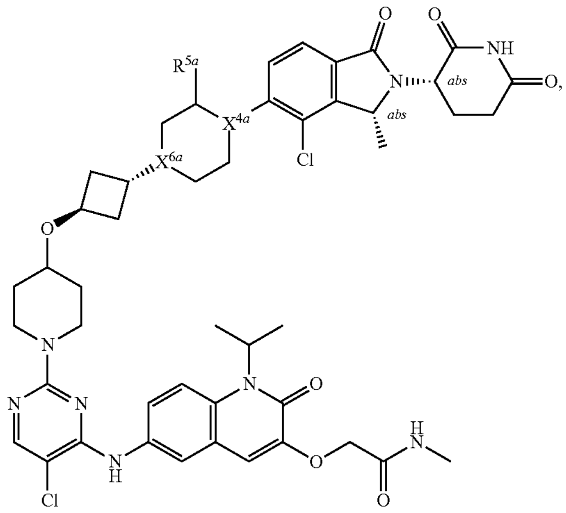

or a pharmaceutically acceptable salt thereof.

In some embodiments, the compound of Formula (II) is a compound of Formula (II-b), Formula (II-c), Formula (II-d), Formula (II-e), Formula (II-f), Formula (II-g), Formula (II-h), Formula (II-i), or Formula (II-j).

In some embodiments, Ria is H. In some embodiments, $R^{1a}$ is halogen.

In some embodiments, $R^{1a}$ is fluorine. In some embodiments, $R^{1a}$ is Cl.

In some embodiments, $R^{2a}$ is H. In some embodiments, $R^{2a}$ is $C_1$-$C_3$ alkyl. In some embodiments, $R^{2a}$ is H or $CH_3$. In some embodiments, $R^{2a}$ is $CH_3$.

In some embodiments, $X^{3a}$ is $CHR^{3a}$. In some embodiments, $X^{3a}$ is C(O). In some embodiments, $X^{3a}$ is $CH_2$ or C(O). In some embodiments, $X^{3a}$ is CH z. In some embodiments, $X^{3a}$ is $CH(CH_3)$.

In some embodiments, $R^{3a}$ is H. In some embodiments, $R^{3a}$ is $C_1$-$C_3$ alkyl. In some embodiments, $R^{3a}$ is $CH_3$.

In some embodiments, Ria is F, $X^{4a}$ and $X^{6a}$ are each N, and $R^{3a}$ and $R^{5a}$ are each $CH_3$.

In some embodiments, $R^{1a}$ is Cl, $X^{4a}$ and $X^{6a}$ are each N, and $R^{3a}$ and $R^{5a}$ are each $CH_3$.

In some embodiments, at least one of $X^{4a}$ and $X^{6a}$ is N. In some embodiments, $X^{4a}$ is N. In some embodiments, $X^{4a}$ is C. In some embodiments, $X^{6a}$ is N. In some embodiments, $X^{6a}$ is C.

In some embodiments, $X^{4a}$ and $X^{6a}$ are each N, and $R^{2a}$ is $CH_3$.

In some embodiments, $R^{5a}$ is H. In some embodiments, Ra is H, $CH_3$ or halogen. In some embodiments, $R^{5a}$ is $CH_3$ or halogen. In some embodiments, $R^{5a}$ is H, $CH_3$ or F. In some embodiments, $R^{5a}$ is $CH_3$ or F. In some embodiments, $R^{5a}$ is $CH_3$. In some embodiments $R^{5a}$ is halogen. In some embodiments $R^{5a}$ is F.

In one aspect, this application pertains to a bifunctional compound of Formula (III):

Formula (III)

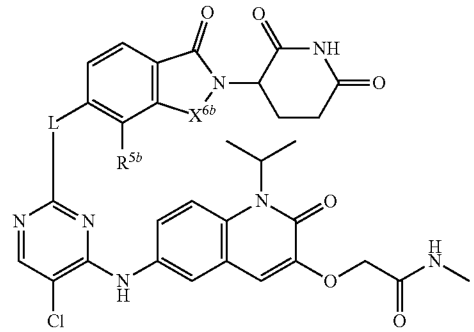

or a pharmaceutically acceptable salt, enantiomer, stereoisomer, or isotopic derivative thereof, wherein:

L is

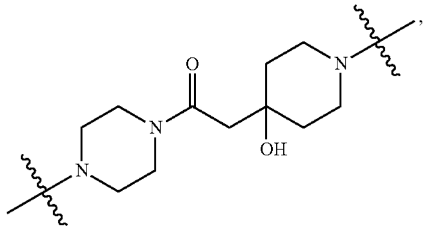

,

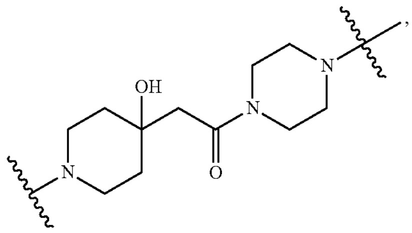

, or

-continued

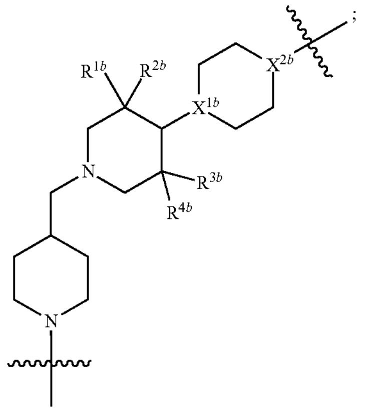

$X^{6b}$ is $CHR^{6b}$ or C(O);

$R^{6b}$ is H or $C_1$-$C_3$ alkyl;

$R^{1b}$, $R^{2b}$, $R^{3b}$, and $R^{4b}$ are each independently H or halogen, wherein at least one of $R^{1b}$, $R^{2b}$, $R^{3b}$, $R^{4b}$ is halogen;

$R^{5b}$ is H or halogen;

$R^{6b}$ is H or $C_1$-$C_3$ alkyl;

$X^{1b}$ and $X^{2b}$ are each independently CH or N, wherein at least one of $X^{1b}$ and $X^{2b}$ is N; and wherein each ∿∿∿ of L indicates a point attachment.

In one aspect, this application pertains to a bifunctional compound of Formula (III):

Formula (III)

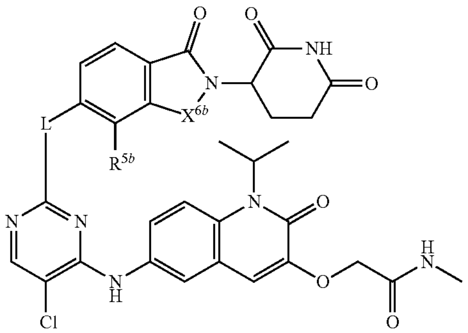

or a pharmaceutically acceptable salt thereof, wherein:

L is

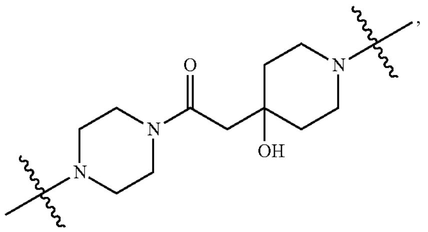

-continued

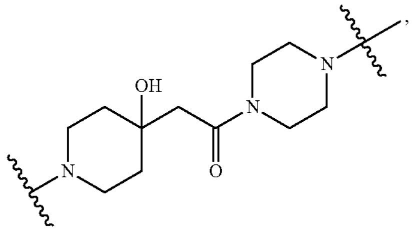

or

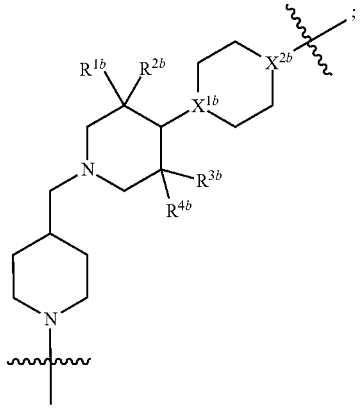

$X^{6b}$ is $CHR^{6b}$ or C(O);

$R^{6b}$ is H or $C_1$-$C_3$ alkyl;

$R^{1b}$, $R^{2b}$, $R^{3b}$, and $R^{4b}$ are each independently H or halogen, wherein at least one of $R^{1b}$, $R^{2b}$, $R^{3b}$, $R^{4b}$ is halogen;

$R^{5b}$ is H or halogen;

$R^{6b}$ is H or $C_1$-$C_3$ alkyl;

$X^{1b}$ and $X^{2b}$ are each independently CH or N, wherein at least one of $X^{1b}$ and $X^{2b}$ is N; and wherein each ∿∿∿ of L indicates a point attachment In one aspect, this application pertains to a bifunctional compound of Formula (III):

Formula (III)

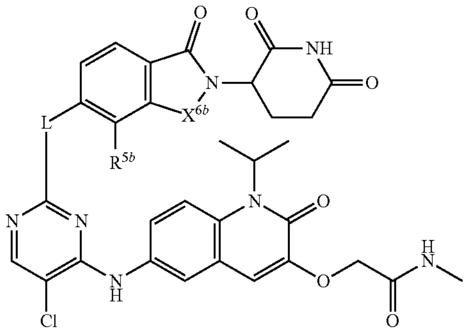

wherein:

L is

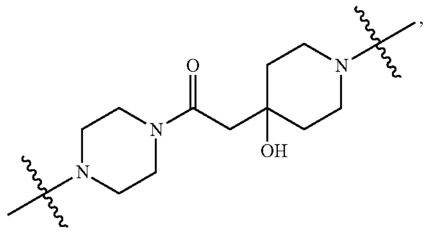

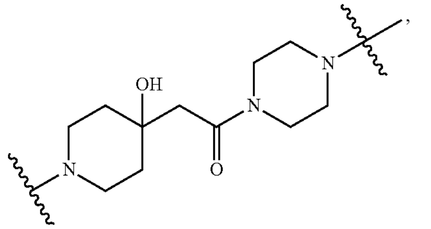

or

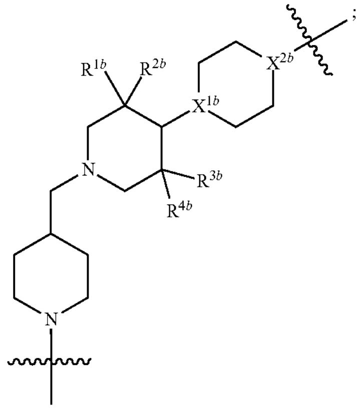

$X^{6b}$ is $CHR^{6b}$ or C(O);

$R^{6b}$ is H or $C_1$-$C_3$ alkyl;

$R^{1b}$, $R^{2b}$, $R^{3b}$, and $R^{4b}$ are each independently H or halogen, wherein at least one of $R^{1b}$, $R^{2b}$, $R^{3b}$, $R^{4b}$ is halogen;

$R^{5b}$ is H or halogen;

$R^{6b}$ is H or $C_1$-$C_3$ alkyl;

$X^{1b}$ and $X^{2b}$ are each independently CH or N, wherein at least one of $X^{1b}$ and $X^{2b}$ is N; and wherein each ∿∿∿ of L indicates a point attachment.

In some embodiments, $R^{5b}$ is H. In some embodiments, $R^{5b}$ is halogen. In some embodiments, $R^{5b}$ is F.

In some embodiments, L is

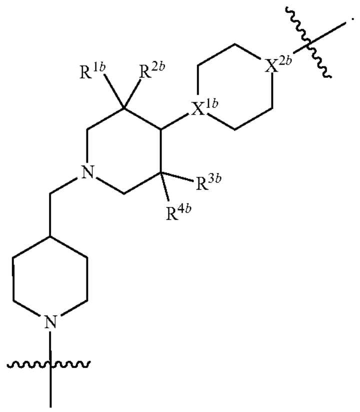

In some embodiments, L is

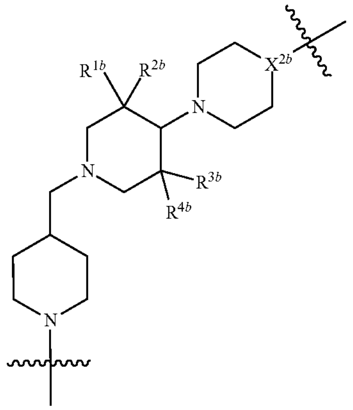

or

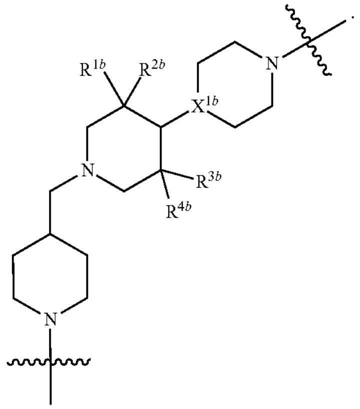

In some embodiments, L is
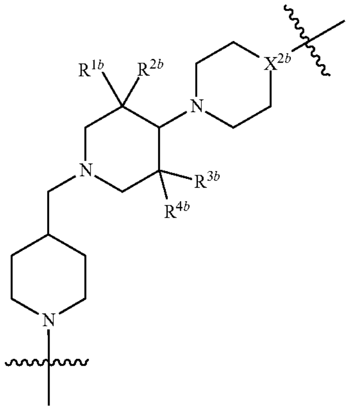
.
In some embodiments, L is
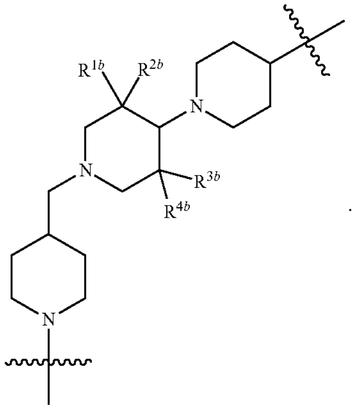
.
In some embodiments, L is
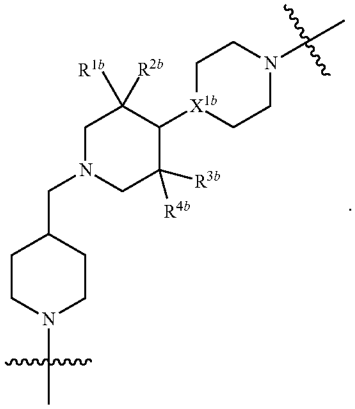
.
In some embodiments, L is
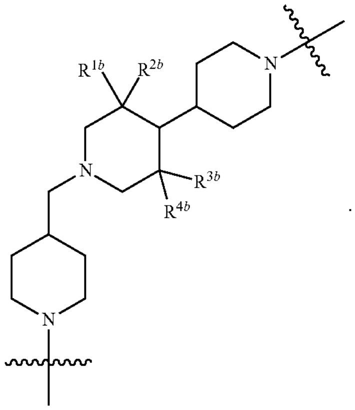
.
In some embodiments, L is
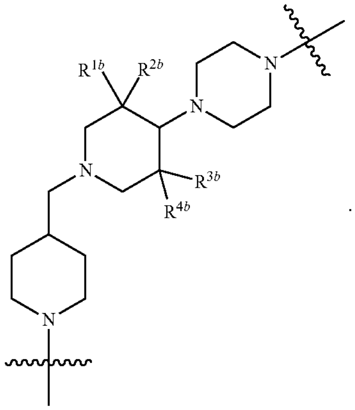
.
In some embodiments, L is
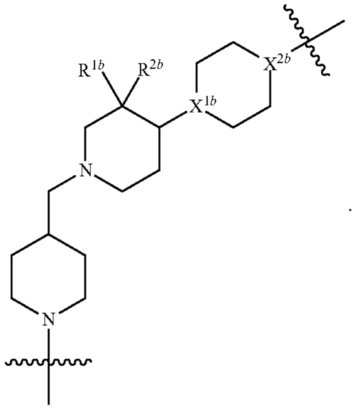
.

In some embodiments, L is

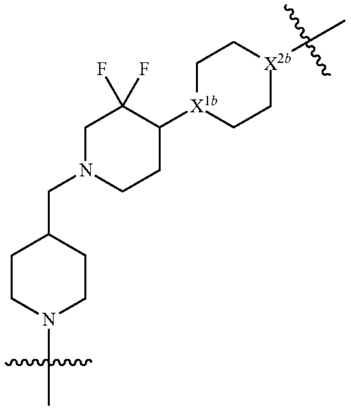

or

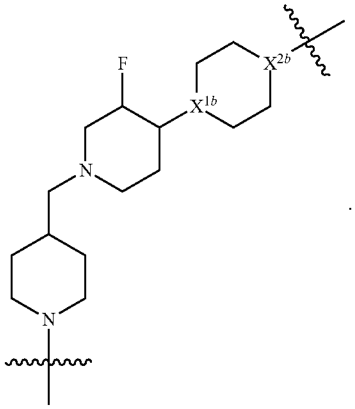

.

In some embodiments, L is

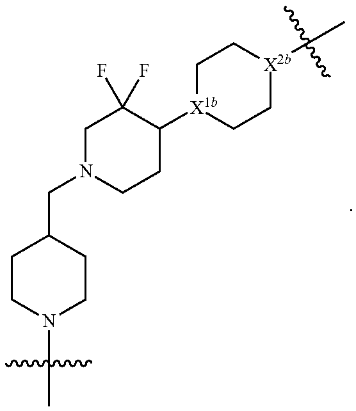

.

In some embodiments, L is

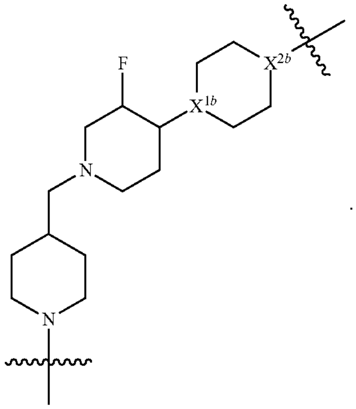

.

In some embodiments, $X^{6b}$ is $CHR^{3a}$. In some embodiments, $X^{6b}$ is C(O). In some embodiments, $X^{6b}$ is $CH_2$ or C(O). In some embodiments, $X^{6b}$ is $CH_2$. In some embodiments, $X^{6b}$ is $CH(CH_3)$.

In some embodiments, $R^{5b}$ is F and $X^{6b}$ is CH.

In some embodiments, at least two of $R^{1b}$, $R^{2b}$, $R^{3b}$, $R^{4b}$ is halogen. In some embodiments, exactly two of $R^{1b}$, $R^{2b}$, $R^{3b}$, $R^{4b}$ are halogen. In some embodiments, at least two of $R^{1b}$, $R^{2b}$, $R^{3b}$, $R^{4b}$ are halogen. In some embodiments, exactly one of $R^{1b}$, $R^{2b}$, $R^{3b}$, $R^{4b}$ is halogen.

In some embodiments, at least two of $R^{1b}$, $R^{2b}$, $R^{3b}$, $R^{4b}$ is F. In some embodiments, exactly two of $R^{1b}$, $R^{2b}$, $R^{3b}$, $R^{4b}$ is F. In some embodiments, at least two of $R^{1b}$, $R^{2b}$, $R^{3b}$, $R^{4b}$ is F. In some embodiments, exactly one of $R^{1b}$, $R^{2b}$, $R^{3b}$, $R^{4b}$ is F.

In some embodiments, $R^{6b}$ is H. In some embodiments, $R^{6b}$ is $C_1$-$C_3$ alkyl. In some embodiments, $R^{6b}$ is $CH_3$.

In some embodiments, at least one of $X^{1b}$ and $X^{2b}$ is N. In some embodiments, $X^{1b}$ is N. In some embodiments, $X^{1b}$ is CH. In some embodiments, $X^{2b}$ is N. In some embodiments, $X^{2b}$ is CH.

In some embodiments, L is

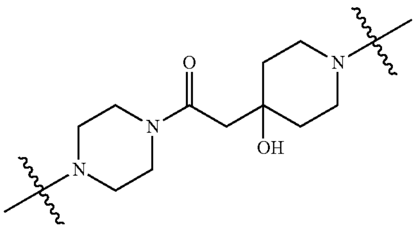

or

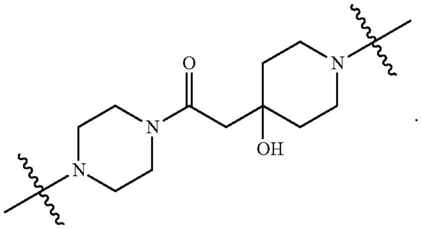

.

In some embodiments, L is
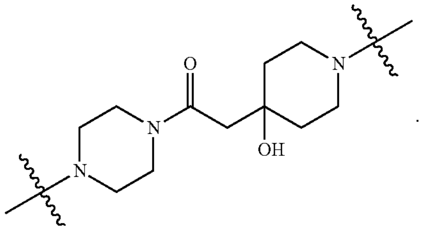 [SMILES: *N1CCN(C(=O)CC2(O)CCN(*)CC2)CC1]
.
In some embodiments, L is
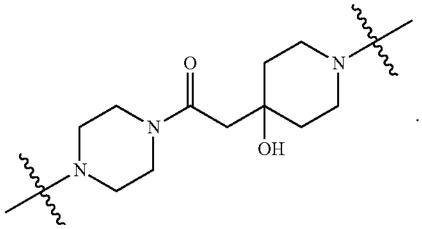 [SMILES: *N1CCN(C(=O)CC2(O)CCN(*)CC2)CC1]
.
In some embodiments, L is,
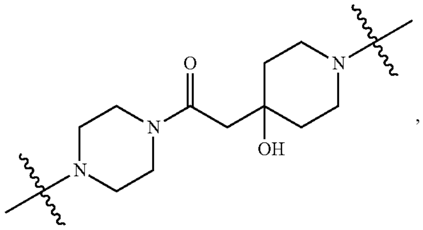
,
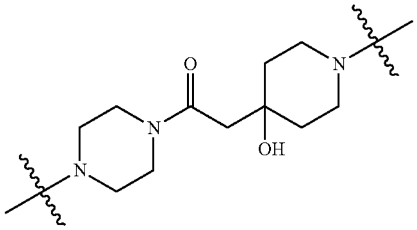
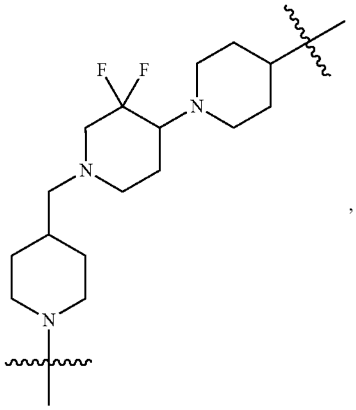
,
-continued
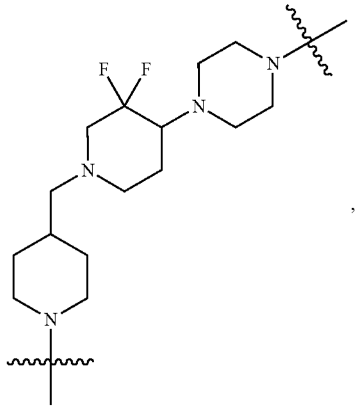
, or
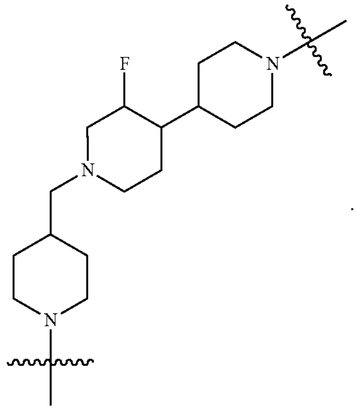
.
In some embodiments, L is
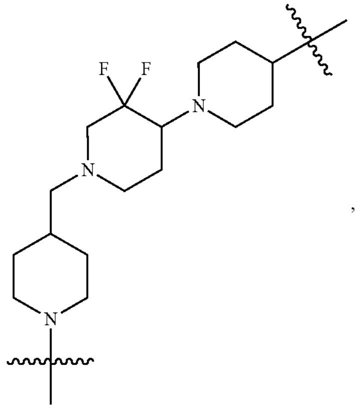
, -continued
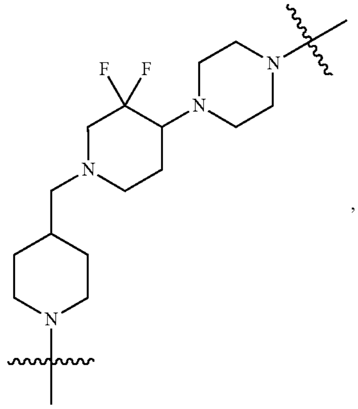
, or
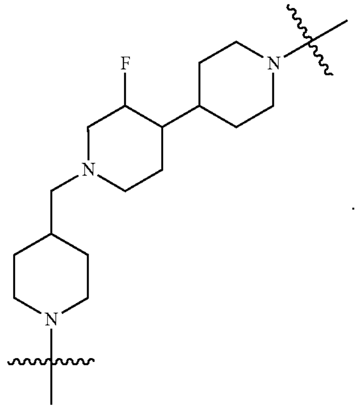
.
In some embodiments, L is
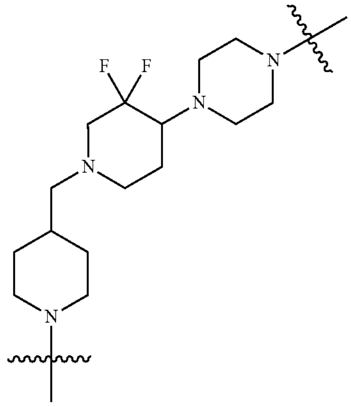
or
-continued
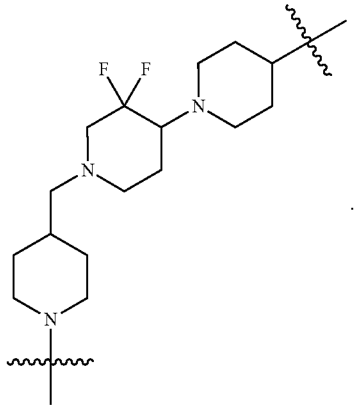
.
In some embodiments, L is
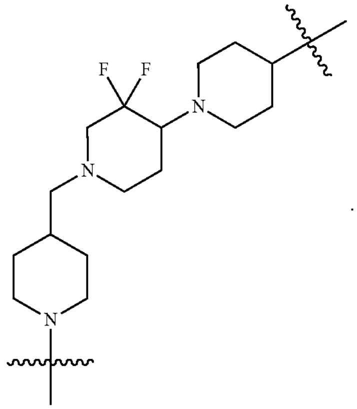 [SMILES: *C1CCN(C2CCN(CC3CCN(*)CC3)CC2(F)F)CC1]
.
In some embodiments, L is
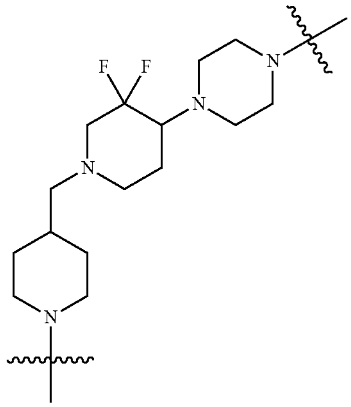
.

In some embodiments, L is
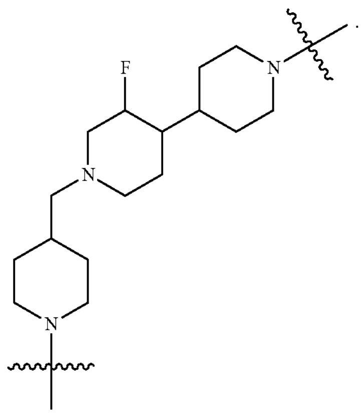 [SMILES: *N1CCC(CN2CCC(C3CCN(*)CC3)C(F)C2)CC1]
In another aspect, the application pertains to a compound, wherein the compound is as shown in Table 1, or a pharmaceutically acceptable salt enantiomer, stereoisomer, solvate, or isotopic derivative thereof.
TABLE 1
1
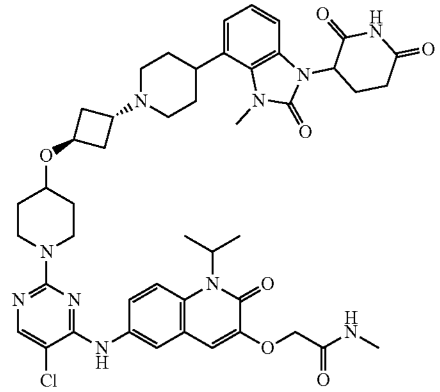 [SMILES: CNC(=O)COc1cc2cc(Nc3nc(N4CCC(O[C@H]5C[C@H](N6CCC(c7cccc8c7n(C)c(=O)n8C7CCC(=O)NC7=O)CC6)C5)CC4)ncc3Cl)ccc2n(C(C)C)c1=O]
2
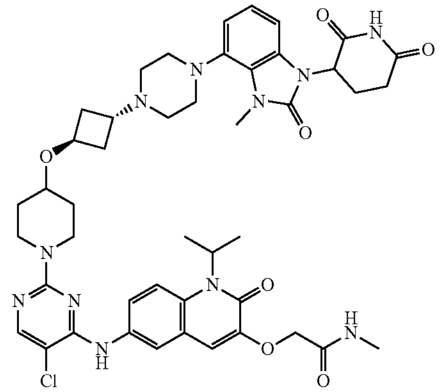 [SMILES: CNC(=O)COc1cc2cc(Nc3nc(N4CCC(O[C@H]5C[C@H](N6CCN(c7cccc8c7n(C)c(=O)n8C7CCC(=O)NC7=O)CC6)C5)CC4)ncc3Cl)ccc2n(C(C)C)c1=O]
TABLE 1-continued
3
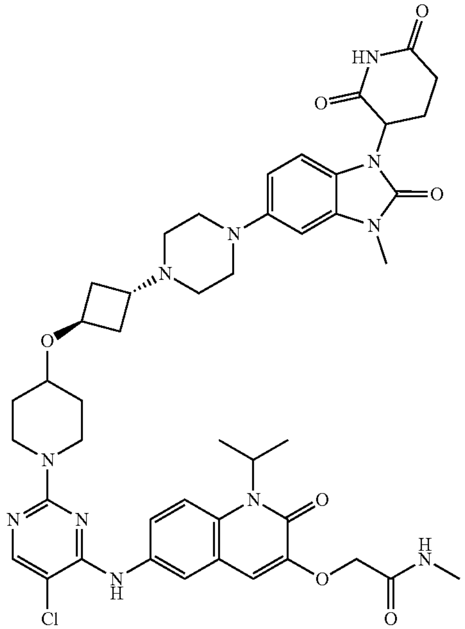 [SMILES: CNC(=O)COc1cc2cc(Nc3nc(N4CCC(O[C@H]5C[C@H](N6CCN(c7ccc8c(c7)n(C)c(=O)n8C7CCC(=O)NC7=O)CC6)C5)CC4)ncc3Cl)ccc2n(C(C)C)c1=O]
4
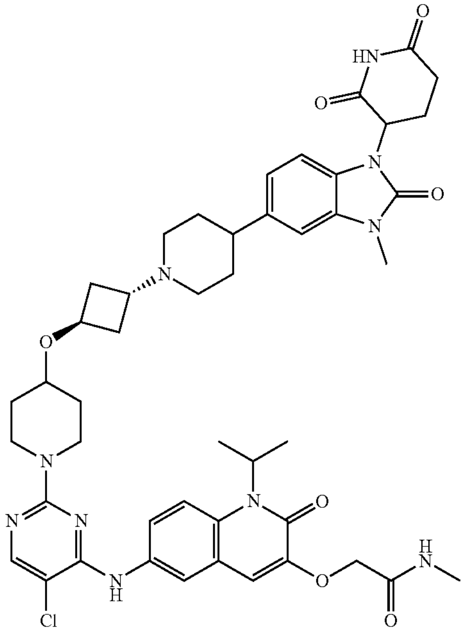 [SMILES: CNC(=O)COc1cc2cc(Nc3nc(N4CCC(O[C@H]5C[C@H](N6CCC(c7ccc8c(c7)n(C)c(=O)n8C7CCC(=O)NC7=O)CC6)C5)CC4)ncc3Cl)ccc2n(C(C)C)c1=O]

TABLE 1-continued
5
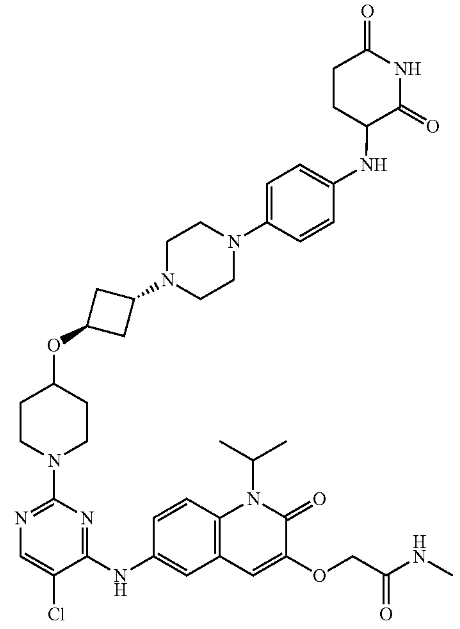 [SMILES: CNC(=O)COc1cc2cc(Nc3nc(N4CCC(O[C@H]5C[C@H](N6CCN(c7ccc(NC8CCC(=O)NC8=O)cc7)CC6)C5)CC4)ncc3Cl)ccc2n(C(C)C)c1=O]
6
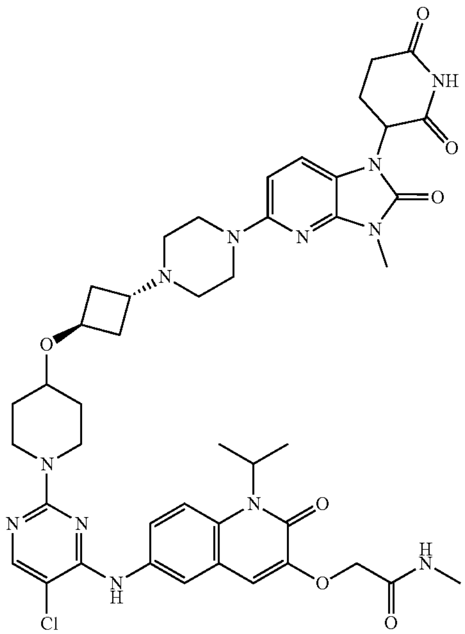 [SMILES: CNC(=O)COc1cc2cc(Nc3nc(N4CCC(O[C@H]5C[C@H](N6CCN(c7ccc8c(n7)n(C)c(=O)n8C7CCC(=O)NC7=O)CC6)C5)CC4)ncc3Cl)ccc2n(C(C)C)c1=O]
TABLE 1-continued
7
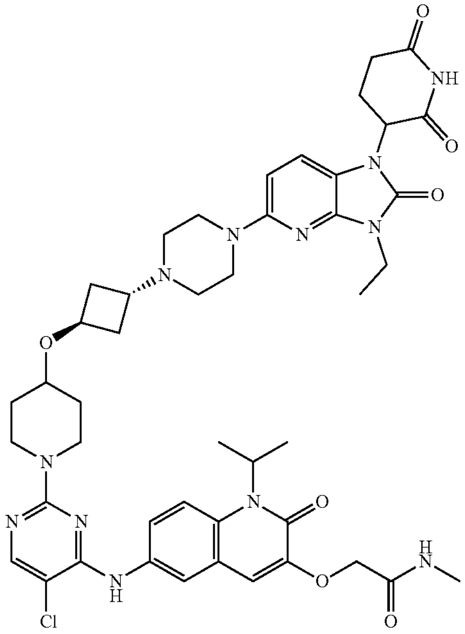 [SMILES: CCn1c(=O)n(C2CCC(=O)NC2=O)c2ccc(N3CCN([C@H]4C[C@H](OC5CCN(c6ncc(Cl)c(Nc7ccc8c(c7)cc(OCC(=O)NC)c(=O)n8C(C)C)n6)CC5)C4)CC3)nc21]
8
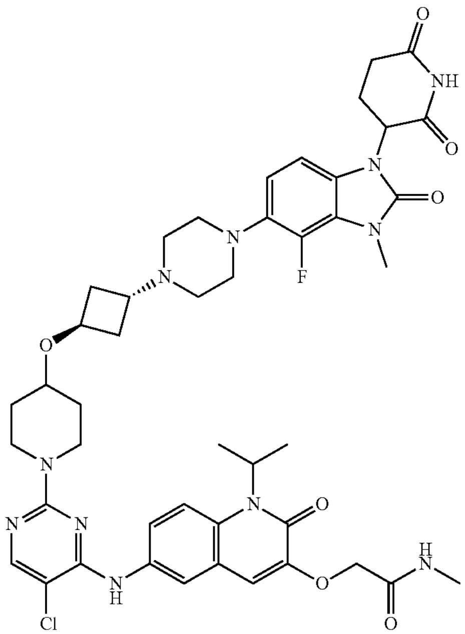

TABLE 1-continued
9
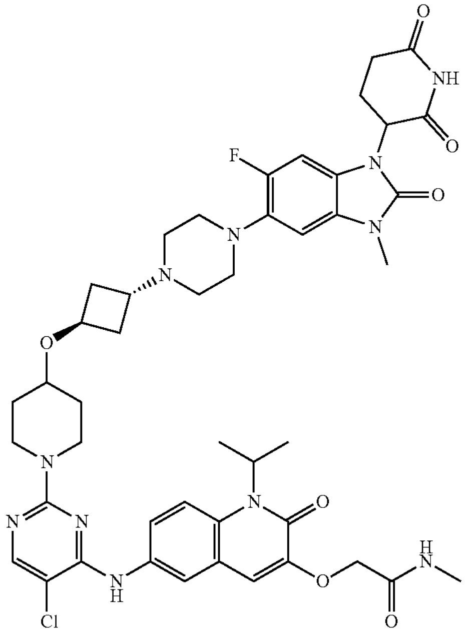
10
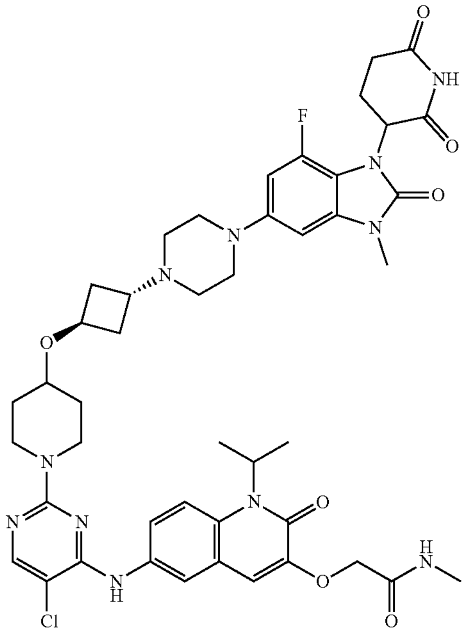
TABLE 1-continued
11
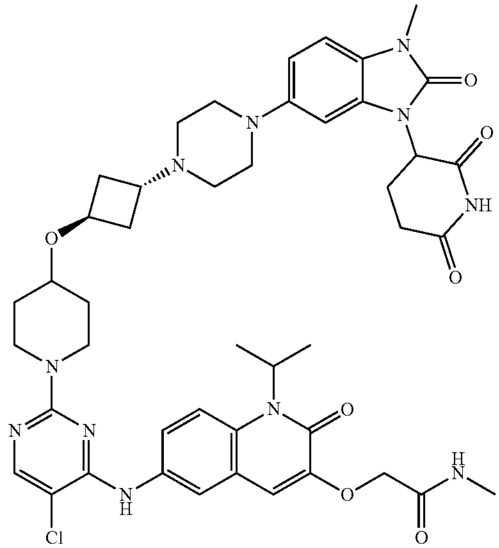 [SMILES: CNC(=O)COc1cc2cc(Nc3nc(N4CCC(O[C@H]5C[C@H](N6CCN(c7ccc8c(c7)n(C7CCC(=O)NC7=O)c(=O)n8C)CC6)C5)CC4)ncc3Cl)ccc2n(C(C)C)c1=O]
12
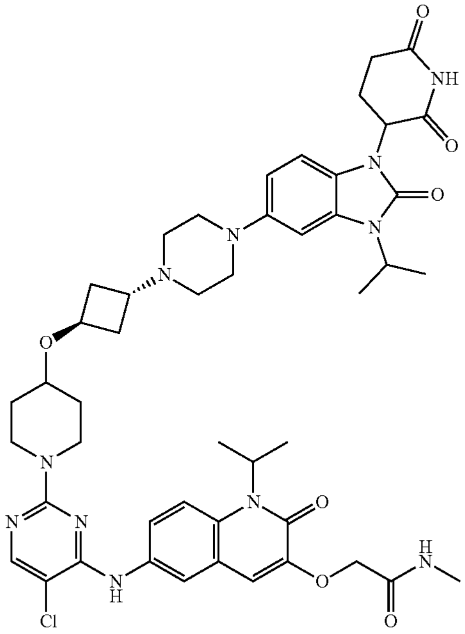 [SMILES: CNC(=O)COc1cc2cc(Nc3nc(N4CCC(O[C@H]5C[C@H](N6CCN(c7ccc8c(c7)n(C(C)C)c(=O)n8C7CCC(=O)NC7=O)CC6)C5)CC4)ncc3Cl)ccc2n(C(C)C)c1=O]

TABLE 1-continued
13
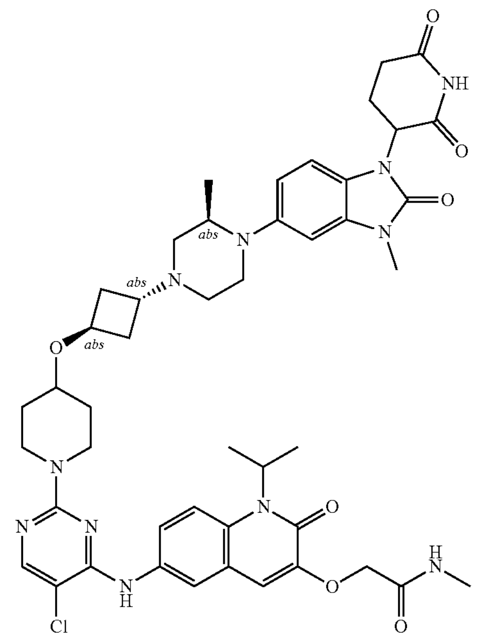 [SMILES: CNC(=O)COc1cc2cc(Nc3nc(N4CCC(O[C@H]5C[C@H](N6CCN(c7ccc8c(c7)n(C)c(=O)n8C7CCC(=O)NC7=O)[C@H](C)C6)C5)CC4)ncc3Cl)ccc2n(C(C)C)c1=O]
14
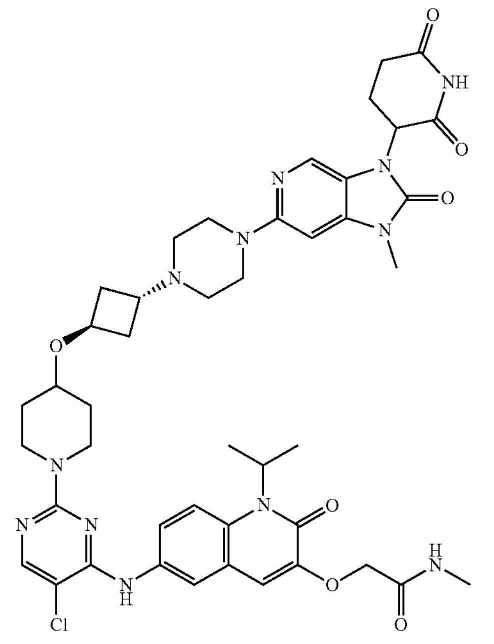 [SMILES: CNC(=O)COc1cc2cc(Nc3nc(N4CCC(O[C@H]5C[C@H](N6CCN(c7cc8c(cn7)n(C7CCC(=O)NC7=O)c(=O)n8C)CC6)C5)CC4)ncc3Cl)ccc2n(C(C)C)c1=O]
TABLE 1-continued
15
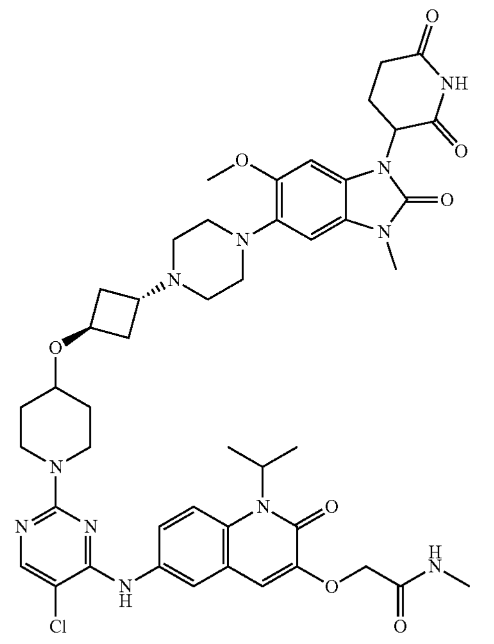 [SMILES: CNC(=O)COc1cc2cc(Nc3nc(N4CCC(O[C@H]5C[C@H](N6CCN(c7cc8c(cc7OC)n(C7CCC(=O)NC7=O)c(=O)n8C)CC6)C5)CC4)ncc3Cl)ccc2n(C(C)C)c1=O]
16
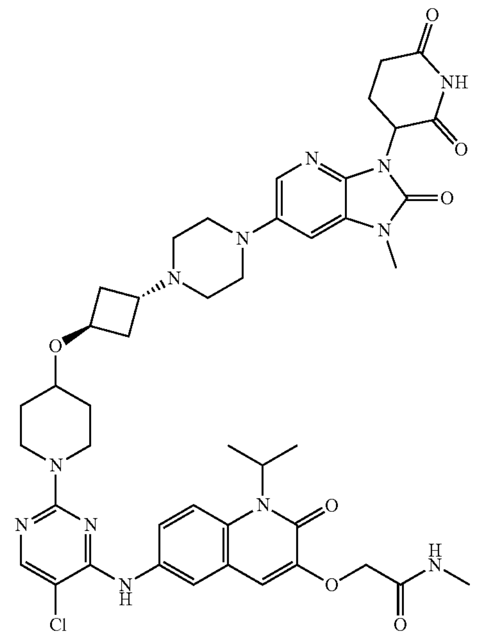 [SMILES: CNC(=O)COc1cc2cc(Nc3nc(N4CCC(O[C@H]5C[C@H](N6CCN(c7cnc8c(c7)n(C)c(=O)n8C7CCC(=O)NC7=O)CC6)C5)CC4)ncc3Cl)ccc2n(C(C)C)c1=O]

17
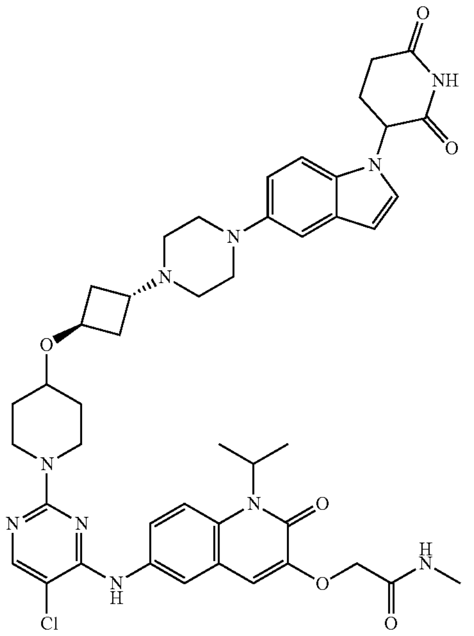
18
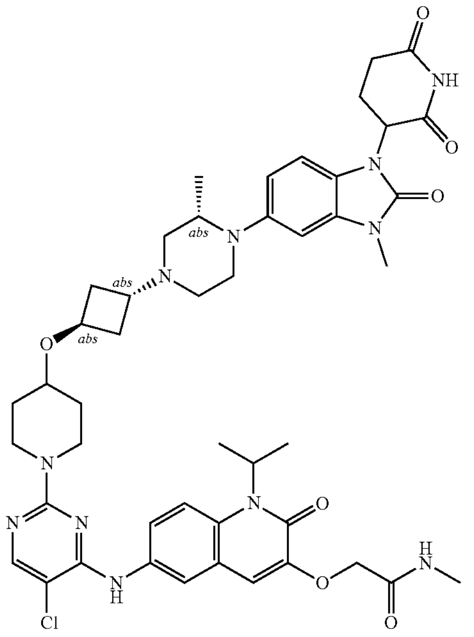 [SMILES: CNC(=O)COc1cc2cc(Nc3nc(N4CCC(O[C@H]5C[C@H](N6CCN(c7ccc8c(c7)n(C)c(=O)n8C7CCC(=O)NC7=O)[C@@H](C)C6)C5)CC4)ncc3Cl)ccc2n(C(C)C)c1=O]
19
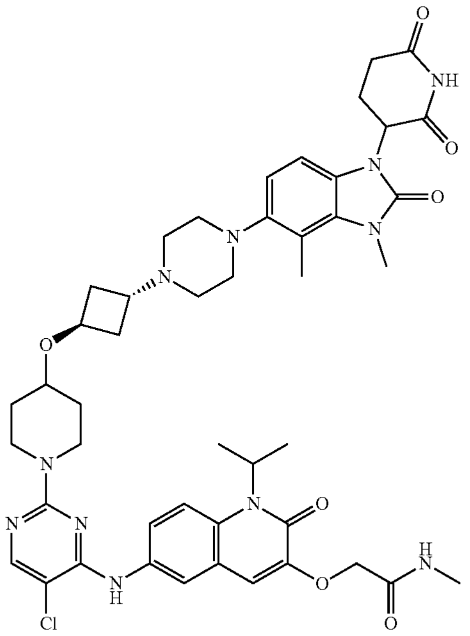 [SMILES: CNC(=O)COc1cc2cc(Nc3nc(N4CCC(O[C@H]5C[C@H](N6CCN(c7ccc8c(c7C)n(C)c(=O)n8C7CCC(=O)NC7=O)CC6)C5)CC4)ncc3Cl)ccc2n(C(C)C)c1=O]
20
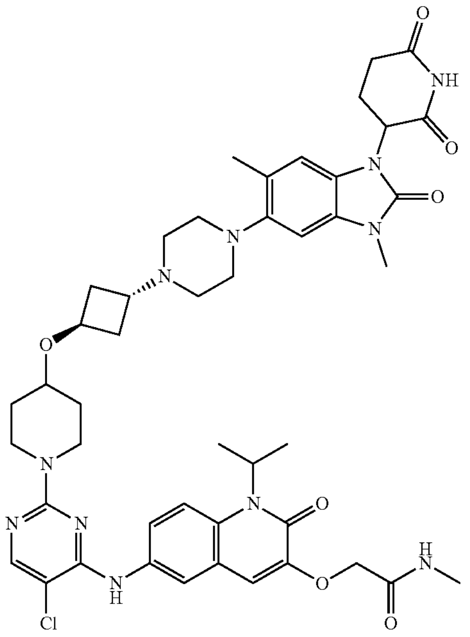 [SMILES: CNC(=O)COc1cc2cc(Nc3nc(N4CCC(O[C@H]5C[C@H](N6CCN(c7cc8c(cc7C)n(C7CCC(=O)NC7=O)c(=O)n8C)CC6)C5)CC4)ncc3Cl)ccc2n(C(C)C)c1=O]

TABLE 1-continued
21
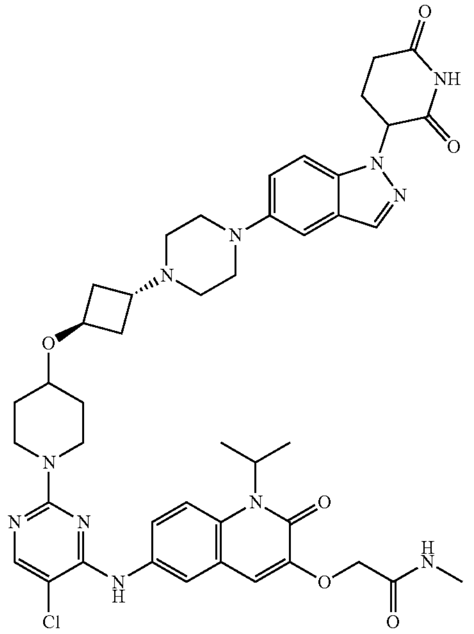
22
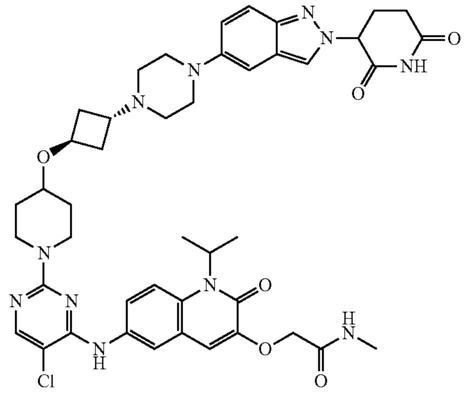 [SMILES: CNC(=O)COc1cc2cc(Nc3nc(N4CCC(O[C@H]5C[C@H](N6CCN(c7ccc8nn(C9CCC(=O)NC9=O)cc8c7)CC6)C5)CC4)ncc3Cl)ccc2n(C(C)C)c1=O]
23
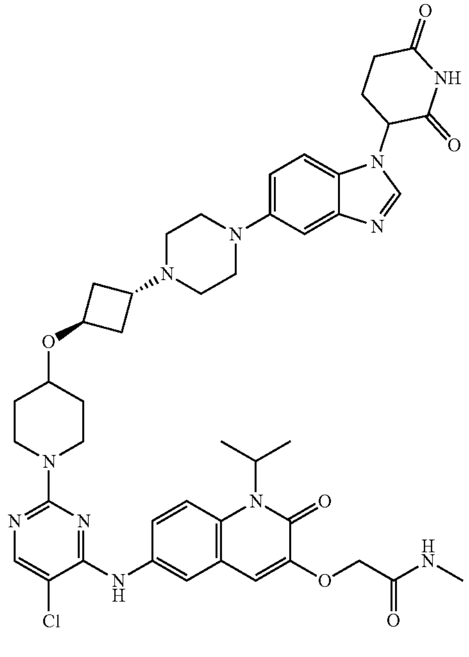
TABLE 1-continued
24
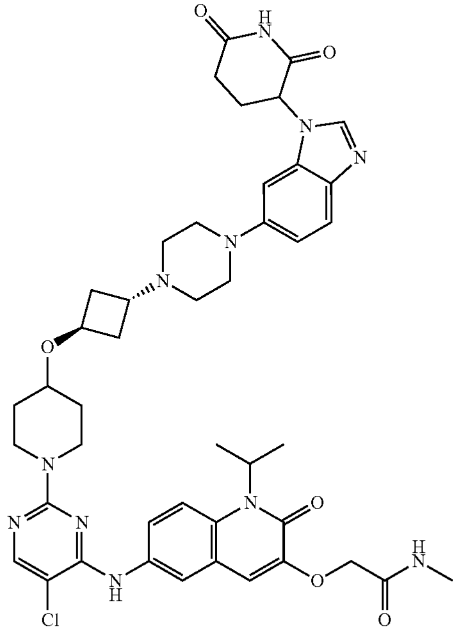 [SMILES: CNC(=O)COc1cc2cc(Nc3nc(N4CCC(O[C@H]5C[C@H](N6CCN(c7ccc8ncn(C9CCC(=O)NC9=O)c8c7)CC6)C5)CC4)ncc3Cl)ccc2n(C(C)C)c1=O]
25
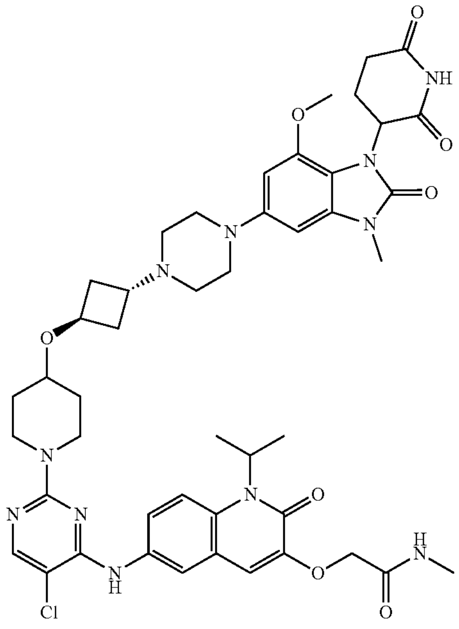 [SMILES: CNC(=O)COc1cc2cc(Nc3nc(N4CCC(O[C@H]5C[C@H](N6CCN(c7cc(OC)c8c(c7)n(C)c(=O)n8C7CCC(=O)NC7=O)CC6)C5)CC4)ncc3Cl)ccc2n(C(C)C)c1=O]

26
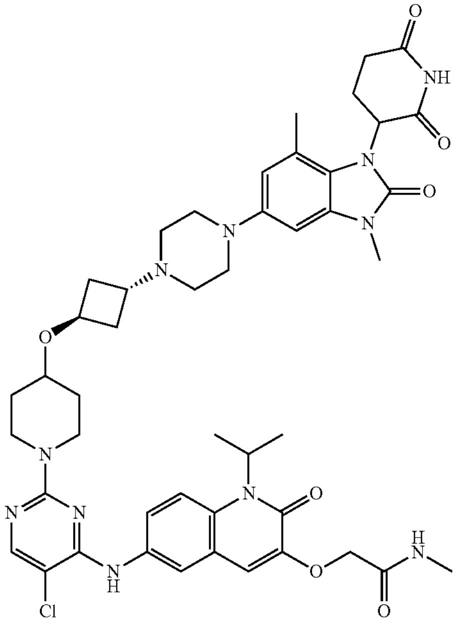 [SMILES: CNC(=O)COc1cc2cc(Nc3nc(N4CCC(O[C@H]5C[C@H](N6CCN(c7cc(C)c8c(c7)n(C)c(=O)n8C7CCC(=O)NC7=O)CC6)C5)CC4)ncc3Cl)ccc2n(C(C)C)c1=O]
27
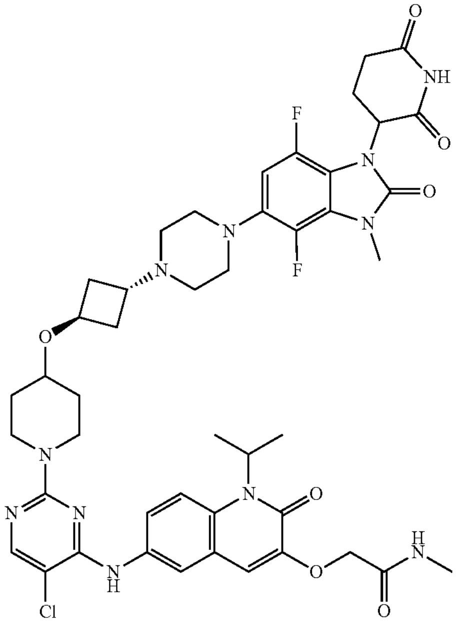 [SMILES: CNC(=O)COc1cc2cc(Nc3nc(N4CCC(O[C@H]5C[C@H](N6CCN(c7cc(F)c8c(c7F)n(C)c(=O)n8C7CCC(=O)NC7=O)CC6)C5)CC4)ncc3Cl)ccc2n(C(C)C)c1=O]
28
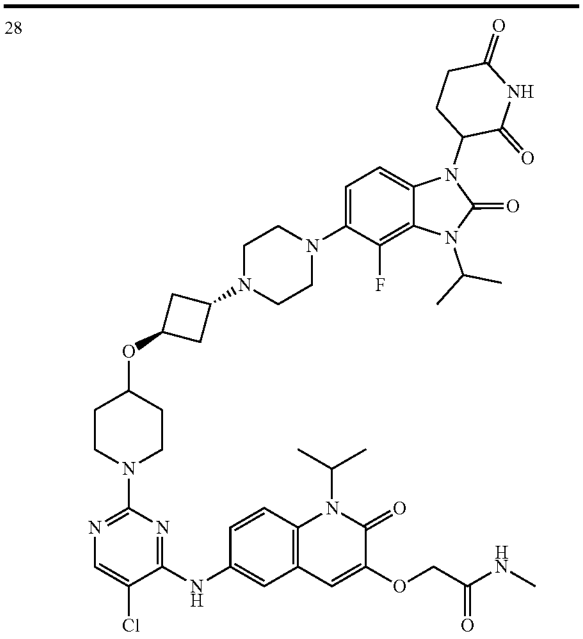
29
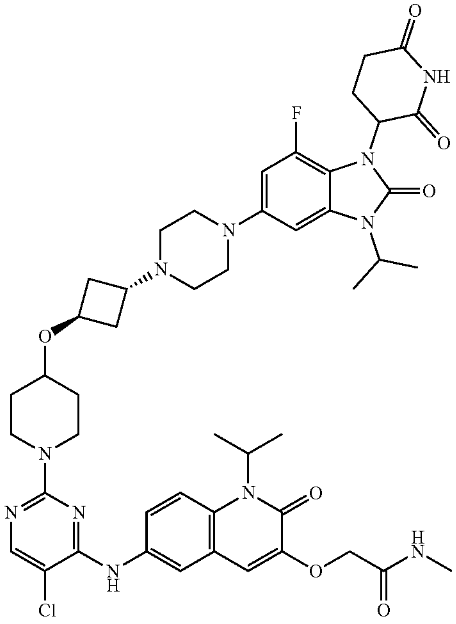 [SMILES: CNC(=O)COc1cc2cc(Nc3nc(N4CCC(O[C@H]5C[C@H](N6CCN(c7cc(F)c8c(c7)n(C(C)C)c(=O)n8C7CCC(=O)NC7=O)CC6)C5)CC4)ncc3Cl)ccc2n(C(C)C)c1=O]
30
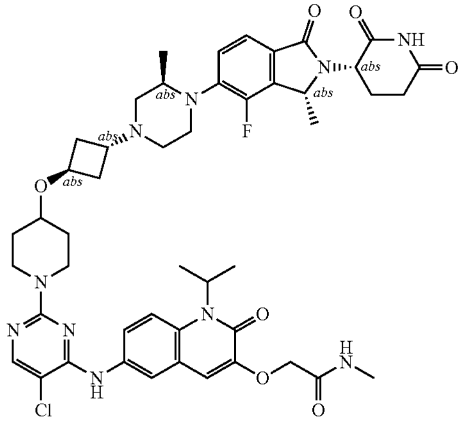 [SMILES: CNC(=O)COc1cc2cc(Nc3nc(N4CCC(O[C@H]5C[C@H](N6CCN(c7ccc8c(c7F)[C@@H](C)N([C@H]7CCC(=O)NC7=O)C8=O)[C@H](C)C6)C5)CC4)ncc3Cl)ccc2n(C(C)C)c1=O]

TABLE 1-continued
31
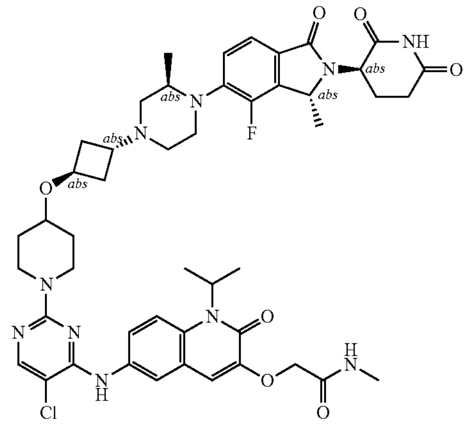 [SMILES: CNC(=O)COc1cc2cc(Nc3nc(N4CCC(O[C@H]5C[C@H](N6CCN(c7ccc8c(c7F)[C@@H](C)N([C@@H]7CCC(=O)NC7=O)C8=O)[C@H](C)C6)C5)CC4)ncc3Cl)ccc2n(C(C)C)c1=O]
32
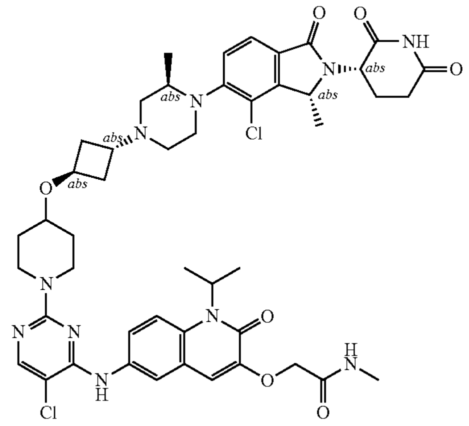 [SMILES: CNC(=O)COc1cc2cc(Nc3nc(N4CCC(O[C@H]5C[C@H](N6CCN(c7ccc8c(c7Cl)[C@@H](C)N([C@H]7CCC(=O)NC7=O)C8=O)[C@H](C)C6)C5)CC4)ncc3Cl)ccc2n(C(C)C)c1=O]
33
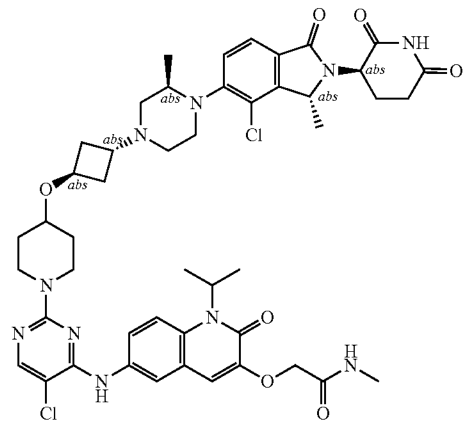 [SMILES: CNC(=O)COc1cc2cc(Nc3nc(N4CCC(O[C@H]5C[C@H](N6CCN(c7ccc8c(c7Cl)[C@@H](C)N([C@@H]7CCC(=O)NC7=O)C8=O)[C@H](C)C6)C5)CC4)ncc3Cl)ccc2n(C(C)C)c1=O]
TABLE 1-continued
34
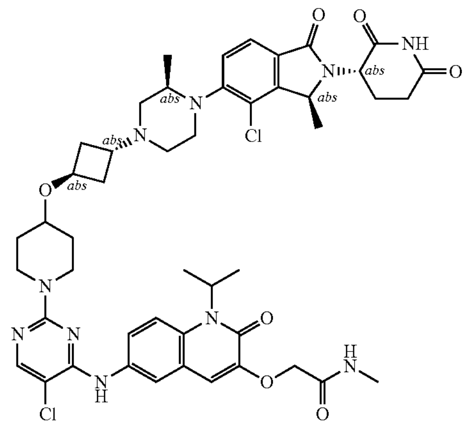 [SMILES: CNC(=O)COc1cc2cc(Nc3nc(N4CCC(O[C@H]5C[C@H](N6CCN(c7ccc8c(c7Cl)[C@H](C)N([C@H]7CCC(=O)NC7=O)C8=O)[C@H](C)C6)C5)CC4)ncc3Cl)ccc2n(C(C)C)c1=O]
35
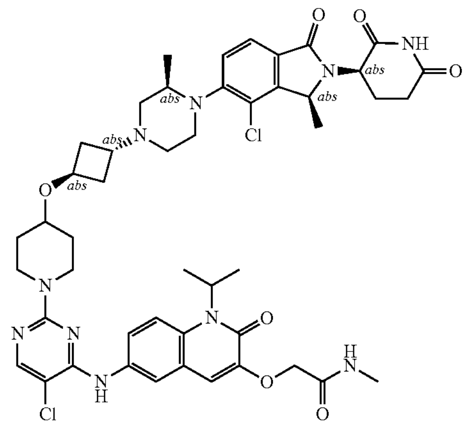 [SMILES: CNC(=O)COc1cc2cc(Nc3nc(N4CCC(O[C@H]5C[C@H](N6CCN(c7ccc8c(c7Cl)[C@H](C)N([C@@H]7CCC(=O)NC7=O)C8=O)[C@H](C)C6)C5)CC4)ncc3Cl)ccc2n(C(C)C)c1=O]
36
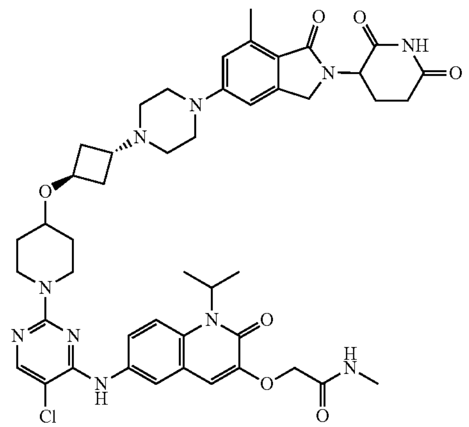 [SMILES: CNC(=O)COc1cc2cc(Nc3nc(N4CCC(O[C@H]5C[C@H](N6CCN(c7cc(C)c8c(c7)CN(C7CCC(=O)NC7=O)C8=O)CC6)C5)CC4)ncc3Cl)ccc2n(C(C)C)c1=O]

37
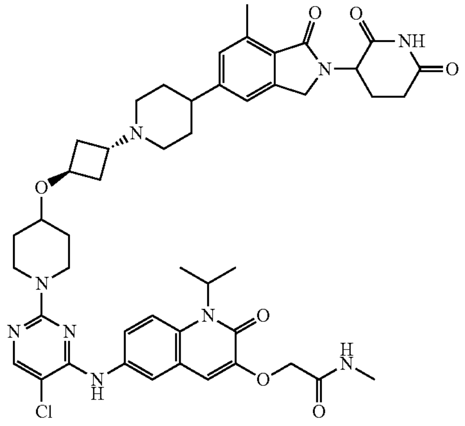 [SMILES: CNC(=O)COc1cc2cc(Nc3nc(N4CCC(O[C@H]5C[C@H](N6CCC(c7cc(C)c8c(c7)CN(C7CCC(=O)NC7=O)C8=O)CC6)C5)CC4)ncc3Cl)ccc2n(C(C)C)c1=O]
38
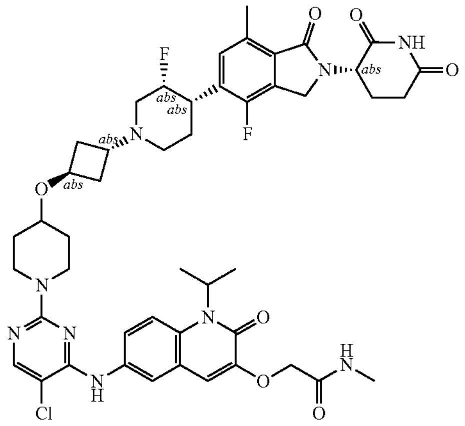 [SMILES: CNC(=O)COc1cc2cc(Nc3nc(N4CCC(O[C@H]5C[C@H](N6CC[C@@H](c7cc(C)c8c(c7F)CN([C@H]7CCC(=O)NC7=O)C8=O)[C@@H](F)C6)C5)CC4)ncc3Cl)ccc2n(C(C)C)c1=O]
39
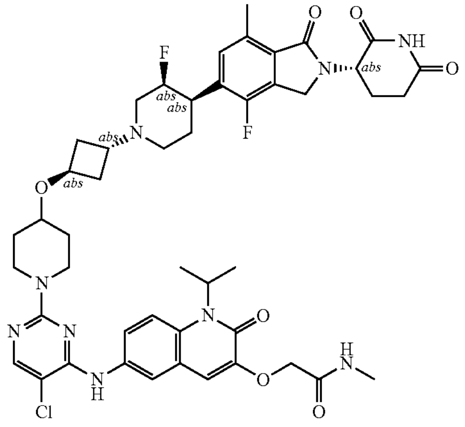 [SMILES: CNC(=O)COc1cc2cc(Nc3nc(N4CCC(O[C@H]5C[C@H](N6CC[C@H](c7cc(C)c8c(c7F)CN([C@H]7CCC(=O)NC7=O)C8=O)[C@H](F)C6)C5)CC4)ncc3Cl)ccc2n(C(C)C)c1=O]
40
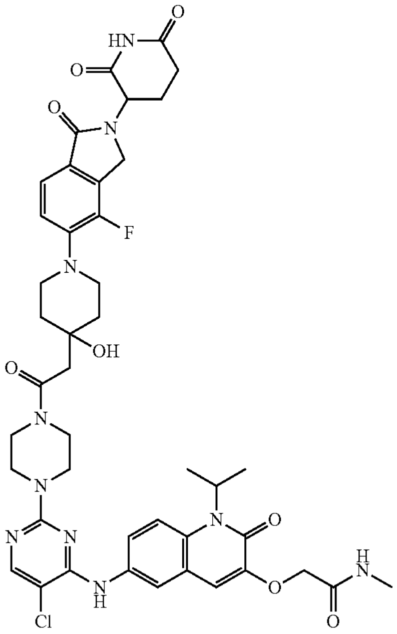 [SMILES: CNC(=O)COc1cc2cc(Nc3nc(N4CCN(C(=O)CC5(O)CCN(c6ccc7c(c6F)CN(C6CCC(=O)NC6=O)C7=O)CC5)CC4)ncc3Cl)ccc2n(C(C)C)c1=O]
41
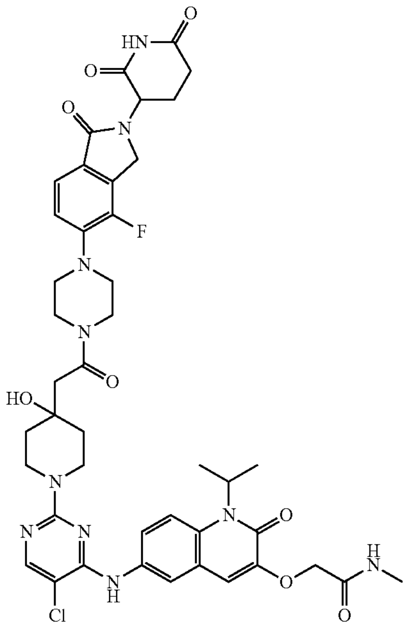 [SMILES: CNC(=O)COc1cc2cc(Nc3nc(N4CCC(O)(CC(=O)N5CCN(c6ccc7c(c6F)CN(C6CCC(=O)NC6=O)C7=O)CC5)CC4)ncc3Cl)ccc2n(C(C)C)c1=O]

TABLE 1-continued

| | |
|---|---|
| 42 | 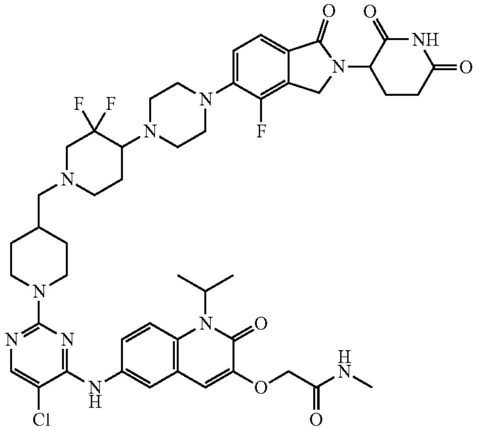 [SMILES: CNC(=O)COc1cc2cc(Nc3nc(N4CCC(CN5CCC(N6CCN(c7ccc8c(c7F)CN(C7CCC(=O)NC7=O)C8=O)CC6)C(F)(F)C5)CC4)ncc3Cl)ccc2n(C(C)C)c1=O] |
| 43 | 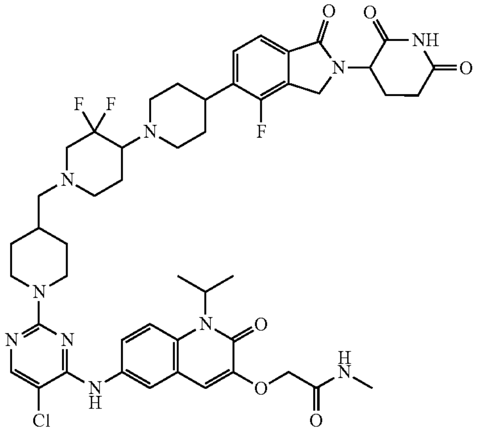 [SMILES: CNC(=O)COc1cc2cc(Nc3nc(N4CCC(CN5CCC(N6CCC(c7ccc8c(c7F)CN(C7CCC(=O)NC7=O)C8=O)CC6)C(F)(F)C5)CC4)ncc3Cl)ccc2n(C(C)C)c1=O] |
| 44 | 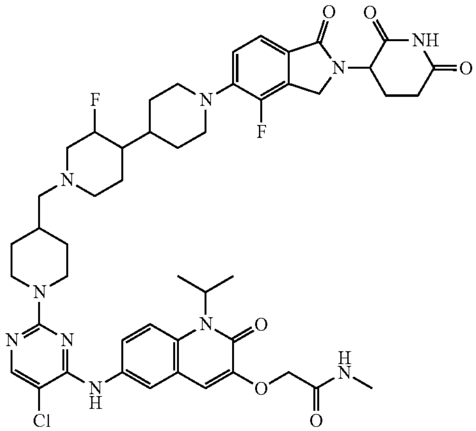 [SMILES: CNC(=O)COc1cc2cc(Nc3nc(N4CCC(CN5CCC(C6CCN(c7ccc8c(c7F)CN(C7CCC(=O)NC7=O)C8=O)CC6)C(F)C5)CC4)ncc3Cl)ccc2n(C(C)C)c1=O] |

In another aspect, the application pertains to a compound, wherein the compound is as shown in Table 1, or a pharmaceutically acceptable salt thereof.

In another aspect, the application pertains to a compound, wherein the compound is as shown in Table 1.

In another aspect, the application pertains to a compound, wherein the compound is as shown in Table 2, or a pharmaceutically acceptable salt enantiomer, stereoisomer, solvate, or isotopic derivative thereof.

TABLE 2

| | |
|---|---|
| 1 | 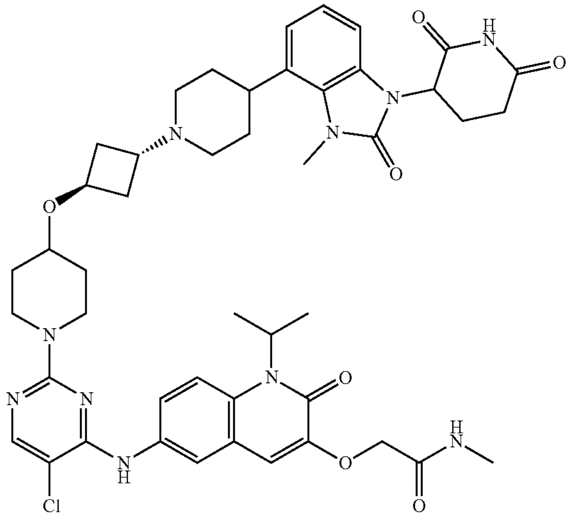 |

TABLE 2-continued
2
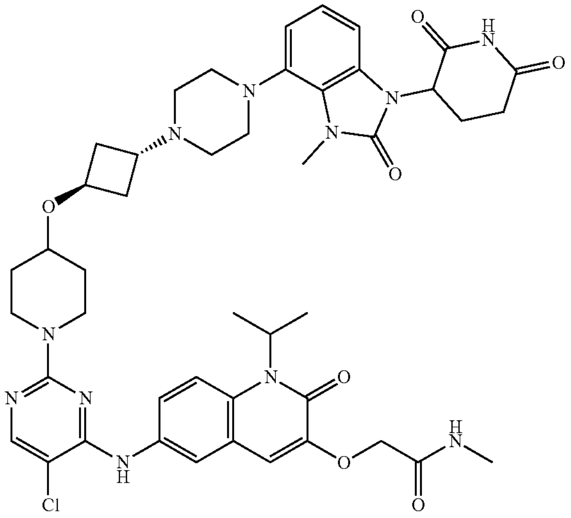
3
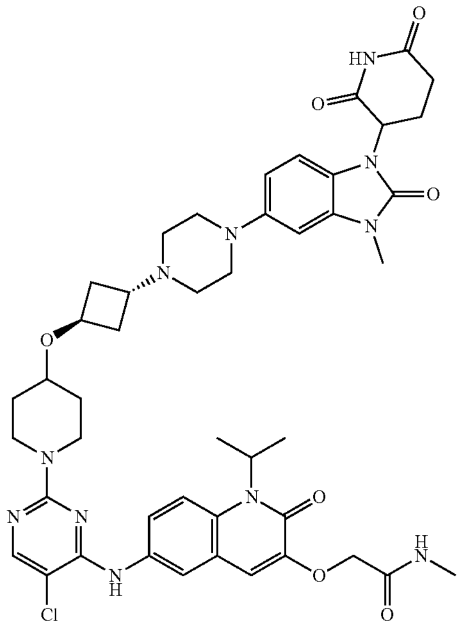

TABLE 2-continued
4
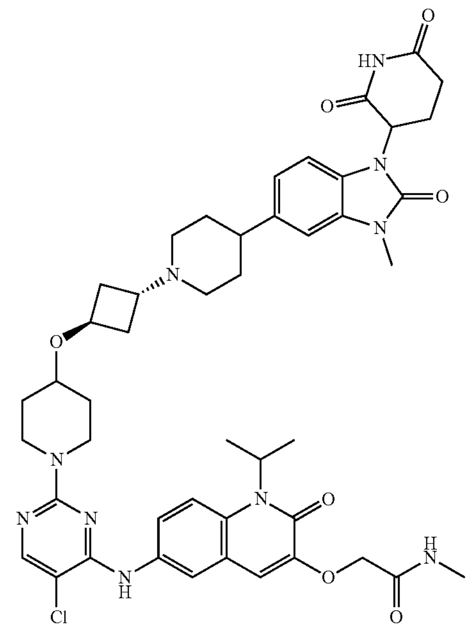
5
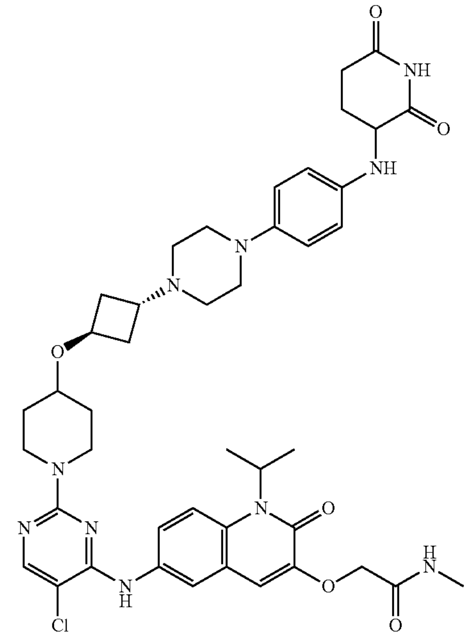 [SMILES: CNC(=O)COc1cc2cc(Nc3nc(N4CCC(O[C@H]5C[C@H](N6CCN(c7ccc(NC8CCC(=O)NC8=O)cc7)CC6)C5)CC4)ncc3Cl)ccc2n(C(C)C)c1=O]

TABLE 2-continued
6
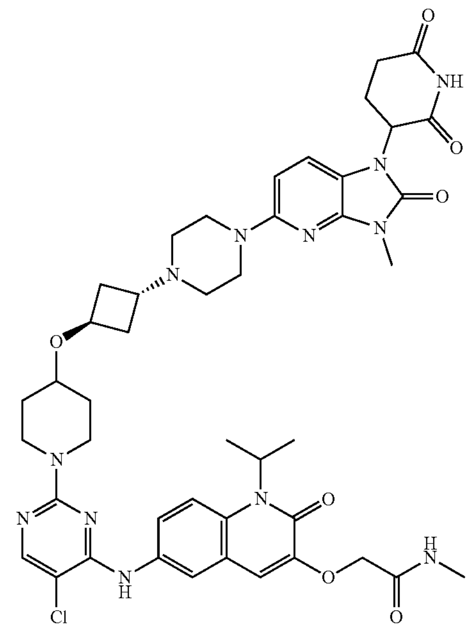 [SMILES: CNC(=O)COc1cc2cc(Nc3nc(N4CCC(O[C@H]5C[C@H](N6CCN(c7ccc8c(n7)n(C)c(=O)n8C7CCC(=O)NC7=O)CC6)C5)CC4)ncc3Cl)ccc2n(C(C)C)c1=O]
7
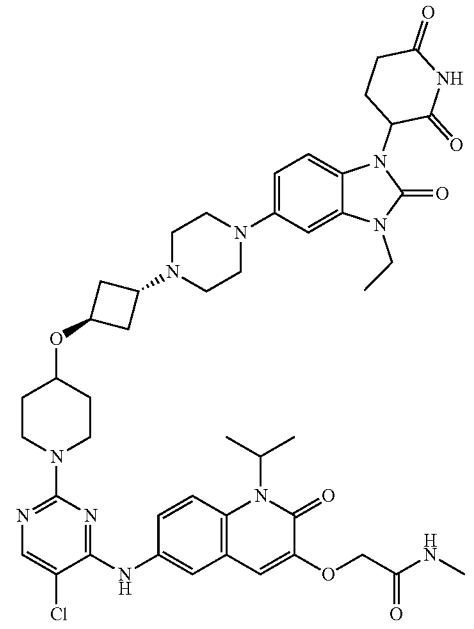 [SMILES: CCn1c(=O)n(C2CCC(=O)NC2=O)c2ccc(N3CCN([C@H]4C[C@H](OC5CCN(c6ncc(Cl)c(Nc7ccc8c(c7)cc(OCC(=O)NC)c(=O)n8C(C)C)n6)CC5)C4)CC3)cc21]

TABLE 2-continued
8
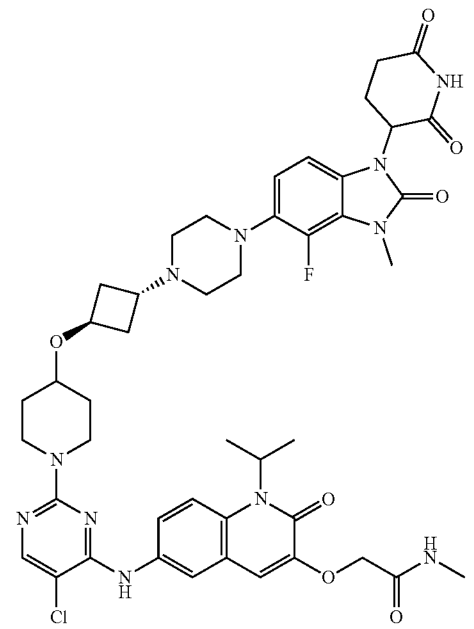
9
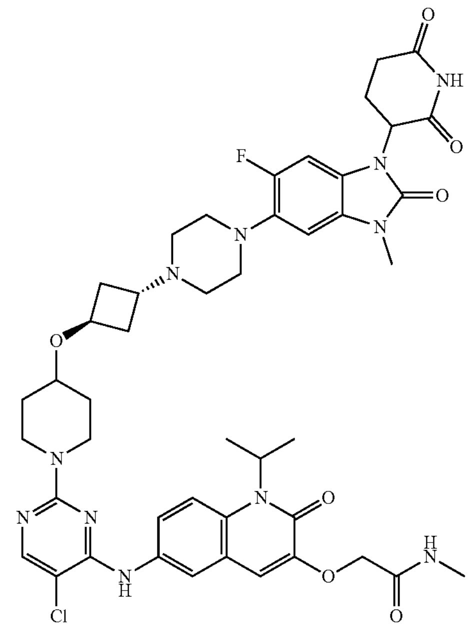

TABLE 2-continued
| | |
|---|---|
| 10 | 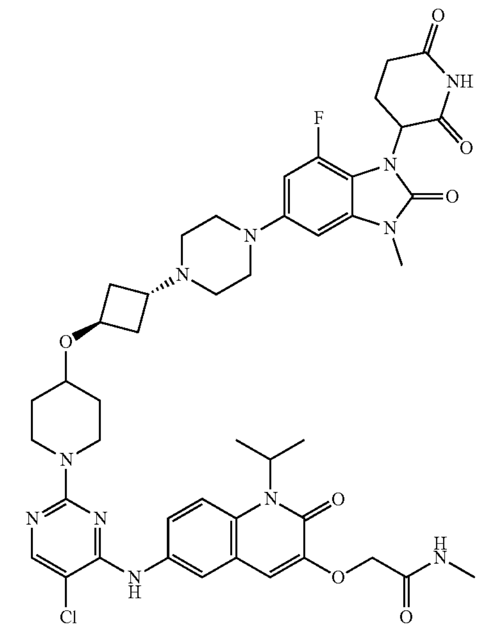 |
| 11 | 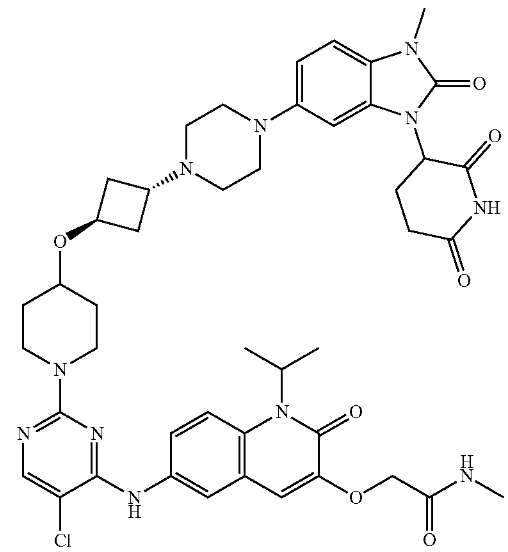 [SMILES: CNC(=O)COc1cc2cc(Nc3nc(N4CCC(O[C@H]5C[C@H](N6CCN(c7ccc8c(c7)n(C7CCC(=O)NC7=O)c(=O)n8C)CC6)C5)CC4)ncc3Cl)ccc2n(C(C)C)c1=O] |

TABLE 2-continued
12
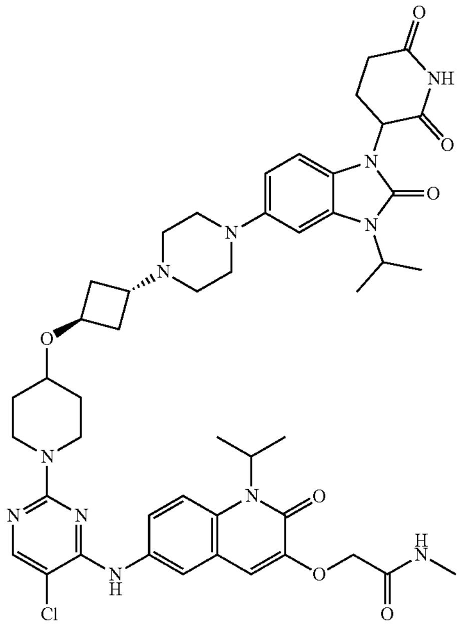 [SMILES: CNC(=O)COc1cc2cc(Nc3nc(N4CCC(O[C@H]5C[C@H](N6CCN(c7ccc8c(c7)n(C(C)C)c(=O)n8C7CCC(=O)NC7=O)CC6)C5)CC4)ncc3Cl)ccc2n(C(C)C)c1=O]
13
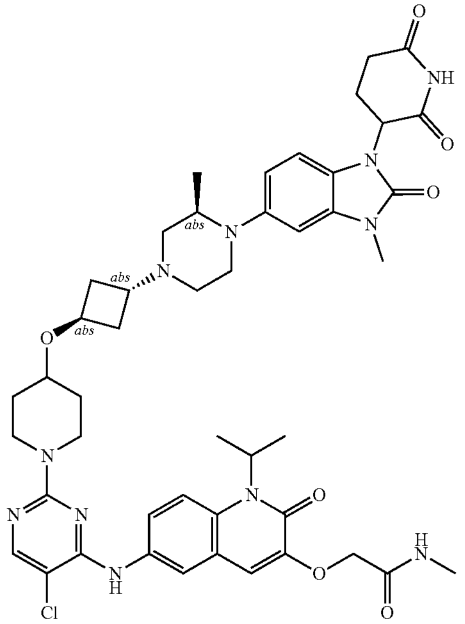 [SMILES: CNC(=O)COc1cc2cc(Nc3nc(N4CCC(O[C@H]5C[C@H](N6CCN(c7ccc8c(c7)n(C)c(=O)n8C7CCC(=O)NC7=O)[C@H](C)C6)C5)CC4)ncc3Cl)ccc2n(C(C)C)c1=O]

TABLE 2-continued
14
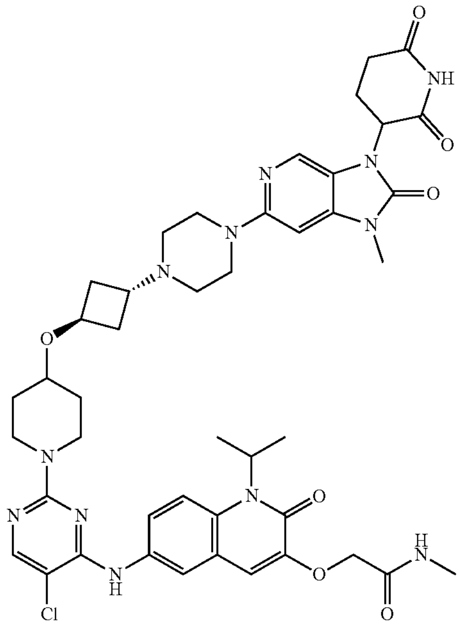 [SMILES: CNC(=O)COc1cc2cc(Nc3nc(N4CCC(O[C@H]5C[C@H](N6CCN(c7cc8c(cn7)n(C7CCC(=O)NC7=O)c(=O)n8C)CC6)C5)CC4)ncc3Cl)ccc2n(C(C)C)c1=O]
15
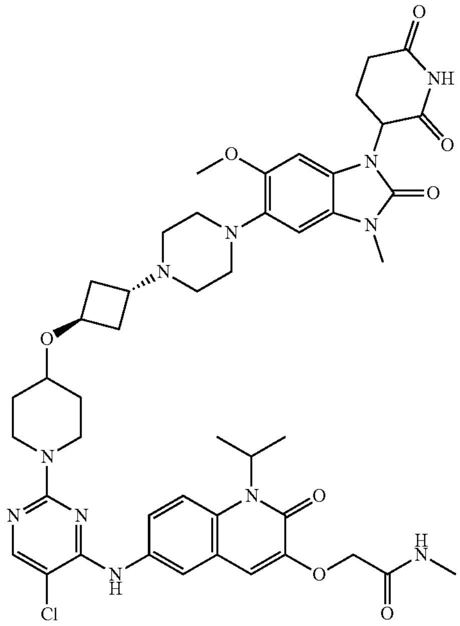 [SMILES: CNC(=O)COc1cc2cc(Nc3nc(N4CCC(O[C@H]5C[C@H](N6CCN(c7cc8c(cc7OC)n(C7CCC(=O)NC7=O)c(=O)n8C)CC6)C5)CC4)ncc3Cl)ccc2n(C(C)C)c1=O]

TABLE 2-continued
16
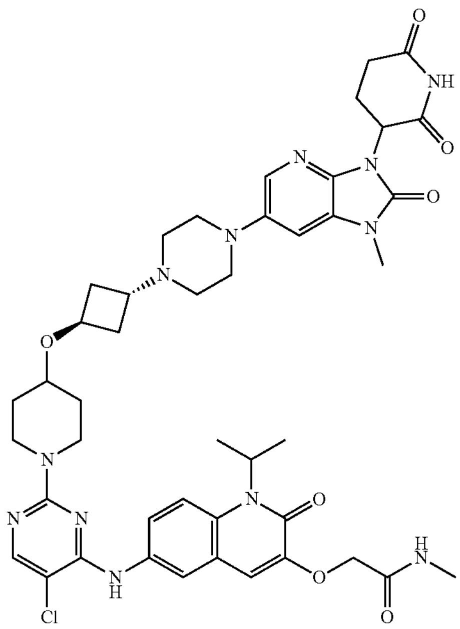 [SMILES: CNC(=O)COc1cc2cc(Nc3nc(N4CCC(O[C@H]5C[C@H](N6CCN(c7cnc8c(c7)n(C)c(=O)n8C7CCC(=O)NC7=O)CC6)C5)CC4)ncc3Cl)ccc2n(C(C)C)c1=O]
17
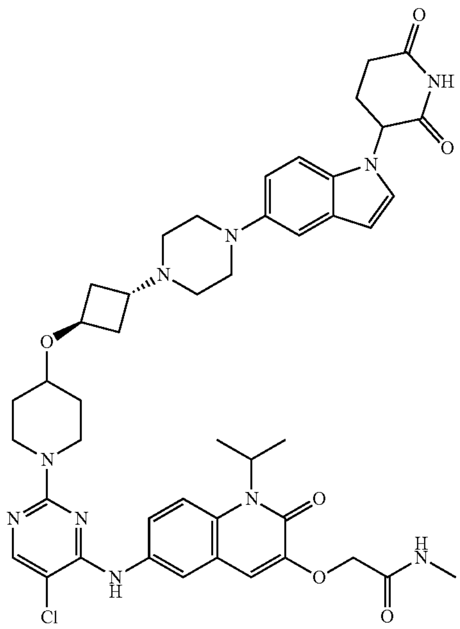

TABLE 2-continued
18
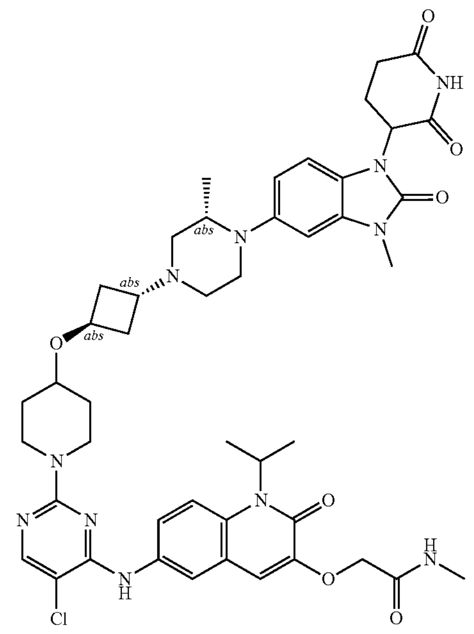 [SMILES: CNC(=O)COc1cc2cc(Nc3nc(N4CCC(O[C@H]5C[C@H](N6CCN(c7ccc8c(c7)n(C)c(=O)n8C7CCC(=O)NC7=O)[C@@H](C)C6)C5)CC4)ncc3Cl)ccc2n(C(C)C)c1=O]
19
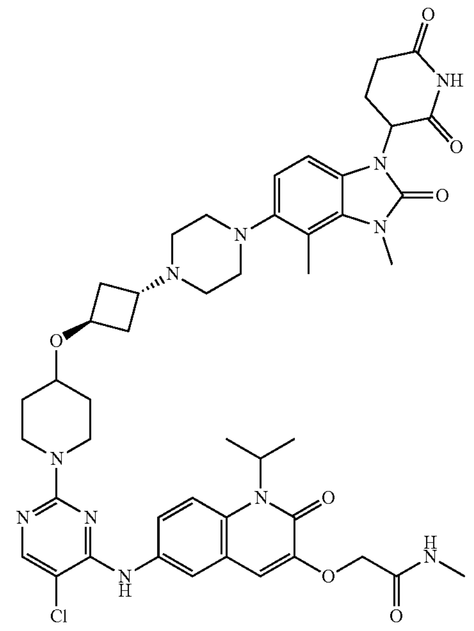

TABLE 2-continued
20
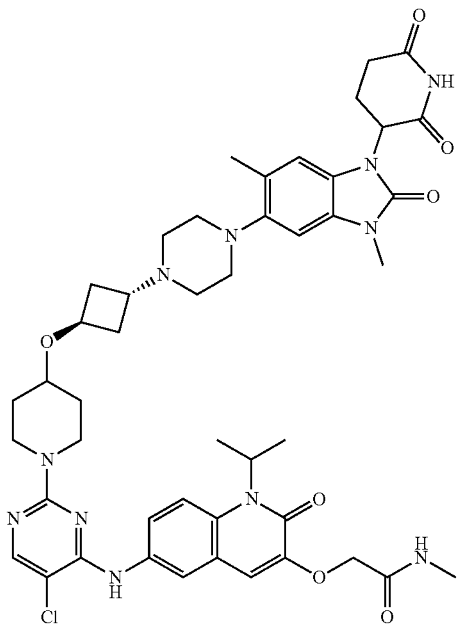 [SMILES: CNC(=O)COc1cc2cc(Nc3nc(N4CCC(O[C@H]5C[C@H](N6CCN(c7cc8c(cc7C)n(C7CCC(=O)NC7=O)c(=O)n8C)CC6)C5)CC4)ncc3Cl)ccc2n(C(C)C)c1=O]
21
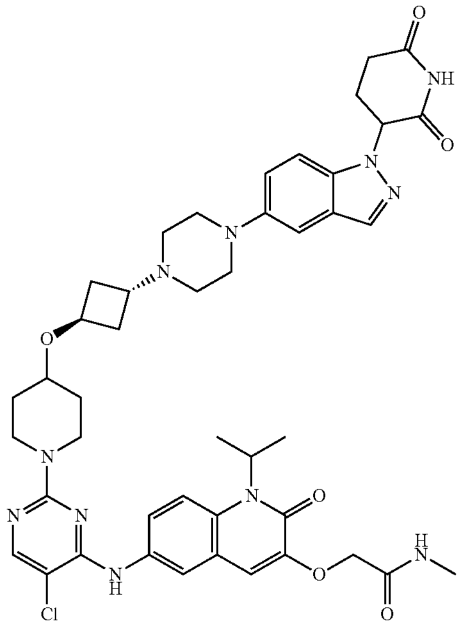

TABLE 2-continued
22
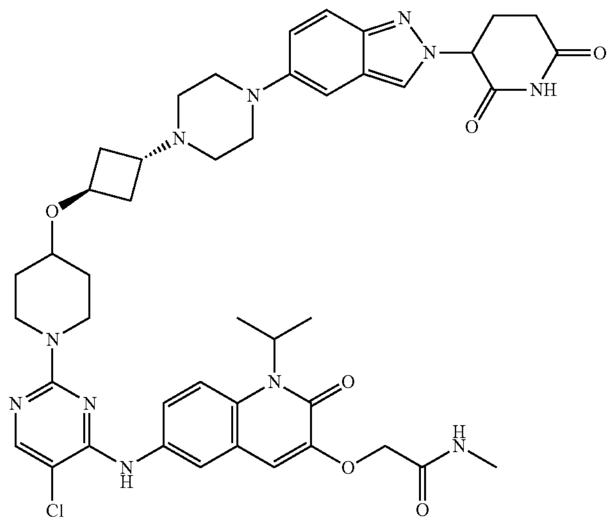 [SMILES: CNC(=O)COc1cc2cc(Nc3nc(N4CCC(O[C@H]5C[C@H](N6CCN(c7ccc8nn(C9CCC(=O)NC9=O)cc8c7)CC6)C5)CC4)ncc3Cl)ccc2n(C(C)C)c1=O]
23
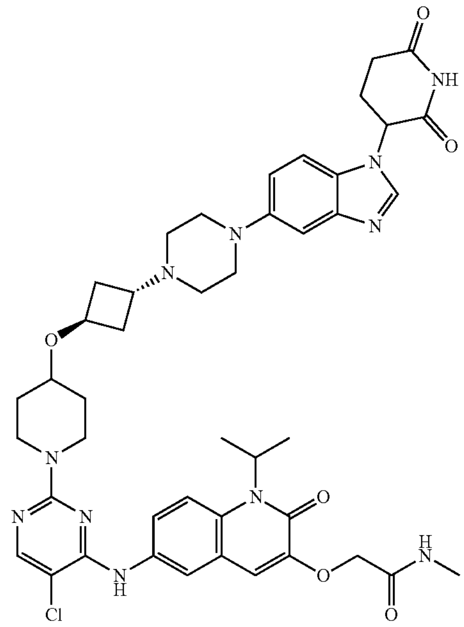

TABLE 2-continued
24
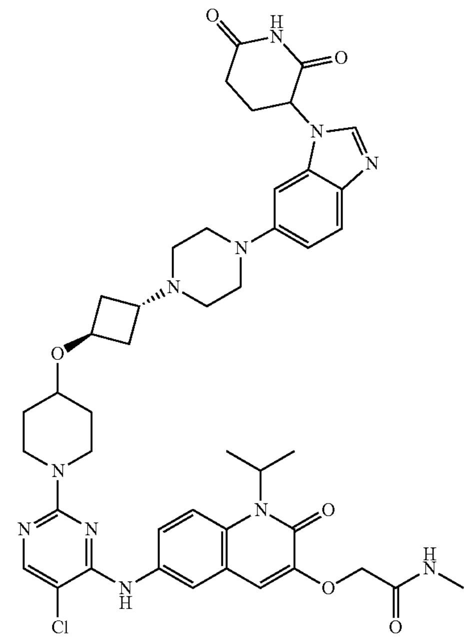 [SMILES: CNC(=O)COc1cc2cc(Nc3nc(N4CCC(O[C@H]5C[C@H](N6CCN(c7ccc8ncn(C9CCC(=O)NC9=O)c8c7)CC6)C5)CC4)ncc3Cl)ccc2n(C(C)C)c1=O]
25
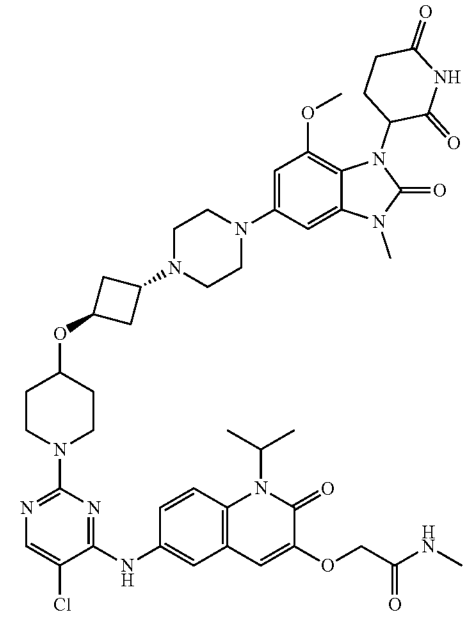 [SMILES: CNC(=O)COc1cc2cc(Nc3nc(N4CCC(O[C@H]5C[C@H](N6CCN(c7cc(OC)c8c(c7)n(C)c(=O)n8C7CCC(=O)NC7=O)CC6)C5)CC4)ncc3Cl)ccc2n(C(C)C)c1=O]

TABLE 2-continued
26
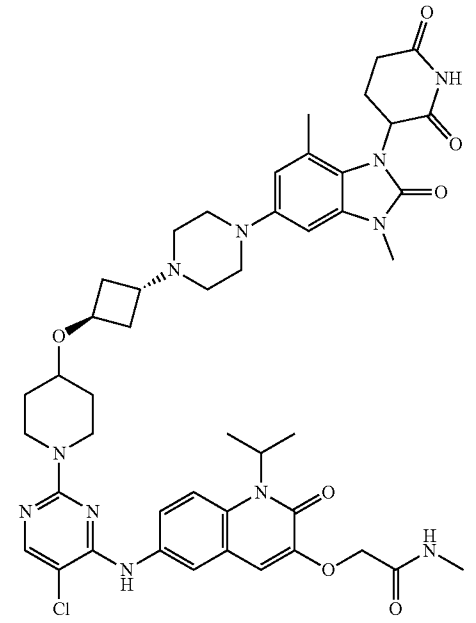 [SMILES: CNC(=O)COc1cc2cc(Nc3nc(N4CCC(O[C@H]5C[C@H](N6CCN(c7cc(C)c8c(c7)n(C)c(=O)n8C7CCC(=O)NC7=O)CC6)C5)CC4)ncc3Cl)ccc2n(C(C)C)c1=O]
27
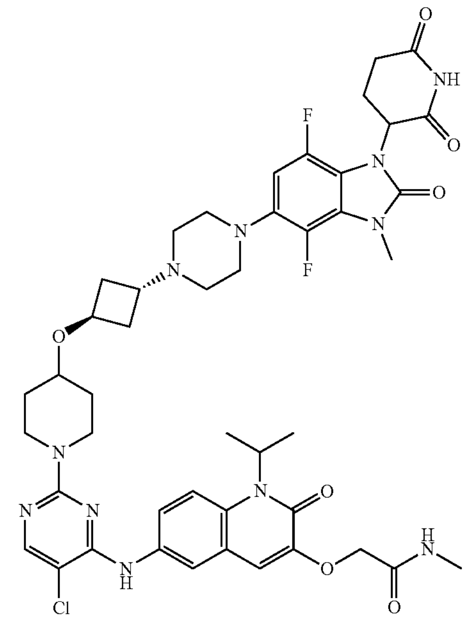

TABLE 2-continued

28

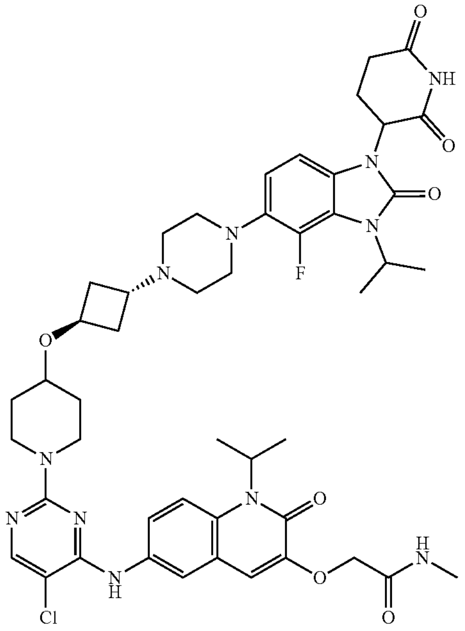 [SMILES: CNC(=O)COc1cc2cc(Nc3nc(N4CCC(O[C@H]5C[C@H](N6CCN(c7ccc8c(c7F)n(C(C)C)c(=O)n8C7CCC(=O)NC7=O)CC6)C5)CC4)ncc3Cl)ccc2n(C(C)C)c1=O]

29

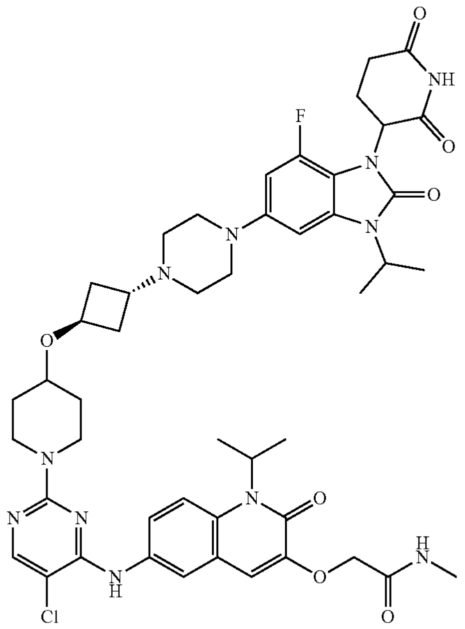 [SMILES: CNC(=O)COc1cc2cc(Nc3nc(N4CCC(O[C@H]5C[C@H](N6CCN(c7cc(F)c8c(c7)n(C(C)C)c(=O)n8C7CCC(=O)NC7=O)CC6)C5)CC4)ncc3Cl)ccc2n(C(C)C)c1=O]

In another aspect, the application pertains to a compound, wherein the compound is as shown in Table 2, or a pharmaceutically acceptable salt thereof.

In another aspect, the application pertains to a compound, wherein the compound is as shown in Table 2.

In another aspect, the application pertains to a compound, wherein the compound is as shown in Table 3, or a pharmaceutically acceptable salt enantiomer, stereoisomer, solvate, or isotopic derivative thereof.

TABLE 3
30
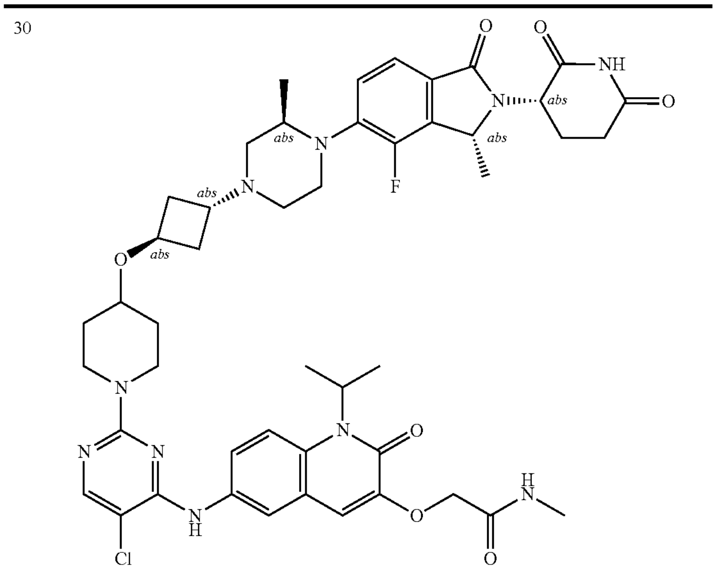
31
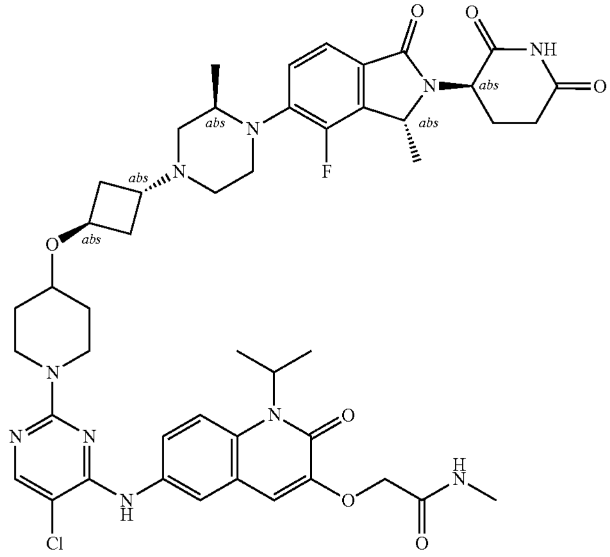 [SMILES: CNC(=O)COc1cc2cc(Nc3nc(N4CCC(O[C@H]5C[C@H](N6CCN(c7ccc8c(c7F)[C@@H](C)N([C@@H]7CCC(=O)NC7=O)C8=O)[C@H](C)C6)C5)CC4)ncc3Cl)ccc2n(C(C)C)c1=O]
32
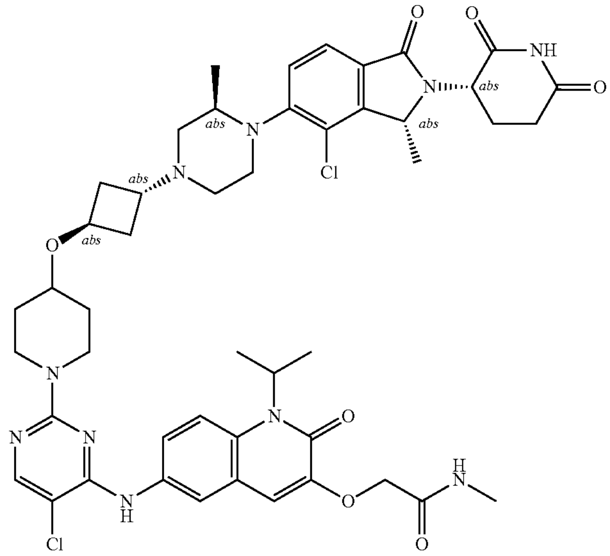 [SMILES: CNC(=O)COc1cc2cc(Nc3nc(N4CCC(O[C@H]5C[C@H](N6CCN(c7ccc8c(c7Cl)[C@@H](C)N([C@H]7CCC(=O)NC7=O)C8=O)[C@H](C)C6)C5)CC4)ncc3Cl)ccc2n(C(C)C)c1=O]

TABLE 3-continued
33
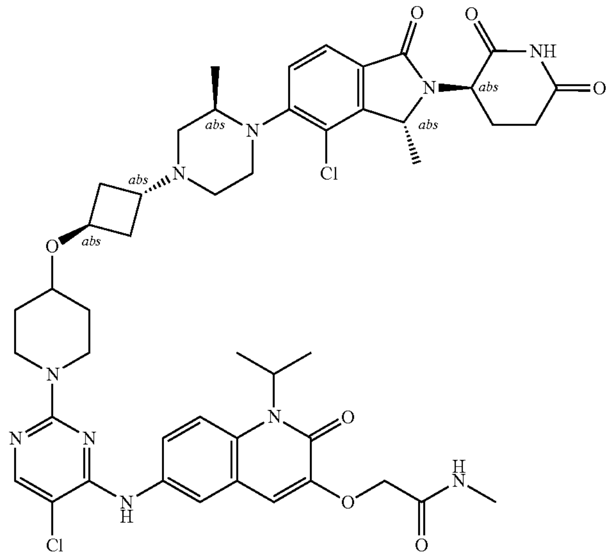
34
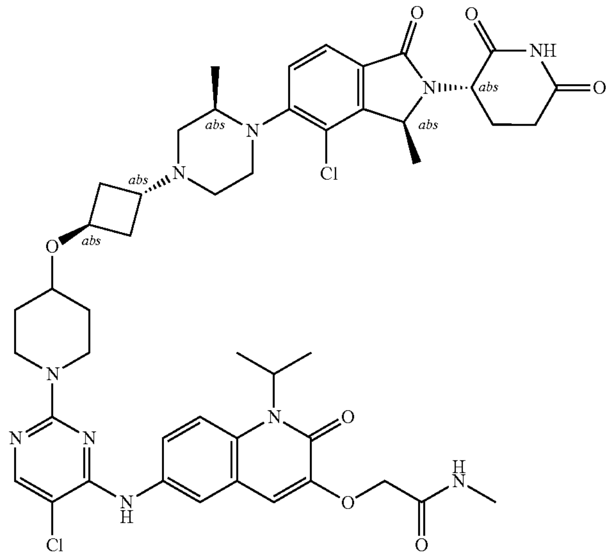 [SMILES: CNC(=O)COc1cc2cc(Nc3nc(N4CCC(O[C@H]5C[C@H](N6CCN(c7ccc8c(c7Cl)[C@H](C)N([C@H]7CCC(=O)NC7=O)C8=O)[C@H](C)C6)C5)CC4)ncc3Cl)ccc2n(C(C)C)c1=O]

TABLE 3-continued
35
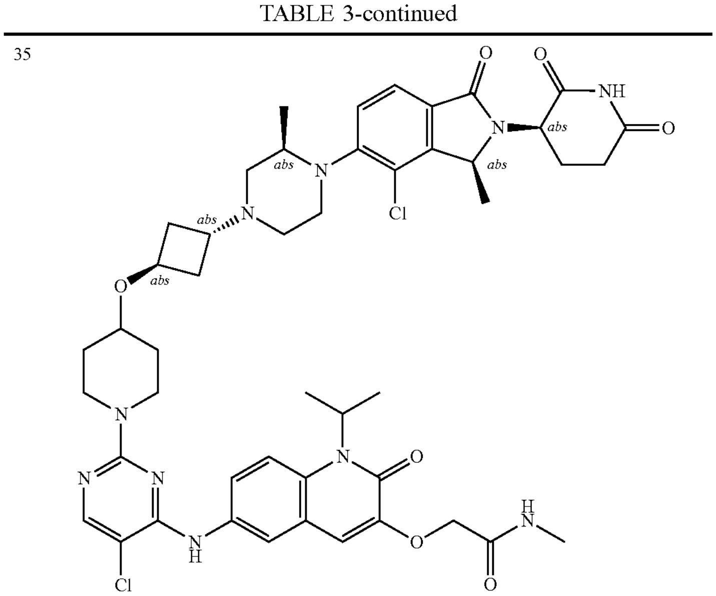
36
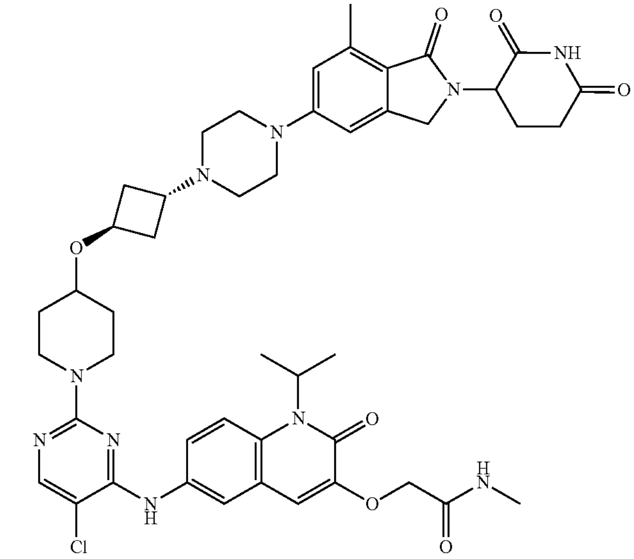
37
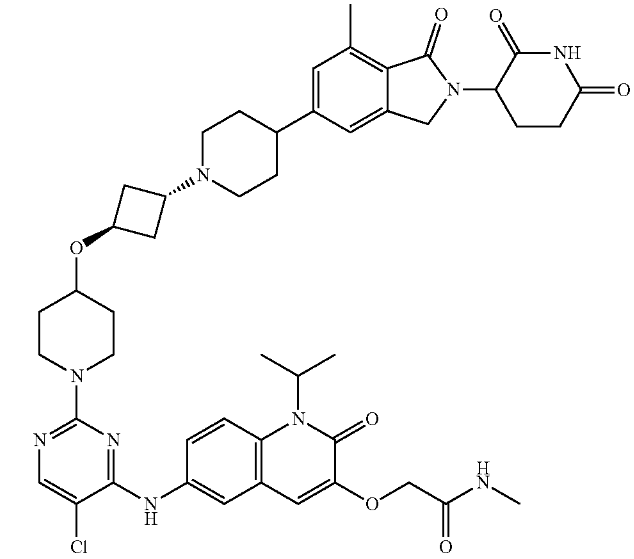

TABLE 3-continued
38
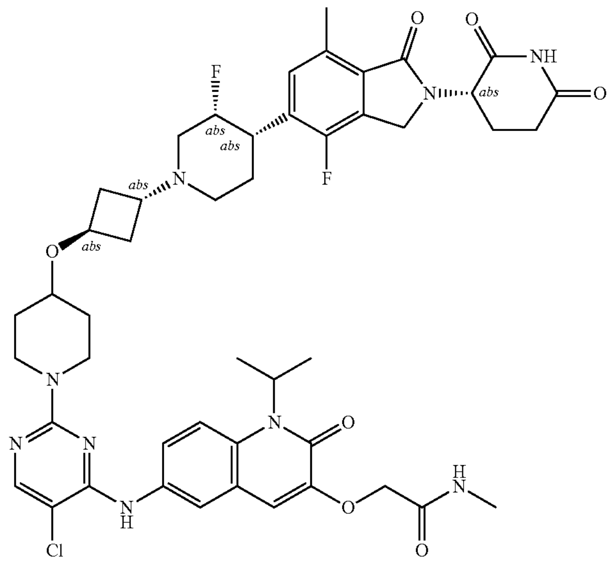 [SMILES: CNC(=O)COc1cc2cc(Nc3nc(N4CCC(O[C@H]5C[C@H](N6CC[C@@H](c7cc(C)c8c(c7F)CN([C@H]7CCC(=O)NC7=O)C8=O)[C@@H](F)C6)C5)CC4)ncc3Cl)ccc2n(C(C)C)c1=O]
39
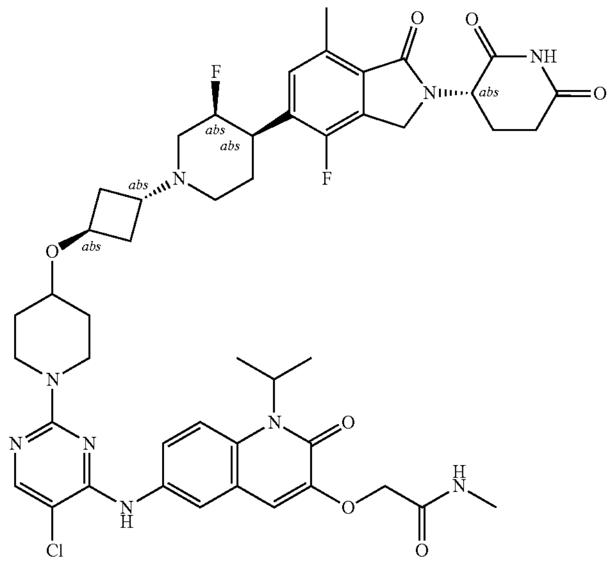 [SMILES: CNC(=O)COc1cc2cc(Nc3nc(N4CCC(O[C@H]5C[C@H](N6CC[C@H](c7cc(C)c8c(c7F)CN([C@H]7CCC(=O)NC7=O)C8=O)[C@H](F)C6)C5)CC4)ncc3Cl)ccc2n(C(C)C)c1=O]

TABLE 3-continued
40
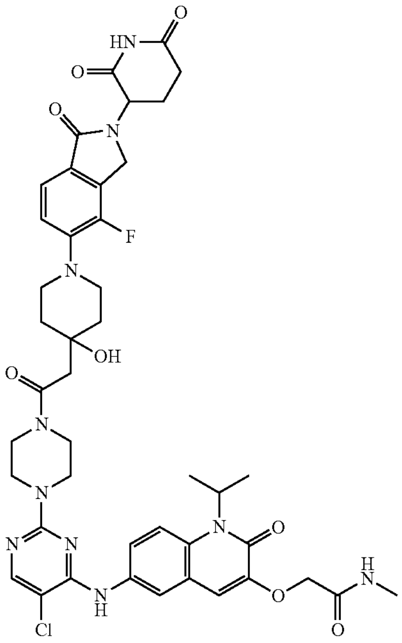 [SMILES: CNC(=O)COc1cc2cc(Nc3nc(N4CCN(C(=O)CC5(O)CCN(c6ccc7c(c6F)CN(C6CCC(=O)NC6=O)C7=O)CC5)CC4)ncc3Cl)ccc2n(C(C)C)c1=O]
41
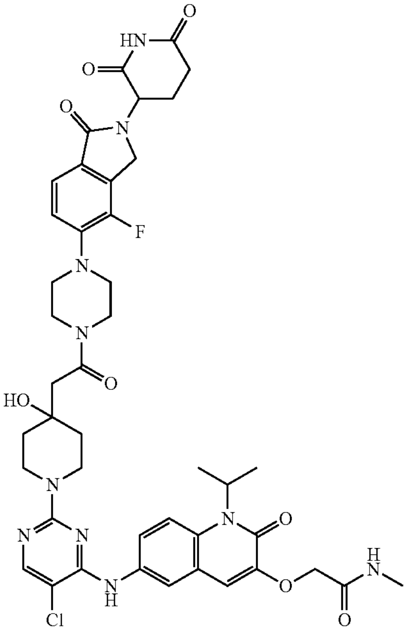 [SMILES: CNC(=O)COc1cc2cc(Nc3nc(N4CCC(O)(CC(=O)N5CCN(c6ccc7c(c6F)CN(C6CCC(=O)NC6=O)C7=O)CC5)CC4)ncc3Cl)ccc2n(C(C)C)c1=O]

TABLE 3-continued
42
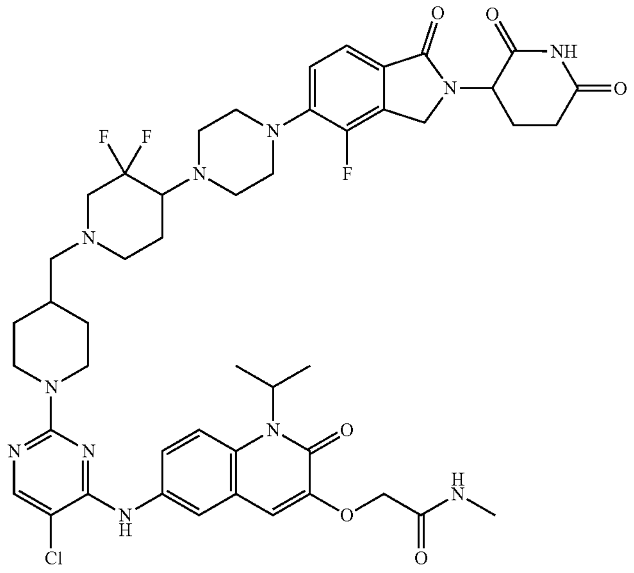 [SMILES: CNC(=O)COc1cc2cc(Nc3nc(N4CCC(CN5CCC(N6CCN(c7ccc8c(c7F)CN(C7CCC(=O)NC7=O)C8=O)CC6)C(F)(F)C5)CC4)ncc3Cl)ccc2n(C(C)C)c1=O]
43
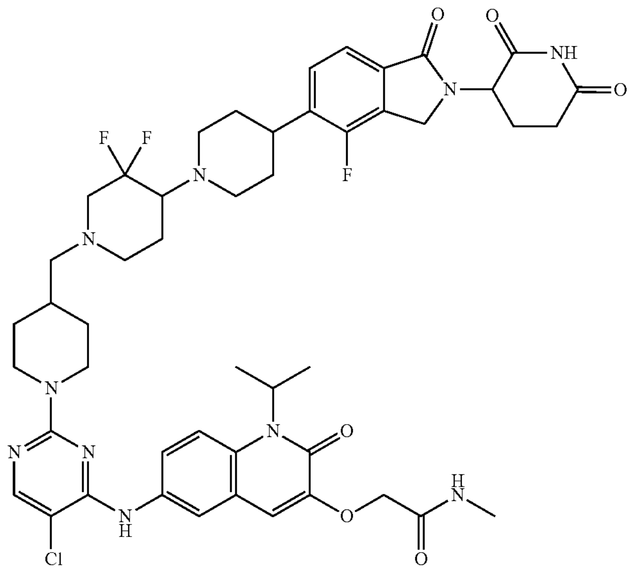 [SMILES: CNC(=O)COc1cc2cc(Nc3nc(N4CCC(CN5CCC(N6CCC(c7ccc8c(c7F)CN(C7CCC(=O)NC7=O)C8=O)CC6)C(F)(F)C5)CC4)ncc3Cl)ccc2n(C(C)C)c1=O]

TABLE 3-continued

| | |
|---|---|
| 44 | 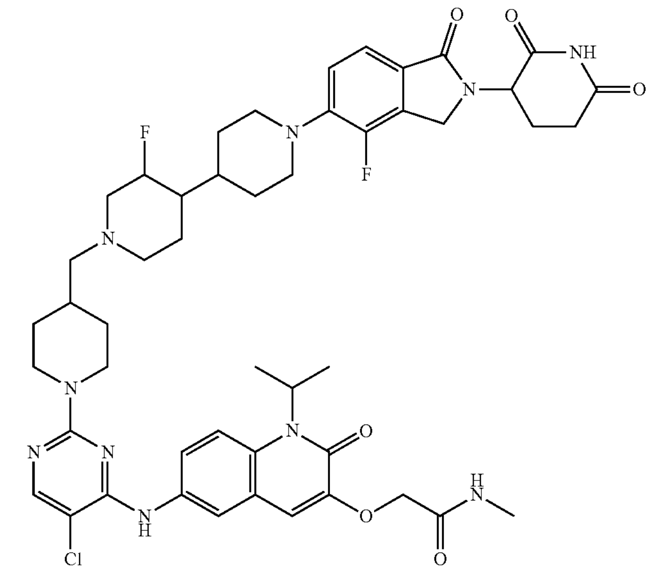 [SMILES: CNC(=O)COc1cc2cc(Nc3nc(N4CCC(CN5CCC(C6CCN(c7ccc8c(c7F)CN(C7CCC(=O)NC7=O)C8=O)CC6)C(F)C5)CC4)ncc3Cl)ccc2n(C(C)C)c1=O] |

In another aspect, the application pertains to a compound, wherein the compound is as shown in Table 3, or a pharmaceutically acceptable salt thereof.

In another aspect, the application pertains to a compound, wherein the compound is as shown in Table 3.

A compound of the disclosure may be synthesized using standard synthetic methods and procedures for the preparation of organic molecules and functional group transformations and manipulations, including the use of protective groups, as can be obtained from the relevant scientific literature or from standard reference textbooks in the field in view of this disclosure. Although not limited to any one or several sources, recognized reference textbooks of organic synthesis include: Smith, M. B.; March, J. March's Advanced Organic Chemistry: Reactions, Mechanisms, and Structure, 5th ed.; John Wiley & Sons: New York, 2001; and Greene, T. W.; Wuts, P. G. M. Protective Groups in Organic Synthesis, 3rd; John Wiley & Sons: New York, 1999. The synthetic methods described in International Applications Nos. PCT/US2020/056145 and PCT/US2022/025041 are incorporated herein by reference in their entireties.

In one embodiment, the compounds of the disclosure may be prepared according to the procedures and methods disclosed herein. Other bifunctional compounds of the disclosure can be prepared using similar methods from common intermediates or derivatives thereof.

General Synthetic Routes to Prepare Compounds of the Disclosure

Scheme 1

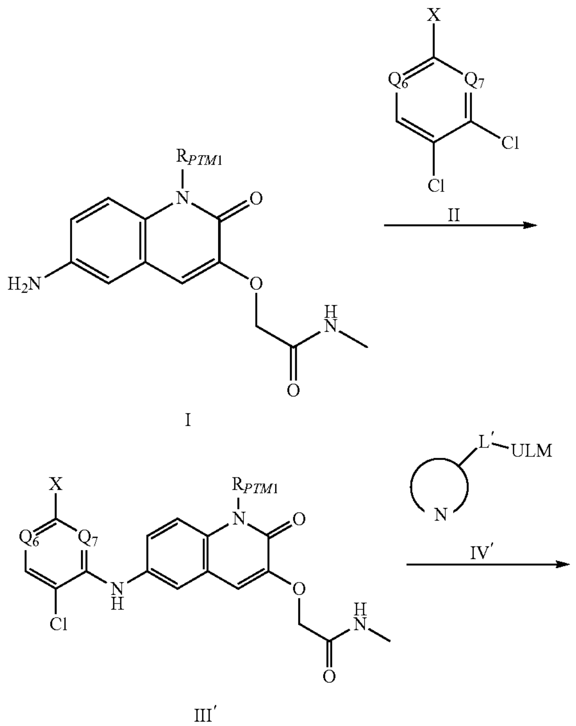

I

III′

-continued

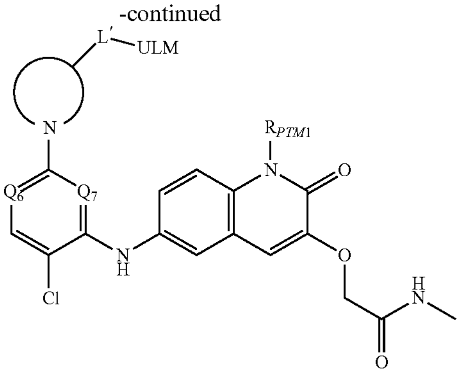

V'

A compound of formula I' (commercially available or readily prepared) may be reacted with a compound of formula II' (also commercially available or readily prepared) in a solvent such as DMSO or DMF, with a base such as triethylamine or DIEA and with heating to produce a compound of formula III'. In this case, the X on compound II' can be a leaving group such as a halogen and $Q_6$ and $Q_7$ are such that the selective displacement shown here is favored. Non-limiting examples are where X═Cl and $Q_6$ and $Q_7$ are both N. Compounds of formula III' can generate a PROTAC™ of formula V by reaction with a compound of formula IV' by heating in a solvent such as DMSO, in the presence of a base such as DIEA. Compounds of formula IV' are advanced building blocks where the ULM, linker and part of the PTM form a complete subunit. Wherein

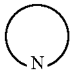

represents a 4-8 membered cyclic amine or a spirocyclic amine of any 2-ring combination selected from 4,4; 4,5; 4,6; 5,4; 5,5; 5,6; 6,4; 6,5; and 6,6, optionally including a second nitrogen atom (N) if more than 2 carbons are between them. L' can be a bond, linker, or part of linker.

Scheme 2

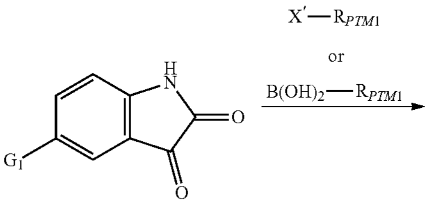

VI'

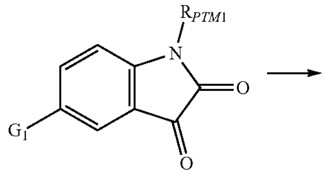

VII'

-continued

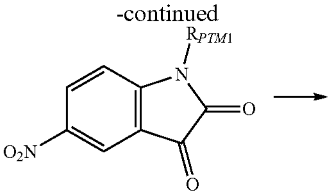

VIII'

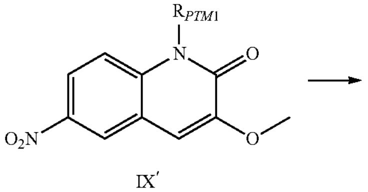

IX'

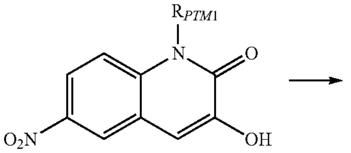

X'

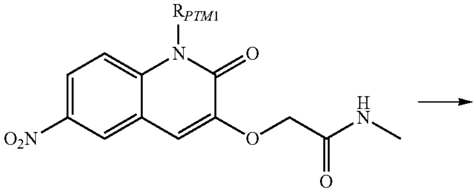

XI'

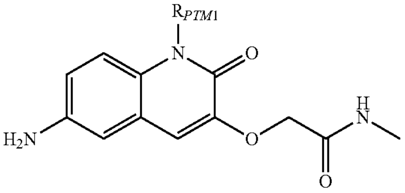

I'

Compounds of formula I' in Scheme 1 can be prepared using procedures found and/or adapted from Kerres et al., 2017, *Cell Reports* 20, 2860-2875 and are shown in Scheme 2. When $G_1$ is $NO_2$, a compound of formula VI' can be dissolved in a solvent such as DMF, treated with a base such as, but not limited to, $K_2CO_3$ and alkylated with an $R_{PTM1}$-X'. In this case X' can be a leaving group such as, but not limited to, iodo or bromo. Generally, $R_{PTM1}$-X' are commercially available or readily prepared. Alternatively, the boronic acid analogue of $R_{PTM1}$ can be attached to a compound of formula VI' using the Chan-Lam coupling reaction (Chen et al., 2020, Advanced Synthesis and Catalysis 62 (16), 3311-3331) wherein the boronic acid and compound of formula VI' are combined with a copper salt such as $Cu(OAc)_2$, a base such as $Na_2CO_3$ in a solvent such as DCE and heated. In this case it may be preferable to have $G_1$=H and conduct a nitration as shown in the third step of scheme 2 using $KNO_3$ under acidic conditions. The skilled artisan will realize that the nitration step is skipped when alkylating a 5-nitroisatin (VI' with $G_1$=$NO_2$) with $R_{PTM1}$-X' as compounds of formula VIII' are generated directly. Compounds of formula VIII can be reacted with TMS-diazomethane under basic conditions (See Duplantier et al., 2009, *J. Med. Chem.* 52, 3576-3585 and references cited therein) to give the ring expanded compounds of formula IX'. The hydroxy group of compounds of formula X' can be unmasked by treating compounds of formula IX' with $BBR_3$. Compounds of formula I can be obtained in 2 additional steps by alkylation of the hydroxy group of X' with a 2-haloacetamide followed by reduction of the nitro group. Numerous methods are available to the skilled artisan to accomplish the nitro reduction.

Methods of Ubiquitinating/Degrading a Target Protein in a Cell

The present disclosure provides a method of ubiquitinating/degrading a target protein in a cell. The method comprises administering a bifunctional composition comprising an E3 ubiquitin ligase binding moiety and a protein targeting moiety, preferably linked through a linker moiety, as otherwise described herein, wherein the E3 ubiquitin ligase binding moiety is coupled to the protein targeting moiety and wherein the E3 ubiquitin ligase binding moiety recognizes a ubiquitin pathway protein (e.g., an ubiquitin ligase, preferably an E3 ubiquitin ligase) and the protein targeting moiety recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In one embodiment, the present disclosure is directed to a method of treating a patient in need, for a disease state or condition modulated through a protein where the degradation of that protein will produce a therapeutic effect in that patient, the method comprising administering to a patient in need an effective amount of a compound of any one of Formula (I-III) or disclosed herein, or a pharmaceutically acceptable salt, enantiomer, stereoisomer, solvate, or isotopic derivative thereof, optionally in combination with another anti-cancer agent. The disease state or condition may be a disease caused by a microbial agent or other exogenous agent such as a virus, bacteria, fungus, protozoa, or other microbe or may be a disease state caused by overexpression of a protein, which leads to a disease state and/or condition.

Methods of Treatment

In one aspect, the present application pertains to a method of treating and/or preventing cancer comprising administering to a subject in need thereof a therapeutically effective amount of a compound of the disclosure, or a pharmaceutically acceptable salt, enantiomer, stereoisomer, solvate, or isotopic derivative thereof.

In one aspect, the present application pertains to a method of treating and/or preventing cancer comprising administering to a subject in need thereof a therapeutically effective amount of a compound of the disclosure, or a pharmaceutically acceptable salt, enantiomer, stereoisomer, solvate, polymorph, or isotopic derivative thereof, in combination with one or more additional anti-cancer agents.

In one aspect, the cancer that is treated or prevented is breast cancer, ovarian cancer, leukemia, lymphoma, benign lymphoma, malignant lymphoma, Burkitt's lymphoma, non-Hodgkin's lymphoma, B-cell non-Hodgkin's lymphoma, sarcomas, Ewing's sarcoma, hemangiosarcoma, Kaposi's sarcoma, liposarcoma, myosarcomas, synovial sarcoma, meningeal sarcomas, carcinosarcoma, acute myeloid leukemia (AML), acute lymphoblastic leukemia (ALL), T-lineage acute lymphoblastic leukemia (T-ALL), T-lineage lymphoblastic lymphoma (T-LL), peripheral T-cell lymphoma, adult T-cell leukemia, Pre-B acute lymphoblastic leukemia, pre-B lymphomas, B-cell lymphoma, large B-cell lymphoma, diffuse large B-cell lymphoma, B-cell acute lymphoblastic leukemia (ALL), Philadelphia chromosome positive acute lymphoblastic leukemia (ALL), Philadelphia chromosome positive chronic myeloid leukemia (CML), follicular lymphoma, intravascular large B-cell lymphoma, angioimmunoblastic T-cell lymphoma (AITL), T-cell lymphoma, B-cell leukemia, chronic myeloid leukemia, non-small cell lung cancer, systemic lupus erythematosus (SLE), brain tumors, or central nervous system cancers.

In one aspect, the cancer that is treated or prevented is large B-cell lymphoma, diffuse large B-cell lymphoma, Burkitt's lymphoma, follicular lymphoma, or angioimmunoblastic T-cell lymphoma (AITL).

The methods of treating cancer described herein result in a reduction in tumor size. Alternatively, or in addition, the cancer is metastatic cancer and this method of treatment includes inhibition of metastatic cancer cell invasion.

In one aspect, the application pertains to a method of treating cancer comprising administering to a subject in need thereof a therapeutically effective amount of a bifunctional compound the disclosure, i.e., a compound of any of Formulas (I)-(III) or Tables 1-3, as defined herein, or a pharmaceutically acceptable salt, enantiomer, stereoisomer, solvate, or isotopic derivative thereof.

In one aspect, the application pertains to a method of treating cancer comprising administering to a subject in need thereof a therapeutically effective amount of a bifunctional compound of the disclosure, i.e., a compound of any of Formulas (I)-(III) or Tables 1-3, as defined herein, or a pharmaceutically acceptable salt thereof.

In one aspect, the application pertains to a method of treating cancer comprising administering to a subject in need thereof a therapeutically effective amount of a bifunctional compound of the disclosure, i.e., a compound of any of Formulas (I)-(III) or Tables 1-3, as defined herein.

In one aspect, the application pertains to a method of treating cancer comprising administering to a subject in need thereof a therapeutically effective amount of a bifunctional compound the disclosure, i.e., a compound of any of Formula (I), as defined herein, or a pharmaceutically acceptable salt, enantiomer, stereoisomer, solvate, or isotopic derivative thereof.

In one aspect, the application pertains to a method of treating cancer comprising administering to a subject in need thereof a therapeutically effective amount of a bifunctional compound of the disclosure, i.e., a compound of any of Formulas (I), as defined herein, or a pharmaceutically acceptable salt thereof.

In one aspect, the application pertains to a method of treating cancer comprising administering to a subject in need thereof a therapeutically effective amount of a bifunctional compound of the disclosure, i.e., a compound of any of Formulas (I), as defined herein.

In one aspect, the application pertains to a method of treating cancer comprising administering to a subject in need thereof a therapeutically effective amount of a bifunctional compound the disclosure, i.e., a compound of any of Formula (II), as defined herein, or a pharmaceutically acceptable salt, enantiomer, stereoisomer, solvate, or isotopic derivative thereof.

In one aspect, the application pertains to a method of treating cancer comprising administering to a subject in need thereof a therapeutically effective amount of a bifunctional compound of the disclosure, i.e., a compound of any of Formulas (II), as defined herein, or a pharmaceutically acceptable salt thereof.

In one aspect, the application pertains to a method of treating cancer comprising administering to a subject in need thereof a therapeutically effective amount of a bifunctional compound of the disclosure, i.e., a compound of any of Formulas (II), as defined herein.

In one aspect, the application pertains to a method of treating cancer comprising administering to a subject in need thereof a therapeutically effective amount of a bifunctional compound the disclosure, i.e., a compound of any of Formula (III), as defined herein, or a pharmaceutically acceptable salt, enantiomer, stereoisomer, solvate, or isotopic derivative thereof.

In one aspect, the application pertains to a method of treating cancer comprising administering to a subject in need thereof a therapeutically effective amount of a bifunctional compound of the disclosure, i.e., a compound of any of Formulas (III), as defined herein, or a pharmaceutically acceptable salt thereof.

In one aspect, the application pertains to a method of treating cancer comprising administering to a subject in need thereof a therapeutically effective amount of a bifunctional compound of the disclosure, i.e., a compound of any of Formulas (III), as defined herein.

In one aspect, the application pertains to a method of treating cancer comprising administering to a subject in need thereof a therapeutically effective amount of a bifunctional compound that is selected from any of Tables 1-3, or a pharmaceutically acceptable salt, enantiomer, stereoisomer, solvate, or isotopic derivative thereof.

In one aspect, the application pertains to a method of treating cancer comprising administering to a subject in need thereof a therapeutically effective amount of a bifunctional compound that is selected from any of Tables 1-3, or a pharmaceutically acceptable salt thereof.

In one aspect, the application pertains to a method of treating cancer comprising administering to a subject in need thereof a therapeutically effective amount of a bifunctional compound that is selected from any of Tables 1-3.

In one aspect, the application pertains to a method of treating cancer comprising administering to a subject in need thereof a therapeutically effective amount of a bifunctional compound that is selected from Table 1, or a pharmaceutically acceptable salt, enantiomer, stereoisomer, solvate, or isotopic derivative thereof.

In one aspect, the application pertains to a method of treating cancer comprising administering to a subject in need thereof a therapeutically effective amount of a bifunctional compound that is selected from Table 1, or a pharmaceutically acceptable salt thereof.

In one aspect, the application pertains to a method of treating cancer comprising administering to a subject in need thereof a therapeutically effective amount of a bifunctional compound that is selected from Table 1.

In one aspect, the application pertains to a method of treating cancer comprising administering to a subject in need thereof a therapeutically effective amount of a bifunctional compound that is selected from Table 2, or a pharmaceutically acceptable salt, enantiomer, stereoisomer, solvate, or isotopic derivative thereof.

In one aspect, the application pertains to a method of treating cancer comprising administering to a subject in need thereof a therapeutically effective amount of a bifunctional compound that is selected from Table 2, or a pharmaceutically acceptable salt thereof.

In one aspect, the application pertains to a method of treating cancer comprising administering to a subject in need thereof a therapeutically effective amount of a bifunctional compound that is selected from Table 2.

In one aspect, the application pertains to a method of treating cancer comprising administering to a subject in need thereof a therapeutically effective amount of a bifunctional compound that is selected from Table 3, or a pharmaceutically acceptable salt, enantiomer, stereoisomer, solvate, or isotopic derivative thereof.

In one aspect, the application pertains to a method of treating cancer comprising administering to a subject in need thereof a therapeutically effective amount of a bifunctional compound that is selected from Table 3, or a pharmaceutically acceptable salt thereof.

In one aspect, the application pertains to a method of treating cancer comprising administering to a subject in need thereof a therapeutically effective amount of a bifunctional compound that is selected from Table 3.

In one aspect, the application pertains to treating cancer with a compound of the disclosure in combination with another anti-cancer agent. In one embodiment, the cancer treated with the combination of a compound of the disclosure and another anti-cancer agent is lymphoma.

In one embodiment, the cancer treated with the combination of a compound of the disclosure and another anti-cancer agent is multiple myeloma. In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its volume prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active agent or compound of the disclosure. In another preferred aspect, an increase in average survival time of a population may also be measured, for example, by calculating for a population the average length of survival following completion of a first round of treatment with an active agent or compound of the disclosure.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured by calculating for a population the average length of survival following initiation of treatment with an active agent or compound of the disclosure. In another preferred aspect, an increase in average survival time of a population may be measured by calculating for a population the average length of survival following completion of a first round of treatment with a compound of the disclosure.

In another aspect, treating cancer results in a decrease in tumor growth rate. Preferably, after treatment, tumor growth rate is reduced by at least 5% relative to growth rate prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured by measuring an increase in the diameter of a tumor after a prior tumor shrinkage that followed treatment. In another preferred aspect, a decrease in tumor regrowth is indicated by failure of tumors to reoccur after treatment has stopped.

The dosages of the compound of the disclosure for any of the methods and uses described herein vary depending on the agent, the age, weight, and clinical condition of the recipient subject, and the experience and judgment of the clinician or practitioner administering the therapy, among other factors affecting the selected dosage.

The therapeutically effective amount of the compound of the disclosure may be administered one or more times over a day for up to 30 or more days, followed by 1 or more days of non-administration of the compound. This type of treatment schedule, i.e., administration of a the compound of the disclosure on consecutive days followed by non-administration of the compound on consecutive days may be referred to as a treatment cycle. A treatment cycle may be repeated as many times as necessary to achieve the intended affect.

In one embodiment, the therapeutically effective amount of the compound of the disclosure is 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1,000 mg administered once, twice, three times, four times, or more daily for one, two, three, four, five, six, seven, eight, nine, ten, eleven, twelve, thirteen, fourteen, fifteen, twenty, twenty-five, thirty consecutive days, or, once, twice, three times, four times, or more daily, in single or divided doses, for 2 months, 3 months, 4 months, 5 months, 6 months, or longer.

In one embodiment, the therapeutically effective amount of the compound of the disclosure is about 10 to about 40 mg, about 20 to about 50 mg, about 30 to about 60 mg, about 40 to about 70 mg, about 50 to about 80 mg, about 60 to about 90 mg, about 70 to about 100 mg, about 80 to about 110 mg, about 90 to about 120 mg, about 100 to about 130 mg, about 110 to about 140 mg, about 120 to about 150 mg, about 130 to about 160 mg, about 140 to about 170 mg, about 150 to about 180 mg, about 160 to about 190 mg, about 170 to about 200 mg, about 180 to about 210 mg, about 190 to about 220 mg, about 200 to about 230 mg, about 210 to about 240 mg, about 220 to about 250 mg, about 230 to about 260 mg, about 240 to about 270 mg, about 250 to about 280 mg, about 260 to about 290 mg, about 270 to about 300 mg, about 280 to about 310 mg, about 290 to about 320 mg, about 300 to about 330 mg, about 310 to about 340 mg, about 320 to about 350 mg, about 330 to about 360 mg, about 340 to about 370 mg, about 350 to about 380 mg, about 360 to about 390 mg, about 370 to about 400 mg, about 380 to about 410 mg, about 390 to about 420 mg, about 400 to about 430 mg, about 410 to about 440 mg, about 420 to about 450 mg, about 430 to about 460 mg, about 440 to about 470 mg, about 450 to about 480 mg, about 460 to about 490 mg, about 470 to about 500 mg, about 480 to about 510 mg, about 490 to about 520 mg, about 500 to about 530 mg, about 510 to about 540 mg, about 520 to about 550 mg, about 530 to about 560 mg, about 540 to about 570 mg, about 550 to about 580 mg, about 560 to about 590 mg, about 570 to about 600 mg, about 580 to about 610 mg, about 590 to about 620 mg, about 600 to about 630 mg, about 610 to about 640 mg, about 620 to about 650 mg, about 630 to about 660 mg, about 640 to about 670 mg, about 650 to about 680 mg, about 660 to about 690 mg, about 670 to about 700 mg, about 680 to about 710 mg, about 690 to about 720 mg, about 700 to about 730 mg, about 710 to about 740 mg, about 720 to about 750 mg, about 730 to about 760 mg, about 740 to about 770 mg, about 750 to about 780 mg, about 760 to about 790 mg, about 770 to about 800 mg, about 780 to about 810 mg, about 790 to about 820 mg, about 800 to about 830 mg, about 810 to about 840 mg, about 820 to about 850 mg, about 830 to about 860 mg, about 840 to about 870 mg, about 850 to about 880 mg, about 860 to about 890 mg, about 870 to about 900 mg, about 880 to about 910 mg, about 890 to about 920 mg, about 900 to about 930 mg, about 910 to about 940 mg, about 920 to about 950 mg, about 930 to about 960 mg, about 940 to about 970 mg, about 950 to about 980 mg, about 960 to about 990 mg, or about 970 to about 1,000 mg administered once, twice, three times, four times, or more daily in single or divided doses (which dose may be adjusted for the patient's weight in kg, body surface area in $m^2$, and/or age in years).

In one embodiment, the therapeutically effective amount of the compound of the disclosure is about 70 mg to about 1000 mg administered once, twice, three times, four times, or more daily in single or divided doses (which dose may be adjusted for the patient's weight in kg, body surface area in $m^2$, and/or age in years).

The therapeutically effective amount of the compound of the disclosure can also range from about 0.01 mg/kg per day to about 100 mg/kg per day. In an aspect, therapeutically effective amount of the compound of the disclosure can range from about 0.05 mg/kg per day to about 10 mg/kg per day. In an aspect, therapeutically effective amount of the compound of the disclosure can range from about 0.075 mg/kg per day to about 5 mg/kg per day. In an aspect, therapeutically effective amount of the compound of the disclosure can range from about 0.10 mg/kg per day to about 1 mg/kg per day. In an aspect, therapeutically effective amount of the compound of the disclosure can range from about 0.20 mg/kg per day to about 0.70 mg/kg per day.

In one embodiment, the therapeutically effective amount of the compound of the disclosure is about 0.10 mg/kg per day, about 0.15 mg/kg per day, about 0.20 mg/kg per day, about 0.25 mg/kg per day, about 0.30 mg/kg per day, about 0.35 mg/kg per day, about 0.40 mg/kg per day, about 0.45 mg/kg per day, about 0.50 mg/kg per day, about 0.55 mg/kg per day, about 0.60 mg/kg per day, about 0.65 mg/kg per day, about 0.70 mg/kg per day, about 0.75 mg/kg per day, about 0.80 mg/kg per day, about 0.85 mg/kg per day, about 0.90 mg/kg per day, about 0.95 mg/kg per day, or about 1.00 mg/kg per day.

In one embodiment, the therapeutically effective amount of the compound of the disclosure is about 1.05 mg/kg per day, about 1.10 mg/kg per day, about 1.15 mg/kg per day, about 1.20 mg/kg per day, about 1.25 mg/kg per day, about 1.30 mg/kg per day, about 1.35 mg/kg per day, about 1.40 mg/kg per day, about 1.45 mg/kg per day, about 1.50 mg/kg per day, about 1.55 mg/kg per day, about 1.60 mg/kg per day, about 1.65 mg/kg per day, about 1.70 mg/kg per day, about 1.75 mg/kg per day, about 1.80 mg/kg per day, about 1.85 mg/kg per day, about 1.90 mg/kg per day, about 1.95 mg/kg per day, or about 2.00 mg/kg per day.

In one embodiment, the therapeutically effective amount of the compound of the disclosure is about 2 mg/kg per day, about 2.5 mg/kg per day, about 3 mg/kg per day, about 3.5 mg/kg per day, about 4 mg/kg per day, about 4.5 mg/kg per day, about 5 mg/kg per day, about 5.5 mg/kg per day, about 6 mg/kg per day, about 6.5 mg/kg per day, about 7 mg/kg per day, about 7.5 mg/kg per day, about 8.0 mg/kg per day, about 8.5 mg/kg per day, about 9.0 mg/kg per day, about 9.5 mg/kg per day, or about 10 mg/kg per day.

In one embodiment, the therapeutically effective amount of the compound of the disclosure is administered to the subject once daily. In one embodiment, this daily dose of a compound of the compound of the disclosure may administered to the subject all at once. In one embodiment, this daily dose of the compound of the disclosure may administered to the subject in two portions (i.e., a divided dose). In one embodiment, this daily dose of the compound of the disclosure may administered to the subject in three divided doses. In one embodiment, this daily dose of the compound of the disclosure may administered to the subject in four divided doses. In one embodiment, this daily dose of the compound of the disclosure may be administered to the subject in five or more divided doses. In one embodiment, these portions or divided doses are administered to the subject at regular intervals throughout the day, for example, every 12 hours, every 8 hours, every 6 hours, every 5 hours, every 4 hours, etc.

The therapeutically effective amount of the compound of the disclosure can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the compound of the disclosure or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, once every two weeks, or monthly depending on half-life and clearance rate of the particular formulation.

In one embodiment, for the methods of treating cancer with the combination of the compound of the disclosure and an effective amount of at least one additional anti-cancer agent, the therapeutically effective amount of the compound of the disclosure is described herein, and the therapeutically effective amount of the at least one additional anti-cancer agent is 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1,000 mg administered once, twice, three times, four times, or more daily for one, two, three, four, five, six, seven, eight, nine, ten, eleven, twelve, thirteen, fourteen, fifteen, or thirty consecutive days, or, once, twice, three times, four times, or more daily, in single or divided doses, for 2 months, 3 months, 4 months, 5 months, 6 months, or longer.

In one embodiment, for the methods of treating cancer with the combination of the compound of the disclosure and at least one additional anti-cancer agent, the therapeutically effective amount of the at least one additional anti-cancer agent is administered orally once daily for one, two, three, four, five, six, seven, eight, nine, ten, eleven, twelve, thirteen, fourteen, fifteen, twenty, twenty-five, thirty, or more consecutive days, in single or divided doses. In one embodiment, the combination of the compound of the disclosure and the at least one additional anti-cancer agent is administered to the subject in need thereof in the fasted state. In one embodiment, the subject does not eat for at least two hours before, and at least one hour after, the administration of the combination of the compound of the disclosure and the at least one additional anti-cancer agent.

In one embodiment, the compound of the disclosure and the at least one additional anti-cancer agent are administered to the subject simultaneously. In one embodiment, the compound of the disclosure and the at least one additional anti-cancer agent are administered to the subject sequentially.

In one embodiment, the compound of the disclosure and the at least one additional anti-cancer agent are administered to the subject in temporal proximity.

In some embodiments, "temporal proximity" means that administration of the compound of the disclosure occurs within a time period before or after the administration of the at least one additional anti-cancer agent, such that the therapeutic effect of the compound of the disclosure overlaps with the therapeutic effect of the at least one additional anti-cancer agent. In some embodiments, the therapeutic effect of the compound of the disclosure completely overlaps with the therapeutic effect of the at least one additional anti-cancer agent. In some embodiments, "temporal proximity" means that administration of the compound of the disclosure occurs within a time period before or after the administration of the at least one additional anti-cancer agent, such that there is a synergistic effect between the compound of the disclosure and the at least one additional anti-cancer agent.

"Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

Pharmaceutical Compositions

In one embodiment, the compound of the disclosure is formulated for oral administration. For example, in one embodiment, the compound of the disclosure is formulated as a tablet that comprises zero, one, two, or more of each of the following: emulsifier; surfactant, binder; disintegrant, glidant; and lubricant.

In one embodiment, the emulsifier is hypromellose.

In one embodiment, the surfactant is vitamin E polyethylene glycol succinate.

In one embodiment, the binder (also referred to herein as a filler) is selected from the group consisting of microcrystalline cellulose, lactose monohydrate, sucrose, glucose, and sorbitol.

In one embodiment, the disintegrant is croscarmellose sodium.

In one embodiment, the glidant refers to a substance used to promote powder flow by reducing interparticle cohesion. In one embodiment, in the dosage forms of the disclosure, the glidant is selected from the group consisting of silicon dioxide, silica colloidal anhydrous, starch, and talc.

In one embodiment, the lubricant refers to a substance that prevents ingredients from sticking and/or clumping together in the machines used in preparation of the dosage forms of the disclosure. In one embodiment, in the dosage forms of the disclosure, the lubricant is selected from the group consisting of magnesium stearate, sodium stearyl fumarate, stearic acid, and vegetable stearin.

The pharmaceutical compositions containing the compound of the disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the compound of the disclosure into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the compound of the disclosure in the required amount in an appropriate solvent with one or a combination of ingredients enumerated above, as required, followed by filtered sterilization. Generally, dispersions are prepared by incorporating the active agent or compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the compound of the disclosure can be incorporated with excipients and used in the form of tablets, troches, or capsules. Oral compositions can also be prepared using a fluid carrier for use as a mouthwash, wherein the agent or compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

For administration by inhalation, the agents or compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active agents or compounds are formulated into ointments, salves, gels, or creams as generally known in the art.

In one aspect, the compound of the disclosure is prepared with pharmaceutically acceptable carriers that will protect the agent or compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active agent or compound calculated to produce the desired therapeutic effect in association with the required pharmaceutical carrier. The specification for the dosage unit forms of the application are dictated by and directly dependent on the unique characteristics of the compound of the disclosure and the particular therapeutic effect to be achieved.

The pharmaceutical compositions can be included in a container, pack, or dispenser together with instructions for administration.

Illustrative modes of administration for the compound of the disclosure includes systemic or local administration such as oral, nasal, parenteral, transdermal, subcutaneous, vaginal, buccal, rectal or topical administration modes. In one embodiment, the compound of the disclosure is administered orally. In one embodiment, the compound of the disclosure is administered as a tablet, capsule, caplet, solution, suspension, syrup, granule, bead, powder, or pellet.

Illustrative pharmaceutical compositions are tablets and gelatin capsules comprising a salt of the compound of the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also;

c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the salt such as cyclodextrin, hydroxypropyl-cyclodextrin, PEG400, and/or PEG200.

For preparing pharmaceutical compositions from the compound of the disclosure, or a salt or hydrate thereof, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. For example, water or water-propylene glycol solutions for parenteral injection or addition of sweeteners and opacifiers for oral solutions, suspensions and emulsions. Liquid form preparations may also include solutions for intranasal administration.

Liquid, particularly injectable, compositions can, for example, be prepared by dissolution, dispersion, etc. For example, the disclosed salt is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, intrathecal, subcutaneous or intramuscular form, and all using forms well known to those skilled in the pharmaceutical arts.

Pharmaceutical compositions can be prepared according to conventional mixing, granulating or coating methods, respectively, and the present pharmaceutical compositions can contain from about 0.1% to about 99%, from about 5% to about 90%, or from about 1% to about 20% of the disclosed free base or salt by weight or volume.

The pharmaceutical compositions containing the compound of the disclosure may further comprising one or more additional anti-cancer agents, including any of those disclosed herein.

All amounts of any component of an oral dosage form described herein, e.g., a tablet, that are indicated based on % w/w refer to the total weight of the oral dosage form, unless otherwise indicated.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations

ACN: acetonitrile
ADDP: 1,1'-(azodicarbonyl)dipiperidine
BAST: N,N-bis(2-methoxyethyl)aminosulfur trifluoride
Binap: 2,2'-bis(diphenylphosphino)-1,1'-binaphthyl
Boc: tert-butoxycarbonyl
BPO: benzoyl peroxide
Cbz: Carbonylbezyloxy
DAST: diethylaminosulfur trifluoride
DBE: 1,2-dibromoethane
DCE: 1,2-dichloroethane
DCM: dichloromethane
DEAD: diethyl azodicarboxylate
DIAD: diisopropyl azodicarboxylate
DIBAL: disiobutylaluminium hydride
DIEA or DIPEA: diisopropylethylamine
DMA: N,N-dimethylacetamide
DMF: N,N-dimethylformamide
DMP: Dess-Martin periodinane
DMSO: Dimethylsulfoxide
dtbpf: 1,1'-bis(di-tert-butylphosphino)ferrocene
EA: ethyl acetate
EDCI: 1-ethyl-3-(3-dimethylaminopropyl)carbodiimide
EtOAc: Ethyl acetate
HATU: 1-[bis(dimethylamino)methylene]-1H-1,2,3-triazolo[4,5-b]pyridinium 3-oxide hexafluorophosphate
HBTU: N,N,N'N'-tetramethyl-O-(1H-benzotriazol-1-yl) uronium hexafluorophosphate HMDS: bis(trimethylsilyl)amine
HOBt: hydroxybenzotriazole
HPLC: High Performance Liquid Chromatography
HMPA: hexamethylphosphoramide
LDA: lithium diisopropylamide LCMS: Liquid Chromatography-Mass Spectrometry
MCPBA: meta-chloroperoxybenzoic acid
MeCN: acetonitrile
MsCl: methanesulfonyl chloride
M.W: microwave
NBS: N-bromosuccinimide
NMM: N-methylmorpholine
NMP: N-methylpyrrolidone
Pd-PEPPSI-IPent: Dichloro[1,3-bis(2,6-Di-3-pentylphenyl)imidazol-2-ylidene](3-chloropyridyl)palladium (II), [1,3-Bis(2,6-Di-3-pentylphenyl)imidazol-2-ylidene](3-chloropyridyl)dichloropalladium(I), [1,3-Bis(2,6-Di-3-pentylphenyl)imidazol-2-ylidene](3-chloropyridyl)palladium(II) dichloride
PCC: pyridinium chlorochromate Pd-118 or Pd(dtpf)$Cl_2$: 1,1'-bis(di-tert-butylphosphino)ferrocene dichloropalladium
Pd(dppf)$Cl_2$: 1,1'-bis(diphenylphosphino)ferrocene dichloropalladium
Pd$(dba)_2$: bis(dibenzylideneacetone)palladium
$Pd_2(dba)_3$: Tris(dibenzylideneacetone)dipalladium
PPTS: pyridium p-tolunesulfonate
PTSA: p-toluenesulfonic acid
RuPhos-Pd-G3: XPhos-Pd-G3: [(2-dicyclohexylphosphino-2',6'-diisopropoxy-1,1'-biphenyl)-2-(2'-amino-1,1'-biphenyl)] palladium(II) methanesulfonate
RuPhos-Pd-G2: Chloro[(2-dicyclohexylphosphino-2',6'-diisopropoxy-1,1'-biphenyl)-2-(2'-amino-1,1'-biphenyl)] palladium(II)
SEM-Cl: 2-(trimethylsilyl)ethoxymethyl chloride
SFC: supercritical fluid chromatography
STAB: sodium triacetoxyborohydride
t-BuXPhos-Pd-G3: [(2-di-tert-butylphosphino-2',4',6'-triisopropyl-1,1'-biphenyl)-2-(2'-amino-1,1'-biphenyl)] palladium(II) methanesulfonate
TEA: triethylamine
THF: tetrahydrofuran
TFA: trifluoroacetic acid
TLC: thin layer chromatography
TMP: 2,2,6,6-tetramethylpiperidine
TEMPO: 2,2,6,6-tetramethylpiperidine-N-oxide
TosCl or TsCl: p-toluenesulfonyl chloride
TsOH: p-toluenesulfonic acid
XantPhos: 4,5-bis(diphenylphosphino)-9,9-dimethylxanthene
XPhos: 2-dicyclohexylphosphino-2'4'6'-triisopropylbiphenyl
XPhos-Pd-G3: [(2-dicyclohexylphosphino-2',4',6'-triisopropyl-1,1'-biphenyl)-2-(2'-amino-1,1'-biphenyl)] palladium(II) methanesulfonate 12354-85-7: bis(pentamethylcyclopentadienylrhodium dichloride)

Example 1—Synthesis of Compounds 30 and 31

Step 1: 4-bromo-2-ethyl-3-fluorobenzoic acid

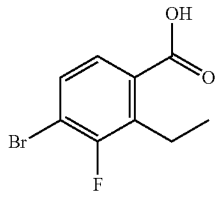

A solution of 2,2,6,6-tetramethylpiperidine (13.48 g, 95 mmol) in tetrahydrofuran (100 mL) was treated with n-BuLi (6.11 g, 95 mmol) for 30 min at −20° C. under nitrogen atmosphere, followed by the addition of 4-bromo-3-fluorobenzoic acid (9.5 g, 43 mmol) dropwise at −50° C. The resulting mixture was stirred for 2 h at −50° C. under nitrogen atmosphere. To the above mixture was dropwise added iodoethane (33.83 g, 217 mmol) over 5 min at −50° C. The resulting mixture was stirred for 2 h at room temperature, then acidified to pH 4 with concentrated hydrochloric acid. The aqueous layer was extracted with ethyl acetate. The resulting mixture was concentrated under vacuum to afford 4-bromo-2-ethyl-3-fluorobenzoic acid (10 g, 93%) as a colorless solid. MS (ESI): m/z 244.90 $[M+H]^+$.

Step 2: methyl 4-bromo-2-ethyl-3-fluorobenzoate

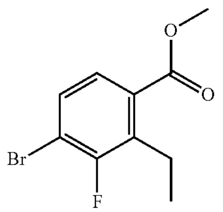

To a stirred solution of 4-bromo-2-ethyl-3-fluorobenzoic acid (12 g, 49 mmol) in methanol (100 mL) was added sulfuric acid (10.0 mL, 187 mmol). The resulting mixture was stirred overnight at 60° C. under nitrogen atmosphere, then concentrated under vacuum. The residue was extracted with ethyl acetate, concentrated. The residue was purified by silica gel column chromatography, eluted with petroleum ether/ethyl acetate (8:1) to afford methyl 4-bromo-2-ethyl-3-fluorobenzoate (7.6 g, 60%) as an off-white solid.

Step 3: methyl 4-bromo-2-(I-bromoethyl)-3-fluorobenzoate

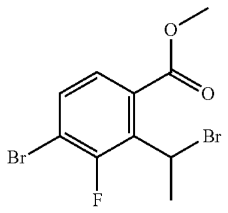

To a stirred solution of methyl 4-bromo-2-ethyl-3-fluorobenzoate (7.5 g, 29 mmol) and N-bromosuccinimide (6.14 g, 34 mmol) in dichloroethane (100 mL) was added azobisisobutyronitrile (0.94 g, 6 mmol). The resulting mixture was stirred overnight at 70° C. under nitrogen atmosphere. Diluted with saturated ammonium chloride solution and extracted with dichloromethane. The combined organic layers were dried over anhydrous sodium sulfate, filtered, and concentrated under reduced pressure to afford methyl 4-bromo-2-(1-bromoethyl)-3-fluorobenzoate (9 g, 92%) as a brown oil.

Step 4: 2-[2,6-bis(benzyloxy)pyridin-3-yl]-5-bromo-4-fluoro-3-methyl-3H-isoindol-1-one

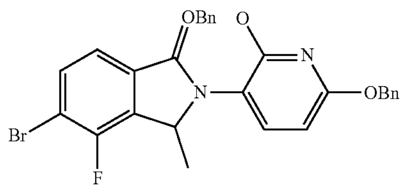

To a stirred solution of methyl 4-bromo-2-(1-bromoethyl)-3-fluorobenzoate (5.0 g, 15 mmol) and 2,6-bis(benzyloxy)pyridin-3-amine (5.4 g, 18 mmol) in acetonitrile (100 mL) were added N,N-diisopropylethylamine (5.1 mL, 29 mmol). The resulting mixture was stirred overnight at 70° C. under nitrogen atmosphere, then concentrated under vacuum. The resulting mixture was extracted with dichloromethane. The combined organic layers were dried over anhydrous sodium sulfate, filtered, and concentrated. The residue was purified by reverse flash chromatography (column: C18 silica gel; mobile phase: acetonitrile in water (10 mmol/L $NH_4HCO_3$), 10% to 100% in 30 min) to afford 2-[2,6-bis(benzyloxy)pyridin-3-yl]-5-bromo-4-fluoro-3-methyl-3H-isoindol-1-one (7.8 g, 99%) as a brown solid. MS (ESI): m/z 535.15 $[M+H]^+$.

Step 5: tert-butyl 4-[(1r,3r)-3-[(3R)-4-{2-[2,6-bis(benzyloxy)pyridin-3-yl]-4-fluoro-3-methyl-1-oxo-3H-isoindol-5-yl}-3-methylpiperazin-1-yl]cyclobutoxy]piperidine-1-carboxylate

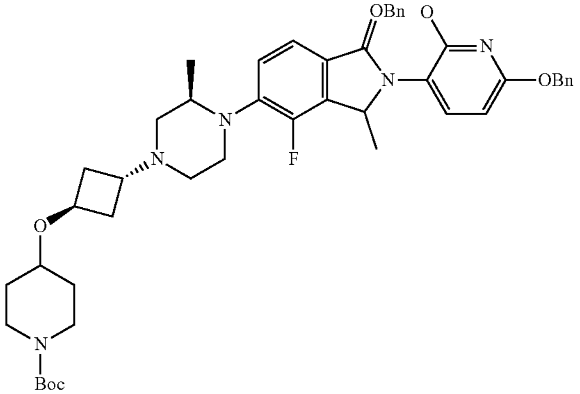

To a degassed solution of 2-[2,6-bis(benzyloxy)pyridin-3-yl]-5-bromo-4-fluoro-3-methyl-3H-isoindol-1-one (1.2 g, 2 mmol) in dioxane (20 mL) was added tert-butyl 4-[(1r,3r)-3-[(3R)-3-methylpiperazin-1-yl]cyclobutoxy]piperidine-1-carboxylate (0.95 g, 2.7 mmol) followed by $Cs_2CO_3$ (2.20 g, 7 mmol) and dichloro[1,3-bis(2,6-di-3-pentylphenyl)imidazol-2-ylidene](3-chloropyridyl)palladium(II) (3.15 g, 3.8 mmol) at room temperature. The reaction mixture was stirred at 100° C. for 6 h. The resulting mixture was filtered, the filter cake was washed with ethyl acetate. The filtrate was concentrated under reduced pressure. The residue was purified by reverse flash chromatography (column: C18 silica gel; mobile phase: acetonitrile in water (10 mmol/L $NH_4HCO_3$), 10% to 70% gradient in 30 min). to afford tert-butyl 4-[(1r,3r)-3-[(3R)-4-{2-[2,6-bis(benzyloxy)pyridin-3-yl]-4-fluoro-3-methyl-1-oxo-3H-isoindol-5-yl}-3-methylpiperazin-1-yl]cyclobutoxy]piperidine-1-carboxylate (1.1 g, 61%) as a brown solid.

Step 6: tert-butyl 4-((1R,3r)-3-((R)-4-((S)-2-(2,6-bis(benzyloxy)pyridin-3-yl)-4-fluoro-3-methyl-1-oxoisoindolin-5-yl)-3-methylpiperazin-1-yl)cyclobutoxy)piperidine-1-carboxylate and tert-butyl 4-((1R,3r)-3-((R)-4-((R)-2-(2,6-bis(benzyloxy)pyridin-3-yl)-4-fluoro-3-methyl-1-oxoisoindolin-5-yl)-3-methylpiperazin-1-yl)cyclobutoxy)piperidine-1-carboxylate

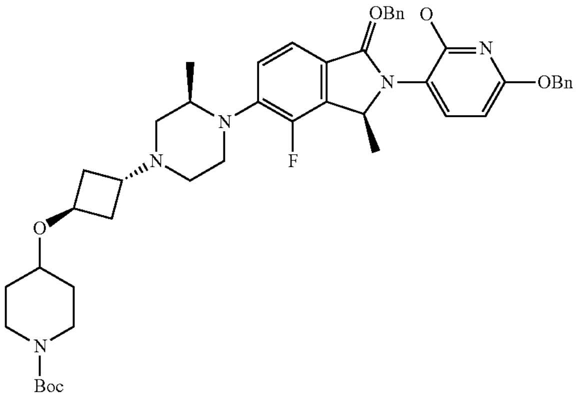

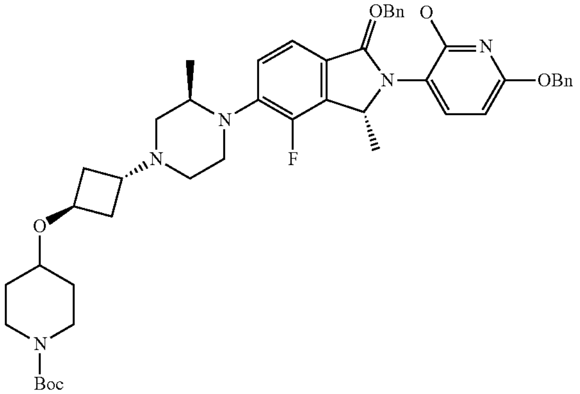

The racemate product (1.1 g) was purified by prep-HPLC (column: (S,S) Whelk-O1 4.6×50 mm, 3.5 μm; co-solvent: methanol (0.1% diethylamine); 4 mL/min; gradient (B %): 10% to 50% in 2.0 min). The first peak (1.635 min) was collected to afford tert-butyl 4-[(1r,3r)-3-[(3R)-4-[(3R)-2-[2,6-bis(benzyloxy)pyridin-3-yl]-4-fluoro-3-methyl-1-oxo-3H-isoindol-5-yl]-3-methylpiperazin-1-yl]cyclobutoxy]piperidine-1-carboxylate (tentatively assigned, 610 mg, 55%) as a brown solid. The second peak (1.999 min) was collected to afford tert-butyl 4-[(1r,3r)-3-[(3R)-4-[(3S)-2-[2,6-bis(benzyloxy)pyridin-3-yl]-4-fluoro-3-methyl-1-oxo-3H-isoindol-5-yl]-3-methylpiperazin-1-yl]cyclobutoxy]piperidine-1-carboxylate (tentatively assigned, 450 mg, 41%) as a brown solid.

Step 7: tert-butyl 4-[(1r,3r)-3-[(3R)-4-[(3R)-2-(2,6-dioxopiperidin-3-yl)-4-fluoro-3-methyl-1-oxo-3H-isoindol-5-yl]-3-methylpiperazin-1-yl]cyclobutoxy] piperidine-1-carboxylate

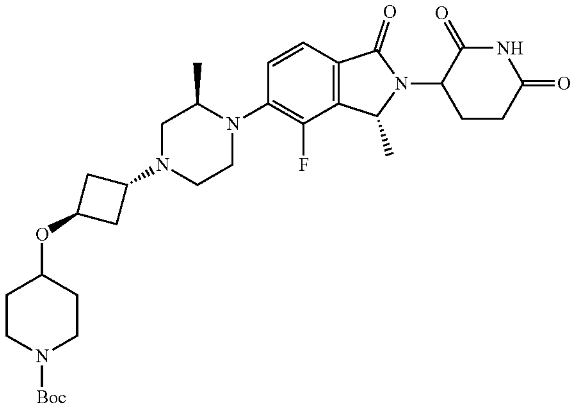 [SMILES: C[C@@H]1CN([C@H]2C[C@H](OC3CCN(C(=O)OC(C)(C)C)CC3)C2)CCN1c1ccc2c(c1F)[C@@H](C)N(C1CCC(=O)NC1=O)C2=O]

To a solution of tert-butyl 4-[(1r,3r)-3-[(3R)-4-[(3R)-2-[2,6-bis(benzyloxy)pyridin-3-yl]-4-fluoro-3-methyl-1-oxo-3H-isoindol-5-yl]-3-methylpiperazin-1-yl]cyclobutoxy]piperidine-1-carboxylate (450 mg, 0.6 mmol) in ethanol (8 mL) was added 10% Pd/C (200 mg, 1.9 mmol) under nitrogen atmosphere. The mixture was degassed and purged with hydrogen for a few times before stirring at room temperature overnight under hydrogen atmosphere using a hydrogen balloon. The mixture was filtered through a Celite pad and concentrated under reduced pressure to afford tert-butyl 4-[(1r,3r)-3-[(3R)-4-[(3R)-2-(2,6-dioxopiperidin-3-yl)-4-fluoro-3-methyl-1-oxo-3H-isoindol-5-yl]-3-methylpiperazin-1-yl]cyclobutoxy]piperidine-1-carboxylate (130 mg, 37%) as a brown solid.

Step 8: 3-[(3R)-4-fluoro-3-methyl-5-[(2R)-2-methyl-4-[(1r,3r)-3-(piperidin-4-yloxy) cyclobutyl] piperazin-1-yl]-1-oxo-3H-isoindol-2-yl]piperidine-2,6-dione

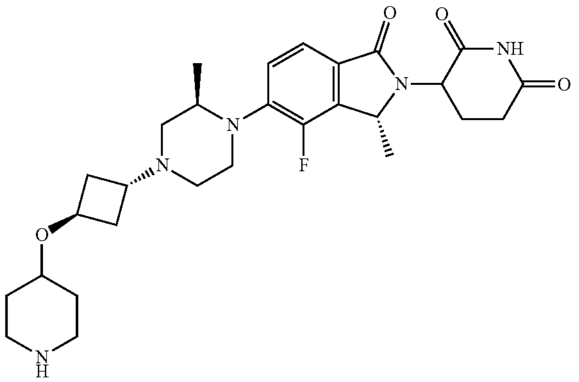 [SMILES: C[C@@H]1CN([C@H]2C[C@H](OC3CCNCC3)C2)CCN1c1ccc2c(c1F)[C@@H](C)N(C1CCC(=O)NC1=O)C2=O]

Toa stirred solution of tert-butyl 4-[(1r,3r)-3-[(3R)-4-[(3R)-2-(2,6-dioxopiperidin-3-yl)-4-fluoro-3-methyl-1-oxo-3H-isoindol-5-yl]-3-methylpiperazin-1-yl]cyclobutoxy]piperidine-1-carboxylate (130 mg, 0.2 mmol) in dioxane (3 mL) was added hydrochloric acid (3 mL). The resulting mixture was stirred for 2 h at room temperature, then concentrated under reduced pressure to afford 3-[(3R)-4-fluoro-3-methyl-5-[(2R)-2-methyl-4-[(1r,3r)-3-(piperidin-4-yloxy)cyclobutyl]piperazin-1-yl]-1-oxo-3H-isoindol-2-yl]piperidine-2,6-dione hydrochloride (109 mg, 99%) as a white solid. MS (ESI), m/z 528.40 $[M+H]^+$.

Step 9: 1-isopropyl-5-nitro-indoline-2,3-dione

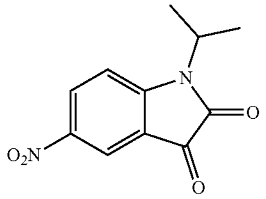 [SMILES: CC(C)N1C(=O)C(=O)c2cc([N+](=O)[O-])ccc21]

To a mixture of 5-nitroindoline-2,3-dione (5.00 g, 26 mmol) in N,N-dimethylformamide (50 mL) was added potassium carbonate (7.19 g, 52 mmol) and 2-iodopropane (3.9 mL, 39 mmol). The mixture was stirred at 25° C. for 48 h. The mixture was poured into water (300 mL) and extracted with ethyl acetate (50 mL×3). The organic layer was washed with brine (100 mL), dried over anhydrous sodium sulfate, filtered, and concentrated under reduced pressure to give 1-isopropyl-5-nitro-indoline-2,3-dione (4.00 g, 66%) as yellow solid, which was used in the next step directly. $^1$H NMR (400 MHz, DMSO) δ 8.46 (dd, J=8.8, 2.4 Hz, 1H), 8.21 (d, J=2.4 Hz, 1H), 7.52 (d, J=8.8 Hz, 1H), 4.60-4.45 (m, 1H), 1.46 (d, J=6.8 Hz, 6H).

Step 10: 1-isopropyl-3-methoxy-6-nitro-quinolin-2-one

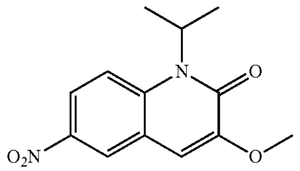 [SMILES: COc1cc2cc([N+](=O)[O-])ccc2n(C(C)C)c1=O]

To a stirred solution of 1-isopropyl-5-nitro-indoline-2,3-dione (25.0 g, 107 mmol) in ethanol (400 mL) was added triethylamine (33 mL) followed by trimethylsilanediazomethane in hexane (2 M, 117 mL) at 25° C. After stirring for 12 h at 25° C., the reaction mixture was poured into water (1500 mL) and extracted with dichloromethane (500 mL×3). The organic layers were combined and concentrated under reduced pressure. The residue was stirred in a mixture of ethyl acetate (50 mL) and petroleum ether (500 mL) at 25° C. for 2 h then filtered. The filter cake was dried under reduced pressure to give 1-isopropyl-3-methoxy-6-nitro-quinolin-2-one as a yellow solid (45 g, crude). MS (ESI) m/z: 263.1 $[M+H]^+$; $^1$H NMR (400 MHz, DMSO) δ 8.59 (d, J=2.8 Hz, 1H), 8.17 (dd, J=9.6, 2.8 Hz, 1H), 7.52 (d, J=9.6 Hz, 1H), 7.49 (s, 1H), 5.45-5.28 (m, 1H), 3.84 (s, 3H), 1.55 (d, J=6.8 Hz, 6H).

Step 11: 3-hydroxy-1-isopropyl-6-nitro-quinolin-2-one

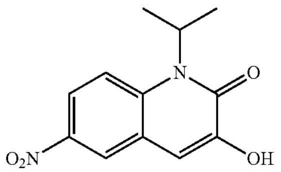 [SMILES: CC(C)n1c(=O)c(O)cc2cc([N+](=O)[O-])ccc21]

A solution of boron tribromide (4.5 mL 46 mmol) in dichloromethane (40 mL) was dropwise added to a mixture of 1-isopropyl-3-methoxy-6-nitro-quinolin-2-one (11 g, 42 mmol) in dichloromethane (400 mL) at 0° C. After stirring at 0° C. for 2 h, the mixture was poured into saturated sodium bicarbonate (1000 mL) and extracted with dichloromethane (500 mL×3). The organic layers were combined, washed with brine (100 mL), dried over anhydrous sodium sulfate, filtered, and concentrated under reduced pressure. The residue was triturated with a mixture of ethyl acetate (50 mL), petroleum ether (500 mL) and acetonitrile (50 mL) at 25° C. for 12 h then filtered. The filtrate was concentrated under reduced pressure to give 3-hydroxy-1-isopropyl-6-nitro-quinolin-2-one (28 g, 90%) as brown solid. MS (ESI) m/z: 280.2 $[M+Na]^+$; $^1H$ NMR (400 MHz, DMSO) δ 9.95 (s, 1H), 8.54 (d, J=2.8 Hz, 1H), 8.14 (dd, J=9.2, 2.4 Hz, 1H), 7.92 (d, J=9.2 Hz, 1H), 7.33 (s, 1H), 5.58-5.14 (m, 1H), 1.59 (d, J=6.8 Hz, 6H).

Step 12: 2-[(1-isopropyl-6-nitro-2-oxo-3-quinolyl)oxy]-N-methyl-acetamide

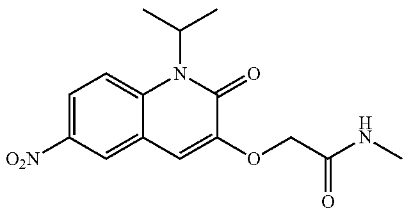 [SMILES: CNC(=O)COc1cc2cc(N)ccc2n(C(C)C)c1=O]

To a solution of 3-hydroxy-1-isopropyl-6-nitroquinolin-2-one (15 g, 60 mmol) and potassium carbonate (16.5 g, 120 mmol) in DMF (500 mL) was added 2-bromo-N-methylacetamide (9.1 g, 60 mmol). The resulting was stirred for 2 h at room temperature. The mixture was suspended in ice water, filtered and dried to afford 2-[(1-isopropyl-6-nitro-2-oxoquinolin-3-yl)oxy]-N-methylacetamide (13 g, 67%) as a yellow solid. MS (ESI) m/z: 320.1 $[M+1]^+$; $^1H$ NMR (400 MHz, DMSO) δ 8.60 (d, J=2.8 Hz, 1H), 8.21 (dd, J=9.6, 2.8 Hz, 1H), 8.01-7.88 (m, 2H), 7.48 (s, 1H), 5.70-5.15 (m, 1H), 4.57 (s, 2H), 2.68 (d, J=4.8 Hz, 3H), 1.58 (d, J=7.2 Hz, 6H).

Step 13: 2-[(6-amino-1-isopropyl-2-oxoquinolin-3-yl)oxy]-N-methylacetamide

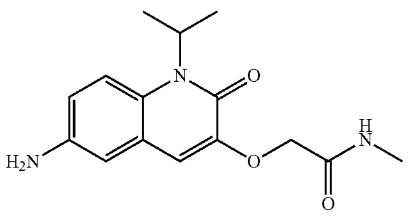

Combined 2-[(1-isopropyl-6-nitro-2-oxoquinolin-3-yl)oxy]-N-methylacetamide (13 g) and 10% Pd/C (2 g) under nitrogen atmosphere. The mixture was degassed and purged with hydrogen for three time before stirring at room temperature overnight under hydrogen using a hydrogen balloon. The mixture was filtered through a Celite pad and concentrated under reduced pressure to afford 2-[(6-amino-1-isopropyl-2-oxoquinolin-3-yl)oxy]-N-methylacetamide (10 g, 84%) as a brown solid.

Step 14: 2-[(6-amino-1-isopropyl-2-oxoquinolin-3-yl)oxy]-N-methylacetamide

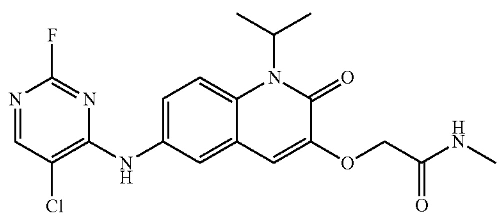 [SMILES: CNC(=O)COc1cc2cc(Nc3nc(F)ncc3Cl)ccc2n(C(C)C)c1=O]

To a stirred solution/mixture of 2-[(6-amino-1-isopropyl-2-oxoquinolin-3-yl)oxy]-N-methylacetamide (10 g, 34 mmol) and 5-chloro-2,4-difluoropyrimidine (5.2 g, 34 mmol) in N, N-dimethylformamide was added N,N-diisopropylethylamine (18.1 mL, 104 mmol) at room temperature. The resulting mixture was stirred for 2 h at room temperature under nitrogen atmosphere. The mixture was suspended in water, filtered and washed with water (2×20 mL). The resulting solid was dried under infrared light to afford 2-({6-[(5-chloro-2-fluoropyrimidin-4-yl)amino]-1-isopropyl-2-oxoquinolin-3-yl}oxy)-N-methylacetamide (11 g, 76%) as a yellow solid. MS (ESI): m/z 420.05 $[M+H]^+$.

Step 15: 2-({6-[(5-chloro-2-{4-[(1r,3r)-3-[(3R)-4-[(3R)-2-(2,6-dioxopiperidin-3-yl)-4-fluoro-3-methyl-1-oxo-3H-isoindol-5-yl]-3-methylpiperazin-1-yl]cyclobutoxy]piperidin-1-yl}pyrimidin-4-yl)amino]-1-isopropyl-2-oxoquinolin-3-yl}oxy)-N-methylacetamide

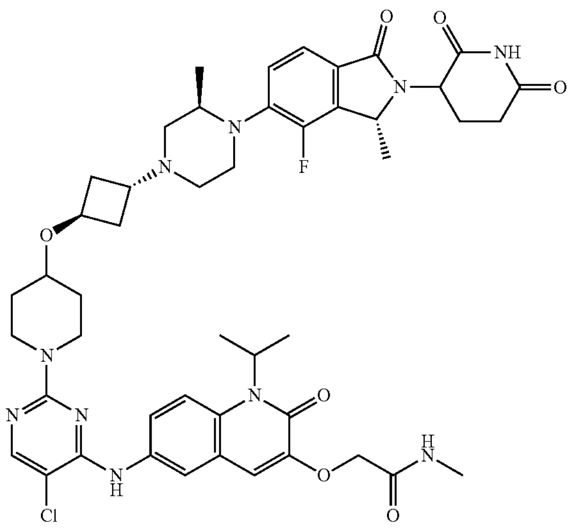 [SMILES: CNC(=O)COc1cc2cc(Nc3nc(N4CCC(O[C@H]5C[C@H](N6CCN(c7ccc8c(c7F)[C@@H](C)N(C7CCC(=O)NC7=O)C8=O)[C@H](C)C6)C5)CC4)ncc3Cl)ccc2n(C(C)C)c1=O]

To a stirred solution of 3-[(3R)-4-fluoro-3-methyl-5-[(2R)-2-methyl-4-[(1r,3r)-3-(piperidin-4-yloxy)cyclobutyl]piperazin-1-yl]-1-oxo-3H-isoindol-2-yl]piperidine-2,6-dione (80 mg, 0.2 mmol) and 2-({6-[(5-chloro-2-fluoropyrimidin-4-yl)amino]-1-isopropyl-2-oxoquinolin-3-yl}oxy)-N-methylacetamide (58 mg, 0.1 mmol) in dimethyl sulfoxide (5 mL) was added N,N-diisopropylethylamine (0.5 mL). The resulting mixture was stirred for 2 h at 50° C. under nitrogen atmosphere. The residue was purified by reverse flash chromatography (column: C18 silica gel; mobile phase: acetonitrile in water (10 mmol/L $NH_4HCO_3$), 10% to 50% gradient in 30 min) to afford 2-({6-[(5-chloro-2-{4-[(1r,3r)-3-[(3R)-4-[(3R)-2-(2,6-dioxopiperidin-3-yl)-4-fluoro-3-methyl-1-oxo-3H-isoindol-5-yl]-3-methylpiperazin-1-yl]cyclobutoxy]piperidin-1-yl}pyrimidin-4-yl)amino]-1-isopropyl-2-oxoquinolin-3-yl}oxy)-N-methylacetamide (100 mg, 78%) as a brown solid. MS (ESI) m/z 927.55 [M+H]$^+$.

-continued

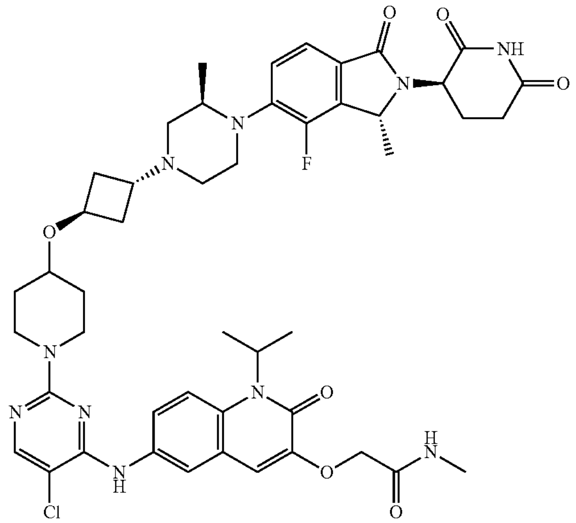

Step 16: 2-({6-[(5-chloro-2-{4-[(1r,3r)-3-[(3R)-4-[(3R)-2-[(3S)-2,6-dioxopiperidin-3-yl]-4-fluoro-3-methyl-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide and 2-({6-[(5-chloro-2-{4-[(1r,3r)-3-[(3R)-4-[(3R)-2-[(3R)-2,6-dioxopiperidin-3-yl]-4-fluoro-3-methyl-1-oxo-3H-isoindol-5-yl]-3-methylpiperazin-1-yl]cyclobutoxy]piperidin-1-yl}pyrimidin-4-yl)amino]-1-isopropyl-2-oxoquinolin-3-yl}oxy)-N-methylacetamide

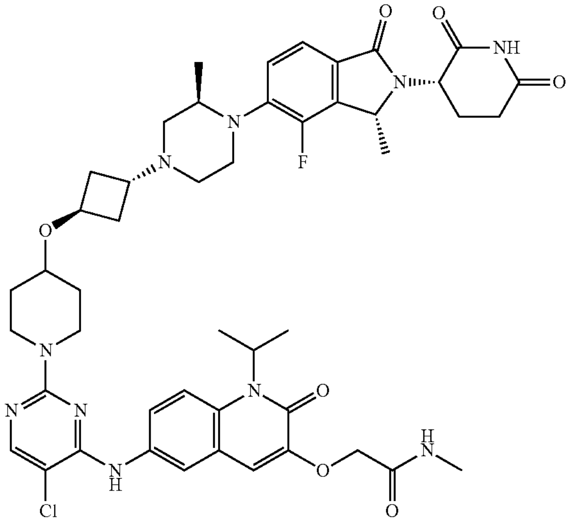

The crude product (50 mg) was purified by prep-HPLC (column: CHIRALPAK ID-3, Column Size: 4.6×50 mm, 3 μm, mobile phase: (hexane:dichloromethane=1:1, 0.1% diethylamine): ethanol=60:40, 1.0 mL/min). The first peak (3.421 min) was collected to afford 2-({6-[(5-chloro-2-{4-[(1r,3r)-3-[(3R)-4-[(3R)-2-[(3S)-2,6-dioxopiperidin-3-yl]-4-fluoro-3-methyl-1-oxo-3H-isoindol-5-yl]-3-methylpiperazin-1-yl]cyclobutoxy]piperidin-1-yl}pyrimidin-4-yl)amino]-1-isopropyl-2-oxoquinolin-3-yl}oxy)-N-methylacetamide (assumed) (19.5 mg, 18%) as an off-white solid. MS (ESI): m/z 925.65 [M+H]$^+$; $^1$H NMR (400 MHz, DMSO) δ 10.71 (s, 1H), 8.83 (s, 1H), 8.04 (s, 1H), 7.96-7.95 (m, 2H), 7.69 (s, 2H), 7.43-7.41 (m, 1H), 7.20-7.17 (m, 1H), 7.03 (s, 1H), 5.42-5.53 (m, 1H), 4.90-4.88 (m, 1H), 4.67-4.65 (m, 1H), 4.53 (s, 2H), 4.20-4.10 (m, 2H), 3.53-3.51 (m, 1H), 3.33-3.32 (m, 1H), 3.27-3.26 (m, 2H), 2.99-2.80 (m, 2H), 2.69-2.67 (m, 2H), 2.59-2.50 (m, 5H), 2.39-2.38 (m, 2H), 2.27-2.22 (m, 3H), 2.21-2.01 (m, 3H), 1.99-1.82 (m, 2H), 1.58-1.56 (m, 6H), 1.48-1.46 (m, 3H), 1.37-1.35 (m, 2H), 1.00-0.98 (m, 3H). The second peak (5.15 min) was collected to afford 2-({6-[(5-chloro-2-{4-[(1r,3r)-3-[(3R)-4-[(3R)-2-[(3R)-2,6-dioxopiperidin-3-yl]-4-fluoro-3-methyl-1-oxo-3H-isoindol-5-yl]-3-methylpiperazin-1-yl]cyclobutoxy]piperidin-1-yl}pyrimidin-4-yl)amino]-1-isopropyl-2-oxoquinolin-3-yl}oxy)-N-methylacetamide (assumed) (21.5 mg, 43%) as an off-white solid. MS (ESI): m/z 925.65 [M+H]$^+$; $^1$H NMR (400 MHz, DMSO) δ 10.71 (s, 1H), 8.83 (s, 1H), 8.04 (s, 1H), 7.96-7.95 (m, 2H), 7.69 (s, 2H), 7.43-7.41 (m, 1H), 7.20-7.17 (m, 1H), 7.03 (s, 1H)), 5.42-5.53 (m, 1H), 4.90-4.88 (m, 1H), 4.67-4.65 (m, 1H), 4.53 (s, 2H), 4.20-4.10 (m, 2H), 3.53-3.51 (m, 1H), 3.33-3.32 (m, 1H), 3.27-3.26 (m, 2H), 2.99-2.80 (m, 2H), 2.69-2.67 (m, 2H), 2.59-2.50 (m, 5H), 2.39-2.38 (m, 2H), 2.27-2.22 (m, 3H), 2.21-2.01 (m, 3H), 1.99-1.82 (m, 2H), 1.58-1.56 (m, 6H), 1.48-1.46 (m, 3H), 1.37-1.35 (m, 2H), 1.00-0.98 (m, 3H).

Example 2—Synthesis of Compounds 32 and 33

Step 1: 4-bromo-2-ethylbenzoic acid

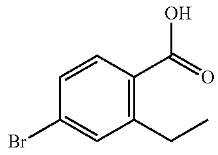

To a stirred solution of butyllithium (2.5 M, 46 mL, 115 mmol) in tetrahydrofuran (200 mL) was added 2,2,6,6-tetramethylpiperidine (16.23 g, 115 mmol) dropwise at −40° C. under nitrogen atmosphere. The mixture was stirred for 0.5 h at −40° C. To the above mixture was added 4-bromobenzoic acid (10.5 g, 52 mmol) in THF (20 mL) dropwise over 0.5 h at −40° C. The resulting mixture was stirred for additional 4 h at −40° C. To the above mixture was added ethyl iodide (32.6 g, 209 mmol) dropwise over 0.5 h at −40° C., then stirred for additional 2 h at room temperature. Concentrated hydrochloric acid was added until the pH was 6~7. The resulting mixture was extracted with ethyl acetate (3×100 mL). The combined organic layers were washed with brine (3×100 mL), dried over anhydrous sodium sulfate, filtered, and concentrated under reduced pressure. The residue was purified by silica gel column chromatography (petroleum ether/ethyl acetate=1:1) to afford 4-bromo-2-ethylbenzoic acid (11.5 g, 90%) as a pink solid. MS (ESI): m/z 228.25 $[M+H]^+$.

Step 2: methyl 4-bromo-2-ethylbenzoate

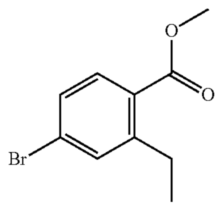

A solution of 4-bromo-2-ethylbenzoic acid (11.5 g, 50 mmol) in methanol (100 mL) was treated with sulfuric acid (1.5 mL, 28 mmol) dropwise at 0° C. under nitrogen atmosphere. The resulting mixture was stirred overnight at 60° C., then concentrated under vacuum. The residue was suspended in water, filtered, and washed with water (3×10 mL). The resulting solid was dried under vacuum to afford methyl 4-bromo-2-ethylbenzoate (12 g) as an off-white solid. MS (ESI): m/z 243.50 $[M+H]^+$.

Step 3: methyl 4-bromo-2-(I-bromoethyl)benzoate

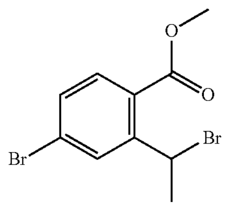

To a stirred solution of methyl 4-bromo-2-ethylbenzoate (4.1 g, 16 mmol) and N-bromosuccinimide (3.60 g, 20 mmol) in ethyl acetate (50 mL) was added BPO (0.86 g, 3.4 mmol). The resulting mixture was stirred for 5 h at 70° C. under nitrogen atmosphere. The reaction was quenched with saturated aqueous ammonium chloride (100 mL). The aqueous layer was extracted with ethyl acetate (100 mL×3). The combined organic layer was concentrated under reduced pressure to afford methyl 4-bromo-2-(1-bromoethyl)benzoate (5.4 g) as a white solid. MS (ESI): m/z 321.50 $[M+H]^+$.

Step 4: 2-[2,6-bis(benzyloxy)pyridin-3-yl]-5-bromo-3-methyl-3H-isoindol-1-one

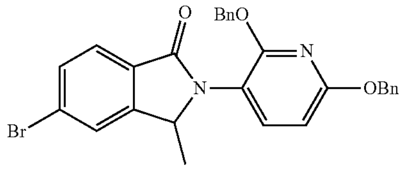 [SMILES: CC1c2cc(Br)ccc2C(=O)N1c1ccc(OCc2ccccc2)nc1OCc1ccccc1]

To a stirred solution of methyl 4-bromo-2-(1-bromoethyl) benzoate (5.4 g, 17 mmol) and 2,6-bis(benzyloxy)pyridin-3-amine (7.71 g, 25 mmol) in acetonitrile (50 mL) was added N,N-diisopropylethylamine (6.50 g, 50 mmol). To the above mixture was added acetic acid (0.5 mL), then stirred overnight at room temperature. The mixture was concentrated under reduced pressure, diluted with water (50 mL) and extracted with dichloromethane (50 mL×3). The combined organic layers were washed with brine (20 mL×3), dried over anhydrous sodium sulfate, filtered, and concentrated under reduced pressure. The residue was purified by reverse flash chromatography (column, C18 silica gel; mobile phase, acetonitrile in water (10 mmol/L $NH_4HCO_3$), 10% to 80% gradient in 30 min) to afford 2-[2,6-bis(benzyloxy)pyridin-3-yl]-5-bromo-3-methyl-3H-isoindol-1-one (6.57 g, 76%) as a yellow solid. MS (ESI): m/z 515.15 $[M+H]^+$.

Step 5: tert-butyl 4-[(1r,3r)-3-[(3R)-4-[(3S)-2-[6-(benzyloxy)-2-oxo-1H-pyridin-3-yl]-3-methyl-1-oxo-3H-isoindol-5-yl]-3-methylpiperazin-1-yl]cyclobutoxy]piperidine-1-carboxylate and tert-butyl 4-[(1r,3r)-3-[(3R)-4-[(3R)-2-[6-(benzyloxy)-2-oxo-1H-pyridin-3-yl]-3-methyl-1-oxo-3H-isoindol-5-yl]-3-methylpiperazin-1-yl]cyclobutoxy]piperidine-1-carboxylate

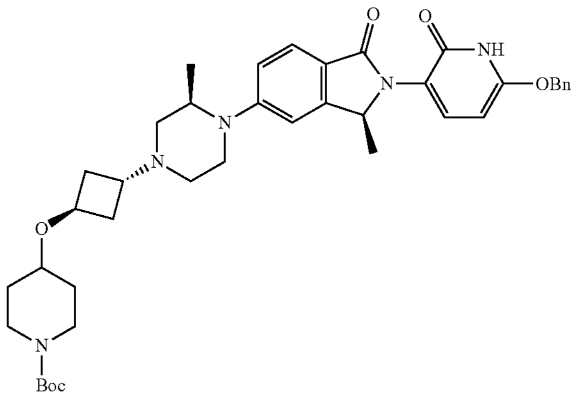

-continued

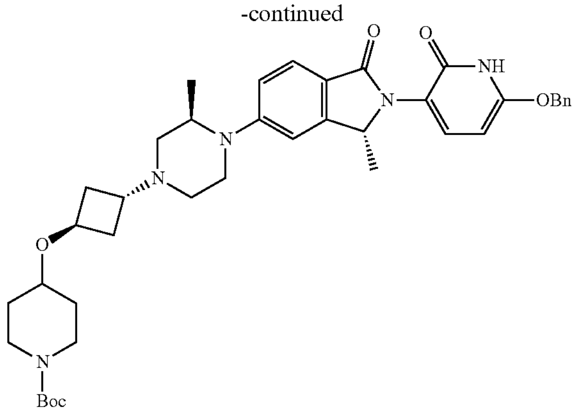

To a stirred solution of 2-[2,6-bis(benzyloxy)pyridin-3-yl]-5-bromo-3-methyl-3H-isoindol-1-one (5.95 g, 11 mmol) and tert-butyl 4-[(1r,3r)-3-[(3R)-3-methylpiperazin-1-yl]cyclobutoxy]piperidine-1-carboxylate (4.36 g, 10 mmol) in dioxane (100 mL) was added dichloro[1,3-bis(2,6-di-3-pentylphenyl)imidazol-2-ylidene](3-chloropyridyl)palladium (II) (0.81 g, 1 mmol) and sodium tert-butoxide (2.77 g, 29 mmol). The resulting mixture was stirred for 2 h at 100° C. under nitrogen atmosphere. The reaction was diluted with water (100 mL), extracted with ethyl acetate (100 mL×3). The combined organic layers were washed with brine, dried over anhydrous sodium sulfate, filtered, and concentrated under reduced pressure. The residue was purified by reverse flash chromatography (column, C18 silica gel; mobile phase, acetonitrile in water (10 mmol/L $NH_4HCO_3$), 10% to 80% gradient in 30 min) to afford tert-butyl 4-[(1r,3r)-3-[(3R)-4-(2-[6-(benzyloxy)-2-oxo-1H-pyridin-3-yl]-3-methyl-1-oxo-3H-isoindol-5-yl)-3-methylpiperazin-1-yl]cyclobutoxy]piperidine-1-carboxylate (3.1 g, 46%) as a yellow solid. The racemate product was purified by prep-HPLC (column: CHIRAL ART Cellulose-SB 3.0×100 mm, 3 μm; isopropanol (0.1% diethylamine); 220 nm). The first peak (0.942 min) was collected to afford tert-butyl 4-[(1r,3r)-3-[(3R)-4-[(3R)-2-[6-(benzyloxy)-2-oxo-1H-pyridin-3-yl]-3-methyl-1-oxo-3H-isoindol-5-yl]-3-methylpiperazin-1-yl]cyclobutoxy]piperidine-1-carboxylate (tentatively assigned, 1.2 g, 39%) as a yellow solid. The second peak (0.372 min) was collected to afford tert-butyl 4-[(1r,3r)-3-[(3R)-4-[(3S)-2-[6-(benzyloxy)-2-oxo-1H-pyridin-3-yl]-3-methyl-1-oxo-3H-isoindol-5-yl]-3-methylpiperazin-1-yl]cyclobutoxy]piperidine-1-carboxylate (tentatively assigned, 1.17 g, 38%) as a yellow solid. MS (ES+): m/z 698.65 $[M+H]^+$.

Step 6: tert-butyl 4-[(1r,3r)-3-[(3R)-4-[(3R)-2-(2,6-dioxopiperidin-3-yl)-3-methyl-1-oxo-3H-isoindol-5-yl]-3-methylpiperazin-1-yl]cyclobutoxy]piperidine-1-carboxylate

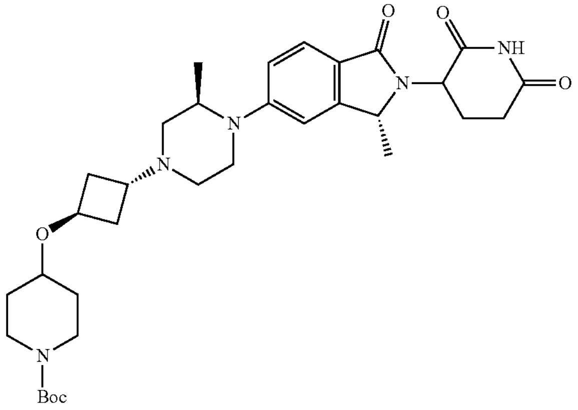 [SMILES: C[C@@H]1CN([C@H]2C[C@H](OC3CCN(C(=O)OC(C)(C)C)CC3)C2)CCN1c1ccc2c(c1)[C@@H](C)N(C1CCC(=O)NC1=O)C2=O]

A mixture of tert-butyl 4-[(1r,3r)-3-[(3R)-4-[(3R)-2-[6-(benzyloxy)-2-oxo-1H-pyridin-3-yl]-3-methyl-1-oxo-3H-isoindol-5-yl]-3-methylpiperazin-1-yl]cyclobutoxy]piperidine-1-carboxylate (1.2 g, 1.7 mmol) and Pd/C (1 g) in ethanol (20 mL) was degassed and purged with hydrogen, then stirred for 2 days at 30° C. under hydrogen atmosphere. The resulting mixture was filtered through Celite, washed with dichloromethane (10 mL×2). The filtrate was concentrated under reduced pressure to afford tert-butyl 4-[(1r,3r)-3-[(3R)-4-[(3R)-2-(2,6-dioxopiperidin-3-yl)-3-methyl-1-oxo-3H-isoindol-5-yl]-3-methylpiperazin-1-yl] cyclobutoxy]piperidine-1-carboxylate (820 mg, 78%) as a colorless oil. MS (ESI): m/z 610.35 $[M+H]^+$.

Step 7: tert-butyl 4-[(1r,3r)-3-[(3R)-4-[(3R)-4-chloro-2-(2,6-dioxopiperidin-3-yl)-3-methyl-1-oxo-3H-isoindol-5-yl]-3-methylpiperazin-1-yl]cyclobutoxy]piperidine-1-carboxylate

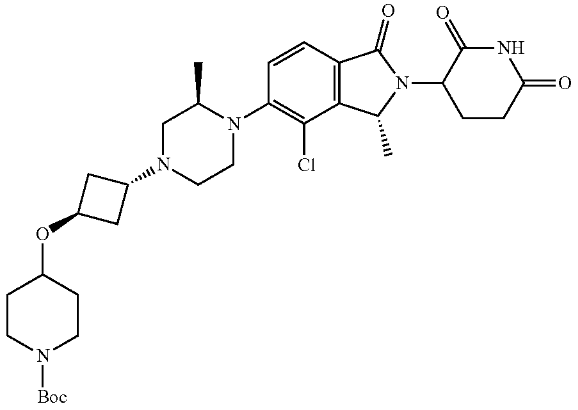 [SMILES: C[C@@H]1CN([C@H]2C[C@H](OC3CCN(C(=O)OC(C)(C)C)CC3)C2)CCN1c1ccc2c(c1Cl)[C@@H](C)N(C1CCC(=O)NC1=O)C2=O]

To a stirred solution of tert-butyl 4-[(1r,3r)-3-[(3R)-4-[(3R)-2-(2,6-dioxopiperidin-3-yl)-3-methyl-1-oxo-3H-isoindol-5-yl]-3-methylpiperazin-1-yl]cyclobutoxy]piperidine-1-carboxylate (720 mg, 1.2 mmol) and trifluoracetic acid (296.20 mg, 2.6 mmol) in dichloromethane (1 mL) were added methanol (1 mL) and N-chlorosuccinimide (204.9 mg, 1.5 mmol). The resulting mixture was stirred overnight at 40° C. under nitrogen atmosphere. The mixture was basified to pH 8 with N,N-diisopropylethylamine. The residue was purified by reverse flash chromatography (column, C18 silica gel; mobile phase, acetonitrile in water (10 mmol/L $NH_4HCO_3$), 10% to 80% gradient in 30 min) to afford tert-butyl 4-[(1r,3r)-3-[(3R)-4-[(3R)-4-chloro-2-(2,6-dioxopiperidin-3-yl)-3-methyl-1-oxo-3H-isoindol-5-yl]-3-methylpiperazin-1-yl]cyclobutoxy]piperidine-1-carboxylate (504 mg, 66%) as a white solid. MS (ESI): m/z 644.40 $[M+H]^+$.

Step 8-9: 2-({6-[(5-chloro-2-{4-[(1r,3r)-3-[(3R)-4-[(3R)-4-chloro-2-[(3S)-2,6-dioxopiperidin-3-yl]-3-methyl-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide and 2-({6-[(5-chloro-2-{4-[(1r,3r)-3-[(3R)-4-[(3R)-4-chloro-2-[(3R)-2,6-dioxopiperidin-3-yl]-3-methyl-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide

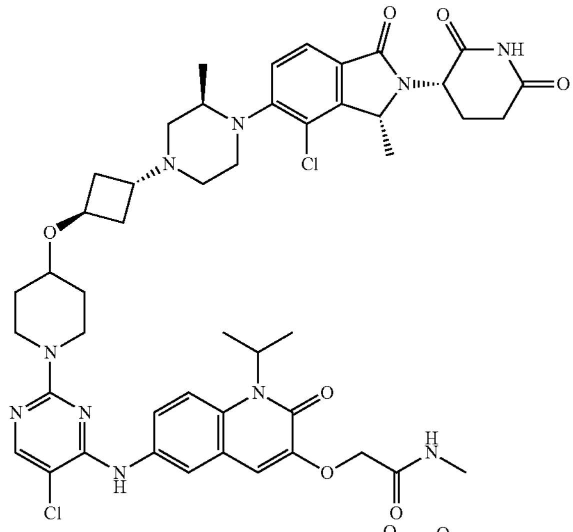

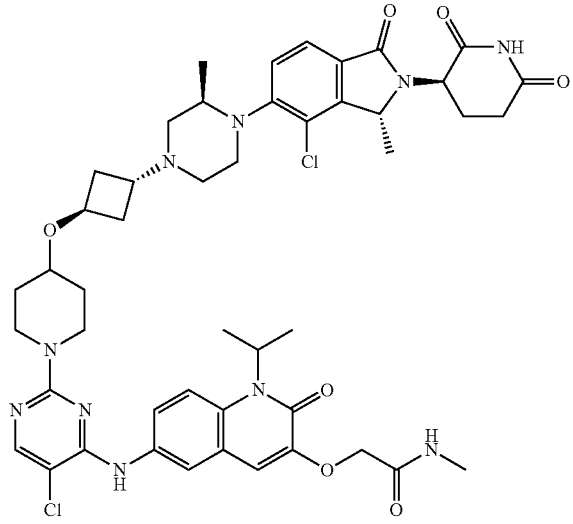

The title compounds are prepared analogously to Compounds 30 and 31. The two diastereomers of 2-({6-[(5-chloro-2-{4-[(1r,3r)-3-[(3R)-4-[(3R)-4-chloro-2-(2,6-dioxopiperidin-3-yl)-3-methyl-1-oxo-3H-isoindol-5-yl]-3-methylpiperazin-1-yl]cyclobutoxy]piperidin-1-yl}pyrimidin-4-yl)amino]-1-isopropyl-2-oxoquinolin-3-yl}oxy)-N-methylacetamide (248 mg) was separated by chiral-HPLC (column: CHIRALPAK IF, 2×25 cm, 5 μm; mobile phase A: methyl tert-butyl ether (0.1% diethylamine), mobile phase B: ethanol:dichloromethane=1:1; 12 mL/min; gradient: 40% B to 40% B in 35 min). The first peak (5.658 min) was collected to afford 2-({6-[(5-chloro-2-{4-[(1r,3r)-3-[(3R)-4-[(3R)-4-chloro-2-[(3S)-2,6-dioxopiperidin-3-yl]-3-methyl-1-oxo-3H-isoindol-5-yl]-3-methylpiperazin-1-yl]cyclobutoxy]piperidin-1-yl}pyrimidin-4-yl)amino]-1-isopropyl-2-oxoquinolin-3-yl}oxy)-N-methylacetamide (tentatively assigned, 84 mg) as white solid. $^1H$ NMR (400 MHz, DMSO) δ 10.97 (s, 1H), 8.84 (s, 1H), 8.05 (s, 1H), 7.96 (m, 2H), 7.69 (m, 2H), 7.63 (m, 1H), 7.37 (m, 1H), 7.03 (s, 1H), 4.77-4.69 (m, 2H), 4.55 (s, 2H), 4.20-4.13 (m, 3H), 3.54 (s, 2H), 3.40 (s, 3H), 2.83 (s, 2H), 2.68 (m, 6H), 2.70 (m, 2H), 2.60 (m, 1H), 2.20 (s, 2H), 2.00 (s, 4H), 1.83 (s, 2H), 1.58 (m, 6H), 1.51 (m, 3H), 1.39 (m, 2H), 0.87 (m, 4H); MS (ESI): m/z 945.05 $[M+H]^+$. The second peak (7.125 min) was collected to afford 2-({6-[(5-chloro-2-{4-[(1r,3r)-3-[(3R)-4-[(3R)-4-chloro-2-[(3R)-2,6-dioxopiperidin-3-yl]-3-methyl-1-oxo-3H-isoindol-5-yl]-3-methylpiperazin-1-yl]cyclobutoxy]piperidin-1-yl}pyrimidin-4-yl)amino]-1-isopropyl-2-oxoquinolin-3-yl}oxy)-N-methylacetamide (tentatively assigned, 77 mg) as white solid. $^1H$ NMR (400 MHz, DMSO) δ 10.93 (s, 1H), 8.84 (s, 1H), 8.05 (s, 1H), 7.96 (m, 2H), 7.69 (m, 2H), 7.61 (m, 1H), 7.36 (m, 1H), 7.03 (s, 1H), 4.82 (m, 1H), 4.69 (d m, 1H), 4.55 (s, 2H), 4.21-4.13 (m, 3H), 3.53 (s, 2H), 3.26-3.21 (m, 3H), 2.82 (s, 1H), 2.68 (m, 6H), 2.63-2.53 (m, 3H), 2.20 (s, 1H), 2.16 (s, 2H), 2.01 (s, 4H), 1.83 (s, 2H), 1.55 (m, 6H), 1.45 (m, 3H), 1.39 (m, 2H), 0.87 (m, 4H); MS (ESI): m/z 945.10 $[M+H]^+$.

Example 3—Synthesis of Compounds 34 and 35

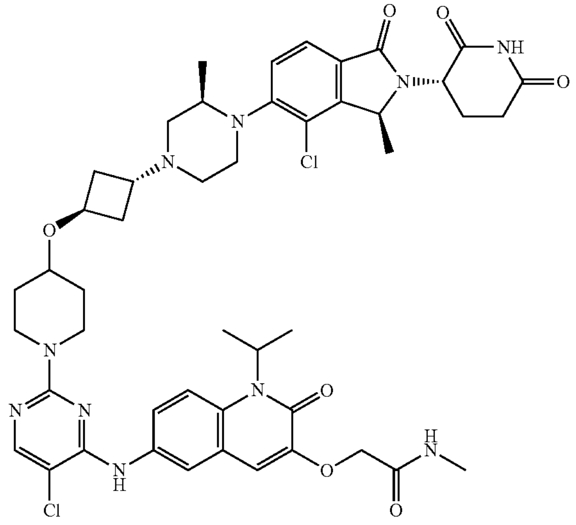

-continued

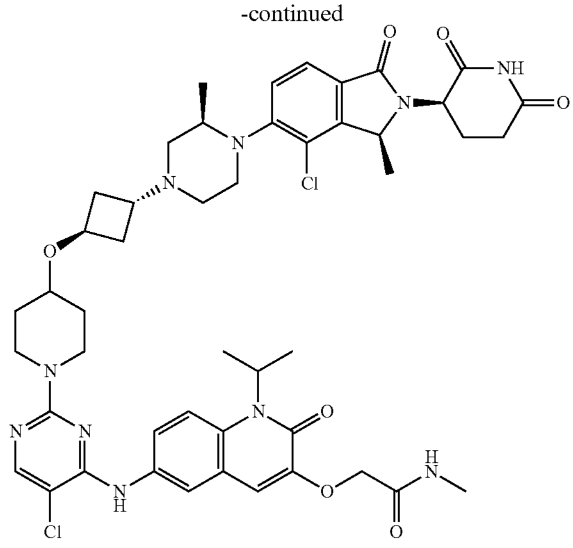

The title compounds are prepared analogously to Compounds 32 and 33 starting from tert-butyl 4-[(1r,3r)-3-[(3R)-4-[(3S)-2-[6-(benzyloxy)-2-oxo-1H-pyridin-3-yl]-3-methyl-1-oxo-3H-isoindol-5-yl]-3-methylpiperazin-1-yl]cyclobutoxy]piperidine-1-carboxylate. The two diastereomers of 2-({6-[(5-chloro-2-{4-[(1r,3r)-3-[(3R)-4-[(3S)-4-chloro-2-(2,6-dioxopiperidin-3-yl)-3-methyl-1-oxo-3H-isoindol-5-yl]-3-methylpiperazin-1-yl]cyclobutoxy]piperidin-1-yl}pyrimidin-4-yl)amino]-1-isopropyl-2-oxoquinolin-3-yl}oxy)-N-methylacetamide (220 mg) was separated by chiral-HPLC (column: CHIRALPAK IF, 2×25 cm, 5 μm; mobile phase A: methyl tert-butyl ether (0.1% diethylamine), mobile phase B: ethanol:dichloromethane=1:1; flow rate: 12 mL/min; gradient: 40% B to 40% B in 50 min). The first peak (3.676 min) was collected to afford 2-({6-[(5-chloro-2-{4-[(1r,3r)-3-[(3R)-4-[(3S)-4-chloro-2-[(3R)-2,6-dioxopiperidin-3-yl]-3-methyl-1-oxo-3H-isoindol-5-yl]-3-methylpiperazin-1-yl]cyclobutoxy]piperidin-1-yl}pyrimidin-4-yl)amino]-1-isopropyl-2-oxoquinolin-3-yl}oxy)-N-methylacetamide (assumed) (56 mg, 25%) as white solid. $^{1}$H NMR (300 MHz, DMSO) δ 10.94 (s, 1H), 8.83 (s, 1H), 8.04 (s, 1H), 7.95 (s, 2H), 7.69-7.61 (m, 3H), 7.38 (d, J=8.2 Hz, 1H), 7.03 (s, 1H), 5.70-5.05 (m, 1H), 4.71 (d, J=21.9 Hz, 2H), 4.53 (s, 2H), 4.21-4.06 (m, 3H), 3.55-3.46 (m, 2H), 3.20 (d, J=10.9 Hz, 3H), 2.85-2.75 (m, 2H), 2.71-2.53 (m, 7H), 2.32 (s, 1H), 2.22-2.02 (m, 7H), 1.82 (d, J=12.0 Hz, 2H), 1.53 (d, J=15.0 Hz, 9H), 1.37 (d, J=9.0 Hz, 2H), 0.87 (d, J=6.3 Hz, 3H); MS (ESI): m/z 943.55 $[M+H]^+$. The second peak (5.243 min) was collected to afford 2-({6-[(5-chloro-2-{4-[(1r,3r)-3-[(3R)-4-[(3S)-4-chloro-2-[(3R)-2,6-dioxopiperidin-3-yl]-3-methyl-1-oxo-3H-isoindol-5-yl]-3-methylpiperazin-1-yl]cyclobutoxy]piperidin-1-yl}pyrimidin-4-yl)amino]-1-isopropyl-2-oxoquinolin-3-yl}oxy)-N-methylacetamide (56.5 mg, 25%) as white solid. MS (ESI): m/z 943.55 $[M+H]^+$; $^{1}$H NMR (300 MHz, DMSO) δ 10.92 (s, 1H), 8.83 (s, 1H), 8.04 (s, 1H), 7.97 (s, 2H), 7.68 (d, J=1.5 Hz, 2H), 7.59 (d, J=8.1 Hz, 1H), 7.36 (d, J=8.1 Hz, 1H), 7.01 (s, 1H), 5.50-5.00 (m, 1H), 4.80 (d, J=6.3 Hz, 1H), 4.66 (d, J=12.4 Hz, 1H), 4.53 (s, 2H), 4.22-4.06 (m, 3H), 3.60 (s, 2H), 3.28-3.15 (m, 3H), 2.90-2.67 (m, 9H), 2.33 (s, 1H), 2.17 (s, 3H), 1.99 (s, 4H), 1.82 (d, J=12.0 Hz, 2H), 1.54 (d, J=9.6 Hz, 9H), 1.37 (d, J=9.3 Hz, 2H), 0.87 (d, J=6.0 Hz, 3H).

Example 4—Synthesis of Compound 36

Step 1: 5-bromo-7-methyl-3H-2-benzofuran-1-one

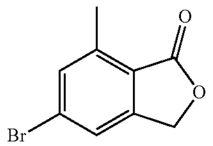

To a stirred solution of 4-bromo-2,6-dimethylbenzoic acid (10 g, 44 mmol) and N-bromosuccinimide (19.0 g, 109 mmol) in chlorobenzene (100 mL) was added benzoyl peroxide (1.12 g, 4.4 mmol). The resulting mixture was stirred overnight at 80° C. under nitrogen atmosphere. Diluted with 40% w/w aqueous sodium bisulfite (100 mL), the phases were separated. The organic phase was washed with saturated aqueous sodium bicarbonate (30 mL). The chlorobenzene phase was concentrated (30 mL) by vacuum distillation, and dimethylacetamide (25 mL) was added before adding this solution to a mixture of sodium borohydride (2.5 g, 1.6 mol) in methyl-tert-butyl ether (40 mL) and dimethylacetamide (25 mL). The mixture quenched with 36% w/w hydrochloric acid (25 mL) in water (35 mL). Removing the solvent by vacuum distillation afforded 5-bromo-7-methyl-3H-2-benzofuran-1-one (4 g, 40%) as a white crystalline solid. MS (ESI): m/z 227.0 $[M+H]^+$.

Step 2: 5-bromo-3-hydroxy-7-methyl-3H-2-benzofuran-1-one

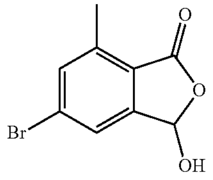

To a stirred solution of 5-bromo-7-methyl-3H-2-benzofuran-1-one (4.0 g, 18 mmol) in methanol (100 mL) was added potassium hydroxide (1.48 g, 26 mmol). The resulting mixture was stirred for 2 h at 60° C. under nitrogen atmosphere. The mixture was acidified to pH 4 with potassium bisulfate (4.80 g, 35 mmol). The aqueous layer was extracted with ethyl acetate and concentrated. The residue was dissolved in dichloromethane (50 mL), manganese dioxide (15.32 g, 176 mmol) was added and stirred overnight at room temperature. The resulting mixture was filtered, the filter cake was washed with dichloromethane. The filtrate was concentrated under reduced pressure. This resulted in 5-bromo-3-hydroxy-7-methyl-3H-2-benzofuran-1-one (0.8 g, 19/a) as an off-white solid. MS (ESI): m-z 242.90 $[M+H]^+$.

Step 3: methyl 4-bromo-2-formyl-6-methylbenzoate

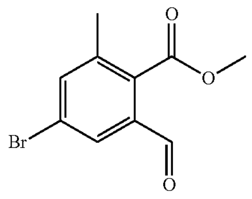

To a stirred solution of 5-bromo-3-hydroxy-7-methyl-3H-2-benzofuran-1-one (1 g, 4 mmol) and potassium carbonate (1.14 g, 8 mmol) in acetone (20 mL) was dropwise added methyl iodide (0.38 mL, 6 mmol) at room temperature. The resulting mixture was stirred for 4 h at room temperature. The reaction was quenched by water (30 mL), extracted with dichloromethane (3×10 mL), the combined organic layers was dried over anhydrous sodium sulfate, filtered, and concentrated under reduced pressure. The residue was purified by reversed-phase flash chromatography (column: C18 silica gel; mobile phase: acetonitrile in water (10 mmol/L $NH_4HCO_3$), 10% to 50% gradient in 30 min) to afford methyl 4-bromo-2-formyl-6-methylbenzoate (0.7 g, 66%) as a colorless oil.

Step 4: 3-(5-bromo-7-methyl-1-oxo-3H-isoindol-2-yl)piperidine-2,6-dione

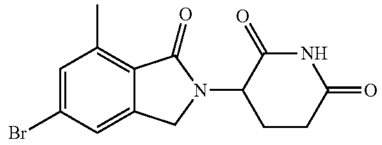 [SMILES: Cc1cc(Br)cc2c1C(=O)N(C1CCC(=O)NC1=O)C2]

To a stirred solution of methyl 4-bromo-2-formyl-6-methylbenzoate (700 mg, 2.7 mmol) in dichloroethane (10 mL) and methanol (3 mL) was added 3-(chloroamino)piperidine-2,6-dione (668 mg, 4.1 mmol). Then acetic acid (0.1 mL, 2 mmol) was added to adjust the pH to 8. The resulting mixture was stirred overnight at room temperature. To the above mixture was added sodium cyanoborohydride (342 mg, 5.4 mmol). The resulting mixture was stirred for an additional 2 h at 50° C. The mixture was filtered, the filter cake was washed with dichloromethane. The filtrate was concentrated under reduced pressure. The residue was purified by reverse flash chromatography (column, C18 silica gel; mobile phase, acetonitrile in water (10 mmol/L $NH_4HCO_3$), 10% to 50% gradient in 30 min) to afford 3-(5-bromo-7-methyl-1-oxo-3H-isoindol-2-yl)piperidine-2,6-dione (420 mg, 46%) as a brown solid.

Step 4: tert-butyl 4-[(1r,3r)-3-{4-[2-(2,6-dioxopiperidin-3-yl)-7-methyl-1-oxo-3H-isoindol-5-yl]piperazin-1-yl}cyclobutoxy]piperidine-1-carboxylate

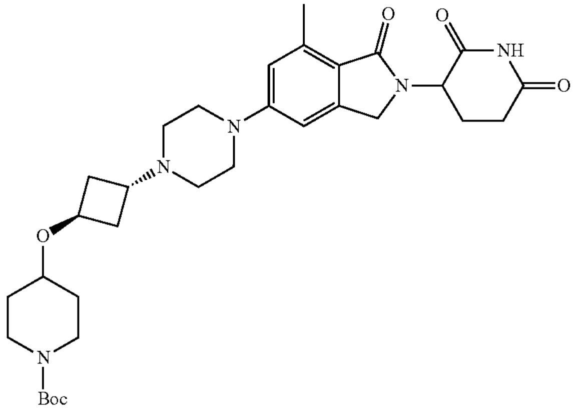 [SMILES: Cc1cc(N2CCN([C@H]3C[C@H](OC4CCN(C(=O)OC(C)(C)C)CC4)C3)CC2)cc2c1C(=O)N(C1CCC(=O)NC1=O)C2]

To a solution of 3-(5-bromo-7-methyl-1-oxo-3H-isoindol-2-yl)piperidine-2,6-dione (180 mg, 0.5 mmol) and tert-butyl 4-[(1r,3r)-3-(piperazin-1-yl)cyclobutoxy]piperidine-1-carboxylate (181 mg, 0.5 mmol) in N, N-dimethylformamide (10 mL) were added cesium carbonate (522 mg, 1.6 mmol) and [1,1'-bis(diphenylphosphino)ferrocene]dichloropalladium(II) (44.91 mg, 0.05 mmol). After stirring for 2 h at 100° C. under a nitrogen atmosphere, the mixture was diluted with ethyl acetate. The resulting mixture was filtered, the filter cake was washed with ethyl acetate. The mixture was acidified to pH 6 with saturated ammonium chloride solution. The mixture was extracted with ethyl acetate. The combined organic layers were dried over anhydrous sodium sulfate, filtered, and concentrated. The residue was purified by reverse flash chromatography (column, C18 silica gel; mobile phase, acetonitrile in water (10 mmol/L $NH_4HCO_3$), 10% to 50% gradient in 30 min) to afford tert-butyl 4-[(1r, 3r)-3-{4-[2-(2,6-dioxopiperidin-3-yl)-7-methyl-1-oxo-3H-isoindol-5-yl]piperazin-1-yl}cyclobutoxy]piperidine-1-carboxylate (140 mg, 44%) as a brown solid. MS (ESI): m/z 596.40 $[M+H]^+$.

Step 5: 3-(7-methyl-1-oxo-5-{4-[(1r,3r)-3-(piperidin-4-yloxy)cyclobutyl]piperazin-1-yl}-3H-isoindol-2-yl)piperidine-2,6-dione

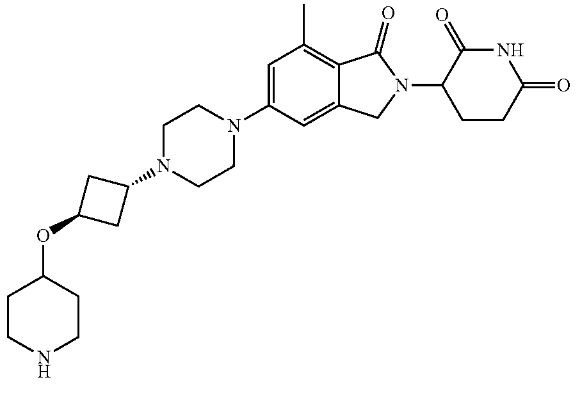 [SMILES: Cc1cc(N2CCN([C@H]3C[C@H](OC4CCNCC4)C3)CC2)cc2c1C(=O)N(C1CCC(=O)NC1=O)C2]

To a stirred solution of tert-butyl 4-[(1r,3r)-3-{4-[2-(2,6-dioxopiperidin-3-yl)-7-methyl-1-oxo-3H-isoindol-5-yl]piperazin-1-yl}cyclobutoxy]piperidine-1-carboxylate (140 mg, 0.2 mmol) in dioxane (2.0 mL) was dropwise added hydrochloric acid in dioxane (2 mL). The resulting mixture was stirred for 2 h at room temperature, then concentrated under reduced pressure to afford 3-(7-methyl-1-oxo-5-(4-[(1r,3r)-3-(piperidin-4-yloxy)cyclobutyl]piperazin-1-yl)-3H-isoindol-2-yl)piperidine-2,6-dione hydrochloride (116 mg, 99%) as a white solid. MS (ESI): m/z 496.45 [M+H]$^+$.

Step 6: 2-({6-[(5-chloro-2-{4-[(1r,3r)-3-{4-[2-(2,6-dioxopiperidin-3-yl)-7-methyl-1-oxo-3H-isoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide

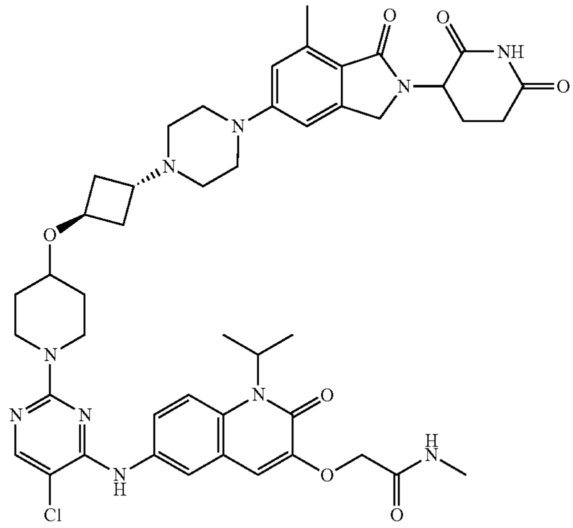 [SMILES: CNC(=O)COc1cc2cc(Nc3nc(N4CCC(O[C@H]5C[C@H](N6CCN(c7cc(C)c8c(c7)CN(C7CCC(=O)NC7=O)C8=O)CC6)C5)CC4)ncc3Cl)ccc2n(C(C)C)c1=O]

To a stirred solution of 3-(7-methyl-1-oxo-5-{4-[(1r,3r)-3-(piperidin-4-yloxy)cyclobutyl]piperazin-1-yl}-3H-isoindol-2-yl)piperidine-2,6-dione (110 mg, 0.2 mmol) and 2-({6-[(5-chloro-2-fluoropyrimidin-4-yl)amino]-1-isopropyl-2-oxoquinolin-3-yl}oxy)-N-methylacetamide (71.7 mg, 0.171 mmol) in dimethyl sulfoxide (5 mL) was dropwise added N,N-diisopropylethylamine (1 mL). The resulting mixture was stirred for 2 h at 50° C. The residue was purified by reverse flash chromatography (column, C18 silica gel, mobile phase, acetonitrile in water (10 mmol/L $NH_4HCO_3$), 10% to 50% gradient in 10 min) to afford 2-({6-[(5-chloro-2-{4-[(1r,3r)-3-{4-[2-(2,6-dioxopiperidin-3-yl)-7-methyl-1-oxo-3H-isoindol-5-yl]piperazin-1-yl}cyclobutoxy]piperidin-1-yl}pyrimidin-4-yl)amino]-1-isopropyl-2-oxoquinolin-3-yl}oxy)-N-methylacetamide (52.7 mg, 34%) as a white solid. $^1$H NMR (400 MHz, DMSO-d6) δ 11.32 (s, 1H), 10.93 (s, 1H), 8.84 (s, 1H), 8.05 (s, 1H), 7.97 (d, J=8.3 Hz, 2H), 7.69 (s, 2H), 7.32 (s, 1H), 7.20 (s, 1H), 7.05 (d, J=16.9 Hz, 2H), 6.93 (s, 1H), 6.86 (s, 1H), 5.01 (dd, J=13.3, 5.1 Hz, 1H), 4.55 (s, 2H), 4.28 (d, J=16.9 Hz, 1H), 4.17 (d, J=17.1 Hz, 2H), 4.11 (s, 1H), 3.56 (s, 1H), 3.24 (t, J=11.3 Hz, 3H), 2.97-2.83 (m, 1H), 2.68 (d, J=4.6 Hz, 3H), 2.59 (d, J=16.0 Hz, 1H), 2.55 (s, 3H), 2.44-2.32 (m, 1H), 2.20 (s, 2H), 1.95 (d, J=12.3 Hz, 1H), 1.87-1.80 (m, 2H), 1.58 (d, J=6.8 Hz, 6H), 1.39 (d, J=9.8 Hz, 3H). MS (ESI): m/z 843.25 [M+H]$^+$.

Example 5—Synthesis of Compound 37

Step 1: (1s,3s)-3-(benzyloxy)cyclobutan-1-ol

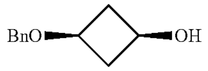 [SMILES: O[C@H]1C[C@@H](OCc2ccccc2)C1]

To a solution of 3-(benzyloxy)cyclobutan-1-one (100 g, 567 mmol) in methanol (500 mL) was added sodium borohydride (13.5 g, 357 mmol) in portions at 0° C. The resulting mixture was stirred overnight at room temperature. After filtration, the filtrate was concentrated under reduced pressure. The residue was diluted with water at 0° C., extracted with ethyl acetate (3×400 mL). The combined organic layers were washed with brine (3×200 mL), dried over anhydrous sodium sulfate to afford (1s,3s)-3-(benzyloxy)cyclobutan-1-ol (99 g, 98%) as a colorless oil.

Step 2: trimethyl[(1s,3s)-3-(benzyloxy)cyclobutoxy]silane

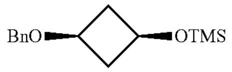

To a solution of (1s,3s)-3-(benzyloxy)cyclobutan-1-ol (79.0 g, 443 mmol) in dichloromethane (700 mL) was added triethylamine (134.0 g, 1.3 mol) at 0° C. under nitrogen atmosphere followed by the addition of trimethylsilane chloride (53.0 g, 488 mmol) dropwise at 0° C. The resulting mixture was stirred for 2 h at room temperature under nitrogen atmosphere, then diluted with water (500 mL) and extracted with ethyl acetate (500 mL×2). The combined organic phase was washed with saturated brine (300 mL), dried with anhydrous sodium sulfate, filtered, and concentrated in vacuum to afford trimethyl[(1s,3s)-3-(benzyloxy)cyclobutoxy]silane (110 g, 99%) as an off-white oil.

Step 3: benzyl 4-[(1s,3s)-3-(benzyloxy)cyclobutoxy]piperidine-1-carboxylate

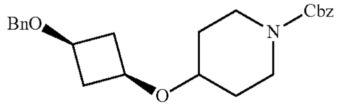 [SMILES: O=C(OCc1ccccc1)N1CCC(O[C@H]2C[C@@H](OCc3ccccc3)C2)CC1]

To a solution of trimethyl[(1s,3s)-3-(benzyloxy)cyclobutoxy]silane (67.6 g, 270 mmol) and benzyl 4-oxopiperidine-1-carboxylate (69.3 g, 297 mmol) in dichloromethane (600 mL) was added triethylsilane (34.5 g, 297 mmol) dropwise at −78° C. under nitrogen atmosphere. The resulting mixture was stirred at −78° C. for 5 min, then trimethylsilyl trifluoromethanesulfonate (30.0 g, 135 mmol) in dichloromethane (50 mL) was dropwise added. The reaction mixture was stirred for 10 min at −78° C., slowly warmed up to 0° C. and stirred for another 2 h. The mixture was diluted with water (500 mL) and extracted with ethyl acetate (500 mL×3). The combined organic layers were washed with brine (200 mL×3), dried over anhydrous sodium sulfate, filtered, and concentrated under reduced pressure. The residue was purified by silica gel column chromatography (petroleum ether/ethyl acetate=10/1 to 4/1) to afford benzyl 4-[(1s,3s)-3-(benzyloxy)cyclobutoxy]piperidine-1-carboxylate (81 g, 76%) as an oil.

Step 4: tert-butyl 4-[(1s,3s)-3-hyroxycyclobutoxy]piperidine-1-carboxylate

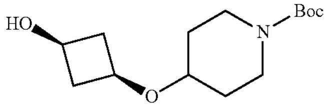 [SMILES: CC(C)(C)OC(=O)N1CCC(O[C@H]2C[C@@H](O)C2)CC1]

To a solution of benzyl 4-[(1s,3s)-3-(benzyloxy)cyclobutoxy]piperidine-1-carboxylate (20 g, 51 mmol) and di-tert-butyl dicarbonate (16.6 g, 76 mmol) in ethanol (200 mL) and tetrahydrofuran (150 mL) was added Pd/C (10 g) and $Pd(OH)_2/C$ (10 g) under nitrogen atmosphere. The mixture was degassed and purged with hydrogen, then stirred at 55° C. under hydrogen (15 psi) for 48 h. Then reaction mixture was cooled to room temperature and filtered through Celite, concentrated. The residue was purified by reverse flash chromatography (column, C18 silica gel; mobile phase, acetonitrile/water (10 mmol/L $NH_4HCO_3$), 5% to 40% gradient in 30 min) to afford tert-butyl 4-[(1s,3s)-3-hyroxycyclobutoxy]piperidine-1-carboxylate (28 g, 82%) as an off-white solid.

Step 5: tert-butyl 4-[(1s,3s)-3-(trifluoromethanesulfonyloxy)cyclobutoxy]piperidine-1-carboxylate

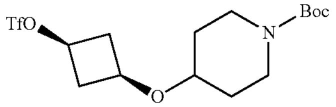 [SMILES: CC(C)(C)OC(=O)N1CCC(O[C@H]2C[C@@H](OS(=O)(=O)C(F)(F)F)C2)CC1]

To a solution of tert-butyl 4-[(1s,3s)-3-hydroxycyclobutoxy]piperidine-1-carboxylate (10.0 g, 37 mmol) in dichloromethane (150 mL) was added triethylamine (11.2 g, 111 mmol) at room temperature under nitrogen atmosphere, then triflic anhydride (16.6 g, 59 mmol) was dropwise added at −40° C. over a period of 15 min under nitrogen. The mixture was stirred at −40° C. for 2 h, diluted with dichloromethane (200 mL), washed with brine (100 mL×3), dried over anhydrous sodium sulfate, filtered, and concentrated under vacuum. The residue was purified by silica gel column chromatography (petroleum ether/ethyl acetate=9:1) to afford tert-butyl 4-[(1s,3s)-3-(trifluoromethanesulfonyloxy)cyclobutoxy]piperidine-1-carboxylate (9.6 g, 65%) as a yellow solid.

Step 6: tert-butyl 4-[(1r,3r)-3-[4-(4,4,5,5-tetramethyl-1,3,2-dioxaborolan-2-yl)-3,6-dihydro-2H-pyridin-1-yl]cyclobutoxy]piperidine-1-carboxylate

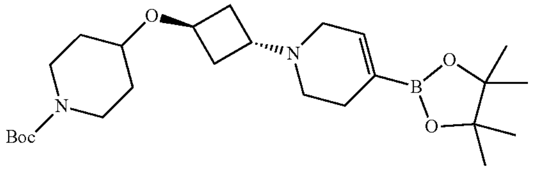 [SMILES: CC(C)(C)OC(=O)N1CCC(O[C@H]2C[C@H](N3CC=C(B4OC(C)(C)C(C)(C)O4)CC3)C2)CC1]

To a stirred mixture of 4-(4,4,5,5-tetramethyl-1,3,2-dioxaborolan-2-yl)-1,2,3,6-tetrahydropyridine (500 mg, 2.4 mmol) and tert-butyl 4-[(1s,3s)-3-(trifluoromethanesulfonyloxy)cyclobutoxy]piperidine-1-carboxylate (964.6 mg, 2.4 mmol) in acetonitrile (30 mL) was added N,N-diisopropylethylamine (2 mL). The resulting mixture was stirred for 5 h at room temperature under nitrogen atmosphere, then concentrated. The residue was diluted with water (10 mL) and extracted with EtOAc (3×10 mL). The combined organic layers were washed with brine (3×10 mL), dried over anhydrous sodium sulfate, filtered, and concentrated under reduced pressure to afford tert-butyl 4-[(1r,3r)-3-[4-(4,4,5,5-tetramethyl-1,3,2-dioxaborolan-2-yl)-3,6-dihydro-2H-pyridin-1-yl]cyclobutoxy]piperidine-1-carboxylate (1 g, 90%) as a yellow oil. MS (ESI): m/z 418.21 $[M+H]^+$.

Step 7: tert-butyl 4-[(1r,3r)-3-{4-[2-(2,6-dioxopiperidin-3-yl)-7-methyl-1-oxo-3H-isoindol-5-yl]-3,6-dihydro-2H-pyridin-1-yl}cyclobutoxy]piperidine-1-carboxylate

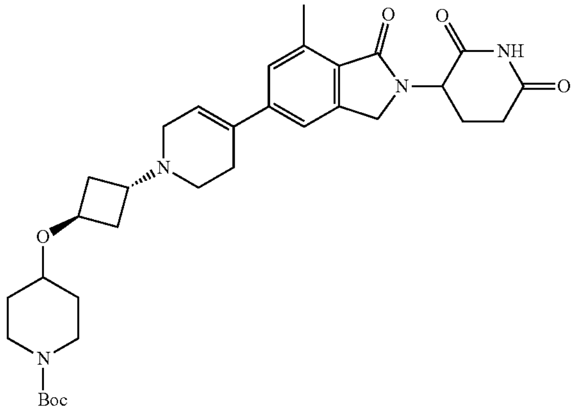 [SMILES: Cc1cc(C2=CCN([C@H]3C[C@H](OC4CCN(C(=O)OC(C)(C)C)CC4)C3)CC2)cc2c1C(=O)N(C1CCC(=O)NC1=O)C2]

To a solution of tert-butyl 4-[(1r,3r)-3-[4-(4,4,5,5-tetramethyl-1,3,2-dioxaborolan-2-yl)-3,6-dihydro-2H-pyridin-1-yl]cyclobutoxy]piperidine-1-carboxylate (170 mg, 0.4 mmol) and 3-(5-bromo-7-methyl-1-oxo-3H-isoindol-2-yl)piperidine-2,6-dione (247 mg, 0.7 mmol) in dioxane (4 mL) and water (0.5 mL) were added cesium fluoride (111 mg, 0.7 mmol) and $Pd(dtbpf)Cl_2$ (24 mg, 0.04 mmol). After stirring for 2 h at 90° C. under a nitrogen atmosphere, the resulting mixture was concentrated under reduced pressure. The residue was purified by silica gel column chromatography (petroleum ether/ethyl acetate=1:1) to afford tert-butyl 4-[(1r,3r)-3-{4-[2-(2,6-dioxopiperidin-3-yl)-7-methyl-1-oxo-3H-isoindol-5-yl]-3,6-dihydro-2H-pyridin-1-yl}cyclobutoxy]piperidine-1-carboxylate (140 mg, 64%) as a brown solid. MS (ESI): m/z 593.35 $[M+H]^+$.

Step 8: tert-butyl 4-[(1r,3r)-3-{4-[2-(2,6-dioxopiperidin-3-yl)-7-methyl-1-oxo-3H-isoindol-5-yl]piperidin-1-yl}cyclobutoxy]piperidine-1-carboxylate

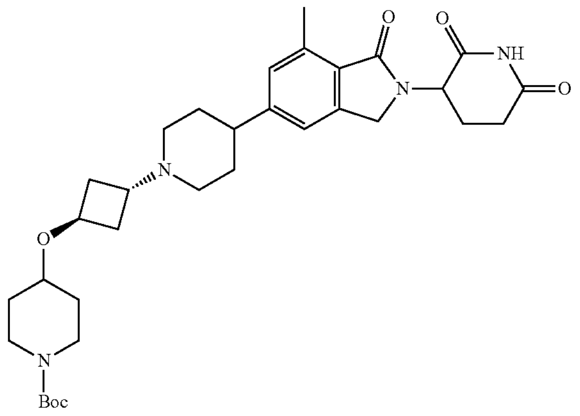 [SMILES: Cc1cc(C2CCN([C@H]3C[C@H](OC4CCN(C(=O)OC(C)(C)C)CC4)C3)CC2)cc2c1C(=O)N(C1CCC(=O)NC1=O)C2]

To a solution of tert-butyl 4-[(1r,3r)-3-{4-[2-(2,6-dioxopiperidin-3-yl)-7-methyl-1-oxo-3H-isoindol-5-yl]-3,6-dihydro-2H-pyridin-1-yl}cyclobutoxy]piperidine-1-carboxylate (140 mg, 0.2 mmol) in tetrahydrofuran (5 mL) and isopropanol (5 mL) was added 10% Pd/C (0.1 g) under nitrogen atmosphere. The mixture was degassed and purged with hydrogen for three times before stirring at room temperature overnight under hydrogen atmosphere using a hydrogen balloon. The mixture was filtered through a Celite pad and washed with tetrahydrofuran, concentrated under reduced pressure to afford tert-butyl 4-[(1r,3r)-3-{4-[2-(2,6-dioxopiperidin-3-yl)-7-methyl-1-oxo-3H-isoindol-5-yl]piperidin-1-yl}cyclobutoxy]piperidine-1-carboxylate (140 mg, 99%) as a brown oil. MS (ESI): m/z 595.35 $[M+H]^+$.

Step 9: 3-(7-methyl-1-oxo-5-{1-[(1r,3r)-3-(piperidin-4-yloxy)cyclobutyl]piperidin-4-yl}-3H-isoindol-2-yl)piperidine-2,6-dione

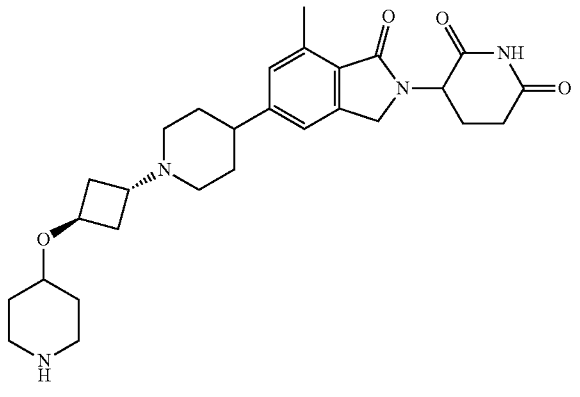 [SMILES: Cc1cc(C2CCN([C@H]3C[C@H](OC4CCNCC4)C3)CC2)cc2c1C(=O)N(C1CCC(=O)NC1=O)C2]

To a stirred solution of tert-butyl 4-[(1r,3r)-3-(4-[2-(2,6-dioxopiperidin-3-yl)-7-methyl-1-oxo-3H-isoindol-5-yl]piperidin-1-yl}cyclobutoxy]piperidine-1-carboxylate (140 mg, 0.2 mmol) in dioxane (2 mL) was added HCl gas in 1,4-dioxane (2 mL). The resulting mixture was stirred for 2 h at room temperature, then concentrated under vacuum to afford 3-(7-methyl-1-oxo-5-{1-[(1r,3r)-3-(piperidin-4-yloxy)cyclobutyl]piperidin-4-yl}-3H-isoindol-2-yl)piperidine-2,6-dione hydrochloride (100 mg, 85%) as a brown solid. MS (ESI): m/z 495.35 $[M+H]^+$.

Step 10: 2-({6-[(5-chloro-2-{4-[(1r,3r)-3-{4-[2-(2,6-dioxopiperidin-3-yl)-7-methyl-1-oxo-3H-isoindol-5-yl]piperidin-1-yl}cyclobutoxy]piperidin-1-yl}pyrimidin-4-yl)amino]-1-isopropyl-2-oxoquinolin-3-yl}oxy)-N-methylacetamide

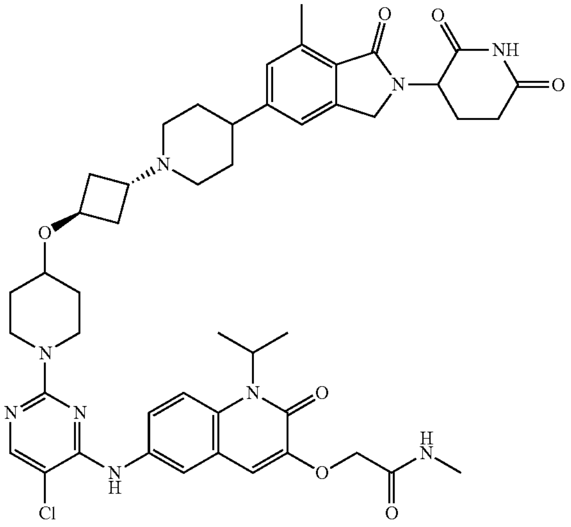 [SMILES: CNC(=O)COc1cc2cc(Nc3nc(N4CCC(O[C@H]5C[C@H](N6CCC(c7cc(C)c8c(c7)CN(C7CCC(=O)NC7=O)C8=O)CC6)C5)CC4)ncc3Cl)ccc2n(C(C)C)c1=O]

To a stirred solution of 3-(7-methyl-1-oxo-5-{1-[(1r,3r)-3-(piperidin-4-yloxy)cyclobutyl]piperidin-4-yl}-3H-isoindol-2-yl)piperidine-2,6-dione (100 mg, 0.2 mmol) and 2-({6-[(5-chloro-2-fluoropyrimidin-4-yl)amino]-1-isopropyl-2-oxoquinolin-3-yl}oxy)-N-methylacetamide (65 mg, 0.2 mmol) in DMSO (5 mL) was dropwise added N,N-diisopropylethylamine (2 mL). The resulting mixture was stirred for 2 h at 50° C. The crude material was purified by reverse flash chromatography (column: C18 silica gel; mobile phase: acetonitrile in water (10 mmol/L $NH_4HCO_3$), 10% to 50% gradient in 30 min) to afford 2-({6-[(5-chloro-2-{4-[(1r,3r)-3-{4-[2-(2,6-dioxopiperidin-3-yl)-7-methyl-1-oxo-3H-isoindol-5-yl]piperidin-1-yl}cyclobutoxy]piperidin-1-yl}pyrimidin-4-yl)amino]-1-isopropyl-2-oxoquinolin-3-yl}oxy)-N-methylacetamide (45.2 mg, 30%) as an off-white solid. MS (ESI): m/z 894.30 $[M+H]^+$; $^1H$ NMR (300 MHz, DMSO) δ 10.97 (s, 1H), 8.83 (s, 1H), 8.05 (s, 1H), 7.96 (m, 2H), 7.69 (m, 2H), 7.27 (s, 1H), 7.15 (s, 1H), 7.03 (s, 1H), 5.34 (s, 1H), 5.06 (m, 1H), 4.55 (s, 2H), 4.35 (m, 1H), 4.22 (m, 1H), 4.15 (s, 2H), 4.10 (s, 1H), 3.53 (s, 1H), 2.99 (m, 2H), 2.82 (s, 2H), 2.68 (m, 3H), 2.59 (s, 3H), 2.55 (s, 1H), 2.44-2.29 (m, 1H), 2.20-2.10 (m, 1H), 1.80 (s, 0H), 1.76 (s, 7H), 1.58 (m, 7H), 1.38 (m, 1H).

Example 6—Synthesis of Compounds 38 and 39

Step 1: methyl 4-bromo-5-fluoro-2-methylbenzoate

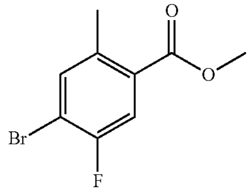

A solution of 4-bromo-5-fluoro-2-methylbenzoic acid (30.0 g, 128 mmol) and sulfuric acid (30 mL) in methanol (300 mL) was stirred overnight at 50° C., then concentrated under vacuum. The residue was diluted with water, extracted with ethyl acetate (100 mL). The combined organic layers were washed with brine (3×10 mL), dried over anhydrous sodium sulfate, filtered, and concentrated under reduced pressure to afford methyl 4-bromo-5-fluoro-2-methylbenzoate (30 g, 94%) as a yellow oil. MS (ESI): m/z 247.2 $[M+H]^+$.

Step 2: methyl 5-fluoro-4-(3-fluoropyridin-4-yl)-2-methylbenzoate

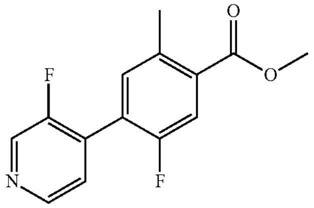 [SMILES: COC(=O)c1cc(F)c(-c2ccncc2F)cc1C]

To a stirred solution of methyl 4-bromo-5-fluoro-2-methylbenzoate (22 g, 87 mmol) and 3-fluoro-4-(4,4,5,5-tetramethyl-1,3,2-dioxaborolan-2-yl)pyridine (19.5 g, 87 mmol) in dioxane (200 mL) and water (20 mL) was added [1,1'-bis(diphenylphosphino)ferrocene]dichloropalladium(II) (7.1 g, 8.7 mmol) and sodium carbonate (18.4 g, 175 mmol). The reaction was stirred at 80° C. overnight, diluted with water and extracted with ethyl acetate (100 mL×3). The combined organic layers were washed with brine (3×50 mL), dried over anhydrous sodium sulfate, filtered, and concentrated under reduced pressure. The residue was purified by silica gel column chromatography (petroleum ether/ethyl acetate=5:1) to afford methyl 5-fluoro-4-(3-fluoropyridin-4-yl)-2-methylbenzoate (12 g, 54%) as a yellow solid. MS (ESI): m/z 264.3 $[M+H]^+$.

Step 3: methyl 5-fluoro-4-(3-fluoropiperidin-4-yl)-2-methylbenzoate

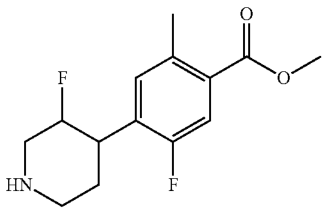 [SMILES: COC(=O)c1cc(F)c(C2CCNCC2F)cc1C]

To a stirred solution of methyl 5-fluoro-4-(3-fluoropyridin-4-yl)-2-methylbenzoate (12 g, 46 mmol) and sulfuric acid (10 mL) in methanol (200 mL) was added $Pd(0H)_2/C$ (1 g) at room temperature. The resulting mixture was degassed and purged with hydrogen before stirring overnight under hydrogen atmosphere. The resulting mixture was filtered, the filter cake was washed with methanol (3×20 mL). The filtrate was concentrated under reduced pressure to afford methyl 5-fluoro-4-(3-fluoropiperidin-4-yl)-2-methylbenzoate (11 g, 80%) as a white oil. MS (ESI): m/z 270.30 $[M+H]^+$.

Step 4: tert-butyl 3-fluoro-4-[2-fluoro-4-(methoxycarbonyl)-5-methylphenyl]piperidine-1-carboxylate

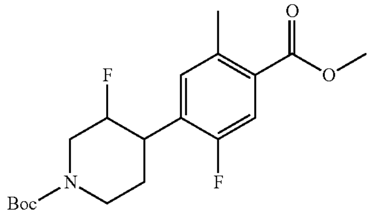 [SMILES: COC(=O)c1cc(F)c(C2CCN(C(=O)OC(C)(C)C)CC2F)cc1C]

To a stirred solution of methyl 5-fluoro-4-(3-fluoropiperidin-4-yl)-2-methylbenzoate (8.0 g, 29 mmol) and sodium carbonate (601 mg, 58 mmol) in tetrahydrofuran (400 mL) and water (400 mL) was added di-tert-butyl dicarbonate (12.6 g, 58 mmol). The resulting mixture was stirred for 2 h at room temperature, then diluted with water, extracted with ethyl acetate (100 mL×3). The combined organic layers were washed with brine (3×20 mL), dried over anhydrous sodium sulfate, filtered, and concentrated under reduced pressure to afford tert-butyl 3-fluoro-4-[2-fluoro-4-(methoxycarbonyl)-5-methylphenyl]piperidine-1-carboxylate (5 g, 50%) as a white solid. MS (ESI): m/z 370.2 $[M+H]^+$.

Step 5: 4-[1-(tert-butoxycarbonyl)-3-fluoropiperidin-4-yl]-5-fluoro-2-methylbenzoic acid

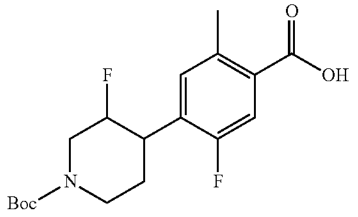 [SMILES: Cc1cc(C2CCN(C(=O)OC(C)(C)C)CC2F)c(F)cc1C(=O)O]

To a stirred solution of tert-butyl 3-fluoro-4-[2-fluoro-4-(methoxycarbonyl)-5-methylphenyl]piperidine-1-carboxylate (5.0 g, 13 mmol) in tetrahydrofuran (200 mL) and water (200 mL) was added caustic soda (2.71 g, 67 mmol). The resulting mixture was stirred overnight at 50° C. The mixture was acidified to pH 6 with hydrochloric acid (50 mL). The resulting mixture was extracted with ethyl acetate (100 mL×3). The combined organic layers were washed with brine (3×50 mL), dried over anhydrous sodium sulfate, filtered, and concentrated under reduced pressure to afford 4-[1-(tert-butoxycarbonyl)-3-fluoropiperidin-4-yl]-5-fluoro-2-methylbenzoic acid (4.5 g, 94%) as a white solid. MS (ESI): m/z 356.3 [M+H]+.

Step 6: tert-butyl 3-fluoro-4-(4-fluoro-3-hydroxy-7-methyl-1-oxo-3H-2-benzofuran-5-yl)piperidine-1-carboxylate

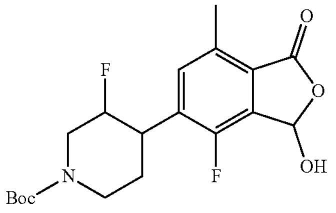 [SMILES: Cc1cc(C2CCN(C(=O)OC(C)(C)C)CC2F)c(F)c2c1C(=O)OC2O]

To a mixture of 4-[1-(tert-butoxycarbonyl)-3-fluoropiperidin-4-yl]-5-fluoro-2-methylbenzoic acid (4.5 g, 13 mmol) and tetrahydrofuran (200 mL) at −78° C. was dropwise added 1.3 M tert-butyl lithium (48 mL, 63 mmol) over 5 min at −78° C. The resulting mixture was stirred for 3 h at −78° C. Then N, N-dimethylformamide (1.8 mL, 25 mmol) was added dropwise over 5 min at −78° C. The resulting mixture was stirred for 3 h at room temperature. The mixture was acidified to pH 6 with hydrochloric acid (50 mL) at 0° C., extracted with ethyl acetate (100 mL×3). The combined organic layers were washed with brine (3×50 mL), dried over anhydrous sodium sulfate, filtered, and concentrated under reduced pressure. The residue was purified by silica gel column chromatography (petroleum ether/ethyl acetate=1:1) to afford tert-butyl 3-fluoro-4-(4-fluoro-3-hydroxy-7-methyl-1-oxo-3H-2-benzofuran-5-yl)piperidine-1-carboxylate (4.5 g, 92%) as a white solid. MS (ESI): m/z 384.30 [M+H]+.

Step 7: tert-butyl 3-fluoro-4-[2-fluoro-3-formyl-4-(methoxycarbonyl)-5-methylphenyl]piperidine-1-carboxylate

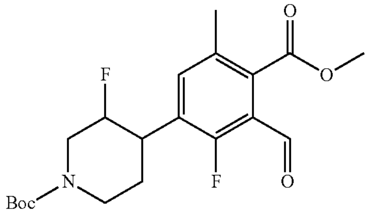 [SMILES: COC(=O)c1c(C)cc(C2CCN(C(=O)OC(C)(C)C)CC2F)c(F)c1C=O]

To a stirred solution of tert-butyl 3-fluoro-4-(4-fluoro-3-hydroxy-7-methyl-1-oxo-3H-2-benzofuran-5-yl)piperidine-1-carboxylate (4.5 g, 12 mmol) and methyl iodide (2.50 g, 18 mmol) in N, N-dimethylformamide (50 mL) was added potassium carbonate (4.87 g, 35 mmol). The resulting mixture was stirred overnight at room temperature, then diluted with water and extracted with ethyl acetate (100 mL×3). The combined organic layers were washed with brine (3×50 mL), dried over anhydrous sodium sulfate, filtered, and concentrated under reduced pressure. The residue was purified by silica gel column chromatography (petroleum ether/ethyl acetate=1:1) to afford tert-butyl 3-fluoro-4-[2-fluoro-3-formyl-4-(methoxycarbonyl)-5-methylphenyl]piperidine-1-carboxylate (4.3 g, 92%) as a white solid. MS (ESI): m/z 398.2 [M+H]+.

Step 8: tert-butyl (3R,4S)-4-{2-[(1S)-4-(tert-butoxy)-1-carbamoyl-4-oxobutyl]-4-fluoro-7-methyl-1-oxo-3H-isoindol-5-yl)-3-fluoropiperidine-1-carboxylate and tert-butyl (3S,4R)-4-(2-[(1S)-4-(tert-butoxy)-1-carbamoyl-4-oxobutyl]-4-fluoro-7-methyl-1-oxo-3H-isoindol-5-yl}-3-fluoropiperidine-1-carboxylate

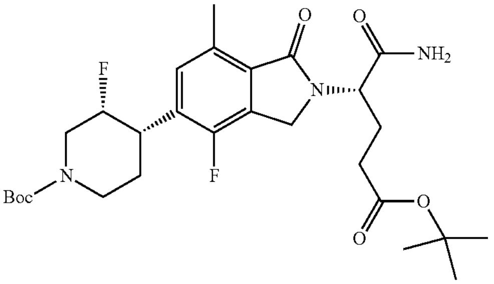

+

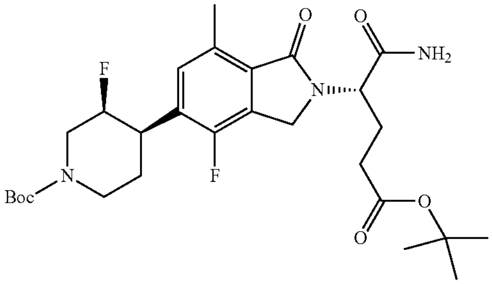

To a solution of tert-butyl 3-fluoro-4-[2-fluoro-3-formyl-4-(methoxycarbonyl)-5-methylphenyl]piperidine-1-carboxylate (5.8 g, 15 mmol) in dichloroethane (50 mL) was added tert-butyl (4S)-4-amino-4-carbamoylbutanoate hydrochloride (3.48 g, 14.5 mmol) and stirred overnight at 40° C. under nitrogen atmosphere. Then sodium cyanoborohydride (2.75 g, 44 mmol) was added, the resulting mixture was stirred overnight at 40° C. The reaction was quenched by water (50 mL) at room temperature, the resulting mixture was extracted with dichloromethane (100 mL×3). The combined organic layers were washed with brine (50 mL×3), dried over anhydrous sodium sulfate, filtered, and concentrated under reduced pressure. The residue was purified by reverse flash chromatography (column, C18 silica gel; mobile phase, acetonitrile/water (10 mmol/L $NH_4HCO_3$), 5% to 70% gradient in 50 min), then purified by SFC (column, (S,S) Whelk-O1 4.6×0 mm, 3.5 μm; mobile phase, isopropanol/hexane=1:2 (0.1% diethylamine), 10% to 50% in 2.0 min). The first peak (2.178 min) was collected to afford tert-butyl (3R,4S)-4-{2-[(1S)-4-(tert-butoxy)-1-carbamoyl-4-oxobutyl]-4-fluoro-7-methyl-1-oxo-3H-isoindol-5-yl}-3-fluoropiperidine-1-carboxylate (1.2 g) as a yellow solid. The second peak (2.308 min) was collected to afford tert-butyl (3S,4R)-4-{2-[(1S)-4-(tert-butoxy)-1-carbamoyl-4-oxobutyl]-4-fluoro-7-methyl-1-oxo-3H-isoindol-5-yl}-3-fluoropiperidine-1-carboxylate (1.3 g) as a yellow solid. MS (ESI): m/z 356.3 [M+H]+.

Step 9: tert-butyl (4S)-4-carbamoyl-4-{4-fluoro-5-[(3R,4S)-3-fluoropiperidin-4-yl]-7-methyl-1-oxo-3H-isoindol-2-yl}butanoate

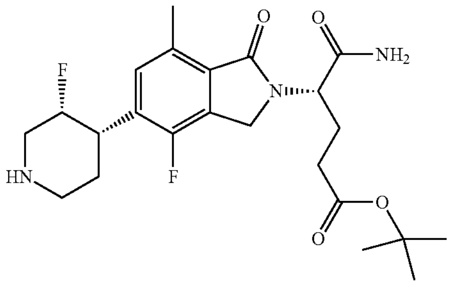 [SMILES: Cc1cc([C@@H]2CCNC[C@@H]2F)c(F)c2c1C(=O)N([C@@H](CCC(=O)OC(C)(C)C)C(N)=O)C2]

A solution of tert-butyl (3R,4S)-4-{2-[(1S)-4-(tert-butoxy)-1-carbamoyl-4-oxobutyl]-4-fluoro-7-methyl-1-oxo-3H-isoindol-5-yl}-3-fluoropiperidine-1-carboxylate (1.2 g, 2.1 mmol) and trimethylsilyl chloride (2.36 g, 22 mmol) in 2-propanol (20 mL) was stirred overnight at room temperature under nitrogen atmosphere. The resulting mixture was diluted with water and extracted with dichloromethane (20 mL×3). The combined organic layers were washed with brine (3×10 mL), dried over anhydrous sodium sulfate, filtered, and concentrated under reduced pressure to afford tert-butyl (4S)-4-carbamoyl-4-{4-fluoro-5-[(3R,4S)-3-fluoropiperidin-4-yl]-7-methyl-1-oxo-3H-isoindol-2-yl}butanoate (860 mg) as a yellow solid. MS (ESI): m/Z 451.30 $[M+H]^+$.

Step 10: tert-butyl 4-[(1r,3r)-3-[(3R,4S)-4-{2-[(1S)-4-(tert-butoxy)-1-carbamoyl-4-oxobutyl]-4-fluoro-7-methyl-1-oxo-3H-isoindol-5-yl}-3-fluoropiperidin-1-yl]cyclobutoxy]piperidine-1-carboxylate

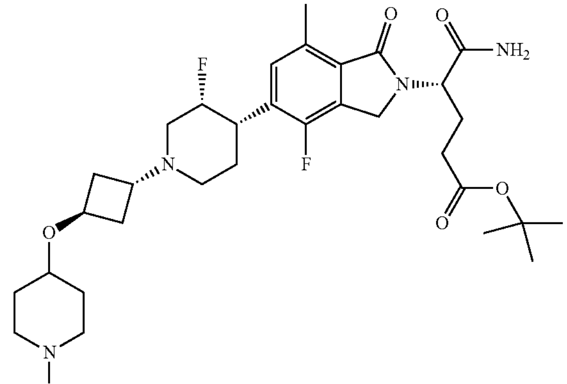

To a stirred solution of tert-butyl (4S)-4-carbamoyl-4-{4-fluoro-5-[(3R,4S)-3-fluoropiperidin-4-yl]-7-methyl-1-oxo-3H-isoindol-2-yl}butanoate (300 mg, 0.7 mmol) and tert-butyl 4-[(1s,3s)-3-(trifluoromethanesulfonyloxy)cyclobutoxy]piperidine-1-carboxylate (670 mg, 1.7 mmol) in acetonitrile (2 mL) was added N,N-diisopropylethylamine (0.5 mL). The resulting mixture was stirred for 2 h at room temperature under nitrogen atmosphere, then diluted with water and extracted with ethyl acetate (10 mL×3). The combined organic layers were washed with brine (3×10 mL), dried over anhydrous sodium sulfate, filtered, and concentrated under reduced pressure. The residue was purified by silica gel column chromatography (petroleum ether/ethyl acetate=5:1) to afford tert-butyl 4-[(1r,3r)-3-[(3R,4S)-4-{2-[(1S)-4-(tert-butoxy)-1-carbamoyl-4-oxobutyl]-4-fluoro-7-methyl-1-oxo-3H-isoindol-5-yl}-3-fluoropiperidin-1-yl]cyclobutoxy]piperidine-1-carboxylate (300 mg, 38%) as a yellow solid. MS (ESI): m/z 705.2 $[M+H]^+$.

Step 11: (3S)-3-{4-fluoro-5-[(3R,4S)-3-fluoro-1-[(1r,3r)-3-(piperidin-4-yloxy)cyclobutyl]piperidin-4-yl]-7-methyl-1-oxo-3H-isoindol-2-yl}piperidine-2,6-dione

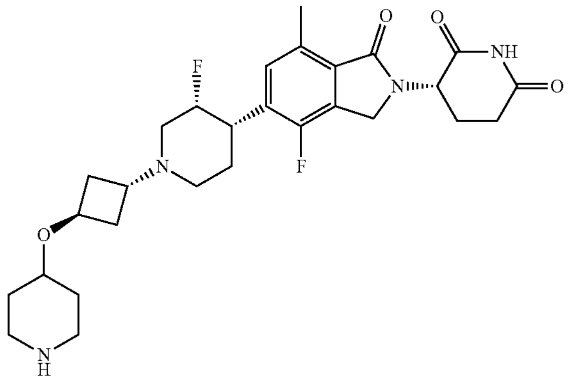 [SMILES: Cc1cc([C@@H]2CCN([C@H]3C[C@H](OC4CCNCC4)C3)C[C@@H]2F)c(F)c2c1C(=O)N([C@H]1CCC(=O)NC1=O)C2]

To a stirred solution of tert-butyl 4-[(1r,3r)-3-[(3R,4S)-4-{2-[(1S)-4-(tert-butoxy)-1-carbamoyl-4-oxobutyl]-4-fluoro-7-methyl-1-oxo-3H-isoindol-5-yl}-3-fluoropiperidin-1-yl]cyclobutoxy]piperidine-1-carboxylate (300 mg, 0.4 mmol) in acetonitrile (10 mL) was added (1R)-(−)-10-Camphorsulfonic acid (19.7 mg, 1.3 mmol). The resulting mixture was stirred for 3 h at 80° C. under nitrogen atmosphere, then concentrated under vacuum to afford (3S)-3-{4-fluoro-5-[(3R,4S)-3-fluoro-1-[(1r,3r)-3-(piperidin-4-yloxy)cyclobutyl]piperidin-4-yl]-7-methyl-1-oxo-3H-isoindol-2-yl}piperidine-2,6-dione (200 mg, 89/a) as a white solid. MS (ESI): m/z 428.3 $[M+H]^+$.

Step 12: 2-({6-[(5-chloro-2-{4-[(1r,3r)-3-[(3R,4S)-4-{2-[(3S)-2,6-dioxopiperidin-3-yl]-4-fluoro-7-methyl-1-oxo-3H-isoindol-5-yl}-3-fluoropiperidin-1-yl]cyclobutoxy]piperidin-1-yl}pyrimidin-4-yl)amino]-1-isopropyl-2-oxoquinolin-3-yl}oxy)-N-methylacetamide

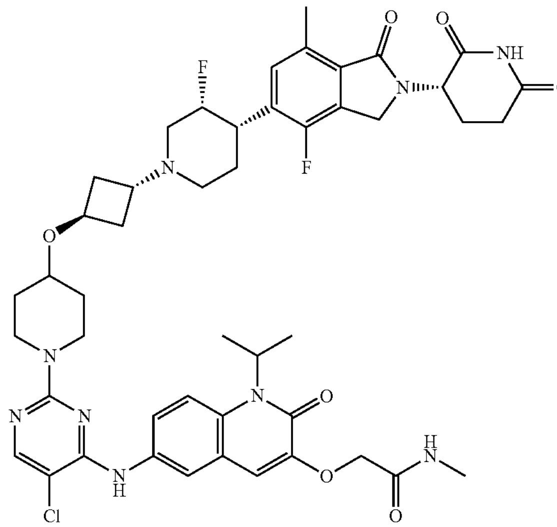

To a stirred solution of (3S)-3-{4-fluoro-5-[(3R,4S)-3-fluoro-1-[(1r,3r)-3-(piperidin-4-yloxy)cyclobutyl]piperidin-4-yl]-7-methyl-1-oxo-3H-isoindol-2-yl}piperidine-2,6-dione (182 mg, 0.3 mmol) and 2-({6-[(5-chloro-2-fluoropyrimidin-4-yl)amino]-1-isopropyl-2-oxoquinolin-3-yl}oxy)-N-methylacetamide (120 mg, 0.3 mmol) in dimethyl sulfoxide (4 mL) was added N,N-diisopropylethylamine (0.5 mL). The resulting mixture was stirred for 2 h at 50° C., then purified by reversed-phase flash chromatography (column, C18 silica gel; mobile phase, acetonitrile in water (10 mmol/L $NH_4HCO_3$), 10% to 50% gradient in 10 min) to afford 2-({6-[(5-chloro-2-{4-[(1r,3r)-3-[(3R,4S)-4-{2-[(3S)-2,6-dioxopiperidin-3-yl]-4-fluoro-7-methyl-1-oxo-3H-isoindol-5-yl}-3-fluoropiperidin-1-yl]cyclobutoxy]piperidin-1-yl}pyrimidin-4-yl)amino]-1-isopropyl-2-oxoquinolin-3-yl}oxy)-N-methylacetamide (72.0 mg, 27%) as an off-white solid. $^1H$ NMR (300 MHz, DMSO) δ 11.01 (s, 1H), 8.85 (s, 1H), 8.05 (s, 1H), 7.97 (d, J=9.6 Hz, 2H), 7.70 (s, 2H), 7.28 (d, J=6.1 Hz, 1H), 7.03 (s, 1H), 5.35 (s, 1H), 5.08 (dd, J=13.2, 5.1 Hz, 1H), 4.89 (s, 1H), 4.50 (d, J=30.0 Hz, 3H), 4.31 (d, J=17.2 Hz, 1H), 4.13 (d, J=13.5 Hz, 3H), 3.54 (s, 2H), 3.22 (d, J=10.8 Hz, 4H), 3.04 (d, J=10.4 Hz, 1H), 2.89 (d, J=10.6 Hz, 2H), 2.68 (d, J=4.6 Hz, 3H), 2.62 (s, 1H), 2.58 (s, 3H), 2.55 (s, 2H), 2.24-2.09 (m, 3H), 1.99 (s, 5H), 1.84 (d, J=12.1 Hz, 2H), 1.66 (s, 2H), 1.57 (d, J=6.8 Hz, 5H), 1.38 (d, J=9.4 Hz, 2H), 1.24 (s, 2H), 0.85 (d, J=6.7 Hz, 1H); MS (ESI): m/z 930.39 $[M+H]^+$.

Step 13: 2-({6-[(5-chloro-2-{4-[(1r,3r)-3-[(3S,4R)-4-{2-[(3S)-2,6-dioxopiperidin-3-yl]-4-fluoro-7-methyl-1-oxo-3H-isoindol-5-yl}-3-fluoropiperidin-1-yl]cyclobutoxy]piperidin-1-yl}pyrimidin-4-yl)amino]-1-isopropyl-2-oxoquinolin-3-yl}oxy)-N-methylacetamide

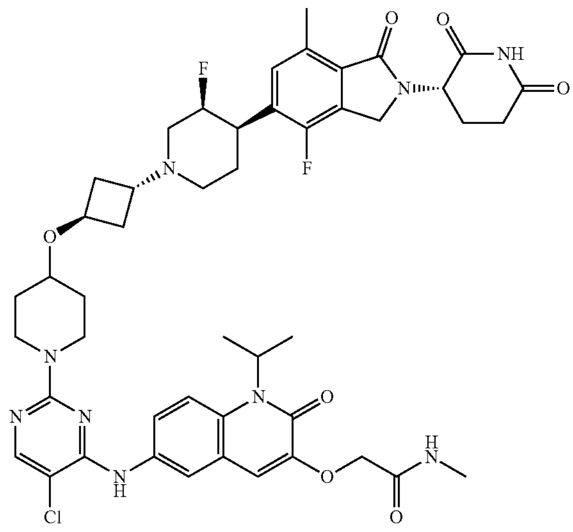 [SMILES: CNC(=O)COc1cc2cc(Nc3nc(N4CCC(O[C@H]5C[C@H](N6CC[C@H](c7cc(C)c8c(c7F)CN([C@H]7CCC(=O)NC7=O)C8=O)[C@H](F)C6)C5)CC4)ncc3Cl)ccc2n(C(C)C)c1=O]

The title compound was prepared analogously to step 9-12 in this example starting from tert-butyl (3S,4R)-4-{2-[(1S)-4-(tert-butoxy)-1-carbamoyl-4-oxobutyl]-4-fluoro-7-methyl-1-oxo-3H-isoindol-5-yl}-3-fluoropiperidine-1-carboxylate. 1H NMR (400 MHz, DMSO) δ 11.00 (s, 1H), 8.83 (s, 1H), 8.04 (s, 1H), 7.96 (d, J=4.8 Hz, 2H), 7.69 (d, J=4.0 Hz, 2H), 7.27 (d, J=6.0 Hz, 1H), 7.03 (s, 1H), 5.50-5.08 (m, 2H), 4.94-4.72 (m, 1H), 4.53-4.45 (m, 3H), 4.40 (s, 1H), 4.31-4.12 (m, 3H), 3.32 (d, J=9.4 Hz, 1H), 3.31 (s, 2H), 3.29-3.18 (m, 3H), 3.03 (d, J=10.4 Hz, 1H), 2.98-2.85 (m, 2H), 2.68 (d, J=4.6 Hz, 3H), 2.62 (d, J=3.7 Hz, 4H), 2.58 (s, 1H), 2.47 (s, 1H), 2.24-2.12 (m, 3H), 2.02-1.95 (m, 4H), 1.83 (d, J=11.6 Hz, 2H), 1.65 (d, J=12.3 Hz, 1H), 1.57 (d, J=6.8 Hz, 6H), 1.38 (d, J=9.2 Hz, 2H); MS (ESI): m/z 930.45 $[M+H]^+$.

Example 7—Synthesis of Compound 40

Step 1: benzyl 4-{2-[1-(tert-butoxycarbonyl)-4-hydroxypiperidin-4-yl]acetyl}piperazine-1-carboxylate

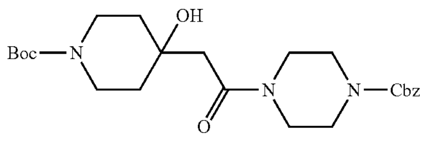 [SMILES: CC(C)(C)OC(=O)N1CCC(O)(CC(=O)N2CCN(C(=O)OCc3ccccc3)CC2)CC1]

To a stirred mixture of [1-(tert-butoxycarbonyl)-4-hydroxypiperidin-4-yl]acetic acid (600 mg, 2.3 mmol) and benzyl piperazine-1-carboxylate (509.7 mg, 2.3 mmol) in N,N-dimethylformamide (10 mL) was added N,N-diisopropylethylamine (2.02 mL, 12 mmol) at room temperature. The resulting mixture was stirred for 5 min at room temperature. Then propanephosphonic acid anhydride (2.94 g, 9.3 mmol) was added to keep the pH over 9. The resulting mixture was stirred for 1 h at room temperature, then diluted with water and extracted with ethyl acetate (2×300 mL). The combined organic layers were washed with brine (2×100 mL), dried over anhydrous sodium sulfate, filtered, and concentrated under reduced pressure. The residue was purified by silica gel column chromatography (dichloromethane/ethyl acetate=1:1) to afford benzyl 4-{2-[1-(tert-butoxycarbonyl)-4-hydroxypiperidin-4-yl]acetyl}piperazine-1-carboxylate (930 mg, 87%) as a light yellow solid. MS (ESI): m/z 462.25 $[M+H]^+$.

Step 2: benzyl 4-[2-(4-hydroxypiperidin-4-yl)acetyl]piperazine-1-carboxylate

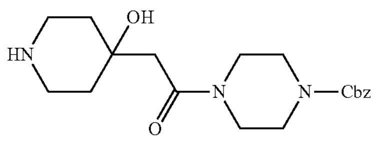 [SMILES: O=C(CC1(O)CCNCC1)N1CCN(C(=O)OCc2ccccc2)CC1]

To a stirred solution of benzyl 4-{2-[1-(tert-butoxycarbonyl)-4-hydroxypiperidin-4-yl]acetyl}piperazine-1-carboxylate (500 mg, 1.1 mmol) in dioxane (4 mL) was added hydrochloric acid in 1,4-dioxane (8 mL) dropwise at room temperature. The resulting mixture was stirred for 1 h at room temperature, then concentrated under vacuum to afford benzyl 4-[2-(4-hydroxypiperidin-4-yl)acetyl]piperazine-1-carboxylate hydrochloride (390 mg) as a light yellow solid. MS (ESI): m/z 362.15 $[M+H]^+$.

Step 3: benzyl 4-(2-{1-[2-(2,6-dioxopiperidin-3-yl)-4-fluoro-1-oxo-3H-isoindol-5-yl]-4-hydroxypiperidin-4-yl}acetyl)piperazine-1-carboxylate

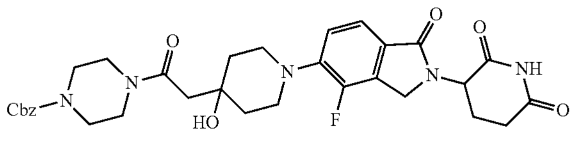 [SMILES: O=C1CCC(N2Cc3c(ccc(N4CCC(O)(CC(=O)N5CCN(C(=O)OCc6ccccc6)CC5)CC4)c3F)C2=O)C(=O)N1]

To a stirred mixture of benzyl 4-[2-(4-hydroxypiperidin-4-yl)acetyl]piperazine-1-carboxylate (212 mg, 0.6 mmol) and 3-(5-bromo-4-fluoro-1-oxo-3H-isoindol-2-yl)piperidine-2,6-dione (200 mg, 0.6 mmol) in N, N-dimethylformamide (10 mL) was added dichloro[1,3-bis(2,6-di-3-pentylphenyl)imidazol-2-ylidene](3-chloropyridyl)palladium (II) (4.93 mg, 0.006 mmol) and cesium carbonate (573 mg, 1.8 mmol) at room temperature. The resulting mixture was stirred for 2 h at 100° C. under nitrogen atmosphere. The reaction was quenched by saturated ammonium chloride solution (300 mL) at room temperature. The resulting mixture was extracted with ethyl acetate (2×300 mL). The combined organic layers were washed with brine (2×50 mL), dried over anhydrous sodium sulfate, filtered, and concentrated under reduced pressure. The residue was purified by reversed-phase flash chromatography (column, C18 silica gel; mobile phase, acetonitrile in water (10 mmol/L $NH_4HCO_3$), 0% to 50% gradient in 40 min) to afford benzyl 4-(2-{1-[2-(2,6-dioxopiperidin-3-yl)-4-fluoro-1-oxo-3H-isoindol-5-yl]-4-hydroxypiperidin-4-yl}acetyl)piperazine-1-carboxylate (190 mg, 52%) as a light yellow solid. MS (ESI): m/z 622.25 $[M+H]^+$.

Step 4: 3-(4-fluoro-5-{4-hydroxy-4-[2-oxo-2-(piperazin-1-yl)ethyl]piperidin-1-yl}-1-oxo-3H-isoindol-2-yl)piperidine-2,6-dione

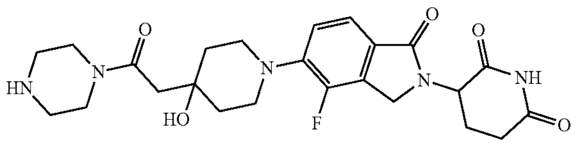 [SMILES: O=C1CCC(N2Cc3c(ccc(N4CCC(O)(CC(=O)N5CCNCC5)CC4)c3F)C2=O)C(=O)N1]

To benzyl 4-(2-{1-[2-(2,6-dioxopiperidin-3-yl)-4-fluoro-1-oxo-3H-isoindol-5-yl]-4-hydroxypiperidin-4-yl}acetyl) piperazine-1-carboxylate (180 mg, 0.3 mmol) was added trifluoroacetic acid (5.0 mL, 67 mmol) at room temperature. The resulting mixture was stirred for 2 h at 60° C., then concentrated under vacuum to afford 3-(4-fluoro-5-{4-hydroxy-4-[2-oxo-2-(piperazin-1-yl)ethyl]piperidin-1-yl}-1-oxo-3H-isoindol-2-yl)piperidine-2,6-dione (140 mg, 99/a) as a brown yellow oil. MS (ESI): m/z 488.25 $[M+H]^+$.

Step 5: 2-{[6-({5-chloro-2-[4-(2-{1-[2-(2,6-dioxopiperidin-3-yl)-4-fluoro-1-oxo-3H-isoindol-5-yl]-4-hydroxypiperidin-4-yl}acetyl)piperazin-1-yl]pyrimidin-4-yl}amino)-1-isopropyl-2-oxoquinolin-3-yl]oxy}-N-methylacetamide

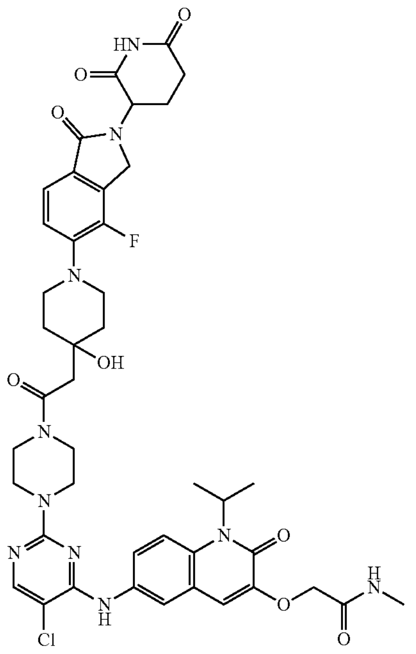 [SMILES: CNC(=O)COc1cc2cc(Nc3nc(N4CCN(C(=O)CC5(O)CCN(c6ccc7c(c6F)CN(C6CCC(=O)NC6=O)C7=O)CC5)CC4)ncc3Cl)ccc2n(C(C)C)c1=O]

To a stirred mixture of 3-(4-fluoro-5-{4-hydroxy-4-[2-oxo-2-(piperazin-1-yl)ethyl]piperidin-1-yl}-1-oxo-3H-isoindol-2-yl)piperidine-2,6-dione (104.51 mg, 0.2 mmol) and 2-({6-[(5-chloro-2-fluoropyrimidin-4-yl)amino]-1-isopropyl-2-oxoquinolin-3-yl}oxy)-N-methylacetamide (60 mg, 0.1 mmol) in dimethyl sulfoxide (4 mL) was added N,N-diisopropylethylamine (2 mL) at room temperature. The reaction was stirred for 6 h at 50° C. The crude material was purified by reversed-phase flash chromatography (column, C18 silica gel; mobile phase, acetonitrile in water (10 mmol/L $NH_4HCO_3$), 0% to 40% gradient in 40 min) to afford 2-([6-({5-chloro-2-[4-(2-{1-[2-(2,6-dioxopiperidin-3-yl)-4-fluoro-1-oxo-3H-isoindol-5-yl]-4-hydroxypiperidin-4-yl}acetyl)piperazin-1-yl]pyrimidin-4-yl}amino)-1-isopropyl-2-oxoquinolin-3-yl]oxy)-N-methylacetamide (53.3 mg, 40%) as an off-white solid. MS (ESI): m/z 887.40 $[M+H]^+$; $^1H$ NMR (300 MHz, DMSO-d6) δ 10.98 (s, 1H), 8.90 (s, 1H), 8.09 (s, 1H), 8.01-7.90 (m, 2H), 7.72 (d, J=3.0 Hz, 2H), 7.46 (d, J=8.1 Hz, 1H), 7.18 (t, J=7.9 Hz, 1H), 7.08 (s, 1H), 5.32 (s, 1H), 5.07 (dd, J=13.2, 5.1 Hz, 1H), 4.96 (s, 1H), 4.56 (s, 2H), 4.48 (d, J=17.0 Hz, 1H), 4.30 (d, J=16.9 Hz, 1H), 3.64 (t, J=13.5 Hz, 8H), 3.13 (t, J=10.7 Hz, 2H), 3.00-2.82 (m, 1H), 2.71-2.51 (m, 6H), 2.47-2.32 (m, 1H), 1.97 (d, J=11.9 Hz, 1H), 1.87-1.66 (m, 4H), 1.58 (d, J=6.8 Hz, 6H), 1.23 (s, 1H).

Example 8—Synthesis of Compound 41

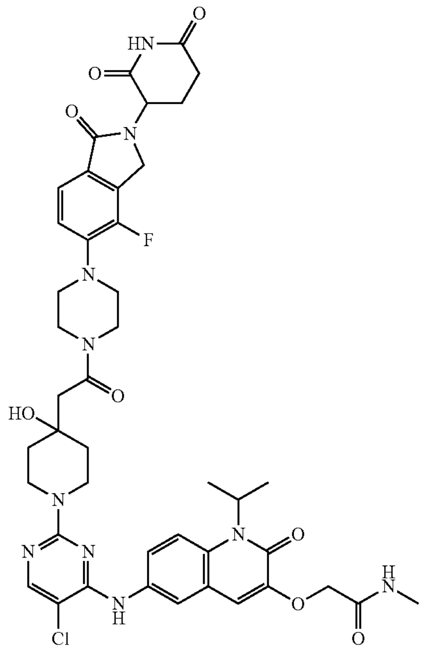 [SMILES: CNC(=O)COc1cc2cc(Nc3nc(N4CCC(O)(CC(=O)N5CCN(c6ccc7c(c6F)CN(C6CCC(=O)NC6=O)C7=O)CC5)CC4)ncc3Cl)ccc2n(C(C)C)c1=O]

The title compound can be prepared analogously to Compound 40 (11) by removing the Cbz protecting group first from the intermediate prepared in step 1. $^1H$ NMR (400 MHz, DMSO) δ 11.00 (s, 1H), 8.83 (s, 1H), 8.05 (s, 1H), 7.98 (d, J=4.8 Hz, 1H), 7.92 (d, J=2.3 Hz, 1H), 7.77-7.66 (m, 2H), 7.49 (d, J=8.1 Hz, 1H), 7.17 (t, J=7.9 Hz, 1H), 7.02 (s, 1H), 5.34 (s, 1H), 5.09 (dd, J=13.3, 5.1 Hz, 1H), 5.00 (s, 1H), 4.51 (d, J=23.6 Hz, 3H), 4.33 (d, J=17.0 Hz, 1H), 4.15 (s, 2H), 3.69 (d, J=16.6 Hz, 4H), 3.34-3.26 (m, 1H), 3.12 (d, J=15.6 Hz, 4H), 2.92 (ddd, J=17.5, 13.6, 5.4 Hz, 1H), 2.68 (d, J=4.7 Hz, 3H), 2.61 (d, J=3.6 Hz, 1H), 2.56 (s, 3H), 2.42 (qd, J=13.1, 4.5 Hz, 1H), 1.98 (d, J=12.6 Hz, 1H), 1.63-1.53 (m, 9H); MS (ESI): m/z 887.40 $[M+H]^+$.

Example 9—Synthesis of Compound 42

Step 1: benzyl 4-[1-(tert-butoxycarbonyl)-3,3-difluoro-2,6-dihydropyridin-4-yl]piperazine-1-carboxylate

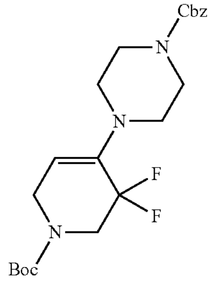 [SMILES: CC(C)(C)OC(=O)N1CC=C(N2CCN(C(=O)OCc3ccccc3)CC2)C(F)(F)C1]

A solution of benzyl piperazine-1-carboxylate (1 g, 4.9 mmol) in toluene (1.5 ml) and acetonitrile (15 mL) was treated with sodium acetate (1.0 g, 12 mmol) for 15 min at room temperature under nitrogen atmosphere, followed by the addition of tert-butyl 3,3-difluoro-4-oxopiperidine-1-carboxylate (1.8 g, 7.5 mmol) in portions at room temperature. The resulting mixture was stirred for 16 h at 100° C. under nitrogen atmosphere. The mixture was allowed to cool down to room temperature, filtered. The filter cake was washed with dichloromethane (3×100 mL), the filtrate was concentrated under reduced pressure to afford benzyl 4-[1-(tert-butoxycarbonyl)-3,3-difluoro-2,6-dihydropyridin-4-yl] piperazine-1-carboxylate (1.1 g, 50%) as light yellow oil. MS (ESI): m: 438.25 $[M+H]^+$.

Step 2: benzyl 4-[1-(tert-butoxycarbonyl)-3,3-difluoropiperidin-4-yl]piperazine-1-carboxylate

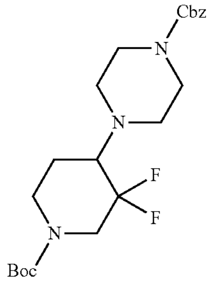 [SMILES: CC(C)(C)OC(=O)N1CCC(N2CCN(C(=O)OCc3ccccc3)CC2)C(F)(F)C1]

A mixture of benzyl 4-[1-(tert-butoxycarbonyl)-3,3-difluoro-2,6-dihydropyridin-4-yl]piperazine-1-carboxylate (1.1 g, 2.5 mmol), acetic acid (1.5 ml) and sodium cyanoborohydride (0.5 g, 7.4 mmol) in dichloroethane (15 mL) was stirred overnight at room temperature. The mixture was diluted with water, extracted with dichloromethane (3×80 mL). The combined organic layers were washed with brine (3×30 mL), dried over anhydrous sodium sulfate, filtered, and concentrated under reduced pressure. The residue was purified by reversed-phase flash chromatography (column: C18 silica gel; mobile phase: acetonitrile in water (10 mmol/L $NH_4HCO_3$), 5% to 60% gradient in 30 min) to afford benzyl 4-[1-(tert-butoxycarbonyl)-3,3-difluoropiperidin-4-yl]piperazine-1-carboxylate (1.5 g, 71%) as light yellow oil. MS (ESI): m/z 440.30 $[M+H]^+$.

Step 3: tert-butyl 3,3-difluoro-4-(piperazin-1-yl) piperidine-1-carboxylate

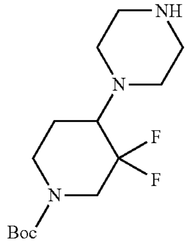 [SMILES: CC(C)(C)OC(=O)N1CCC(N2CCNCC2)C(F)(F)C1]

To a solution of benzyl 4-[1-(tert-butoxycarbonyl)-3,3-difluoropiperidin-4-yl]piperazine-1-carboxylate (1.5 g, 3.4 mmol) in isopropanol (30 mL) was added 10% $Pd(0H)_2/C$ (300 mg) under nitrogen atmosphere. The mixture was then degassed and purged with hydrogen. The reaction mixture was stirred at 30° C. for 2 h under hydrogen atmosphere using a hydrogen balloon, then filtered through a Celite pad and concentrated under reduced pressure to afford tert-butyl 3,3-difluoro-4-(piperazin-1-yl) piperidine-1-carboxylate) (1.05 g, 92%) as colorless oil.

Step 4: tert-butyl 4-{4-[2-(2,6-dioxopiperidin-3-yl)-4-fluoro-1-oxo-3H-isoindol-5-yl]piperazin-1-yl}-3,3-difluoropiperidine-1-carboxylate

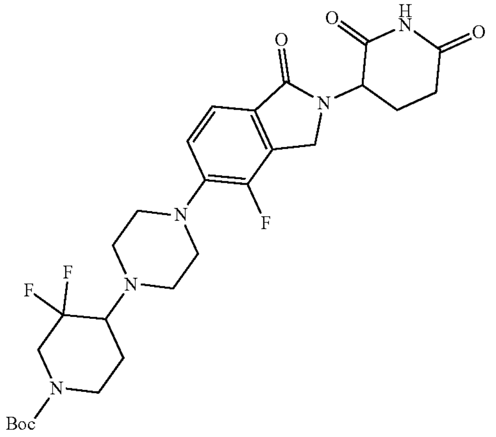 [SMILES: CC(C)(C)OC(=O)N1CCC(N2CCN(c3ccc4c(c3F)CN(C3CCC(=O)NC3=O)C4=O)CC2)C(F)(F)C1]

To a stirred solution of tert-butyl 3,3-difluoro-4-(piperazin-1-yl)piperidine-1-carboxylate (200 mg, 0.7 mmol) and 3-(5-bromo-4-fluoro-1-oxo-3H-isoindol-2-yl)piperidine-2,6-dione (223 mg, 0.7 mmol) in N, N-dimethylformamide (5 mL) was added {1,3-bis[2,6-bis(pentan-3-yl)phenyl]-4,5-dichloro-2,3-dihydro-1H-imidazol-2-yl}dichloro(2-methyl-1lambda4-pyridin-1-yl)palladium (55 mg, 0.1 mmol) and cesium carbonate (640 mg, 2.0 mmol). The resulting mixture was stirred for 2 h at 100° C. under nitrogen atmosphere. The residue was diluted with water (400 mL), extracted with ethyl acetate (2×100 mL). The combined organic layers were washed with brine (1×100 mL), dried over anhydrous sodium sulfate, filtered, and concentrated under reduced pressure. The residue was purified by reverse flash chromatography (column: C18 silica gel; mobile phase: acetonitrile/water (10 mmol/L $NH_4HCO_3$), 5% to 65% gradient in 30 min) to afford tert-butyl 4-{4-[2-(2,6-dioxopiperidin-3-yl)-4-fluoro-1-oxo-3H-isoindol-5-yl]piperazin-1-yl}-3,3-difluoropiperidine-1-carboxylate (110 mg, 30%) as a brown solid. MS (ESI): m/z 566.40 $[M+H]^+$.

Step 5: 3-{5-[4-(3,3-difluoropiperidin-4-yl)piperazin-1-yl]-4-fluoro-1-oxo-3H-isoindol-2-yl}piperidine-2,6-dione

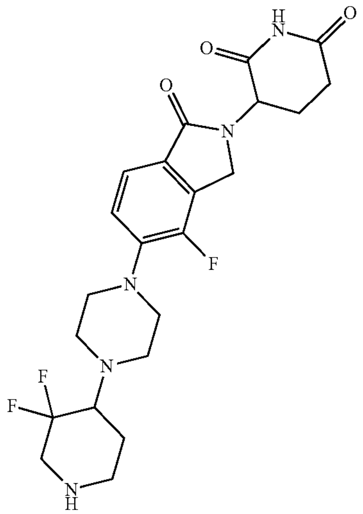 [SMILES: O=C1CCC(N2Cc3c(ccc(N4CCN(C5CCNCC5(F)F)CC4)c3F)C2=O)C(=O)N1]

A solution of tert-butyl 4-{4-[2-(2,6-dioxopiperidin-3-yl)-4-fluoro-1-oxo-3H-isoindol-5-yl]piperazin-1-yl}-3,3-difluoropiperidine-1-carboxylate (110.0 mg, 0.2 mmol) and trifluoroacetic acid (2 mL) in dichloromethane (10 mL) was stirred for 2 h at room temperature. The reaction was concentrated to afford 3-{5-[4-(3,3-difluoropiperidin-4-yl)piperazin-1-yl]-4-fluoro-1-oxo-3H-isoindol-2-yl}piperidine-2,6-dione (88.2 mg, 97%) as brown oil. MS (ESI): m/z 466.25 $[M+H]^+$.

Step 6: 2-({6-[(5-chloro-2-{4-[(4-{4-[2-(2,6-dioxopiperidin-3-yl)-4-fluoro-1-oxo-3H-isoindol-5-yl]piperazin-1-yl}-3,3-difluoropiperidin-1-yl)methyl]piperidin-1-yl}pyrimidin-4-yl)amino]-1-isopropyl-2-oxoquinolin-3-yl}oxy)-N-methylacetamide

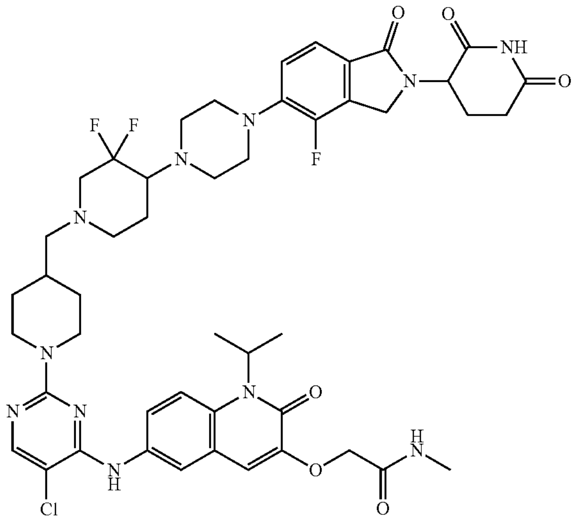

To a mixture of 3-{5-[4-(3,3-difluoropiperidin-4-yl)piperazin-1-yl]-4-fluoro-1-oxo-3H-isoindol-2-yl}piperidine-2, 6-dione (88.2 mg, 0.2 mmol) in dichloroethane (10 mL) and dimethyl sulfoxide (1 mL) was added 2-[(6-{[5-chloro-2-(4-formylpiperidin-1-yl)pyrimidin-4-yl]amino}-1-isopropyl-2-oxoquinolin-3-yl)oxy]-N-methylacetamide (97.0 mg, 0.2 mmol) and N,N-diisopropylethylamine (0.1 mL). The resulting mixture was stirred overnight at room temperature under nitrogen atmosphere. Then sodium triacetoxyborohydride (120.2 mg, 0.6 mmol) was added and stirred for 2 h under nitrogen. The reaction was quenched by water (30 mL), extracted with dichloromethane (50 mL×3). The combined organic layers were washed with brine (30 mL), dried over anhydrous sodium sulfate, filtered, and concentrated under reduced pressure. The residue was purified by reverse flash chromatography (column, C18 silica gel; mobile phase, acetonitrile/water (10 mmol/L $NH_4HCO_3$), 5% to 70% gradient in 30 min) to afford 2-({6-[(5-chloro-2-{4-[(4-(4-[2-(2,6-dioxopiperidin-3-yl)-4-fluoro-1-oxo-3H-isoindol-5-yl] piperazin-1-yl-3,3-difluoropiperidin-1-yl)methyl]piperidin-1-yl}pyrimidin-4-yl)amino]-1-isopropyl-2-oxoquinolin-3-yl}oxy)-N-methylacetamide (69.3 mg, 36%) as an off-white solid. $^1$H NMR (300 MHz, DMSO) δ 11.11-10.82 (m, 1H), 8.78 (s, 1H), 8.02-7.93 (m, 3H), 7.77-7.63 (m, 2H), 7.46 (d, J=8.4 Hz, 1H), 7.14 (d, J=7.8 Hz, 1H), 7.01 (s, 1H), 5.60-5.33 (m, 1H), 5.06 (d, J=13.2 Hz, 1H), 4.48 (d, J=22.2 Hz, 5H), 4.30 (d, J=16.8 Hz, 1H), 3.09 (s, 4H), 2.99-2.79 (m, 10H), 2.66 (d, J=4.6 Hz, 3H), 2.60 (s, 1H), 2.54 (d, J=5.9 Hz, 1H), 2.39-1.98 (m, 5H), 1.74 (s, 5H), 1.55 (d, J=6.9 Hz, 6H), 1.12-0.90 (d, J=12.3 Hz, 2H); MS (ESI): m/z 962.50 $[M+H]^+$.

Example 10—Synthesis of Compound 43

Step 1: 2-([6-({5-chloro-2-[4-(dimethoxymethyl) piperidin-1-yl]pyrimidin-4-yl)amino)-1-isopropyl-2-oxoquinolin-3-yl]oxy}-N-methylacetamide

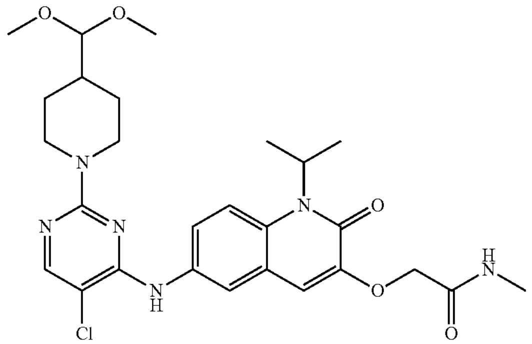

Into a 100 mL round-bottom flask were added 2-({6-[(5-chloro-2-fluoropyrimidin-4-yl)amino]-1-isopropyl-2-oxoquinolin-3-yl}oxy)-N-methylacetamide (500 mg, 1.2 mmol) and DMSO (5 mL) at room temperature. The resulting mixture was stirred for 4 h at 50° C., suspended in water at 0° C., filtered. The resulting solid was dried under infrared light to afford 2-{[6-({5-chloro-2-[4-(dimethoxymethyl)piperidin-1-yl]pyrimidin-4-yl}amino)-1-isopropyl-2-oxoquinolin-3-yl]oxy}-N-methylacetamide (620 mg, 93%) as a brown solid. MS (ESI): m/z 559.05 $[M+H]^+$.

Step 2: 2-((6-((5-chloro-2-(4-formylpiperidin-1-yl) pyrimidin-4-yl)amino)-1-isopropyl-2-oxo-1,2-dihydroquinolin-3-yl)oxy)-N-methylacetamide

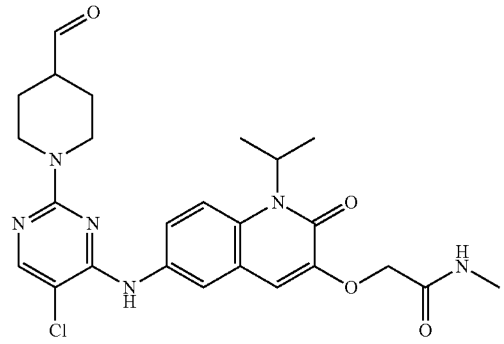 [SMILES: CNC(=O)COc1cc2cc(Nc3nc(N4CCC(C=O)CC4)ncc3Cl)ccc2n(C(C)C)c1=O]

To a mixture of 2-[[6-([5-chloro-2-[4-(dimethoxymethyl) piperidin-1-yl]pyrimidin-4-yl]amino)-1-isopropyl-2-oxoquinolin-3-yl]oxy]-N-methylacetamide (220 mg) in water (1.0 mL) was added trifluroacetic acid (2.0 mL) and dichloromethane (4.0 mL). The resulting mixture was stirred overnight at 40° C. under air atmosphere. Then, the reaction mixture was concentrated under reduced pressure to get 2-[(6-[[5-chloro-2-(4-formylpiperidin-1-yl)pyrimidin-4-yl] amino]-1-isopropyl-2-oxoquinolin-3-yl)oxy]-N-methylacetamide (202 mg) as a yellow oil, which was used in the next step without further purification.

Step 3: 1-[(4E)-1-(tert-butoxycarbonyl)-3,3-difluoropiperidin-4-ylidene]-4-(4,4,5,5-tetramethyl-1,3,2-dioxaborolan-2-yl)-1,2,3,6-tetrahydro-1lambda5-pyridin-1-ylium

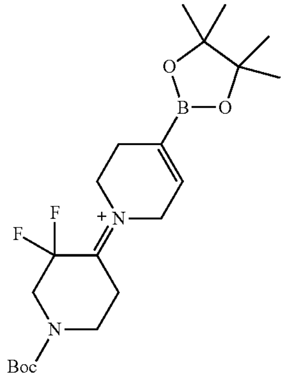

To a stirred solution of 4-(4,4,5,5-tetramethyl-1,3,2-dioxaborolan-2-yl)-1,2,3,6-tetrahydropyridine (4.0 g, 19 mmol) in acetonitrile/toluene (20 mL/40 mL) was added sodium acetate (5.6 g, 68 mmol) and acetic acid (4 mL). The resulting mixture was stirred for 15 min. Then tert-butyl 3,3-difluoro-4-oxopiperidine-1-carboxylate (5.76 g, 24 mmol) was added, stirred for 4 h at 100° C. The mixture was filtered, the filter cake was washed with dichloromethane (20 mL×3). The filtrate was concentrated under reduced pressure to afford 1-[(4E)-1-(tert-butoxycarbonyl)-3,3-difluoropiperidin-4-ylidene]-4-(4,4,5,5-tetramethyl-1,3,2-dioxaborolan-2-yl)-1,2,3,6-tetrahydro-1lambda5-pyridin-1-ylium (1.1 g) as a white solid. MS (ESI): m/z 427.30 $[M+H]^+$.

Step 4: tert-butyl 3,3-difluoro-4-[4-(4,4,5,5-tetramethyl-1,3,2-dioxaborolan-2-yl)-3,6-dihydro-2H-pyridin-1-yl]piperidine-1-carboxylate

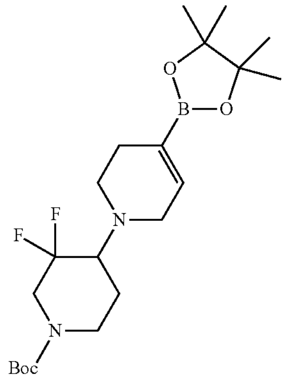 [SMILES: CC(C)(C)OC(=O)N1CCC(N2CC=C(B3OC(C)(C)C(C)(C)O3)CC2)C(F)(F)C1]

A solution of 1-[(4E)-1-(tert-butoxycarbonyl)-3,3-difluoropiperidin-4-ylidene]-4-(4,4,5,5-tetramethyl-1,3,2-dioxaborolan-2-yl)-1,2,3,6-tetrahydro-1lambda5-pyridin-1-ylium (1.1 g, 2.5 mmol) and sodium triacetoxyborohydride (8.6 g, 40 mmol) in dichloroethane (10 mL) was stirred overnight at room temperature. Diluted with water and extracted with dichloromethane (20 mL×3), combined and concentrated. The residue was purified by reversed-phase flash chromatography (column, C18 silica gel; mobile phase, acetonitrile in water (10 mmol/L $NH_4HCO_3$), 10% to 80% gradient in 30 min) to afford tert-butyl 3,3-difluoro-4-[4-(4,4,5,5-tetramethyl-1,3,2-dioxaborolan-2-yl)-3,6-dihydro-2H-pyridin-1-yl]piperidine-1-carboxylate (1.1 g) as a white solid. MS (ESI): m/z 429.20 $[M+H]^+$.

Step 5: tert-butyl 4-{4-[2-(2,6-dioxopiperidin-3-yl)-4-fluoro-1-oxo-3H-isoindol-5-yl]-3,6-dihydro-2H-pyridin-1-yl}-3,3-difluoropiperidine-1-carboxylate

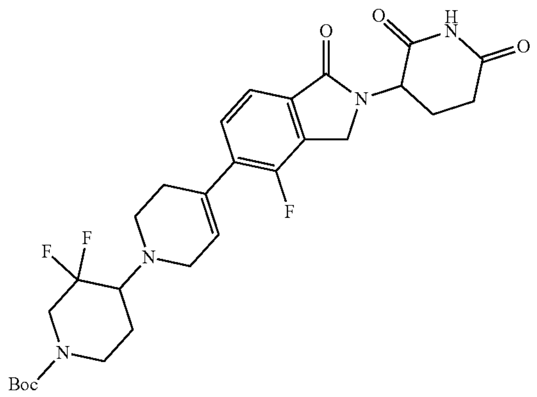 [SMILES: CC(C)(C)OC(=O)N1CCC(N2CC=C(c3ccc4c(c3F)CN(C3CCC(=O)NC3=O)C4=O)CC2)C(F)(F)C1]

To a stirred solution of tert-butyl 3,3-difluoro-4-[4-(4,4,5,5-tetramethyl-1,3,2-dioxaborolan-2-yl)-3,6-dihydro-2H-pyridin-1-yl]piperidine-1-carboxylate (150 mg, 0.4 mmol) and 3-(5-bromo-4-fluoro-1-oxo-3H-isoindol-2-yl)piperidine-2,6-dione (119.5 mg, 0.4 mmol) in dioxane (2 mL) and water (0.2 mL) was added [1,1'-bis(di-tert-butylphosphino)ferrocene]dichloropalladium(II) (45 mg, 0.07 mmol) and cesium fluoride (159.59 mg, 1.0 mmol). The resulting mixture was stirred for 3 h at 90° C. under nitrogen atmosphere, then diluted with water and extracted with ethyl acetate (20 mL×3). The combined organic layers were washed with brine (20 mL×3), dried over anhydrous sodium sulfate, filtered, and concentrated under reduced pressure. The residue was purified by silica gel column chromatography (petroleum ether/ethyl acetate=1:3) to afford tert-butyl 4-{4-[2-(2,6-dioxopiperidin-3-yl)-4-fluoro-1-oxo-3H-isoindol-5-yl]-3,6-dihydro-2H-pyridin-1-yl}-3,3-difluoropiperidine-1-carboxylate (118 mg, 59%) as a white solid. MS (ESI): m/z 563.40 $[M+H]^+$.

Step 6: tert-butyl 4-[2-(2,6-dioxopiperidin-3-yl)-4-fluoro-1-oxo-3H-isoindol-5-yl]-3',3'-difluoro-[1,4'-bipiperidine]-1'-carboxylate

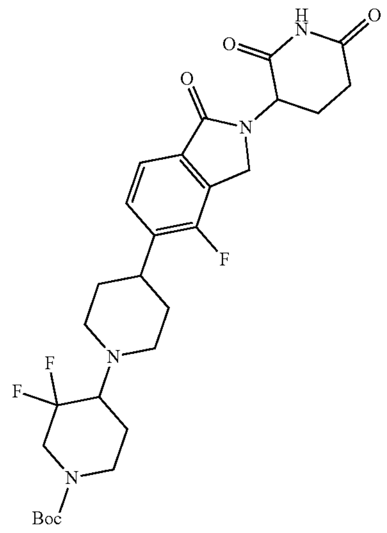 [SMILES: CC(C)(C)OC(=O)N1CCC(N2CCC(c3ccc4c(c3F)CN(C3CCC(=O)NC3=O)C4=O)CC2)C(F)(F)C1]

A mixture of tert-butyl 4-{4-[2-(2,6-dioxopiperidin-3-yl)-4-fluoro-1-oxo-3H-isoindol-5-yl]-3,6-dihydro-2H-pyridin-1-yl}-3,3-difluoropiperidine-1-carboxylate (150 mg, 0.3 mmol) and Pd/C (70 mg) in tetrahydrofuran (1 mL) and isopropanol (5 mL) was degassed and purged with hydrogen, then stirred overnight at 40° C. under hydrogen atmosphere. The resulting mixture was filtered through Celite, washed with dichloromethane (10 mL×3). The filtrate was concentrated under reduced pressure to afford tert-butyl 4-[2-(2,6-dioxopiperidin-3-yl)-4-fluoro-1-oxo-3H-isoindol-5-yl]-3',3'-difluoro-[1,4'-bipiperidine]-1'-carboxylate (118 mg, 78%) as a white solid. MS (ESI): m/z 565.40 $[M+H]^+$.

Step 7: 3-(5-(3',3'-difluoro-[1,4'-bipiperidin]-4-yl)-4-fluoro-1-oxo-3H-isoindol-2-yl)piperidine-2,6-dione

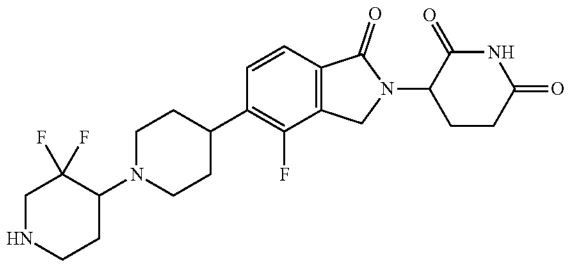 [SMILES: O=C1CCC(N2Cc3c(ccc(C4CCN(C5CCNCC5(F)F)CC4)c3F)C2=O)C(=O)N1]

A solution of tert-butyl 4-[2-(2,6-dioxopiperidin-3-yl)-4-fluoro-1-oxo-3H-isoindol-5-yl]-3',3'-difluoro-[1,4'-bipiperidine]-1'-carboxylate (106 mg, 0.2 mmol) and trifluoracetic acid (2 mL) in dichloromethane (3 mL) was stirred overnight at room temperature. The reaction was concentrated under reduced pressure to afford 3-(5-{3',3'-difluoro-[1,4'-bipiperidin]-4-yl}-4-fluoro-1-oxo-3H-isoindol-2-yl)piperidine-2,6-dione trifluroacetate (87 mg) as a white solid. MS (ESI): m/z 465.25 $[M+H]^+$.

Step 8: 2-{[6-({5-chloro-2-[4-({4-[2-(2,6-dioxopiperidin-3-yl)-4-fluoro-1-oxo-3H-isoindol-5-yl]-3',3'-difluoro-[1,4'-bipiperidin]-1'-yl}methyl)piperidin-1-yl]pyrimidin-4-yl}amino)-1-isopropyl-2-oxoquinolin-3-yl]oxy}-N-methylacetamide

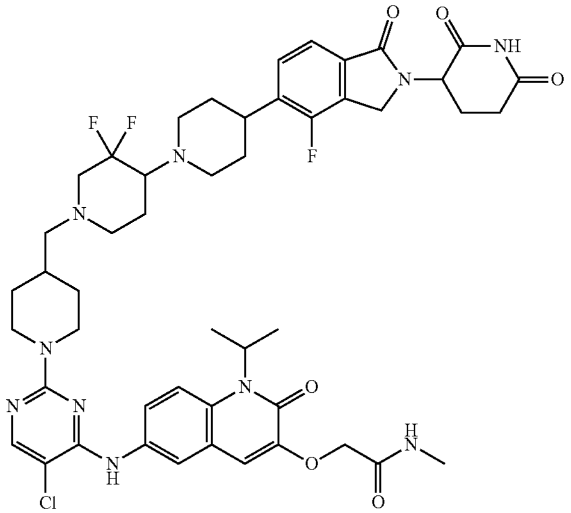

To a stirred mixture of 3-(5-{3',3'-difluoro-[1,4'-bipiperidin]-4-yl}-4-fluoro-1-oxo-3H-isoindol-2-yl)piperidine-2,6-dione (87 mg, 0.2 mmol) in dimethyl sulfoxide (1 mL) and dichloroethane (10 mL) was added 2-[(6-{[5-chloro-2-(4-formylpiperidin-1-yl)pyrimidin-4-yl]amino}-1-isopropyl-2-oxoquinolin-3-yl)oxy]-N-methylacetamide (96 mg, 0.2 mmol) in dichloroethane (2 mL). The mixture was basified to pH 7-8 with N,N-diisopropylethylamine, stirred overnight at room temperature. To the above mixture was added sodium triacetoxyborohydride (119 mg, 0.6 mmol) and stirred for 2 h at room temperature. The reaction mixture was filtered, the filter cake was washed with dichioromethane. The filtrate was concentrated under reduced pressure. The residue was purified by reversed-phase flash chromatography (column, C18 silica gel; mobile phase, acetonitrile in water (10 mmol/L $NH_4HCO_3$), 10% to 80% gradient in 30 min) to afford 2-{[6-({5-chloro-2-[4-({4-[2-(2,6-dioxopiperidin-3-yl)-4-fluoro-1-oxo-3H-isoindol-5-yl]-3',3'-difluoro-[1,4'-bipiperidin]-1'-yl}methyl)piperidin-1-yl]pyrimidin-4-yl}amino)-1-isopropyl-2-oxoquinolin-3-yl]oxy}-N-methylacetamide (50.9 mg) as a white solid. $^1H$ NMR (300 MHz, DMSO) δ 11.01 (s, 1H), 8.81 (s, 1H), 8.04 (s, 1H), 7.95 m, 2H), 7.69 (m, 2H), 7.54 (s, 2H), 7.15 (s, 1H), 5.11 (m, 1H), 4.61-4.36 (m, 6H), 3.01-2.89 (s, 8H), 2.83 (m, 5H), 2.71-2.54 (m, 2H), 2.21-2.02 (s, 6H), 1.73 (s, 9H), 1.57 (m, 7H), 1.02 (s, 2H); MS (ESI): m/z 961.50 $[M+H]^+$.

Example 11—Synthesis of Compound 44

Step 1: tert-butyl 3'-fluoro-3,6-dihydro-2H-[4,4'-bipyridine]-1-carboxylate

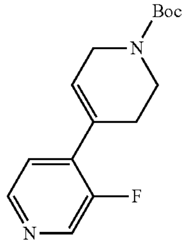 [SMILES: CC(C)(C)OC(=O)N1CC=C(c2ccncc2F)CC1]

To a stirred mixture of 4-bromo-3-fluoropyridine (5.0 g, 28 mmol) and tert-butyl 4-(4,4,5,5-tetramethyl-1,3,2-dioxaborolan-2-yl)-3,6-dihydro-2H-pyridine-1-carboxylate (8.78 g, 28 mmol) in dioxane (20 mL) and water (2 mL) was added sodium carbonate (9.03 g, 85 mmol) and [1,1'-bis(diphenylphosphino)ferrocene]dichloropalladium(II) (2.31 g, 2.8 mmol). The resulting mixture was stirred for 2 h at 80° C. under nitrogen atmosphere, then diluted with water, and extracted with ethyl acetate (3×10 mL). The combined organic layers were washed with brine (3×10 mL), dried over anhydrous sodium sulfate, filtered, and concentrated under reduced pressure. The residue was purified by silica gel column chromatography (petroleum ether/ethyl acetate=10:1) to afford tert-butyl 3'-fluoro-3,6-dihydro-2H-[4,4'-bipyridine]-1-carboxylate (7.3 g, 92%) as a yellow oil. MS (ESI): m, 279.2 $[M+H]^+$.

Step 2: tert-butyl 1-benzyl-1'-(tert-butoxycarbonyl)-3-fluoro-3',6'-dihydro-2'H-[4,4'-bipyridin]-1-ium

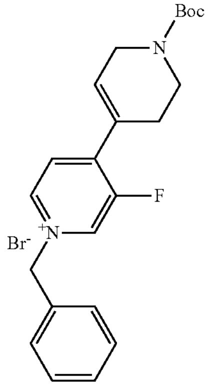 [SMILES: [Br-] ; CC(C)(C)OC(=O)N1CC=C(c2cc[n+](Cc3ccccc3)cc2F)CC1]

To a solution of tert-butyl 3'-fluoro-3,6-dihydro-2H-[4,4'-bipyridine]-1-carboxylate (7.3 g, 26 mmol) and acetone (70 mL) was added benzyl bromide (5.38 g, 31 mmol) dropwise over 3 min at 0° C. The resulting mixture was stirred overnight at 60° C., then concentrated under vacuum. The residue was triturated with petroleum ether (600 mL) to afford 1-benzyl-1'-(tert-butoxycarbonyl)-3-fluoro-3',6'-dihydro-2'H-[4,4'-bipyridin]-1-ium (9 g, 93%) as a brown solid. MS (ESI): m/z 370.3 $[M+H]^+$.

Step 3: tert-butyl 1'-benzyl-3'-fluoro-2H,2'H,3H,3'H,6H,6'H-[4,4'-bipyridine]-1-carboxylate

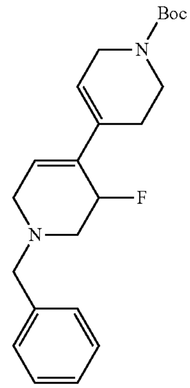 [SMILES: CC(C)(C)OC(=O)N1CC=C(C2=CCN(Cc3ccccc3)CC2F)CC1]

To a solution of 1-benzyl-1'-(tert-butoxycarbonyl)-3-fluoro-3',6'-dihydro-2'H-[4,4'-bipyridin]-1-ium (9 g) in methanol (200 mL) was added $NaBH_4$ (4.61 g, 122 mmol) in batches at room temperature. The resulting mixture was stirred for 2 days at room temperature, then diluted with water, extracted with ethyl acetate (3×10 mL). The combined organic layers were washed with brine (3×10 mL), dried over anhydrous sodium sulfate, filtered, and concentrated under reduced pressure. The residue was purified by silica gel column chromatography (petroleum ether/ethyl acetate=10:1) to afford tert-butyl 1'-benzyl-3'-fluoro-2H,2'H,3H,3'H,6H,6'H-[4,4'-bipyridine]-1-carboxylate (3.5 g, 39%) as a yellow oil. MS (ESI): m/z 373.30 $[M+H]^+$.

Step 4: tert-butyl 3'-fluoro-[4,4'-bipiperidine]-1-carboxylate

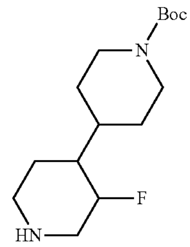 [SMILES: CC(C)(C)OC(=O)N1CCC(C2CCNCC2F)CC1]

A mixture of tert-butyl 1'-benzyl-3'-fluoro-2H,2'H,3H,3'H,6H,6'H-[4,4'-bipyridine]-1-carboxylate (1.8 g, 4.8 mmol) and $Pd(0H)_2/C$ (0.90 g, 6.4 mmol) in methanol (50 mL) was degassed and purged with hydrogen, then stirred overnight at room temperature under hydrogen atmosphere. The resulting mixture was filtered through Celite, washed with dichloromethane (3×10 mL). The filtrate was concentrated under reduced pressure to afford tert-butyl 3'-fluoro-[4,4'-bipiperidine]-1-carboxylate (1.4 g) as a yellow oil. MS ($ES^+$): m/z 287.30 $[M+H]^+$.

Step 5: 1-benzyl 1'-tert-butyl 3-fluoro-[4,4'-bipiperidine]-1,1'-dicarboxylate

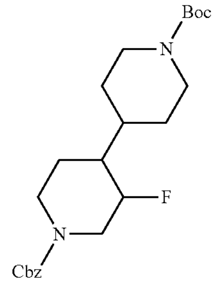 [SMILES: CC(C)(C)OC(=O)N1CCC(C2CCN(C(=O)OCc3ccccc3)CC2F)CC1]

To a stirred solution of tert-butyl 3'-fluoro-[4,4'-bipiperidine]-1-carboxylate (1.2 g, 4.2 mmol) and triethylamine (848 mg, 8.4 mmol) in dichloromethane was added benzyl chloroformate (857.7 mg, 5 mmol) at 0° C. The resulting mixture was stirred for 2 h at room temperature, then concentrated under vacuum. The residue was purified by reversed-phase flash chromatography (column, C18 silica gel; mobile phase, acetonitrile in water (10 mmol/L $NH_4HCO_3$), 10% to 50% gradient in 10 min) to afford 1-benzyl 1'-tert-butyl 3-fluoro-[4,4'-bipiperidine]-1,1'-dicarboxylate (570 mg, 32%) as a white solid. MS (ESI): m-z 421.30 $[M+H]^+$.

Step 6: benzyl 3-fluoro-[4,4'-bipiperidine]-1-carboxylate

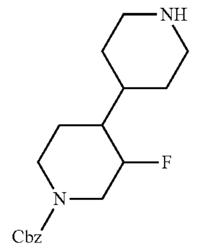 [SMILES: O=C(OCc1ccccc1)N1CCC(C2CCNCC2)C(F)C1]

To a solution of 1-benzyl 1'-tert-butyl 3-fluoro-[4,4'-bipiperidine]-1,1'-dicarboxylate (270 mg, 0.6 mmol) in 1,4-dioxane (5.0 ml) was added HCl (gas) at room temperature. The resulting mixture was stirred for 2 h at room temperature, then concentrated under vacuum to afford benzyl 3-fluoro-[4,4'-bipiperidine]-1-carboxylate (200 mg, 97%) as a white solid. MS (ESI): m/z 321.30 $[M+H]^+$.

Step 7: benzyl 1'-[2-(2,6-dioxopiperidin-3-yl)-4-fluoro-1-oxo-3H-isoindol-5-yl]-3-fluoro-[4,4'-bipiperidine]-1-carboxylate

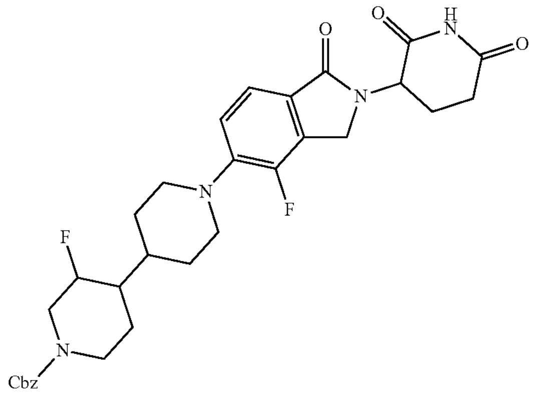 [SMILES: O=C1CCC(N2Cc3c(ccc(N4CCC(C5CCN(C(=O)OCc6ccccc6)CC5F)CC4)c3F)C2=O)C(=O)N1]

To a stirred mixture of benzyl 3-fluoro-[4,4'-bipiperidine]-1-carboxylate (400 mg, 1.2 mmol) and 3-(5-bromo-4-fluoro-1-oxo-3H-isoindol-2-yl)piperidine-2,6-dione (426 mg, 1.2 mmol) in N, N-dimethylformamide were added dichloro[1,3-bis(2,6-di-3-pentylphenyl)imidazol-2-ylidene](3-chloropyridyl)palladium(II) (5.25 mg, 0.006 mmol) and cesium carbonate (814 mg, 2.5 mmol). The resulting mixture was stirred for 2 h at 100° C. under nitrogen atmosphere. Diluted with water and extracted with ethyl acetate (3×10 mL). The combined organic layers were washed with brine (3×10 mL), dried over anhydrous sodium sulfate, filtered, and concentrated under reduced pressure. The residue was purified by reversed-phase flash chromatography (column, C18 silica gel; mobile phase, acetonitrile in water (10 mmol/L $NH_4HCO_3$), 10% to 50% gradient in 10 min) to afford benzyl 1'-[2-(2,6-dioxopiperidin-3-yl)-4-fluoro-1-oxo-3H-isoindol-5-yl]-3-fluoro-[4,4'-bipiperidine]-1-carboxylate (210 mg, 29%) as a white solid. MS (ESI): m/z 581.30 $[M+H]^+$.

Step 8: 3-(4-fluoro-5-(3'-fluoro-[4,4'-bipiperidin]-1-yl)-1-oxo-3H-isoindol-2-yl)piperidine-2,6-dione

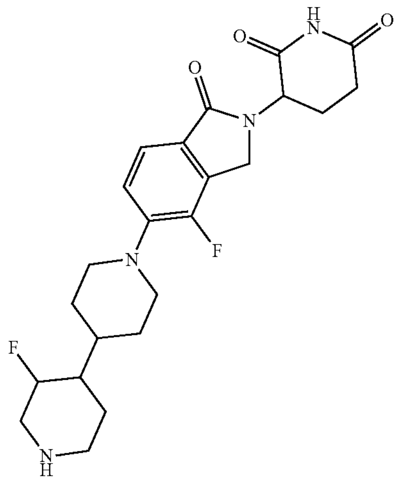 [SMILES: O=C1CCC(N2Cc3c(ccc(N4CCC(C5CCNCC5F)CC4)c3F)C2=O)C(=O)N1]

To benzyl 1'-[2-(2,6-dioxopiperidin-3-yl)-4-fluoro-1-oxo-3H-isoindol-5-yl]-3-fluoro-[4,4'-bipiperidine]-1-carboxylate (150 mg, 0.3 mmol) was added trifluoracetic acid (3 mL, 0.03 mmol). The resulting mixture was stirred for 3 h at 50° C., then concentrated under vacuum. to afford 3-(4-fluoro-5-{3'-fluoro-[4,4'-bipiperidin]-1-yl}-1-oxo-3H-isoindol-2-yl)piperidine-2,6-dione (100 mg, 87%) as a brown oil. MS (ESI): m/z 447.30 $[M+H]^+$.

Step 9: 2-{[6-({5-chloro-2-[4-({1'-[2-(2,6-dioxopiperidin-3-yl)-4-fluoro-1-oxo-3H-isoindol-5-yl]-3-fluoro-[4,4'-bipiperidin]-1-yl}methyl)piperidin-1-yl]pyrimidin-4-yl}amino)-1-isopropyl-2-oxoquinolin-3-yl]oxy}-N-methylacetamide

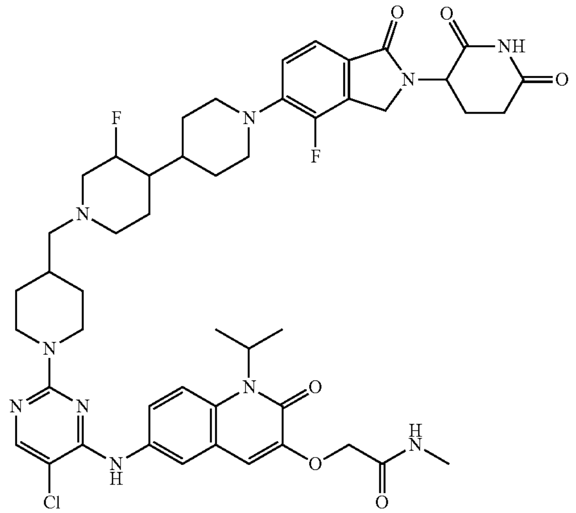 [SMILES: CNC(=O)COc1cc2cc(Nc3nc(N4CCC(CN5CCC(C6CCN(c7ccc8c(c7F)CN(C7CCC(=O)NC7=O)C8=O)CC6)C(F)C5)CC4)ncc3Cl)ccc2n(C(C)C)c1=O]

To a stirred mixture of 3-(4-fluoro-5-{3'-fluoro-[4,4'-bipiperidin]-1-yl}-1-oxo-3H-isoindol-2-yl)piperidine-2,6-dione (70 mg, 0.2 mmol) and 2-[(6-{[5-chloro-2-(4-formylpiperidin-1-yl)pyrimidin-4-yl]amino}-1-isopropyl-2-oxoquinolin-3-yl)oxy]-N-methylacetamide (80.43 mg, 0.2 mmol) in dichloroethane (5 mL) was added N,N-diisopropylethylamine dropwise to adjust the pH to 8. The resulting mixture was stirred overnight at 40° C. To the above mixture was added sodium triacetoxyborohydride (99.68 mg, 0.5 mmol) at room temperature. The resulting mixture was stirred for 2 h at room temperature. The crude material was purified by reversed-phase flash chromatography (column, C18 silica gel; mobile phase, acetonitrile in water (10 mmol/L $NH_4HCO_3$), 10% to 55% gradient in 10 min) to afford 2-{[6-({5-chloro-2-[4-({1'-[2-(2,6-dioxopiperidin-3-yl)-4-fluoro-1-oxo-3H-isoindol-5-yl]-3-fluoro-[4,4'-bipiperidin]-1-yl}methyl)piperidin-1-yl]pyrimidin-4-yl}amino)-1-isopropyl-2-oxoquinolin-3-yl]oxy}-N-methylacetamide (41 mg, 25%) as an off-white solid. $^1H$ NMR (300 MHz, DMSO) δ 10.97 (s, 1H), 7.62 (d, J=7.9 Hz, 1H), 7.52-7.45 (m, 1H), 7.39 (dd, J=7.9, 1.5 Hz, 1H), 7.32 (d, 0.1=4.4 Hz, 4H), 7.31-7.18 (m, 1H), 5.09 (dd, J=13.2, 5.1 Hz, 1H), 4.41 (d, J=17.2 Hz, 1H), 4.27 (d, J=17.2 Hz, 1H), 3.49 (s, 2H), 2.90 (dq, J=13.5, 6.6, 5.3 Hz, 3H), 2.70-2.51 (m, 2H), 2.37 (qd, J=13.1, 4.3 Hz, 1H), 2.02 (dtd, J=17.0, 11.4, 4.1 Hz, 3H), 1.74 (s, 3H), 1.69 (dd, J=12.2, 3.5 Hz, 1H); MS (ESI): m/z 943.39 $[M+H]^+$.

Example 12: Synthesis of Compound 1

Step 1: tert-butyl 4-[(1r,3r)-3-{4-[1-(2,6-dioxopiperidin-3-yl)-3-methyl-2-oxo-1,3-benzodiazol-4-yl]-3,6-dihydro-2H-pyridin-1-yl}cyclobutoxy]piperidine-1-carboxylate

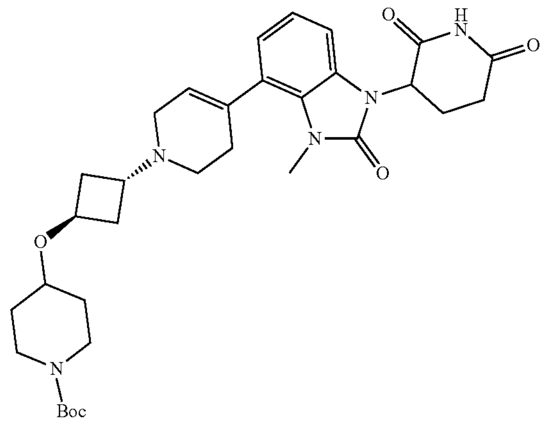 [SMILES: Cn1c(=O)n(C2CCC(=O)NC2=O)c2cccc(C3=CCN([C@H]4C[C@H](OC5CCN(C(=O)OC(C)(C)C)CC5)C4)CC3)c21]

To a stirred solution/mixture of tert-butyl 4-[(1r,3r)-3-[4-(4,4,5,5-tetramethyl-1,3,2-dioxaborolan-2-yl)-3,6-dihydro-2H-pyridin-1-yl]cyclobutoxy]piperidine-1-carboxylate (Example 5, step 6; 512.82 mg, 1.109 mmol, 1.5 equiv) and 3-(4-bromo-3-methyl-2-oxo-1,3-benzodiazol-1-yl)piperidine-2,6-dione (WO2019060693, 250 mg, 0.739 mmol, 1.00 equiv) in 1,4-dioxane and water were added CsF (336.90 mg, 2.217 mmol, 3 equiv) and Pd(dtbpf)$Cl_2$ (48.18 mg, 0.074 mmol, 0.1 equiv) dropwise/in portions at 90° C. under nitrogen atmosphere. The resulting mixture was stirred for 3 h at 90° C. under nitrogen atmosphere. The resulting mixture was extracted with EtOAc (10×mL). The combined organic layers were washed with brine (3×10 mL), dried over anhydrous $Na_2SO_4$. After filtration, the filtrate was concentrated under reduced pressure. The residue was purified by reverse-phase flash chromatography with the following conditions: column, C18 silica gel; mobile phase, MeCN in water (10 mmol/L $NH_4HCO_3$), 10% to 50% gradient in 10 min: detector, UV 254 nm. This afforded tert-butyl 4-[(1r,3r)-3-{4-[1-(2,6-dioxopiperidin-3-yl)-3-methyl-2-oxo-1,3-benzodiazol-4-yl]-3,6-dihydro-2H-pyridin-1-yl}cyclobutoxy]piperidine-1-carboxylate (230 mg, 52.40%) as a white solid. LC-MS ($ES^+$): m/z 594.37 [$MH^+$], $t_R$=1.119 min (2.0 minute run).

Step 2: 2-({6-[(5-chloro-2-{4-[(1r,3r)-3-{4-[4-fluoro-1-oxo-2-(2-oxopiperidin-3-yl)-3H-isoindol-5-yl]piperidin-1-yl}cyclobutoxy]piperidin-1-yl}pyrimidin-4-yl)amino]-1-isopropyl-2-oxoquinolin-3-yl}oxy)-N-methylacetamide

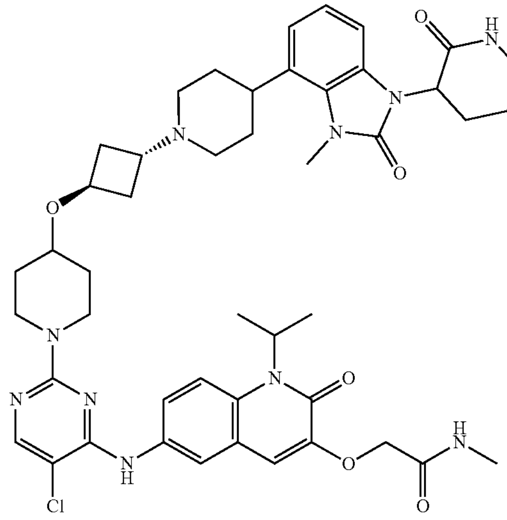

Compound 1 was prepared using the procedures from Example 5/Compound 37, steps 8-10 as 45 mg of an off-white solid (100%). $^1$H NMR (300 MHz, DMSO-d6, ppm): δ 11.08 (s, 1H), 8.84 (s, 1H), 8.05 (s, 1H), 7.97 (d, J=10.4 Hz, 2H), 7.70 (d, J=1.4 Hz, 2H), 7.06-6.89 (m, 4H), 5.37 (dd, J=12.8, 5.3 Hz, 1H), 4.55 (s, 2H), 4.13 (d, J-=14.8 Hz, 3H), 3.57 (s, 3H), 3.53 (s, 1H), 3.22 (d, J=10.0 Hz, 3H), 3.00 (d, J=9.9 Hz, 4H), 2.87 (d, J=14.8 Hz, 2H), 2.69 (d, J=4.6 Hz, 3H), 2.22-2.12 (m, 2H), 2.00 (d, J=5.6 Hz, 3H), 1.82 (d, J=11.3 Hz, 8H), 1.72 (d, J=11.4 Hz, 1H), 1.58 (d, 0.1=6.8 Hz, 5H), 1.38 (d, J=8.7 Hz, 3H).

LC-MS ($ES^+$): m/z 895.39[$MH^+$], $t_R$=1.235 min (3.0 minute run).

Example 13: Synthesis of Compound 5

Step 1: 3-[(4-bromophenyl)amino]piperidine-2,6-dione

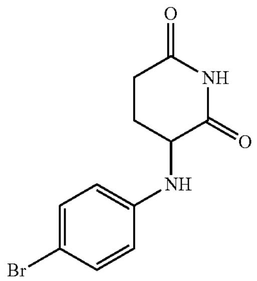 [SMILES: O=C1CCC(Nc2ccc(Br)cc2)C(=O)N1]

To a stirred solution of 4-bromoaniline (2.0 g, 11.6 mmol, 1.0 equiv) and 3-bromopiperidine-2,6-dione (2.2 g, 11.6 mmol, 1.0 equiv) in DMF (50 mL) was added DIEA (4.5 g, 34.9 mmol, 3.0 equiv) at room temperature. The resulting mixture was stirred for overnight at 100° C. The residue was purified by reverse-phase flash chromatography with the following conditions: column, C18 silica gel; mobile phase, $CH_3CN$/water (10 mmol/L FA), 5% to 50% gradient in 45 min; detector, UV 254 nm. This afforded afford 3-[(4-bromophenyl)amino]piperidine-2,6-dione (260 mg) as grey brown solid. LC-MS ($ES^+$): m/z 279.00 [MW], $t_R$=0.908 min (2.0 minute run).

Step 2: tert-butyl 4-[(1r,3r)-3-(4-{4-[(2,6-dioxopiperidin-3-yl)amino]phenyl}piperazin-1-yl)cyclobutoxy]piperidine-1-carboxylate

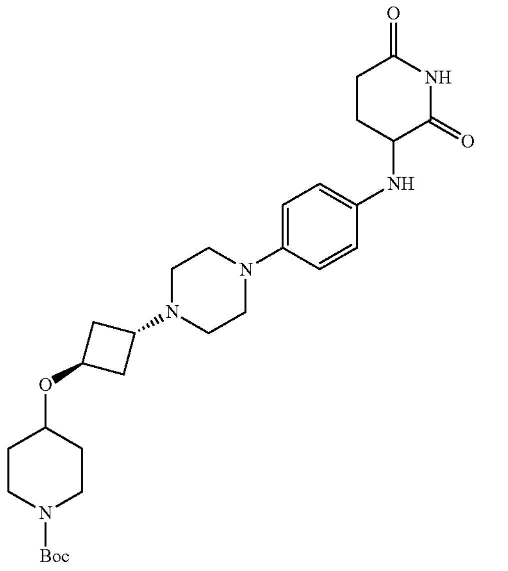 [SMILES: CC(C)(C)OC(=O)N1CCC(O[C@H]2C[C@H](N3CCN(c4ccc(NC5CCC(=O)NC5=O)cc4)CC3)C2)CC1]

A mixture of 3-[(4-bromophenyl)amino]piperidine-2,6-dione (260 mg, 0.8 mmol, 1.0 equiv), tert-butyl 4-[(1r,3r)-3-(piperazin-1-yl)cyclobutoxy]piperidine-1-carboxylate (WO2022221673, 299.8 mg, 0.8 mmol, 1.0 equiv) and $Cs_2CO_3$ (863.10 mg, 2.649 mmol, 3.0 equiv) Pd-PEPPSI-IPentCl (Khadra A, Mayer S, Organ MG. Pd-PEPPSI-$IPent^{Cl}$: A Useful Catalyst for the Coupling of 2-Aminopyridine Derivatives. Chemistry. 2017 Mar. 2; 23(13):3206-3212), 2-methylpyridine (o-picoline) (67.28 mg, 0.08 mmol, 0.1 equiv) in DMF (5.0 mL) was degassed with nitrogen for 3 times. The mixture was stirred at 110° C. for overnight. The mixture was allowed to cool down to room temperature. The resulting mixture was diluted with ethyl acetate (300 mL). The resulting mixture was extracted with EtOAc (200 mL). The combined organic layers were washed with brine (100 mL), dried over anhydrous $Na_2SO_4$. After filtration, the filtrate was concentrated under reduced pressure. The residue was purified by reverse-phase flash chromatography with the following conditions: column, C18 silica gel; mobile phase, MeCN in Water (10 mmol/L $NH_4HCO_3$), 5% to 50% gradient in 30 min; detector, UV 254 nm. This resulted in tert-butyl 4-[(1r,3r)-3-(4-{4-[(2,6-dioxopiperidin-3-yl)amino]phenyl}piperazin-1-yl)cyclobutoxy]piperidine-1-carboxylate (136 mg, 28%) as a black solid. LC-MS ($ES^+$): m/z 542.40 [$MH^+$], $t_R$=0.704 min (1.2 minute run).

Step 3

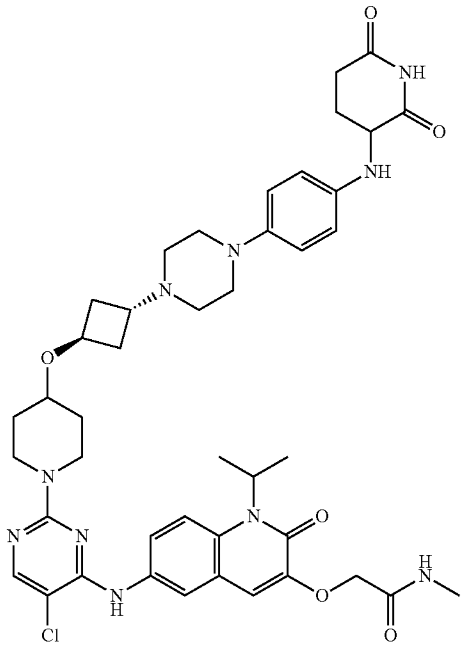 [SMILES: CNC(=O)COc1cc2cc(Nc3nc(N4CCC(O[C@H]5C[C@H](N6CCN(c7ccc(NC8CCC(=O)NC8=O)cc7)CC6)C5)CC4)ncc3Cl)ccc2n(C(C)C)c1=O]

Compound 5 was prepared using the procedures from Example 5/Compound 37, steps 9-10 as 33.8 mg of a white solid. $^1H$ NMR (300 MHz, DMSO-d6, ppm): S 8.83 (s, 1H), 8.04 (s, 1H), 7.97 (s, 2H), 7.69 (d, J=10.2 Hz, 3H), 7.28 (d, J=8.5 Hz, 2H), 7.16 (s, 1H), 7.02 (s, 1H), 6.89 (d, J=8.8 Hz, 2H), 4.54 (d, J=7.3 Hz, 2H), 4.18-4.10 (m, 3H), 3.52 (s, 1H), 3.20 (d, J=10.8 Hz, 2H), 3.08 (s, 3H), 2.78 (s, 1H), 2.66 (d, J=4.5 Hz, 3H), 2.39 (s, 4H), 2.32 (s, 1H), 2.17 (s, 2H), 2.02-1.96 (m, 3H), 1.80 (s, 2H), 1.56 (d, J=6.8 Hz, 6H), 1.37 (s, 2H), 1.22 (s, 4H), 0.82 (s, 2H). LC-MS ($ES^+$): m/z 841.30 [$MH^+$], $t_R$=7.599 min (13.0 minute run).

Example 14: Synthesis of Compound 17

Step 1: 3-(5-bromoindol-1-yl)piperidine-2,6-dione

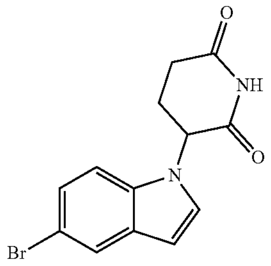 [SMILES: O=C1CCC(n2ccc3cc(Br)ccc32)C(=O)N1]

Into a 30 mL sealed tube was added 5-bromoindole (1.02 g, 5.20 mmol, 2.0 equiv) and NaH (156 mg, 3.90 mmol, 1.5 equiv, 60%) in THF (10 mL) at room temperature. The resulting mixture was stirred for 1 h at room temperature under nitrogen atmosphere. To the above mixture was added 3-bromopiperidine-2,6-dione (0.50 g, 2.60 mmol, 1.0 equiv) in THF (5 mL) dropwise at 0° C. The resulting mixture was stirred for additional overnight at room 60° C. The resulting mixture was extracted with $CH_2Cl_2$/IPA for 4:1 (3×20 mL). The combined organic layers were dried over anhydrous $Na_2SO_4$. After filtration, the filtrate was concentrated under reduced pressure. The residue was purified by silica gel column chromatography, eluted with petroleum ether/ethyl acetate (5:1) to afford 3-(5-bromoindol-1-yl)piperidine-2,6-dione (420 mg, 52.56%) as a white solid. LC-MS ($ES^+$): m/z 306 [$MH^+$], $t_R$=0.91 min (2.00 minutes run).

Step 2: 2-({6-[(5-chloro-2-{4-[(1r,3r)-3-{4-[1-(2,6-dioxopiperidin-3-yl)indol-5-yl]piperazin-1-yl}cyclobutoxy]piperidin-1-yl}pyrimidin-4-yl)amino]-1-isopropyl-2-oxoquinolin-3-yl}oxy)-N-methylacetamide

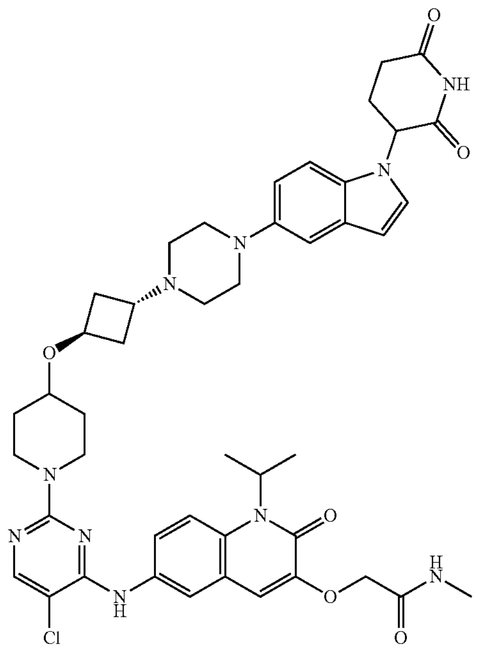 [SMILES: CNC(=O)COc1cc2cc(Nc3nc(N4CCC(O[C@H]5C[C@H](N6CCN(c7ccc8c(ccn8C8CCC(=O)NC8=O)c7)CC6)C5)CC4)ncc3Cl)ccc2n(C(C)C)c1=O]

Compound 17 was prepared analogously to Example 13/Compound 5 to afford 65.9 mg, (46.80%) of a white solid. $^1$H NMR (300 MHz, DMSO-d6) δ 11.04 (s, 1H), 8.83 (s, 1H), 8.05 (s, 1H), 8.00-7.92 (m, 2H), 7.70 (m, 2H), 7.35-7.24 (m, 2H), 7.06-6.99 (m, 2H), 6.91 (m, 1H), 6.36 (m, 1H), 5.53 (m, 1H), 5.33 (s, 1H), 4.55 (s, 2H), 4.25-4.02 (m, 3H), 3.54 (s, 1H), 3.24 (m, 2H), 3.06 (s, 4H), 2.95-2.80 (m, 2H), 2.69 (m, 4H), 2.60 (s, 1H), 2.45 (s, 4H), 2.40 (s, 3H), 2.15 (m, 2H), 1.83 (m, 2H), 1.58 (m, 6H), 1.39 (m, 2H). LC-MS ($ES^+$): m/z 864.38 [$MH^+$], $t_R$=1.13 min (2.00 minutes run).

Example 15: Synthesis of Compound 21

Step 1: 3-(5-bromoindazol-1-yl)piperidine-2,6-dione and 3-(5-bromoindazol-2-yl)piperidine-2,6-dione

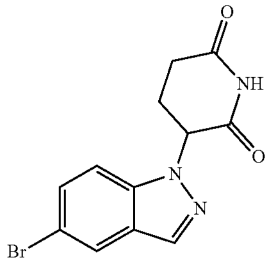

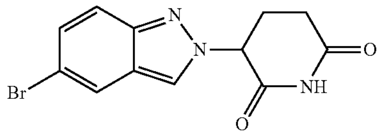

Into a 100 mL 3-necked round-bottom flask were added 5-bromo-1H-indazole (1970.23 mg, 9.999 mmol, 2.00 equiv) and THF (40 mL) at room temperature. To the above mixture was added NaH (239.97 mg, 10.000 mmol, 2.00 equiv) in portions at 0° C. The resulting mixture was stirred for additional 30 min at 60° C. To the above mixture was added 3-bromopiperidine-2,6-dione (960 mg, 5.000 mmol, 1.00 equiv) in THF dropwise at 60° C. The resulting mixture was stirred overnight at 60° C. The resulting mixture was diluted with ethyl acetate (200 mL). The resulting mixture was added to 200 mL 20% HCl(aq.). The aqueous layer was extracted with EtOAc (2×80 mL). The residue was purified by silica gel column chromatography, eluted with petroleum ether/ethyl acetate (2:3) to isolate the 2 regioisomers.

3-(5-bromoindazol-1-yl)piperidine-2,6-dione (1 g, 64.91%) as an off-white solid. LC-MS ($ES^+$): m/z 309.95 [$MH^+$], $t_R$=0.721 min (2.0 minute run).

3-(5-bromoindazol-2-yl)piperidine-2,6-dione (600 mg, 38.95%) as an off-white solid.

LC-MS ($ES^+$): m/z 307.85[$MH^+$], $t_R$=0.687 min (2.0 minute run).

Step 2: Synthesis of 2-({6-[(5-chloro-2-{4-[(1r,3r)-3-{4-[1-(2,6-dioxopiperidin-3-yl)indazol-5-yl]piperazin-1-yl}cyclobutoxy]piperidin-1-yl}pyrimidin-4-yl)amino]-1-isopropyl-2-oxoquinolin-3-yl}oxy)-N-methylacetamide

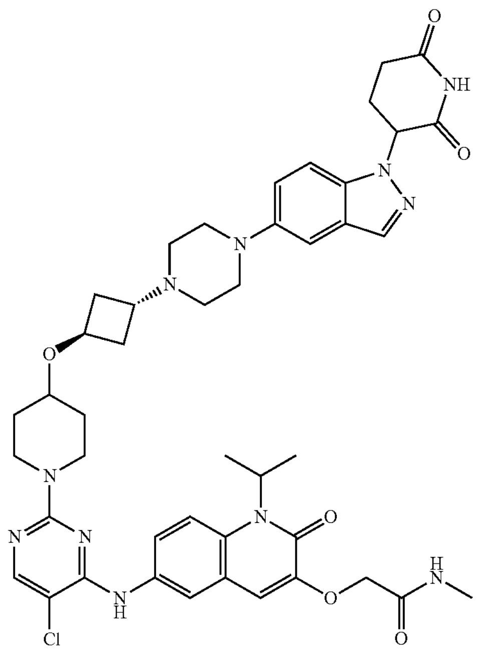 [SMILES: CNC(=O)COc1cc2cc(Nc3nc(N4CCC(O[C@H]5C[C@H](N6CCN(c7ccc8c(cnn8C8CCC(=O)NC8=O)c7)CC6)C5)CC4)ncc3Cl)ccc2n(C(C)C)c1=O]

Compound 21 was prepared by analogously to Example 13/Compound 5 by substituting 3-(5-bromoindazol-1-yl) piperidine-2,6-dione for 3-[(4-bromophenyl)amino]piperidine-2,6-dione in step 1 to afford 55 mg (35.47%) as a light brown solid. $^1$H NMR (300 MHz, DMSO-d6, ppm) δ 11.08 (s, 1H), 8.85 (s, 1H), 8.04-7.91 (m, 4H), 7.69 (m, 2H), 7.49 (m, 1H), 7.26 (m, 1H), 7.10 (m, 1H), 7.02 (s, 1H), 5.76 (m, 1H), 5.32 (s, 1H), 4.55 (s, 2H), 4.25-4.07 (m, 3H), 3.23 (m, 1H), 3.20 (s, 2H), 3.09 (s, 4H), 2.82 (s, 3H), 2.77-2.64 (m, 1H), 2.46 (s, 4H), 2.31-2.19 (m, 3H), 2.19 (s, 3H), 2.00 (m, 2H), 1.83 (m, 2H), 1.57 (m, 6H), 1.38 (m, 2H). LC-MS (ES$^+$): m/z 866.45[MH$^+$], $t_R$=6.315 min (13.0 minute run).

Example 16: Synthesis of Compound 22

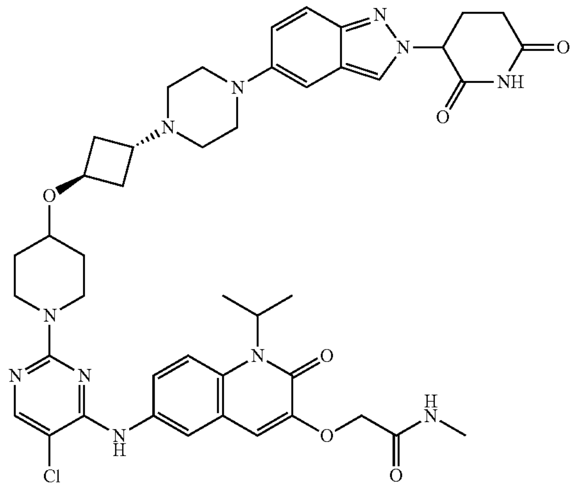 [SMILES: CNC(=O)COc1cc2cc(Nc3nc(N4CCC(O[C@H]5C[C@H](N6CCN(c7ccc8nn(C9CCC(=O)NC9=O)cc8c7)CC6)C5)CC4)ncc3Cl)ccc2n(C(C)C)c1=O]

Compound 22 was prepared by analogously to Example 13/Compound 5 by substituting 3-(5-bromoindazol-2-yl) piperidine-2,6-dione for 3-[(4-bromophenyl)amino]piperidine-2,6-dione in step 1 to afford 27 mg (16%) as a light grey solid. $^1$H NMR (300 MHz, DMSO-d6, ppm) δ 8.84 (s, 1H), 8.20 (s, 1H), 8.05 (s, 1H), 7.97 (m, 2H), 7.70 (s, 2H), 7.47 (m, 1H), 7.17 (m, 1H), 7.03 (s, 1H), 6.90 (s, 1H), 5.64 (m, 1H), 4.55 (s, 2H), 4.11 (m, 3H), 3.54 (s, 1H), 3.26-3.13 (m, 2H), 3.07 (s, 2H), 3.07 (s, 4H), 2.77-2.65 (m, 2H), 2.50 (s, 1H), 2.45 (s, 3H), 2.31 (s, 1H), 2.19 (s, 4H), 1.82 (s, 5H), 1.57 (m, 6H), 1.39 (s, 3H), 1.24 (s, 1H). LC-MS (ES$^+$): m/z 866.45[MH$^+$], $t_R$=5.598 min (10.0 minute run).

Example 17: Synthesis of Compound 23

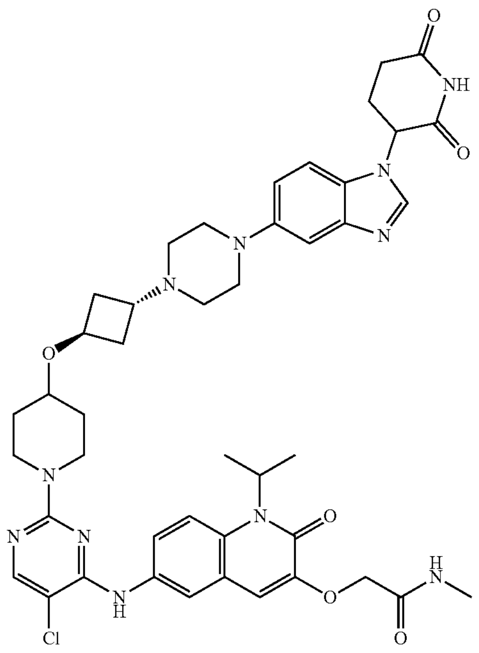 [SMILES: CNC(=O)COc1cc2cc(Nc3nc(N4CCC(O[C@H]5C[C@H](N6CCN(c7ccc8c(c7)ncn8C7CCC(=O)NC7=O)CC6)C5)CC4)ncc3Cl)ccc2n(C(C)C)c1=O]

Compound 23 was prepared analogously to Compound 21 by substituting 3-(5-bromo-1,3-benzodiazol-1-yl)piperidine-2,6-dione for 3-(5-bromoindazol-1-yl)piperidine-2,6-dione in the first step to afford the title compound as 42 mg (23%) of an off white solid. $^1$H NMR (300 MHz, DMSO-$d_6$) δ 11.15 (s, 1H), 8.86 (s, 1H), 8.14 (s, 1H), 8.05 (s, 1H), 7.97 (m, 2H), 7.70 (m, 2H), 7.38 (m, 1H), 7.13 (m, 1H), 7.03 (s, 1H), 5.62 (m, 1H), 5.32 (s, 1H), 4.55 (s, 2H), 4.24-4.07 (m, 2H), 3.54 (s, 1H), 3.23 (m, 2H), 3.10 (s, 3H), 2.75 (m, 6H), 2.45 (s, 3H), 2.25-2.15 (m, 3H), 1.99 (m, 0H), 1.84 (m, 2H), 1.57 (m, 6H), 1.38 (m, 1H). LC-MS (ES$^+$): m/z 866.55 [MH$^+$], $t_R$=2.694 min (9 minute run).

Example 18: Synthesis of Compound 24

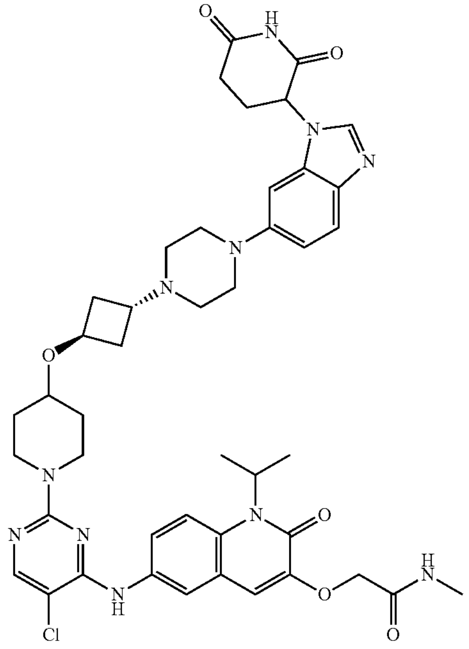 [SMILES: CNC(=O)COc1cc2cc(Nc3nc(N4CCC(O[C@H]5C[C@H](N6CCN(c7ccc8ncn(C9CCC(=O)NC9=O)c8c7)CC6)C5)CC4)ncc3Cl)ccc2n(C(C)C)c1=O]

Compound 24 was prepared analogously to Compound 21 by substituting 3-(6-bromo-1,3-benzodiazol-1-yl)piperidine-2,6-dione for 3-(5-bromoindazol-1-yl)piperidine-2,6-dione in the first step to afford the title compound as 52.6 mg, (44%) of a white solid. $^1$H NMR (300 MHz, DMSO-$d_6$) δ 11.15 (s, 1H), 8.86 (s, 1H), 8.14 (s, 1H), 8.05 (s, 1H), 7.97 (m, 2H), 7.70 (m, 2H), 7.38 (m, 1H), 7.13 (m, 1H), 7.03 (s, 1H), 5.62 (m, 1H), 5.32 (s, 1H), 4.55 (s, 2H), 4.24-4.07 (m, 2H), 3.54 (s, 1H), 3.23 (m, 2H), 3.10 (s, 3H), 2.75 (m, 6H), 2.45 (s, 3H), 2.25-2.15 (m, 3H), 1.99 (m, 0H), 1.84 (m, 2H), 1.57 (m, 6H), 1.38 (m, 1H). LC-MS (ES$^+$): m/z 866.55 [MH$^+$], $t_R$=2.694 min (9 minute run).

Compound Characterization (Mass Spectroscopy)

The mass spectroscopy data for the compounds of the disclosure is provided below in Table 4.

TABLE 4

MASS SPECTROSCOPY DATA FOR THE COMPOUNDS OF THE DISCLOSURE

| Compound No. | Compound Name | Exact Mass | Observed m/z [M + 1]$^+$ |
|---|---|---|---|
| 1 | 2-({6-[(5-chloro-2-{4-[(1r,3r)-3-{4-[1-(2,6-dioxopiperidin-3-yl)-3-methyl-2-oxo-2,3-dihydro-1H-1,3-benzodiazol-4-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 895.44 | 893.50 |
| 2 | 2-({6-[(5-chloro-2-{4-[(1r,3r)-3-{4-[1-(2,6-dioxopiperidin-3-yl)-3-methyl-2-oxo-2,3-dihydro-1H-1,3-benzodiazol-4-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 896.43 | 895.47 |
| 3 | 2-({6-[(5-chloro-2-{4-[(1r,3r)-3-{4-[1-(2,6-dioxopiperidin-3-yl)-3-methyl-2-oxo-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 896.43 | 896.40 |
| 4 | 2-({6-[(5-chloro-2-{4-[(1r,3r)-3-{4-[1-(2,6-dioxopiperidin-3-yl)-3-methyl-2-oxo-2,3-dihydro-1H-1,3-benzodiazol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 895.44 | 894.39 |
| 5 | 2-({6-[(5-chloro-2-{4-[(1r,3r)-3-(4-{4-[(2,6-dioxopiperidin-3-yl)amino]phenyl}piperazin-1-yl)cyclobutoxy]piperidin-1-yl}pyrimidin-4-yl)amino]-2-oxo-1-(propan-2-yl)-1,2-dihydroquinolin-3-yl}oxy)-N-methylacetamide | 841.40 | 841.40 |
| 6 | 2-({6-[(5-chloro-2-{4-[(1r,3r)-3-{4-[1-(2,6-dioxopiperidin-3-yl)-3-methyl-2-oxo-1H,2H,3H-imidazo[4,5-b]pyridin-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 897.42 | 895.40 |
| 7 | 2-({6-[(5-chloro-2-{4-[(1r,3r)-3-{4-[1-(2,6-dioxopiperidin-3-y])-3-ethyl-2-oxo-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 910.46 | 909.41 |
| 8 | 2-({6-[(5-chloro-2-{4-[(1r,3r)-3-{4-[1-(2,6-dioxopiperidin-3-yl)-4-fluoro-3-methyl-2-oxo-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 914.42 | 913.38 |

TABLE 4-continued

MASS SPECTROSCOPY DATA FOR THE COMPOUNDS OF THE DISCLOSURE

| Compound No. | Compound Name | Exact Mass | Observed m/z [M + 1]+ |
|---|---|---|---|
| 9 | 2-({6-[(5-chloro-2-{4-[(1r,3r)-3-{4-[1-(2,6-dioxopiperidin-3-yl)-6-fluoro-3-methyl-2-oxo-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 914.42 | 913.38 |
| 10 | 2-({6-[(5-chloro-2-{4-[(1r,3r)-3-{4-[1-(2,6-dioxopiperidin-3-yl)-7-fluoro-3-methyl-2-oxo-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 914.42 | 913.38 |
| 11 | 2-({6-[(5-chloro-2-{4-[(1r,3r)-3-{4-[3-(2,6-dioxopiperidin-3-yl)-1-methyl-2-oxo-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 896.43 | 895.39 |
| 12 | 2-({6-[(5-chloro-2-{4-[(1r,3r)-3-{4-[1-(2,6-dioxopiperidin-3-yl)-2-oxo-3-(propan-2-yl)-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 924.48 | 924.60 |
| 13 | 2-({6-[(5-chloro-2-{4-[(1r,3r)-3-[(3R)-4-[1-(2,6-dioxopiperidin-3-yl)-3-methyl-2-oxo-2,3-dihydro-1H-1,3-benzodiazol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 910.46 | 910.60 |
| 14 | 2-({6-[(5-chloro-2-{4-[(1r,3r)-3-{4-[3-(2,6-dioxopiperidin-3-yl)-1-methyl-2-oxo-1H,2H,3H-imidazo[4,5-c]pyridin-6-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 897.42 | 897.40 |
| 15 | 2-({6-[(5-chloro-2-{4-[(1r,3r)-3-{4-[1-(2,6-dioxopiperidin-3-yl)-6-methoxy-3-methyl-2-oxo-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 926.46 | 926.35 |
| 16 | 2-({6-[(5-chloro-2-{4-[(1r,3r)-3-{4-[3-(2,6-dioxopiperidin-3-yl)-1-methyl-2-oxo-1H,2H,3H-imidazo[4,5-b]pyridin-6-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 897.42 | 897.50 |
| 17 | 2-({6-[(5-chloro-2-{4-[(1r,3r)-3-{4-[1-(2,6-dioxopiperidin-3-yl)-1H-indol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 865.42 | 865.30 |
| 18 | 2-({6-[(5-chloro-2-{4-[(1r,3r)-3-[(3S)-4-[1-(2,6-dioxopiperidin-3-yl)-3-methyl-2-oxo-2,3-dihydro-1H-1,3-benzodiazol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 910.46 | 910.45 |
| 19 | 2-({6-[(5-chloro-2-{4-[(1r,3r)-3-{4-[1-(2,6-dioxopiperidin-3-yl)-3,4-dimethyl-2-oxo-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 910.46 | 910.50 |
| 20 | 2-({6-[(5-chloro-2-{4-[(1r,3r)-3-{4-[1-(2,6-dioxopiperidin-3-yl)-3,6-dimethyl-2-oxo-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 910.46 | 910.45 |
| 21 | 2-({6-[(5-chloro-2-{4-[(1r,3r)-3-{4-[1-(2,6-dioxopiperidin-3-yl)-1H-indazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 866.40 | 865.38 |
| 22 | 2-({6-[(5-chloro-2-{4-[(1r,3r)-3-{4-[2-(2,6-dioxopiperidin-3-yl)-2H-indazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 866.40 | 865.38 |
| 23 | 2-({6-[(5-chloro-2-{4-[(1r,3r)-3-{4-[1-(2,6-dioxopiperidin-3-y])-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 866.40 | 865.38 |
| 24 | 2-({6-[(5-chloro-2-{4-[(1r,3r)-3-{4-[1-(2,6-dioxopiperidin-3-yl)-1H-1,3-benzodiazol-6-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 866.40 | 865.38 |
| 25 | 2-({6-[(5-chloro-2-{4-[(1r,3r)-3-{4-[1-(2,6-dioxopiperidin-3-yl)-7-methoxy-3-methyl-2-oxo-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 926.46 | 925.40 |
| 26 | 2-({6-[(5-chloro-2-{4-[(1r,3r)-3-{4-[1-(2,6-dioxopiperidin-3-yl)-3,7-dimethyl-2-oxo-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 910.46 | 910.45 |

TABLE 4-continued

MASS SPECTROSCOPY DATA FOR THE COMPOUNDS OF THE DISCLOSURE

| Compound No. | Compound Name | Exact Mass | Observed m/z [M + 1]$^+$ |
|---|---|---|---|
| 27 | 2-({6-[(5-chloro-2-{4-[(1r,3r)-3-{4-[1-(2,6-dioxopiperidin-3-yl)-4,7-difluoro-3-methyl-2-oxo-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 932.41 | 932.30 |
| 28 | 2-({6-[(5-chloro-2-{4-[(1r,3r)-3-{4-[1-(2,6-dioxopiperidin-3-yl)-4-fluoro-2-oxo-3-(propan-2-yl)-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 942.47 | 942.35 |
| 29 | 2-({6-[(5-chloro-2-{4-[(1r,3r)-3-{4-[1-(2,6-dioxopiperidin-3-yl)-7-fluoro-2-oxo-3-(propan-2-yl)-2,3-dihydro-1H-1,3-benzodiazol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 942.47 | 942.20 |
| 30 | 2-({6-[(5-chloro-2-{4-[(1r,3r)-3-[(3R)-4-[(3R)-2-[(3S)-2,6-dioxopiperidin-3-yl]-4-fluoro-3-methyl-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 927.46 | 925.65 |
| 31 | 2-({6-[(5-chloro-2-{4-[(1r,3r)-3-[(3R)-4-[(3R)-2-[(3R)-2,6-dioxopiperidin-3-yl]-4-fluoro-3-methyl-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 927.46 | 927.50 |
| 32 | 2-({6-[(5-chloro-2-{4-[(1r,3r)-3-[(3R)-4-[(3R)-4-chloro-2-[(3S)-2,6-dioxopiperidin-3-yl]-3-methyl-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 943.91 | 943.05 |
| 33 | 2-({6-[(5-chloro-2-{4-[(1r,3r)-3-[(3R)-4-[(3R)-4-chloro-2-[(3R)-2,6-dioxopiperidin-3-yl]-3-methyl-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 943.91 | 945.10 |
| 34 | 2-({6-[(5-chloro-2-{4-[(1r,3r)-3-[(3R)-4-[(3S)-4-chloro-2-[(3S)-2,6-dioxopiperidin-3-yl]-3-methyl-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 943.91 | 943.55 |
| 35 | 2-({6-[(5-chloro-2-{4-[(1r,3r)-3-[(3R)-4-[(3S)-4-chloro-2-[(3R)-2,6-dioxopiperidin-3-yl]-3-methyl-1-oxo-2,3-dihydro-1H-isoindol-5-yl]-3-methylpiperazin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 943.91 | 943.55 |
| 36 | 2-({6-[(5-chloro-2-{4-[(1r,3r)-3-{4-[2-(2,6-dioxopiperidin-3-yl)-7-methyl-1-oxo-2,3-dihydro-1H-isoindol-5-yl]piperazin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 895.44 | 895.50 |
| 37 | 2-({6-[(5-chloro-2-{4-[(1r,3r)-3-{4-[2-(2,6-dioxopiperidin-3-yl)-7-methyl-1-oxo-2,3-dihydro-1H-isoindol-5-yl]piperidin-1-yl}cyclobutoxy]piperidin-1-yl}pyrimidin-4-yl)amino]-2-oxo-1-(propan-2-yl)-1,2-dihydroquinolin-3-yl}oxy)-N-methylacetamide | 894.45 | 894.30 |
| 38 | 2-({6-[(5-chloro-2-{4-[(1r,3r)-3-[(3R,4S)-4-{2-[(3S)-2,6-dioxopiperidin-3-yl]-4-fluoro-7-methyl-1-oxo-2,3-dihydro-1H-isoindol-5-yl}-3-fluoropiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 930.44 | 930.50 |
| 39 | 2-({6-[(5-chloro-2-{4-[(1r,3r)-3-[(3S,4R)-4-{2-[(3S)-2,6-dioxopiperidin-3-yl]-4-fluoro-7-methyl-1-oxo-2,3-dihydro-1H-isoindol-5-yl}-3-fluoropiperidin-1-yl]cyclobutoxy]piperidin-1-yl}pyrimidin-4-yl)amino]-2-oxo-1-(propan-2-yl)-1,2-dihydroquinolin-3-yl}oxy)-N-methylacetamide | 930.44 | 930.45 |
| 40 | 2-{[6-({5-chloro-2-[4-(2-{1-[2-(2,6-dioxopiperidin-3-yl)-4-fluoro-1-oxo-2,3-dihydro-1H-isoindol-5-yl]-4-hydroxypiperidin-4-yl}acetyl)piperazin-1-yl]pyrimidin-4-yl}amino)-2-oxo-1-(propan-2-yl)-1,2-dihydroquinolin-3-yl]oxy}-N-methylacetamide | 887.35 | 887.40 |
| 41 | 2-{[6-({5-chloro-2-[4-(2-{4-[2-(2,6-dioxopiperidin-3-yl)-4-fluoro-1-oxo-2,3-dihydro-1H-isoindol-5-yl]piperazin-1-yl}-2-oxoethyl)-4-hydroxypiperidin-1-yl]pyrimidin-4-yl}amino)-2-oxo-1-(propan-2-yl)-1,2-dihydroquinolin-3-yl]oxy}-N-methylacetamide | 887.35 | 887.40 |
| 42 | 2-({6-[(5-chloro-2-{4-[(4-{4-[2-(2,6-dioxopiperidin-3-yl)-4-fluoro-1-oxo-2,3-dihydro-1H-isoindol-5-yl]piperazin-1-yl}-3,3-difluoropiperidin-1-yl)methyl]piperidin-1-yl}pyrimidin-4-yl)amino]-2-oxo-1-(propan-2-yl)-1,2-dihydroquinolin-3-yl}oxy)-N-methylacetamide | 962.46 | |

TABLE 4-continued

| MASS SPECTROSCOPY DATA FOR THE COMPOUNDS OF THE DISCLOSURE | | | |
|---|---|---|---|
| Compound No. | Compound Name | Exact Mass | Observed m/z $[M + 1]^+$ |
| 43 | 2-{[6-({5-chloro-2-[4-({4-[2-(2,6-dioxopiperidin-3-yl)-4-fluoro-1-oxo-2,3-dihydro-1H-isoindol-5-yl]-3',3'-difluoro-[1,4'-bipiperidin]-1'-yl}methyl)piperidin-1-yl]pyrimidin-4-yl}amino)-2-oxo-1-(propan-2-yl)-1,2-dihydroquinolin-3-yl]oxy}-N-methylacetamide | 961.47 | 960.41 |
| 44 | 2-{[6-({5-chloro-2-[4-({1'-[2-(2,6-dioxopiperidin-3-yl)-4-fluoro-1-oxo-2,3-dihydro-1H-isoindol-5-yl]-3-fluoro-[4,4'-bipiperidin]-1-yl}methyl)piperidin-1-yl]pyrimidin-4-yl}amino)-2-oxo-1-(propan-2-yl)-1,2-dihydroquinolin-3-yl]oxy}-N-methylacetamide | 943.48 | 943.40 |

Bioactivity Data for the Compounds of the Disclosure

Protein Synthesis. BCL6 protein was expressed by transforming Invitrogen One Shot cells with GS63525 pET24a-His-SUMO-TEV-BCLm-Avitag plasmid following manufacturer's instructions. In addition, biotin at a final concentration of 50 μM, and IPTG at a final concentration of 1 mM was added to the culture and incubated at room temperature shaking overnight.

Immunofluorescence Protocol for High Content Imaging of BCL6

T47D cells were seeded in 100 μl volume of RPMI11640-10% FBS in a 96-well black/clear bottom plates for adherent lines (Corning #3904).

Day 1. T47D breast cancer epithelial cells were seeded at a density so that confluence is ~70-90% at endpoint. Cells were seeded at 7K/0.1 mL/well the morning prior to the addition of exemplary bifunctional degradation compounds.

Compound Treatment

Day 2. Prepare an 11 point 3-fold serial dilution of exemplary bifunctional compound in DMSO and aliquot an appropriate volume to cell growth media to generate a 2× final concentration of exemplary bifunctional compound. Add an equal volume (0.1 ml) of 2× exemplary bifunctional compound/media mix to previously plated cells, for a final top concentration in aqueous cell growth media of 0.1 or 1 μM. Incubate for 3 days at 37° C., 5% $CO_2$.

Day 5 Immunofluorescence. Discard cell media. Wash wells with 200 μl of room temperature phosphate-buffered saline (PBS). Prepared 4% paraformaldehyde (PFA) from 16% PFA (Electron Microscopy Sciences #15710) using 1×PBS. Fifty μL of 4% PF was added to each well and incubate for 15 minutes at room temperature to fix the cells. The PFA was aspirated and the cells washed twice with PBS (200 μL)).

Prepared 0.1% Triton X-100 in PBS using 10% triton X-100 stock. The cells were permeabilized by adding 100 μL of the 0.1% Triton X-100 in PBS to each well to permeabilize cells and incubating at room temperature for 15 minutes. Cells were washed twice with PBS.

Prepared 3% BSA/PBS (from Thermofisher #37515 Blocker BSA in TBS, 10%), and 100 μL was added to each well. The cells were incubated for at least 1 hour at room temperature.

Prepared 1% BSA/PBS using Blocker BSA/PBS, and the 3% BSA/PBS removed from the wells.

For no primary antibody controls, 50 μL 1% BSA/PBS was added.

Primary antibody (BCL6 Rb Ab, CST-14895, Cell Signaling) was diluted 1:300 in 1% BSA/PBS using Blocker BSA/PBS.

Fifty μl of primary antibody added to all remaining wells (i.e., all wells other than the primary antibody controls) and the cells were incubated overnight at 4° C. with slow orbital movement.

Day 6. Contents of the wells was removed and the cells washed four times with 200 μL PBS. 1% BSA/PBS was prepared using Blocker BSA in PBS.

Diluted secondary antibody goat anti-Rb IgG Alexa-488 1:1000, and cell mask-Alexa-647 1:3000 in 1% BSA/PBS in the same mix. Add 50 μL to each well and incubate at room temperature for 1 hour in the dark.

Cells were washed three times with 200 μL PBS, and then incubated for 10 minutes with 100 μL Hoechst dye at 1 μg/mL (20 mM stock) to stain cell nuclei. Wells were then washed with 200 μl PBS, and 100 μL of PBS was added to each well and the plate covered plate with a plastic opaque cover. Plates were stored at V° C. and covered in aluminum foil until imaged.

Plates were equilibrated to room temperature prior to reading. The bottom of the plate was wiped with 70% isopropanol immediately prior to imaging.

Imaging:

10×, 4 fields/well, include Top hat smoothing in the analysis protocol.

Supplies/Reagents:

16% paraformaldehyde: Electron Microscopy Sciences #15710

Hoechst: Thermofisher #62249

Blocker BSA in PBS, 10%: Thermofisher #37515

Blocker BSA in TBS, 10%: Thermofisher #37520

Goat anti-rabbit or mouse AlexaFluor-488: Thermofisher #A11008

Cell mask deep red AlexaFluor-647: Thermofisher #C10046

Wash buffer, PBS: 20×PBS, Thermofisher

TABLE 5

| BIOACTIVITY DATA FOR THE COMPOUNDS OF THE DISCLOSURE | | |
|---|---|---|
| Compound No. | High Content T47D BCL6 $DC_{50}$ (nM)* | High Content T47D BCL6 $D_{max}$ (%)** |
| 1 | A | A |
| 2 | A | A |
| 3 | A | A |
| 4 | A | A |
| 5 | C | nd |
| 6 | A | A |
| 7 | A | A |
| 8 | A | A |
| 9 | A | A |
| 10 | A | A |
| 11 | B | C |
| 12 | A | A |
| 13 | A | A |
| 14 | A | B |
| 15 | A | B |
| 16 | A | B |
| 17 | A | A |
| 18 | A | A |
| 19 | A | A |
| 20 | A | A |
| 21 | A | A |
| 22 | B | B |

TABLE 5-continued

BIOACTIVITY DATA FOR THE COMPOUNDS OF THE DISCLOSURE

| Compound No. | High Content T47D BCL6 $DC_{50}$ (nM)* | High Content T47D BCL6 $D_{max}$ (%)** |
|---|---|---|
| 23 | A | B |
| 24 | A | A |
| 25 | A | nd |
| 26 | B | B |
| 27 | A | A |
| 28 | A | A |
| 29 | A | A |
| 30 | B | C |
| 31 | A | nd |
| 32 | A | A |
| 33 | A | A |
| 34 | B | C |
| 35 | A | B |
| 36 | A | B |
| 37 | A | A |
| 38 | A | B |
| 39 | A | A |
| 40 | A | A |
| 41 | A | A |
| 42 | A | B |
| 43 | A | B |
| 44 | A | B |

nd = not determined;

*$DC_{50}$ (nM) ranges: A < 10; 10 ≤ B < 50; 50 ≤ C < 100; D ≥ 100;

**$D_{MAX}$ (%) ranges: A ≥ 70; 50 ≤B < 70; C < 50

ENUMERATED EMBODIMENTS

The aspects of the present disclosure are further described with reference to the following numbered embodiments:

1A. A bifunctional compound of Formula (I), Formula (II), or Formula (III):

Formula (I)

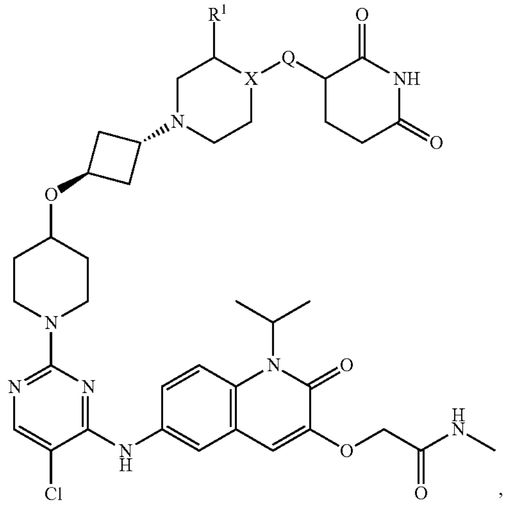

,

-continued

Formula (II)

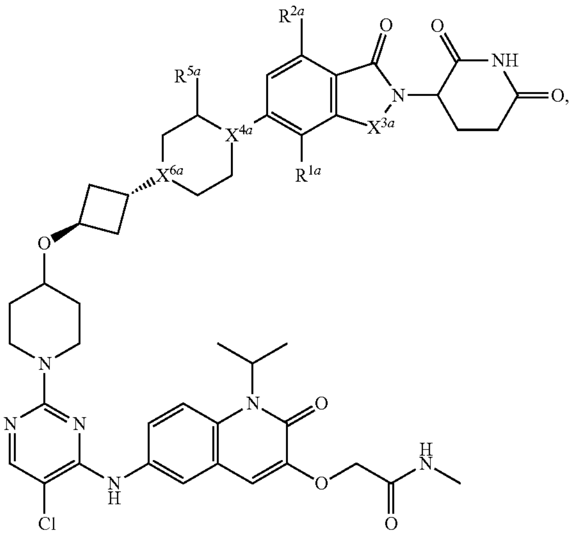

Formula (III)

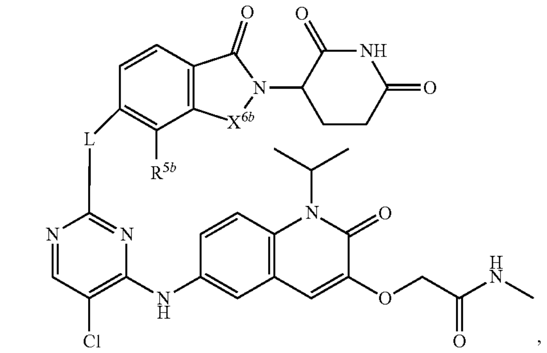

, or a pharmaceutically acceptable salt thereof, wherein:

$R^1$ is H or $C_1$-$C_6$ alkyl;

Q is

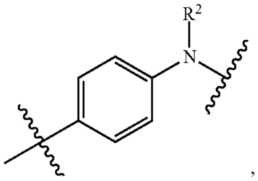

,

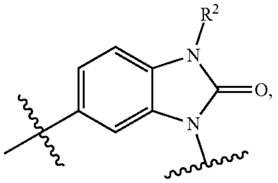

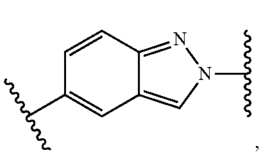

,

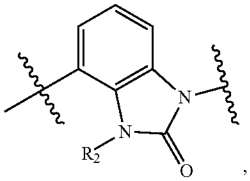

,

-continued

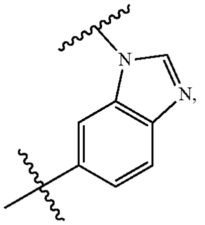

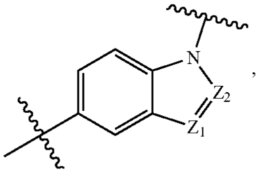

, or

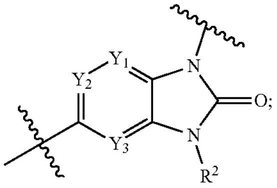

X is N or CH;

$Y_1$, $Y_2$, and $Y_3$ are each, independently, N or $CR^3$;

$Z_1$ and $Z_2$ are each, independently, N or CH;

$R^2$ is H or $C_1$-$C_6$ alkyl;

Each $R^3$ is, independently, H, halogen, $C_1$-$C_6$ alkyl, $C_1$-$C_6$ haloalkyl, —O—($C_1$-$C_6$ alkyl), —O—($C_1$-$C_6$ haloalkyl);

∿∿∿ of the Q indicates the point of attachment with the X or the glutarimide;

$R^{1a}$ is H or halogen;

$R^{2a}$ is H or $C_1$-$C_3$ alkyl;

$X^{3a}$ is $CHR^{3a}$ or C(O);

$R^{3a}$ is H or $C_1$-$C_3$ alkyl;

$X^{4a}$ and $X^{6a}$ are each independently CH or N; and $R^{5a}$ is H, $C_1$-$C_3$ alkyl or halogen;

L is

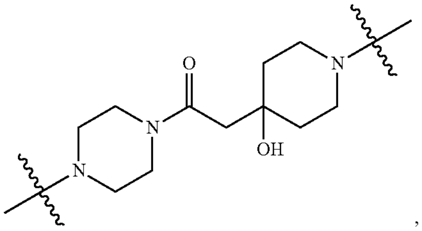

,

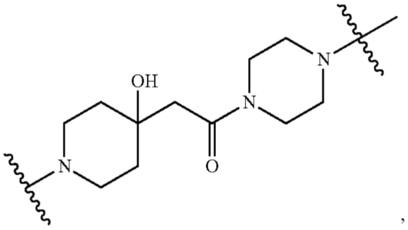

, or

-continued

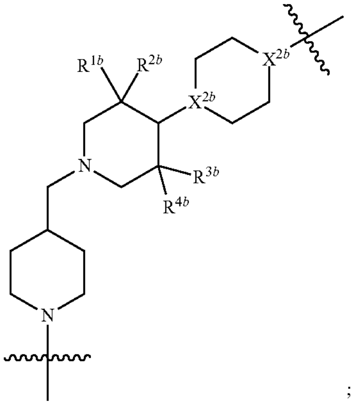

;

$X^{6b}$ is $CHR^{6b}$ or C(O);

$R^{6b}$ is H or $C_1$-$C_3$ alkyl;

$R^{1b}$, $R^{2b}$, $R^{3b}$, and $R^{4b}$ are each independently H or halogen, wherein at least one of $R^{1b}$, $R^{2b}$, $R^{3b}$, $R^{4b}$ is halogen;

$R^{5b}$ is H or halogen;

$R^{6b}$ is H or $C_1$-$C_3$ alkyl;

$X^{1b}$ and $X^{2b}$ are each independently CH or N, wherein at least one of $X^{1b}$ and $X^{2b}$ is N; and wherein each ∿∿∿ of L indicates a point of attachment.

1B. A bifunctional compound of Formula (I):

Formula (I)

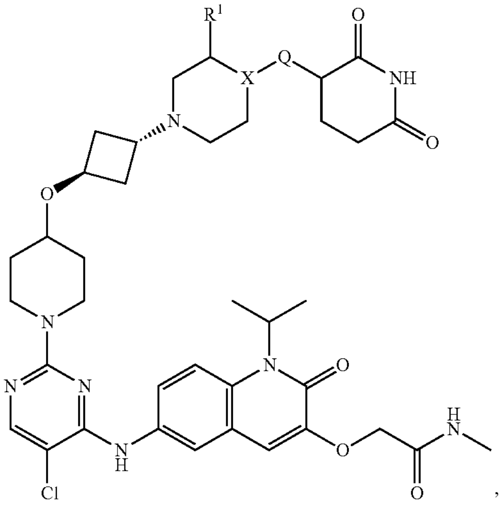

, or a pharmaceutically acceptable salt thereof, wherein:

$R^1$ is H or $C_1$-$C_6$ alkyl;

Q is

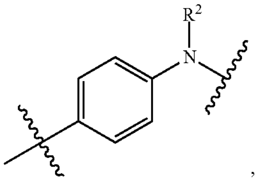

,

-continued

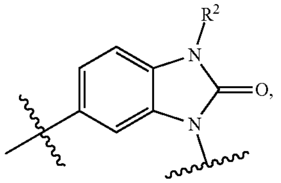

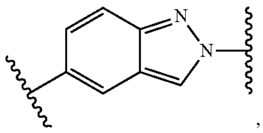
,
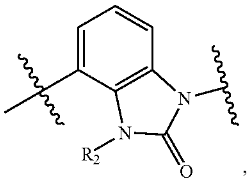
,

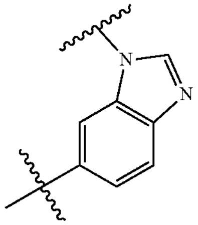

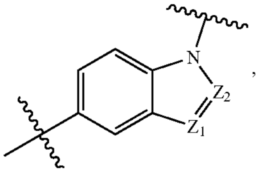
, or

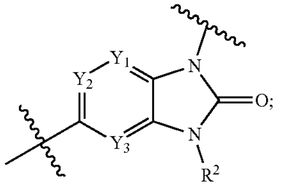

X is N or CH;

$Y_1$, $Y_2$, and $Y_3$ are each, independently, N or $CR^3$;

$Z_1$ and $Z_2$ are each, independently, N or CH;

$R^2$ is H or $C_1$-$C_6$ alkyl;

Each $R^3$ is, independently, H, halogen, $C_1$-$C_6$ alkyl, $C_1$-$C_6$ haloalkyl, —O—($C_1$-$C_6$ alkyl), —O—($C_1$-$C_6$ haloalkyl); and of the Q indicates the point of attachment with the X or the glutarimide.

1C. A bifunctional compound of Formula (II):

Formula (II)

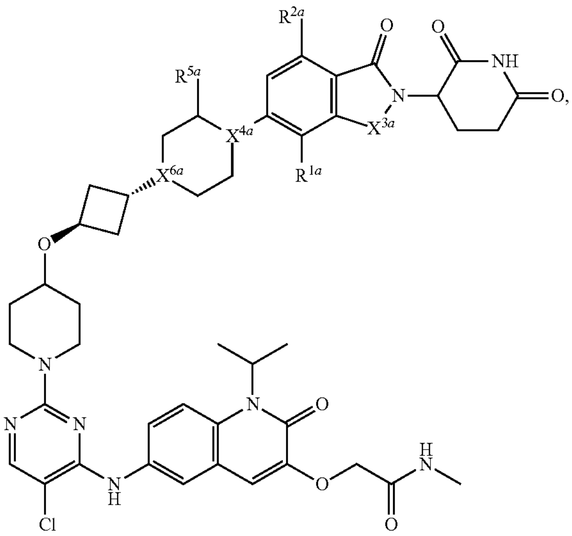
, or a pharmaceutically acceptable salt thereof, wherein:

$R^{1a}$ is H or halogen;

$R^{2a}$ is H or $C_1$-$C_3$ alkyl;

$X^{3a}$ is $CHR^{3a}$ or C(O);

$R^{3a}$ is H or $C_1$-$C_3$ alkyl;

$X^{4a}$ and $X^{6a}$ are each independently CH or N; and $R^{5a}$ is H, $C_1$-$C_3$ alkyl or halogen.

1D. A bifunctional compound of Formula (III):

Formula (III)

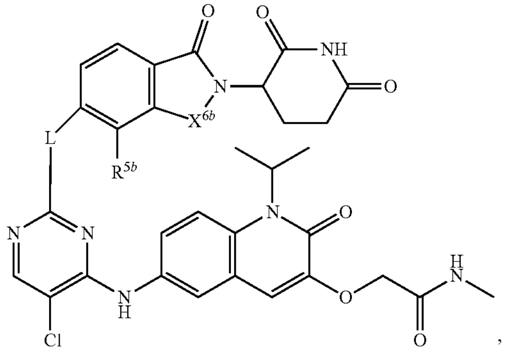
, or a pharmaceutically acceptable salt thereof, wherein:

L is

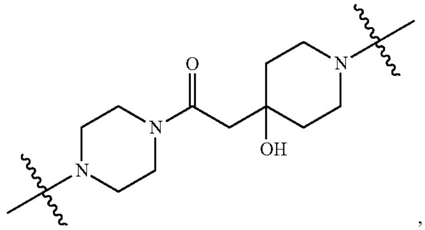
,

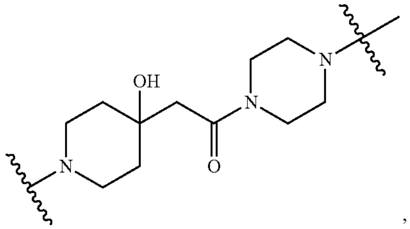
, or

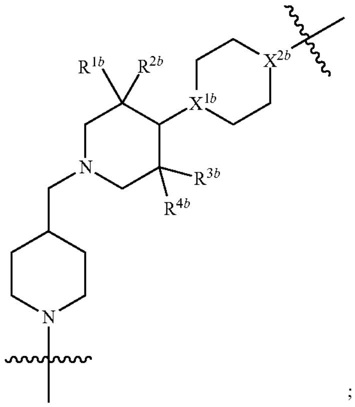
;

$X^{6b}$ is $CHR^{6b}$ or C(O);

$R^{6b}$ is H or $C_1$-$C_3$ alkyl;

$R^{1b}$, $R^{2b}$, $R^{3b}$, and $R^{4b}$ are each independently H or halogen, wherein at least one of $R^{1b}$, $R^{2b}$, $R^{3b}$, $R^{4b}$ is halogen;

$R^{5b}$ is H or halogen;

$R^{6b}$ is H or $C_1$-$C_3$ alkyl;

$X^{1b}$ and $X^{2b}$ are each independently CH or N, wherein at least one of $X^{1b}$ and $X^{2b}$ is N; and wherein each ∿∿∿ of L indicates a point of attachment.

1E. The bifunctional compound of embodiment 1A or 1C, or a pharmaceutically acceptable salt thereof, wherein the compound is a compound of Formula (II-a):

Formula (II-a)

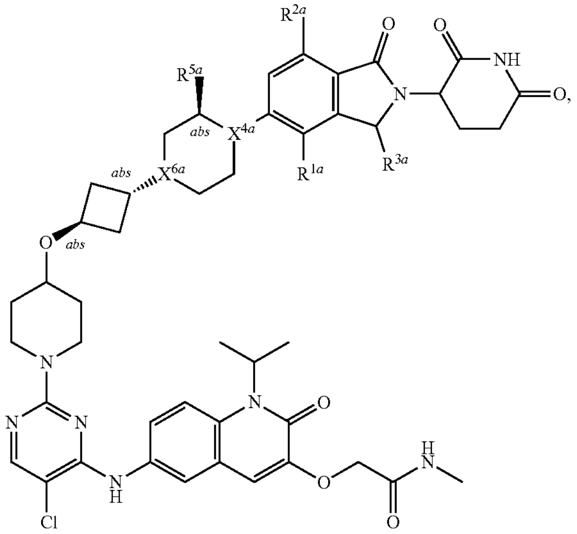

or a pharmaceutically acceptable salt thereof.

1F. The bifunctional compound of embodiment 1A or 1C, or a pharmaceutically acceptable salt thereof, wherein the compound is a compound of Formula (II-b), Formula (II-c), Formula (II-d), Formula (II-e), Formula (II-f), Formula (II-g), Formula (II-h), Formula (II-i), or Formula (II-j):

Formula (II-b)

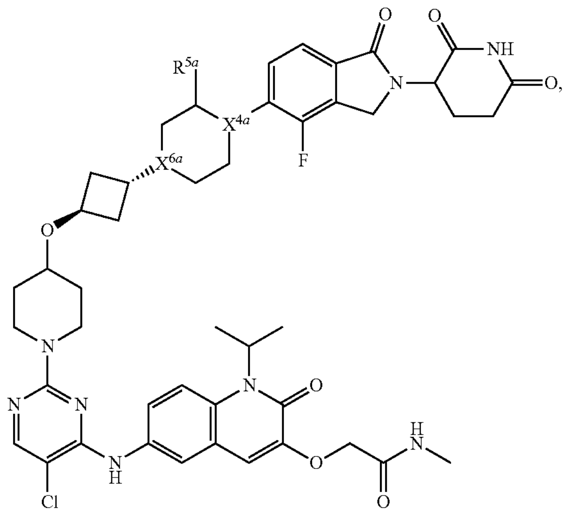

-continued

Formula (II-c)

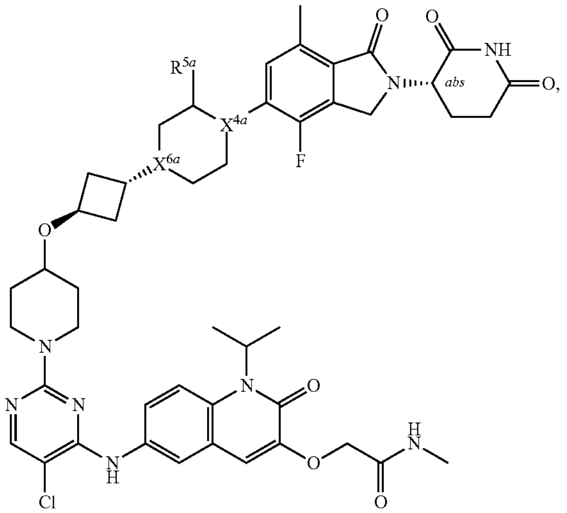

Formula (II-d)

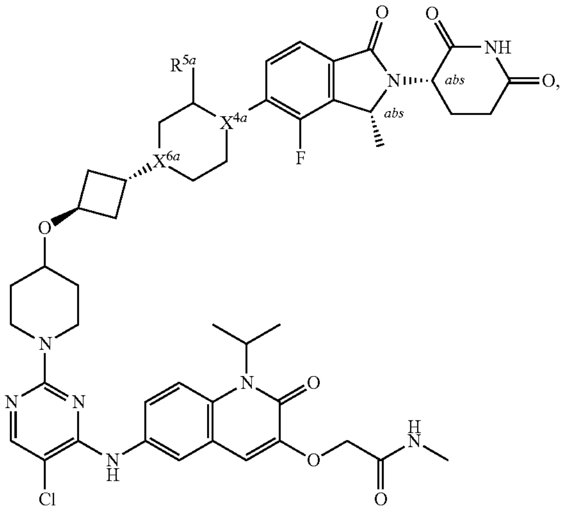

Formula (II-e)

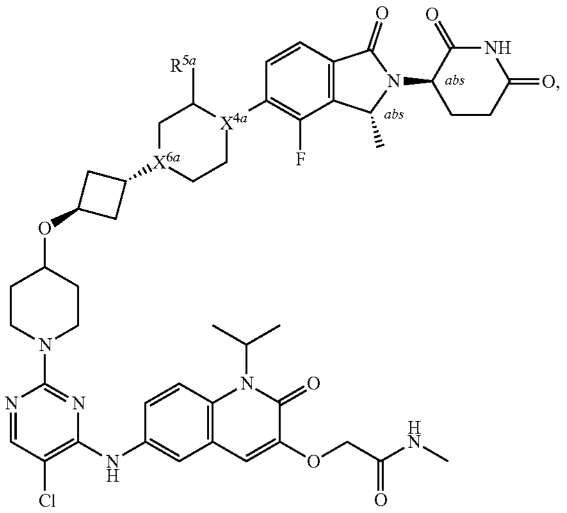

-continued

Formula (II-f)

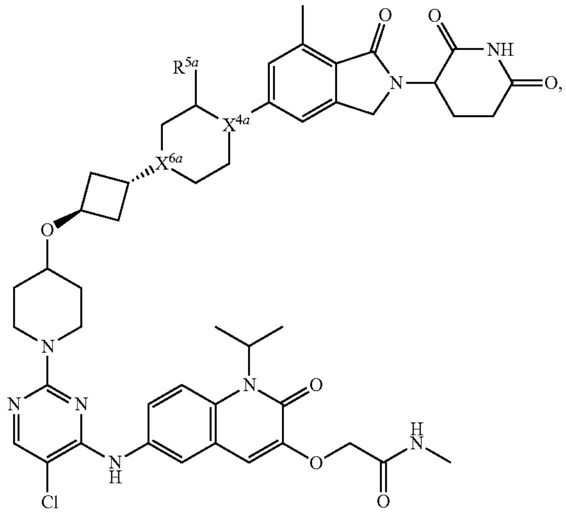

Formula (II-g)

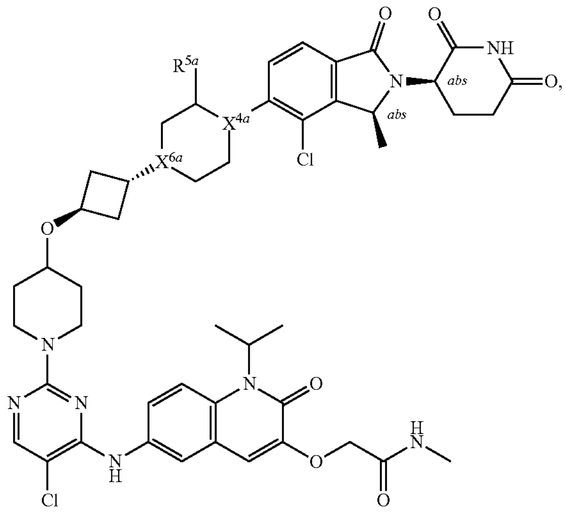

Formula (II-h)

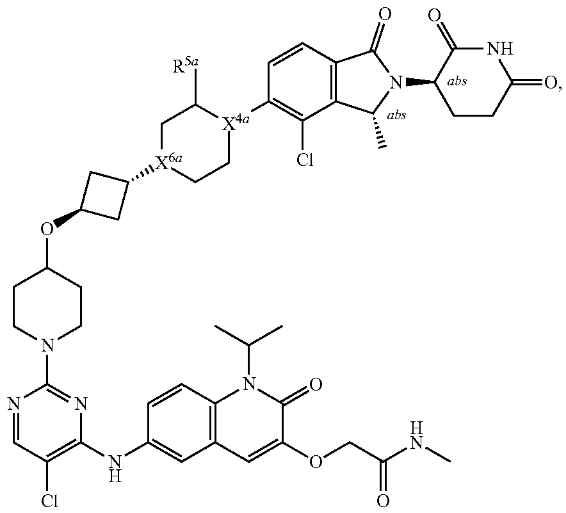

-continued

Formula (II-i)

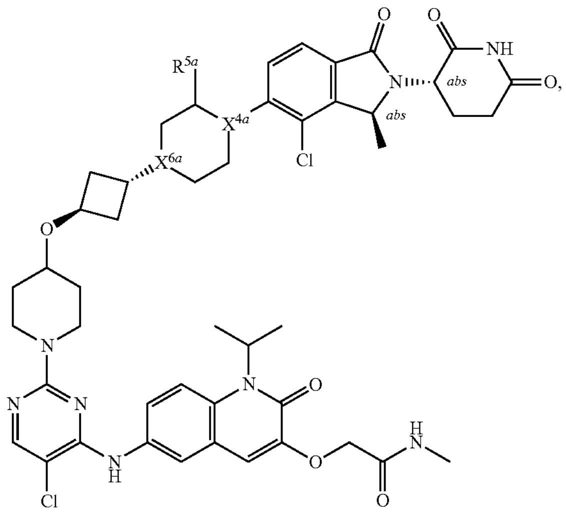

Formula (II-j)

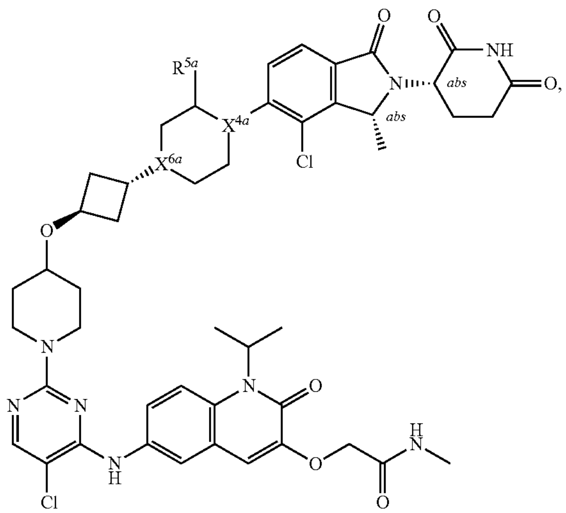

or a pharmaceutically acceptable salt thereof.

1G. The bifunctional compound of embodiment 1A or 1D, or a pharmaceutically acceptable salt thereof, wherein the compound is a compound of Formula (III-a), Formula (III-c), Formula (III-d), Formula (III-f), Formula (III-g), Formula (III-h), or Formula (III-i):

Formula (III-a)

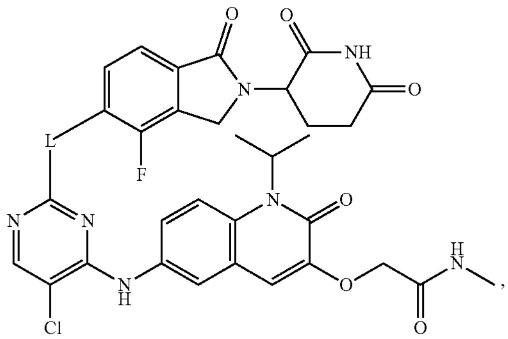

-continued
Formula (III-c)
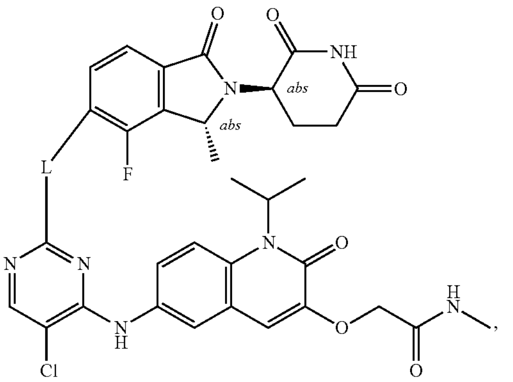
Formula (III-d)
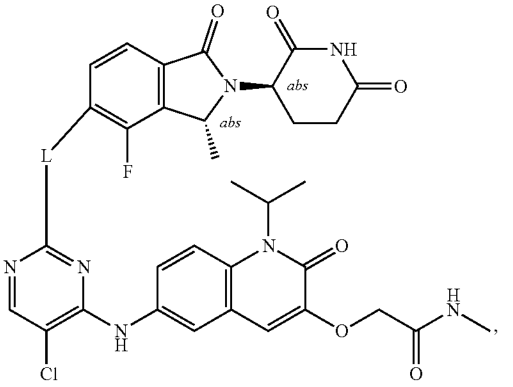
Formula (III-f)
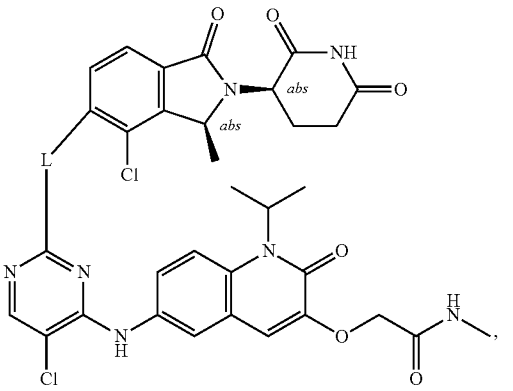
Formula (III-g)
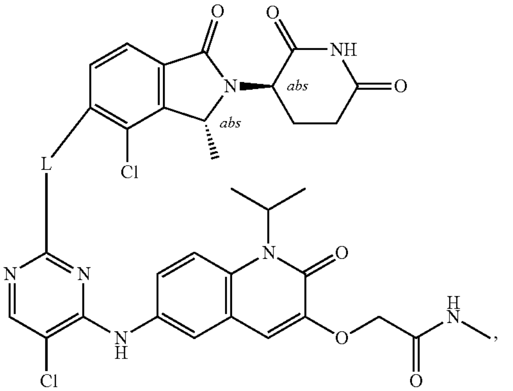
-continued
Formula (III-h)
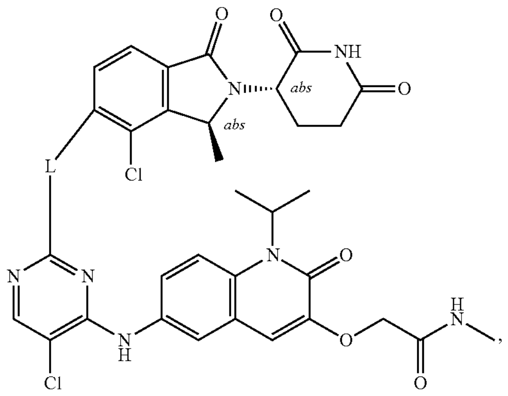
Formula (III-i)
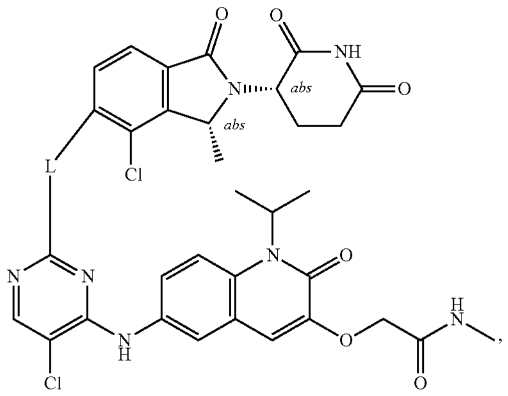
or a pharmaceutically acceptable salt thereof.
1H. A bifunctional compound of Formula (IV-b) or Formula (IV-e):
Formula (IV-b)
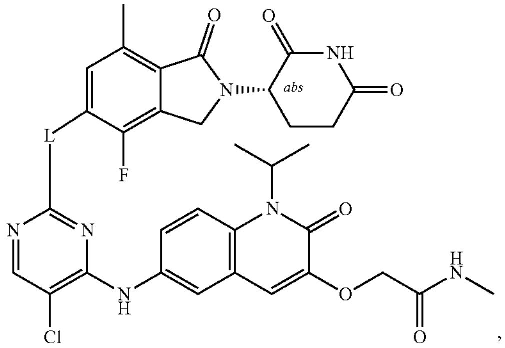
, -continued Formula (IV-e)

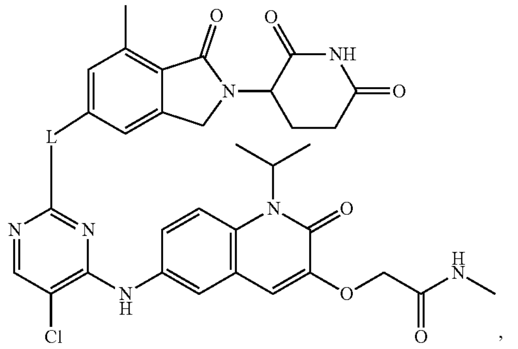

or a pharmaceutically acceptable salt thereof.

2A. A bifunctional compound of Formula (I), Formula (II), or Formula (III):

Formula (I)

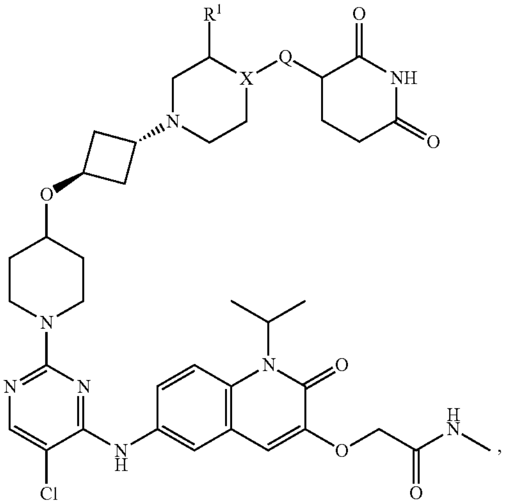

Formula (II)

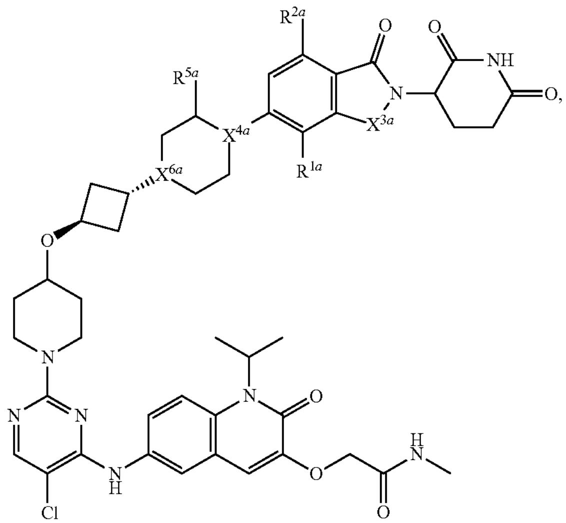

-continued

Formula (III)

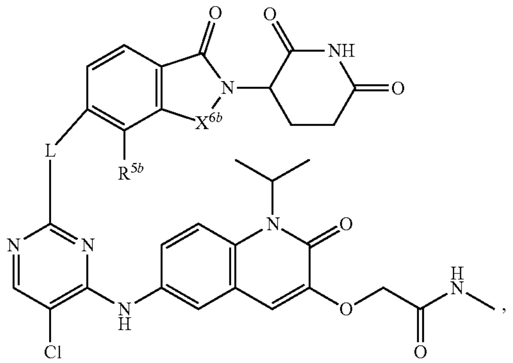

wherein:

$R^1$ is H or $C_1$-$C_6$ alkyl;

Q is

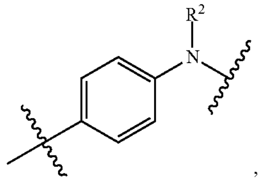

,

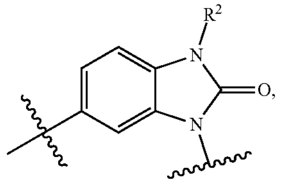

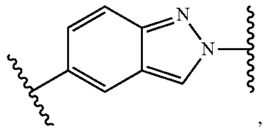

,

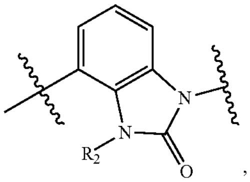

,

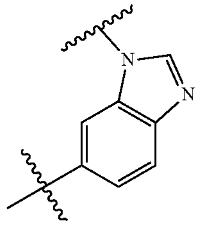

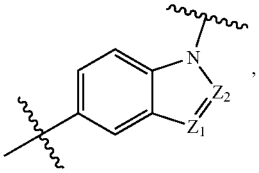

, or

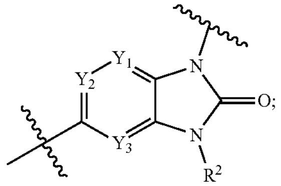

X is N or CH;

$Y_1$, $Y_2$, and $Y_3$ are each, independently, N or $CR^3$;

$Z_1$ and $Z_2$ are each, independently, N or CH;

$R^2$ is H or $C_1$-$C_6$ alkyl;

Each $R^3$ is, independently, H, halogen, $C_1$-$C_6$ alkyl, $C_1$-$C_6$ haloalkyl, —O—($C_1$-$C_6$ alkyl), —O—($C_1$-$C_6$ haloalkyl);

∿∿∿ of the Q indicates the point of attachment with the X or the glutarimide;

$R^{1a}$ is H or halogen;

$R^{2a}$ is H or $C_1$-$C_3$ alkyl;

$X^{3a}$ is $CHR^{3a}$ or C(O);

$R^{3a}$ is H or $C_1$-$C_3$ alkyl;

$X^{4a}$ and $X^{6a}$ are each independently CH or N; and $R^{5a}$ is H, $C_1$-$C_3$ alkyl or halogen;

L is

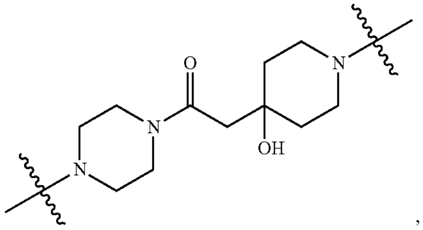

,

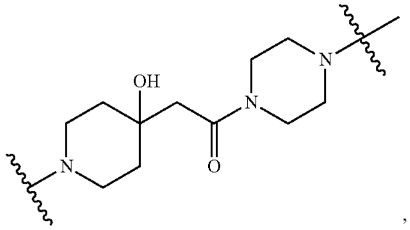

, or

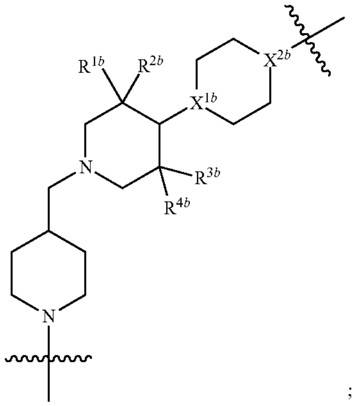

;

$X^{6b}$ is $CHR^{6b}$ or C(O);

$R^{6b}$ is H or $C_1$-$C_3$ alkyl;

$R^{1b}$, $R^{2b}$, $R^{3b}$, and $R^{4b}$ are each independently H or halogen, wherein at least one of $R^{1b}$, $R^{2b}$, $R^{3b}$, $R^{4b}$ is halogen;

$R^{5b}$ is H or halogen;

$R^{5b}$ is H or $C_1$-$C_3$ alkyl;

$X^{1b}$ and $X^{2b}$ are each independently CH or N, wherein at least one of $X^{1b}$ and $X^{2b}$ is N; and wherein each ∿∿∿ of L indicates a point of attachment.

2B. A bifunctional compound of Formula (I):

Formula (I)

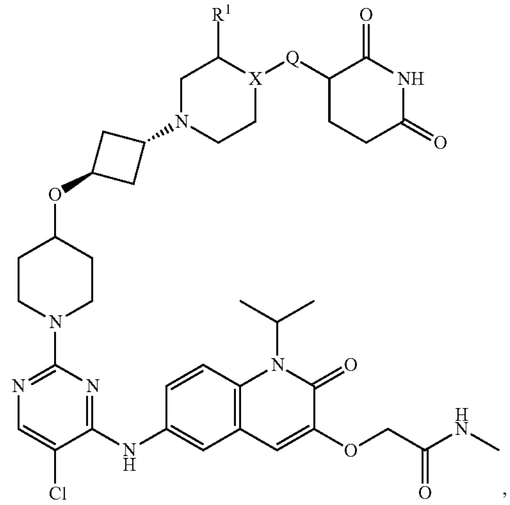

, wherein:

$R^1$ is H or $C_1$-$C_6$ alkyl;

Q is

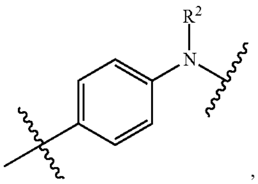

,

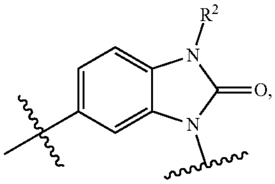

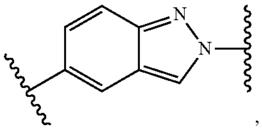

,

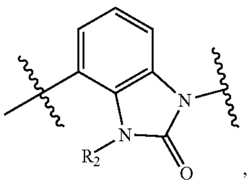

,

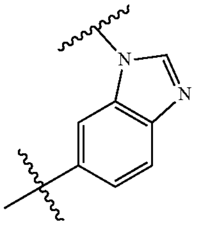

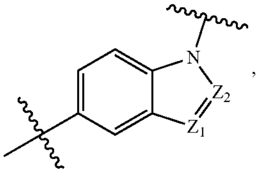

, or

-continued

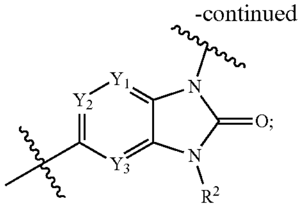

X is N or CH;

$Y_1$, $Y_2$, and $Y_3$ are each, independently, N or $CR^3$;

$Z_1$ and $Z_2$ are each, independently, N or CH;

$R^2$ is H or $C_1$-$C_6$ alkyl;

Each $R^3$ is, independently, H, halogen, $C_1$-$C_6$ alkyl, $C_1$-$C_6$ haloalkyl, —O—($C_1$-$C_6$ alkyl), —O—($C_1$-$C_6$ haloalkyl); and of the Q indicates the point of attachment with the X or the glutarimide.

2C. A bifunctional compound of Formula (II):

Formula (II)

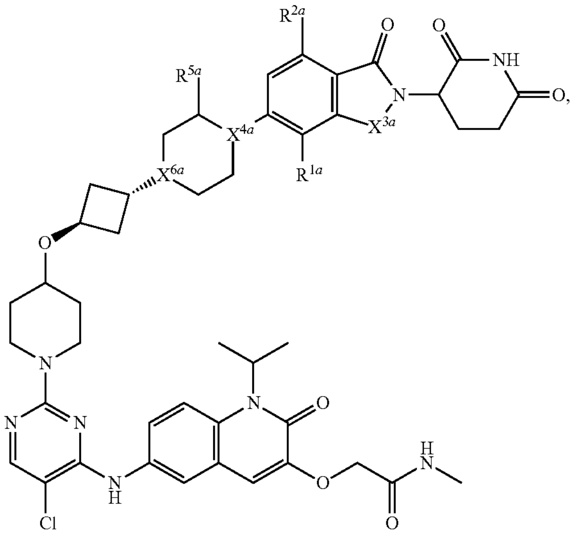

wherein:

$R^{1a}$ is H or halogen;

$R^{2a}$ is H or $C_1$-$C_3$ alkyl;

$X^{3a}$ is $CHR^{3a}$ or C(O);

$R^{3a}$ is H or $C_1$-$C_3$ alkyl;

$X^{4a}$ and $X^{6a}$ are each independently CH or N; and $R^{5a}$ is H, $C_1$-$C_3$ alkyl or halogen.

2D. A bifunctional compound of Formula (III):

Formula (III)

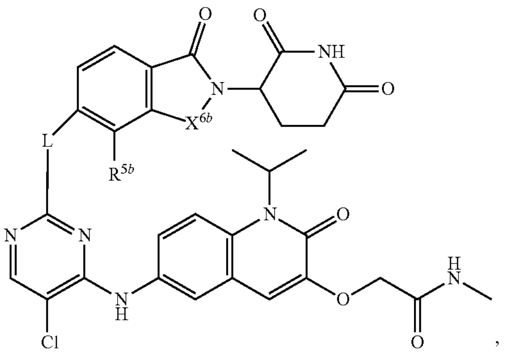

, wherein:

L is

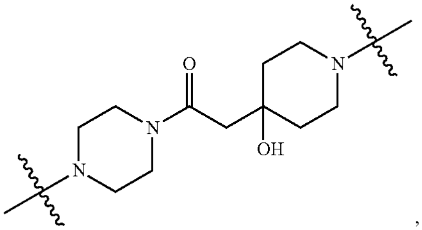

,

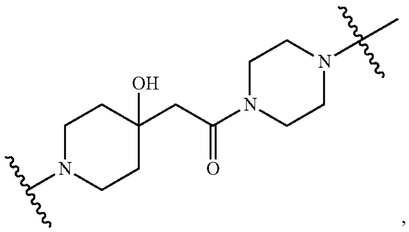

, or

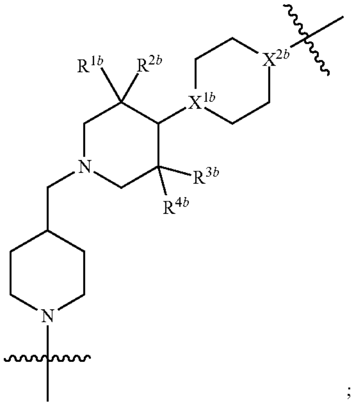

;

$X^{6b}$ is $CHR^{6b}$ or C(O);

$R^{6b}$ is H or Ct-C3 alkyl;

$R^{1b}$, $R^{2b}$, $R^{3b}$, and $R^{4b}$ are each independently H or halogen, wherein at least one of $R^{1b}$, $R^{2b}$, $R^{3b}$, $R^{4b}$ is halogen;

$R^{5b}$ is H or halogen;

$R^{6b}$ is H or $C_1$-$C_3$ alkyl;

$X^{1b}$ and $X^{2b}$ are each independently CH or N, wherein at least one of $X^{1b}$ and $X^{2b}$ is N; and wherein each  of L indicates a point of attachment.

2E. The bifunctional compound of embodiment 2A or 2C, wherein the compound is a compound of Formula (II-a):

Formula (II-a)

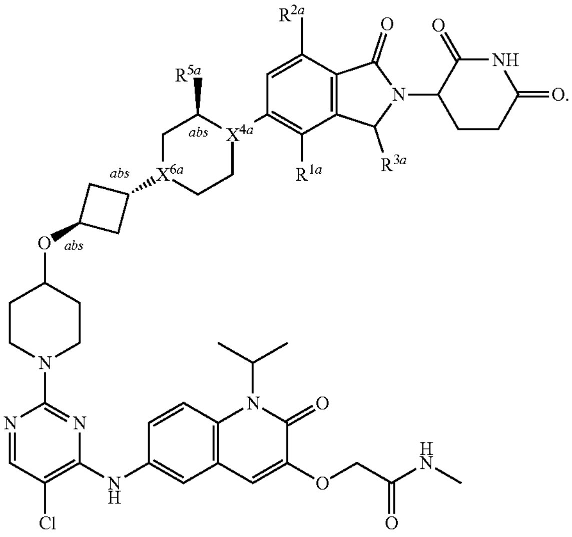

2F. The bifunctional compound of embodiment 2A or 2C, wherein the compound is a compound of Formula (II-b), Formula (II-c), Formula (II-d), Formula (II-e), Formula (II-f), Formula (II-g), Formula (II-h), Formula (II-i), or Formula (II-j):

Formula (II-b)

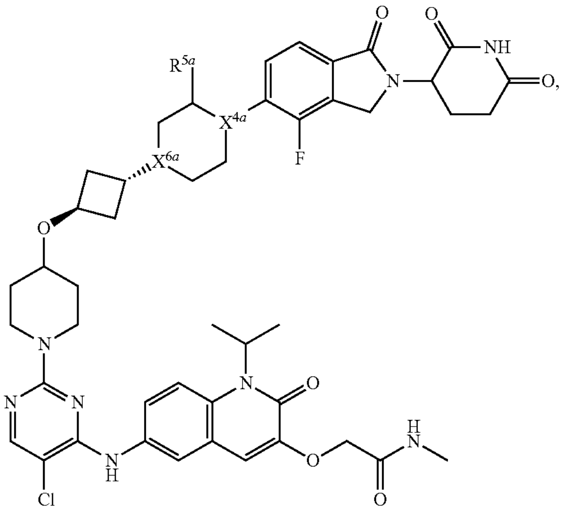

-continued

Formula (II-c)

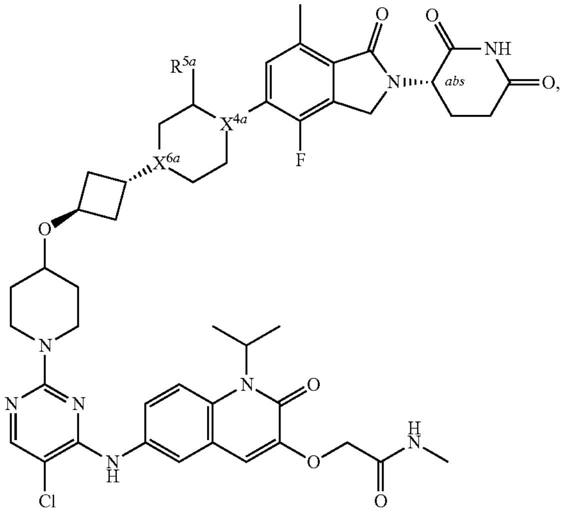

Formula (II-d)

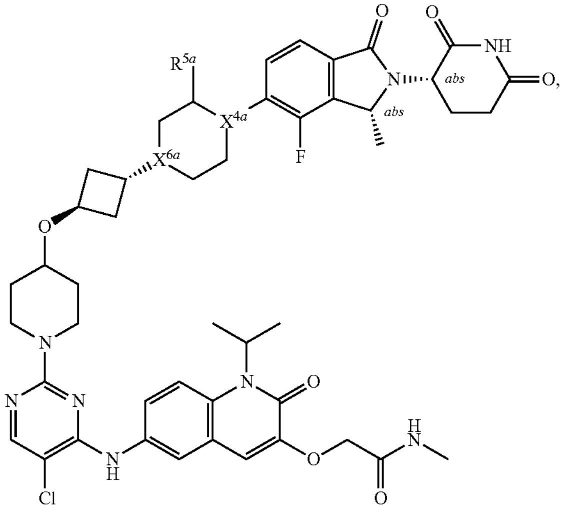

Formula (II-e)

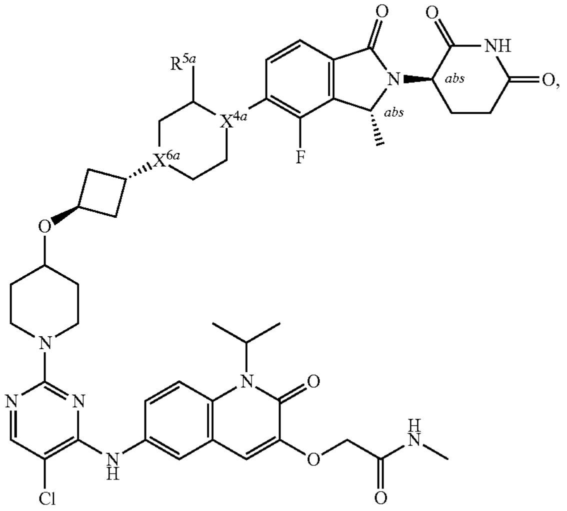

-continued
Formula (II-f)
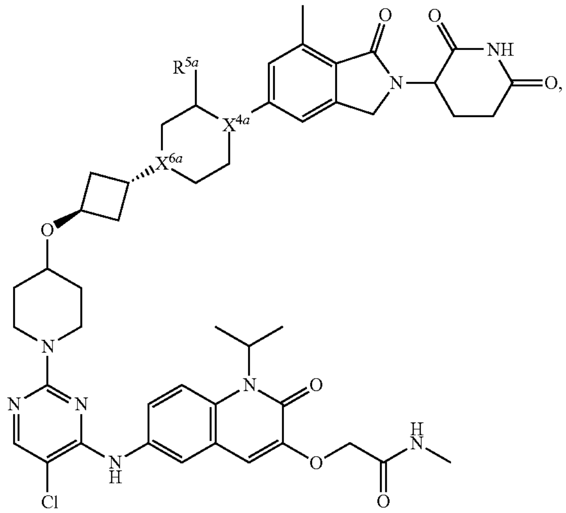
Formula (II-g)
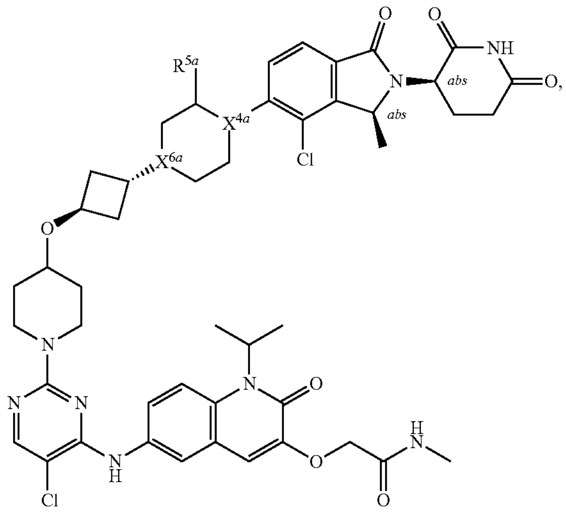
Formula (II-h)
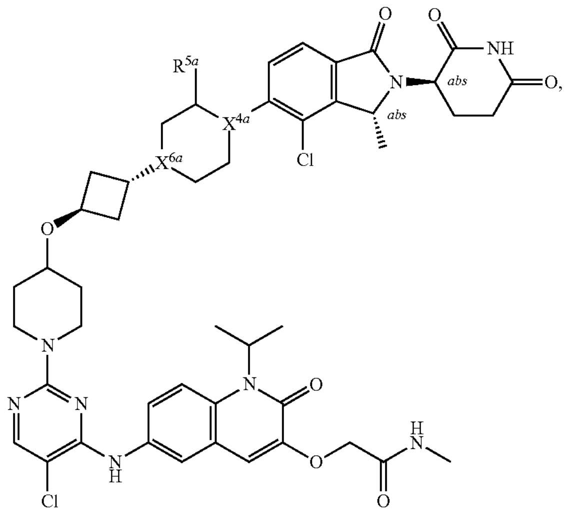
-continued
Formula (II-i)
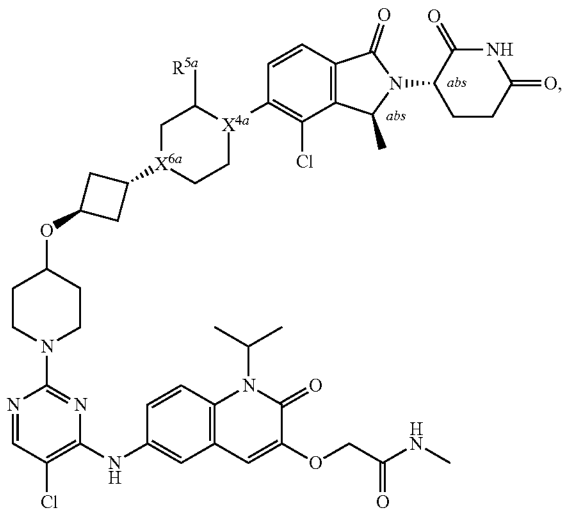
Formula (II-j)
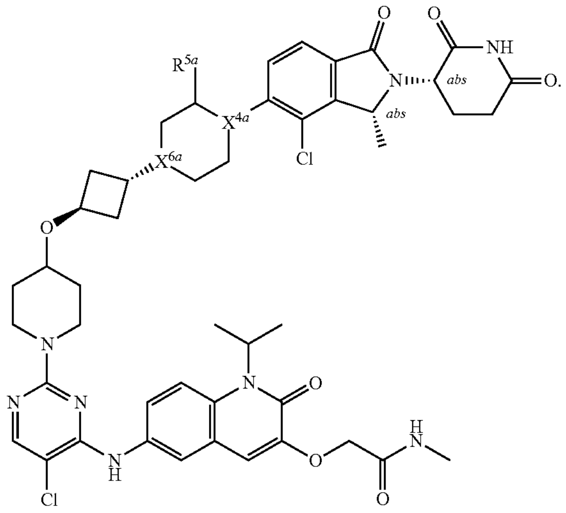
2G. The bifunctional compound of embodiment 2A or 2D, wherein the compound is a compound of Formula (III-a), Formula (III-c), Formula (III-d), Formula (III-f), Formula (III-g), Formula (III-h), or Formula (III-i):
Formula (III-a)
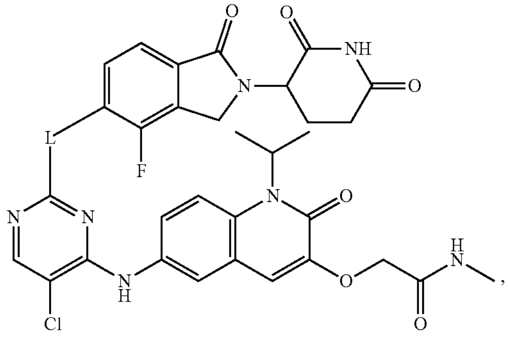

-continued
Formula (III-c)
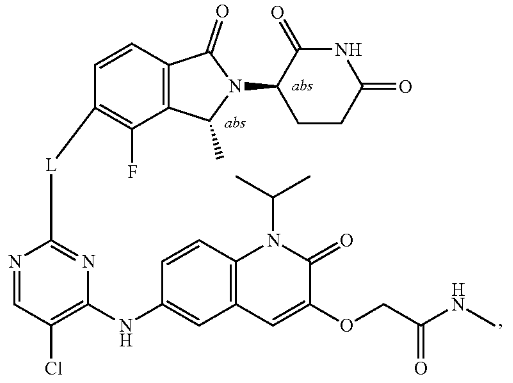
Formula (III-d)
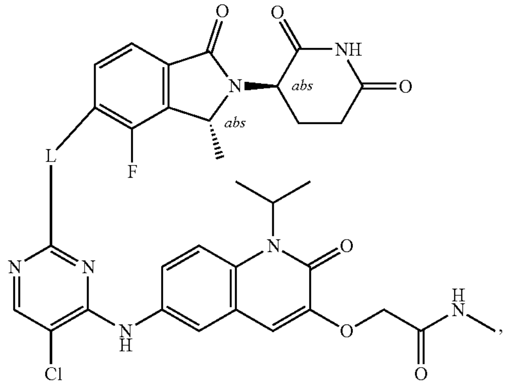
Formula (III-f)
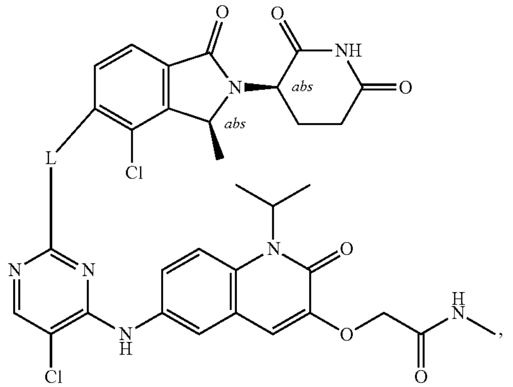
Formula (III-g)
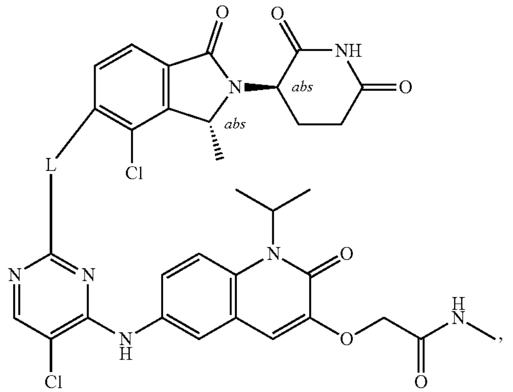
-continued
Formula (III-h)
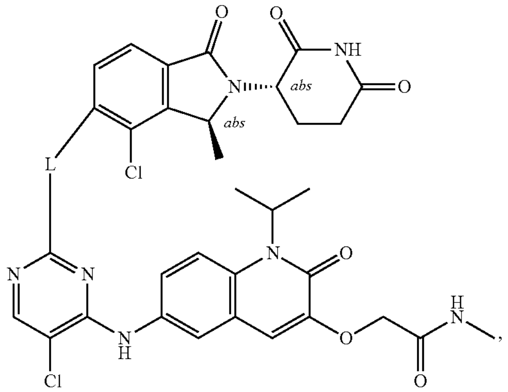
Formula (III-i)
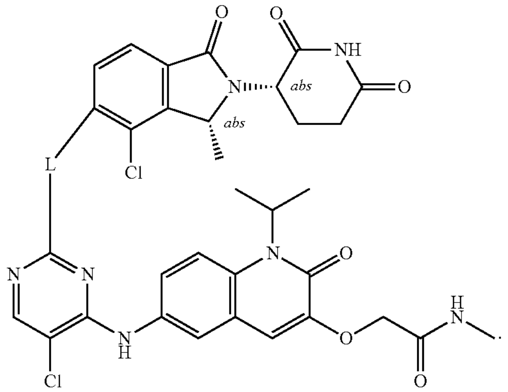
2H. A bifunctional compound of Formula (IV-b) or Formula (IV-e):
Formula (IV-b)
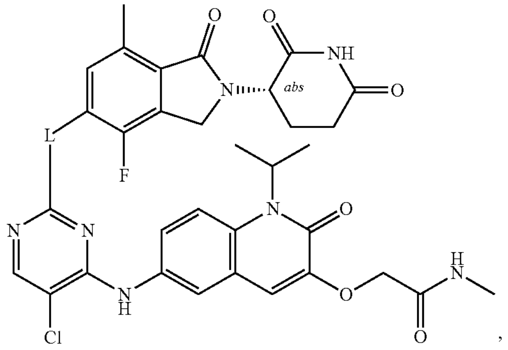

-continued

Formula (IV-e)

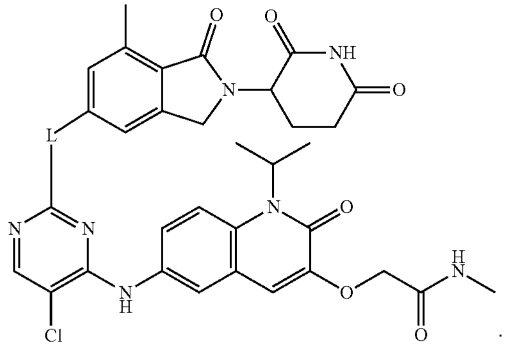

3. The bifunctional compound of any one of embodiments 1A, 1B, 2A or 2B, or a pharmaceutically acceptable salt thereof, wherein Q is

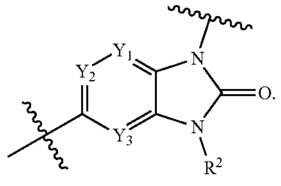

4. The bifunctional compound of any one of embodiments 1A, 1B, 2A or 2B, or a pharmaceutically acceptable salt thereof, wherein each of $Y_1$, $Y_2$, and $Y_3$ is CH.

5. The bifunctional compound of any one of embodiments 11A, 1B, 2A or 2B, or a pharmaceutically acceptable salt thereof, wherein one of $Y_1$, $Y_2$, and $Y_3$ is N, and the other two of $Y_1$, $Y_2$, or $Y_3$ are CH.

6. The bifunctional compound of any one of embodiments 1A, 1B, 2A or 2B, or a pharmaceutically acceptable salt thereof, wherein two of $Y_1$, $Y_2$, and $Y_3$ is N, and the other one of $Y_1$, $Y_2$, or $Y_3$ is CH.

7. The bifunctional compound of any one of embodiments 1A, 1B, 2A or 2B, or a pharmaceutically acceptable salt thereof, wherein $R^1$ is H or $CH_3$.

8. The bifunctional compound of any one of embodiments 1A, 1B, 2A or 2B, or a pharmaceutically acceptable salt thereof, wherein X is N.

9. The bifunctional compound of any one of embodiments 1A, 1B, 2A or 2B, or a pharmaceutically acceptable salt thereof, wherein X is CH.

10. The bifunctional compound of any one of embodiments 1A, 1B, 12A or 2B, or a pharmaceutically acceptable salt thereof, wherein $R^2$ is methyl, ethyl, or isopropyl.

11. The bifunctional compound of any one of embodiments 1A, 1B, 2A or 2B, or a pharmaceutically acceptable salt thereof, wherein each $R^3$ is, independently, H, methyl, fluoro, or methoxy.

12. The bifunctional compound of any one of embodiments 1A, 1C, 1E, 2A, 2C, or 2E or a pharmaceutically acceptable salt thereof, wherein $R^{1a}$ is F.

13. The bifunctional compound of any one of embodiments 1A, 1C, 1E, 2A, 2C, or 2E or a pharmaceutically acceptable salt thereof, wherein $R^{1a}$ is Cl.

14. The bifunctional compound of any one of embodiments 1A, 1C, 1E, 2A, 2C, or 2E or a pharmaceutically acceptable salt thereof, wherein $R^{1a}$ is H.

15. The bifunctional compound of any one of embodiments 1A, 1C, 1E, 1F, 2A, 2C, 2E, or 2F or a pharmaceutically acceptable salt thereof, wherein $X^{4a}$ and $X^{6a}$ are each N.

16. The bifunctional compound of any one of embodiments 1A, 1C, 1E, 1F, 2A, 2C, 2E, or 2F or a pharmaceutically acceptable salt thereof, wherein one of $X^{4a}$ and $X^{6a}$ is N, and the other is CH.

17. The bifunctional compound of any one of embodiments 1A, 1C, 1E, 2A 2C, or 2E or a pharmaceutically acceptable salt thereof, wherein $R^{3a}$ is $CH_3$.

18. The bifunctional compound of any one of embodiments 1A, 1C, 1E, 2A, 2C, or 2E or a pharmaceutically acceptable salt thereof, wherein $R^{3a}$ is H.

19. The bifunctional compound of any one of embodiments 1A, 1C, 1E, 1F, 2A, 2C, 2E, or 2F or a pharmaceutically acceptable salt thereof, wherein $R^{5a}$ is $CH_3$.

20. The bifunctional compound of any one of embodiments 1A, 1C, 1E, 1F, 2A, 2C, 2E, or 2F or a pharmaceutically acceptable salt thereof, wherein $R^{5a}$ is H.

21. The bifunctional compound of any one of embodiments 1A, 1C, 1E, 1F, 2A, 2C, 2E, or 2F or a pharmaceutically acceptable salt thereof, wherein Ra is F.

22. The bifunctional compound of any one of embodiments 1A, 1C, 1E, 2A, 2C, or 2E or a pharmaceutically acceptable salt thereof, wherein $R^{2a}$ is $CH_3$.

23. The bifunctional compound of any one of embodiments 1A, 1C, 1E, 2A, 2C, or 2E or a pharmaceutically acceptable salt thereof, $R^2$ is H.

24. The bifunctional compound of any one of embodiments 1A, 1D, 1G, 1E, 2A, 2D, 2G, or 2E or a pharmaceutically acceptable salt thereof, wherein L is

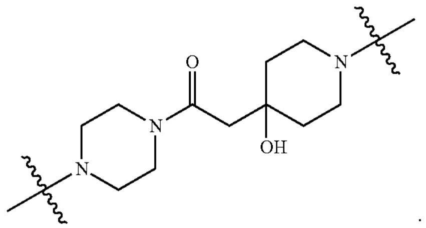 [SMILES: *N1CCN(C(=O)CC2(O)CCN(*)CC2)CC1]

25. The bifunctional compound of any one of embodiments 1A, 1D, 1G, 1E, 2A, 2D, 2G, or 2E or a pharmaceutically acceptable salt thereof, wherein L is

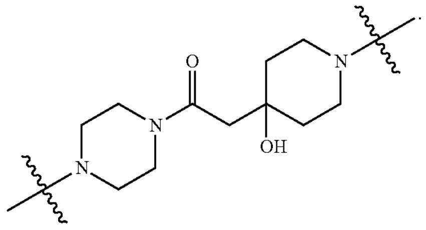 [SMILES: *N1CCN(C(=O)CC2(O)CCN(*)CC2)CC1]

26. The bifunctional compound of any one of embodiments 1A, 1D, 1G, 1E, 2A, 2D, 2G, or 2E or a pharmaceutically acceptable salt thereof, wherein L is

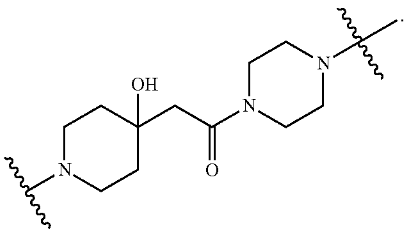 [SMILES: *N1CCN(C(=O)CC2(O)CCN(*)CC2)CC1]

27. The bifunctional compound of any one of embodiments 1A, 1D, 1G, 1E, 2A, 2D, 2G, or 2E or a pharmaceutically acceptable salt thereof, wherein L is

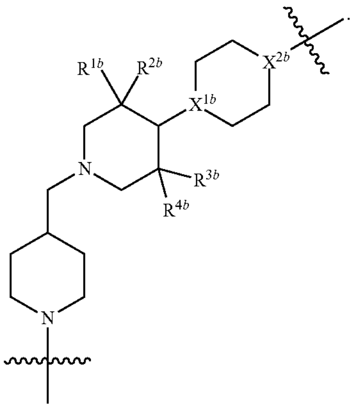

28. The bifunctional compound of any one of embodiments 1A, 1D, 1G, 1E, 2A, 2D, 2G, or 2E or 27 or a pharmaceutically acceptable salt thereof, wherein L is

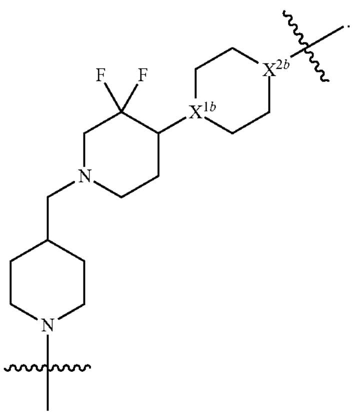

29. The bifunctional compound of any one of embodiments 1A, 1D, 1G, 1E, 2A, 2D, 2G, or 2E or 27 or a pharmaceutically acceptable salt thereof, wherein L is

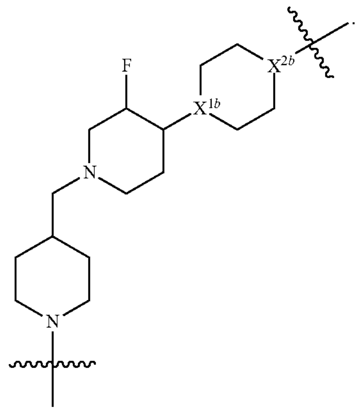

30. A bifunctional compound that is selected from any one of the compounds in Table 1, or a pharmaceutically acceptable salt thereof.

31. A bifunctional compound that is selected from any one of the compounds in Table 1.

32. A pharmaceutical composition comprising the bifunctional compound of any one of embodiments 1A-1D or 3-31, or a pharmaceutically acceptable salt thereof, and one or more pharmaceutically acceptable excipients.

33. A pharmaceutical composition comprising the bifunctional compound of any one of embodiments 2A-2D or 3-31 and one or more pharmaceutically acceptable excipients.

34A. A pharmaceutical composition comprising the bifunctional compound of embodiment 1A or 2A, or a pharmaceutically acceptable salt thereof, and one or more pharmaceutically acceptable excipients.

34B. A pharmaceutical composition comprising the bifunctional compound of embodiment 1B or 2B, or a pharmaceutically acceptable salt thereof, and one or more pharmaceutically acceptable excipients.

34C. A pharmaceutical composition comprising the bifunctional compound of embodiment 1C or 2C, or a pharmaceutically acceptable salt thereof, and one or more pharmaceutically acceptable excipients.

34D. A pharmaceutical composition comprising the bifunctional compound of embodiment 1D or 2D, or a pharmaceutically acceptable salt thereof, and one or more pharmaceutically acceptable excipients.

34E. A pharmaceutical composition comprising the bifunctional compound of embodiment 2A and one or more pharmaceutically acceptable excipients.

34F. A pharmaceutical composition comprising the bifunctional compound of embodiment 2B and one or more pharmaceutically acceptable excipients.

34G. A pharmaceutical composition comprising the bifunctional compound of embodiment 2C and one or more pharmaceutically acceptable excipients.

34H. A pharmaceutical composition comprising the bifunctional compound of embodiment 2D and one or more pharmaceutically acceptable excipients.

36. The pharmaceutical composition of any one of embodiments 31-34H, wherein the composition further comprises an effective amount of at least one additional anti-cancer agent.

37A. A method of treating a disease or disorder in a subject comprising administering to a subject in need thereof a therapeutically effective amount of a bifunctional compound of any one of embodiments 1-31, or a therapeutically effective amount of the pharmaceutical composition of any one of embodiments 32-36.

37B. A method of treating cancer in a subject comprising administering to a subject in need thereof a therapeutically effective amount of a bifunctional compound of any one of embodiments 1-31, or a therapeutically effective amount of the pharmaceutical composition of any one of embodiments 32-36.

38. The method of embodiment 37A or 37B, wherein the therapeutically effective amount of the bifunctional compound or the pharmaceutical composition is administered orally to the subject.

39. The method of embodiment 37A, 37B or 38, wherein the therapeutically effective amount of the bifunctional compound or the pharmaceutical composition is administered to the subject once a day, twice a day, three times a day, or four times a day.

40. The method of any one of embodiments 37A, 37B, or 38-39, wherein the therapeutically effective amount of the bifunctional compound or the pharmaceutical composition is administered to the subject once a day.

41. The method of any one of embodiments 37A, 37B, or 38-39, wherein the therapeutically effective amount of the bifunctional compound or the pharmaceutical composition is administered to the subject all at once or is administered in two, three, or four divided doses.

42. The method of any one of embodiments 37A, 37B, or 38-41, wherein the therapeutically effective amount of the bifunctional compound is about 1 mg to about 1000 mg.

43. The method of any one of embodiments 37A, 37B, or 38-41, wherein the therapeutically effective amount of the bifunctional compound is about 5 mg to about 750 mg.

44. The method of any one of embodiments 37A, 37B, or 38-41, wherein the therapeutically effective amount of the bifunctional compound is about 10 mg to about 500 mg.

45. The method of any one of embodiments 37A, 37B, or 38-41, wherein the therapeutically effective amount of the bifunctional compound is about 20 mg to about 250 mg.

46. The method of any one of embodiments 37A, 37B, or 38-45, wherein the subject is in a fed state at the time of administration.

47. The method of any one of embodiments 37A, 37B, or 38-45, wherein the subject is in a fasted state at the time of administration.

48. The method of any one of embodiments 37A, 37B, or 38-47, further comprising administering an effective amount of at least one additional anti-cancer agent to the subject in need thereof.

49. The method of any one of embodiments 37A, 37B, or 3848, wherein the disease or disorder is associated with aberrant BCL6 expression and/or activity.

50. The method of any one of embodiments 37A, 37B, or 38-48, wherein the disease or disorder is a cancer associated with aberrant BCL6 expression and/or activity.

51. The method of any one of embodiments 37A, 37B, or 38-50, wherein the disease or disorder is breast cancer, ovarian cancer, leukemia, lymphoma, benign lymphoma, malignant lymphoma, Burkitt's lymphoma, non-Hodgkin's lymphoma, B-cell non-Hodgkin's lymphoma, sarcomas, Ewing's sarcoma, hemangiosarcoma, Kaposi's sarcoma, liposarcoma, myosarcomas, synovial sarcoma, meningeal sarcomas, carcinosarcoma, acute myeloid leukemia (AML), acute lymphoblastic leukemia (ALL), T-lineage acute lymphoblastic leukemia (T-ALL), T-lineage lymphoblastic lymphoma (T-LL), peripheral T-cell lymphoma, adult T-cell leukemia, pre-B acute lymphoblastic leukemia, pre-B lymphomas, B-cell lymphoma, large B-cell lymphoma, diffuse large B-cell lymphoma, B-cell acute lymphoblastic leukemia (ALL), Philadelphia chromosome positive acute lymphoblastic leukemia (ALL), Philadelphia chromosome positive chronic myeloid leukemia (CML), follicular lymphoma, intravascular large B-cell lymphoma, angioimmunoblastic T-cell lymphoma (AITL), T-cell lymphoma, B-cell leukemia, chronic myeloid leukemia, non-small cell lung cancer, systemic lupus erythematosus (SLE), brain tumors, or central nervous system cancers.

52. The method of any one of embodiments 37A, 37B, or 38-50, wherein the disease or disorder is large B-cell lymphoma, diffuse large B-cell lymphoma, Burkitt's lymphoma, follicular lymphoma, or angioimmunoblastic T-cell lymphoma (AITL).

The invention claimed is:

1. A bifunctional compound of Formula (I):

Formula (I)

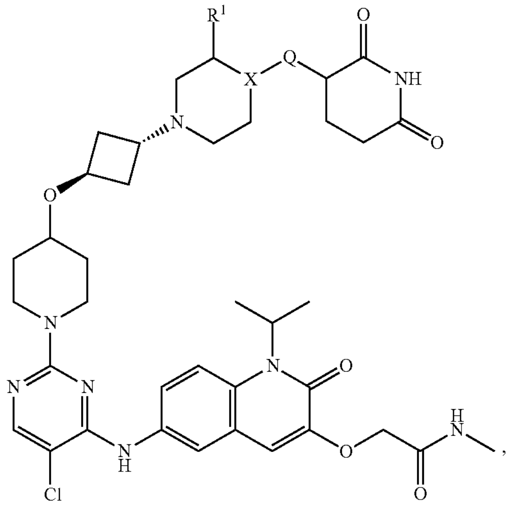

or a pharmaceutically acceptable salt thereof, wherein:

$R^1$ is H or $C_1$-$C_6$ alkyl;

Q is

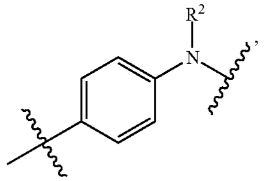

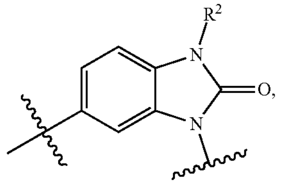

-continued

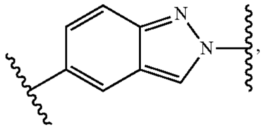

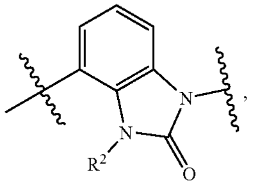

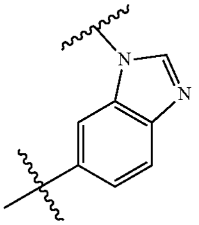

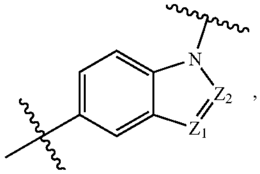

, or

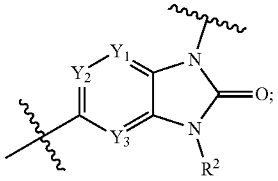

X is N or CH;

$Y_1$, $Y_2$, and $Y_3$ are each, independently, N or $CR^3$;

$Z_1$ and $Z_2$ are each, independently, N or CH;

$R^2$ is H or $C_1$-$C_6$ alkyl;

each $R^3$ is, independently, H, halogen, $C_1$-$C_6$ alkyl, $C_1$-$C_6$ haloalkyl, —O—($C_1$-$C_6$ alkyl), —O—($C_1$-$C_6$ haloalkyl);

∿∿∿ of the Q indicates the point of attachment with the X or the glutarimide.

2. A bifunctional compound of Formula (I:

Formula (I)

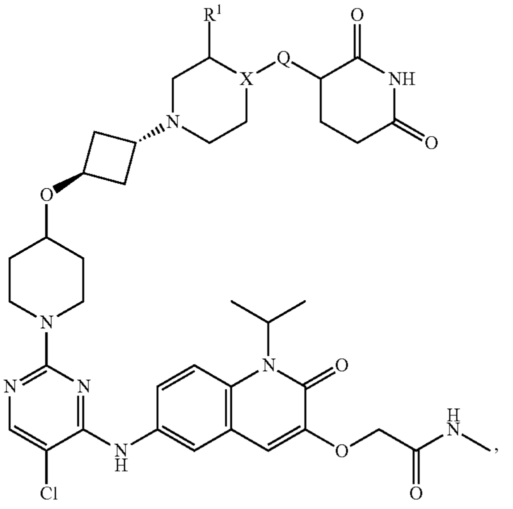

wherein:

$R^1$ is H or $C_1$-$C_6$ alkyl;

Q is

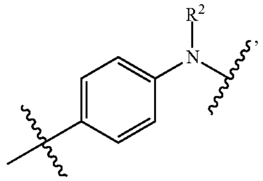

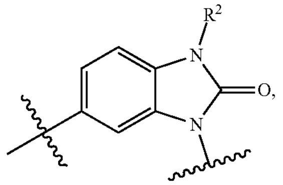

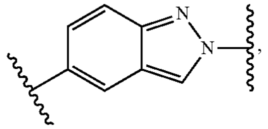

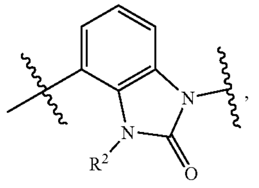

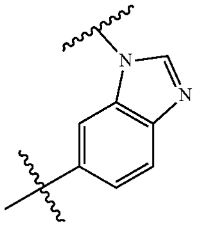

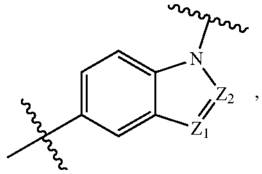

, or

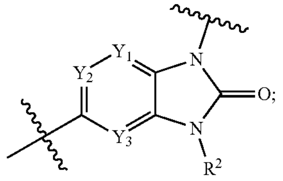

X is N or CH;

$Y_1$, $Y_2$, and $Y_3$ are each, independently, N or $CR^3$;

$Z_1$ and $Z_2$ are each, independently, N or CH;

$R^2$ is H or $C_1$-$C_6$ alkyl;

each $R^3$ is, independently, H, halogen, $C_1$-$C_6$ alkyl, $C_1$-$C_6$ haloalkyl, —O—($C_1$-$C_6$ alkyl), or —O—($C_1$-$C_6$ haloalkyl);

∿∿∿ of the Q indicates the point of attachment with the X or the glutarimide.

3. The bifunctional compound of claim 1, or a pharmaceutically acceptable salt thereof, wherein Q is

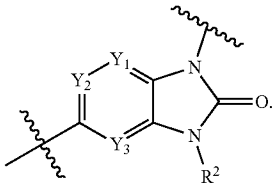

4. The bifunctional compound of claim 1, or a pharmaceutically acceptable salt thereof, wherein each of $Y_1$, $Y_2$, and $Y_3$ is CH.

5. The bifunctional compound of claim 1, or a pharmaceutically acceptable salt thereof, wherein $R^1$ is H or $CH_3$.

6. The bifunctional compound of claim 1, or a pharmaceutically acceptable salt thereof, wherein X is N.

7. The bifunctional compound of claim 1, or a pharmaceutically acceptable salt thereof, wherein $R^2$ is methyl, ethyl, or isopropyl.

8. The bifunctional compound of claim 1, or a pharmaceutically acceptable salt thereof, wherein each $R^3$ is, independently, H, methyl, fluoro, or methoxy.

9. A bifunctional compound that is selected from the group consisting of,

1

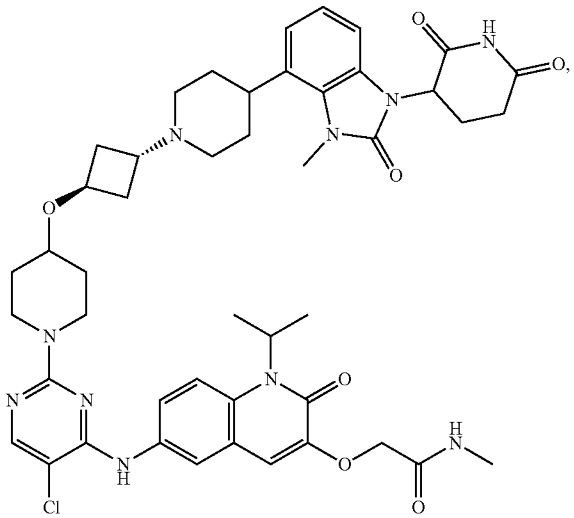

2

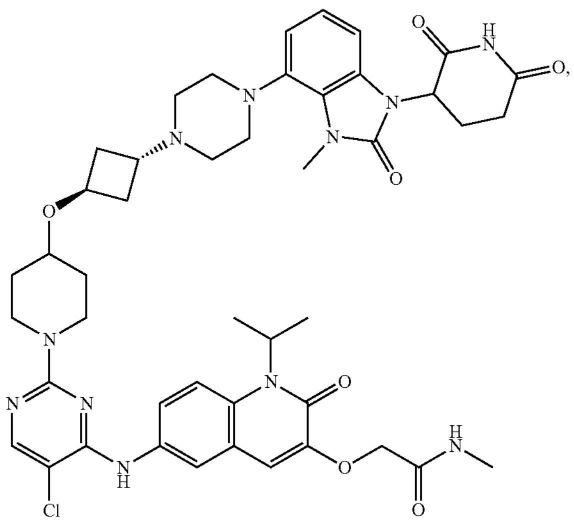

-continued

3

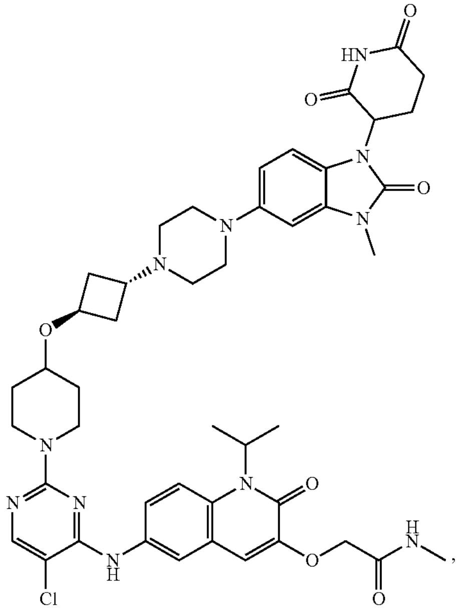

4

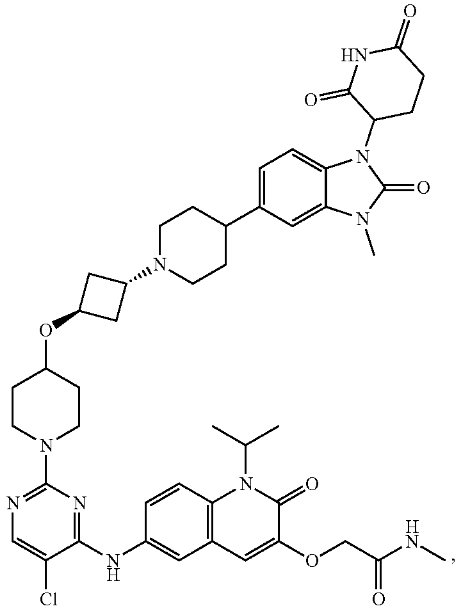

-continued
5
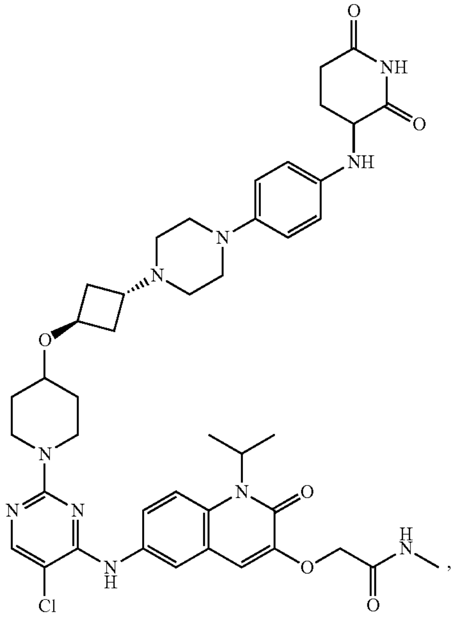
6
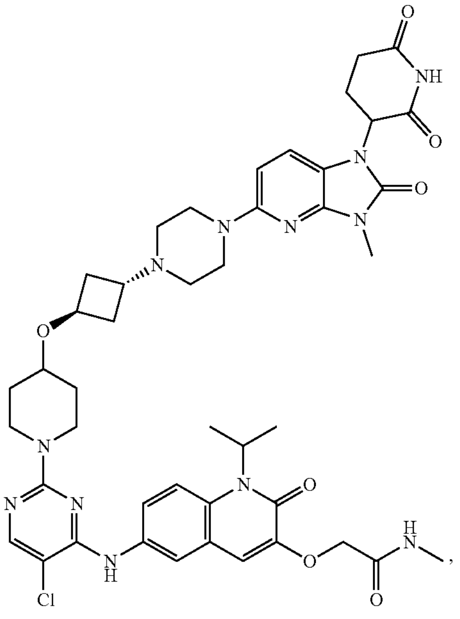
-continued
7
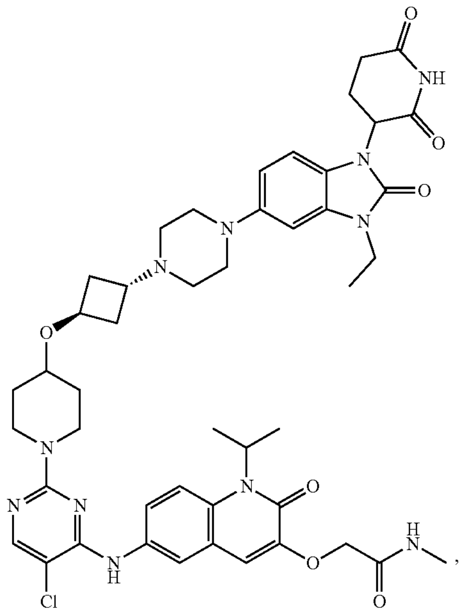
8
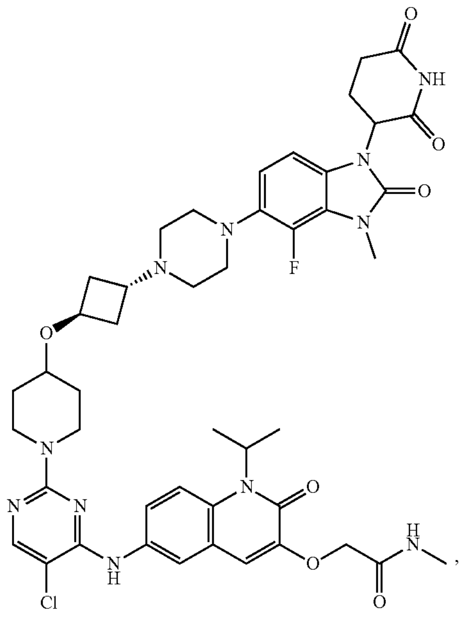

-continued
9
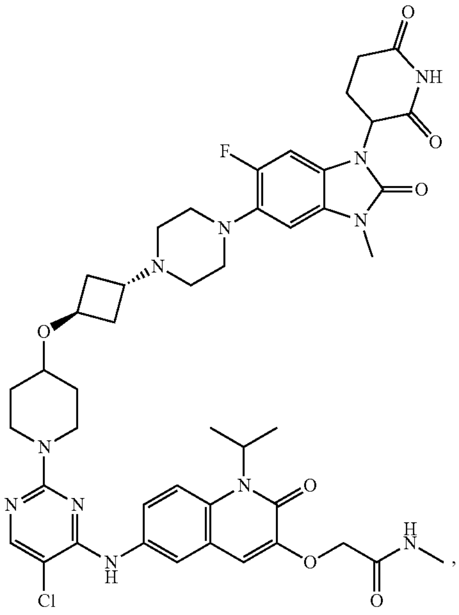
,
10
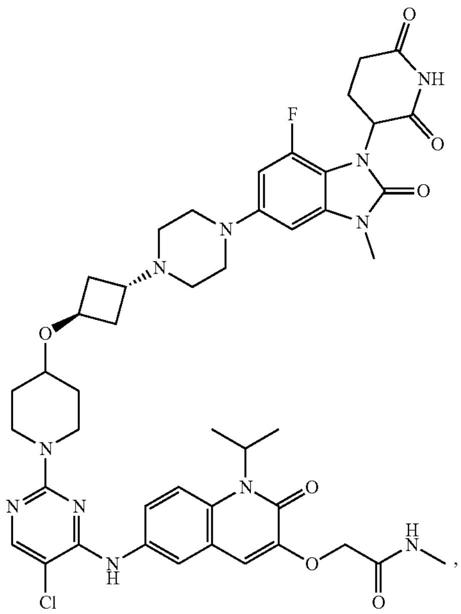
,
-continued
11
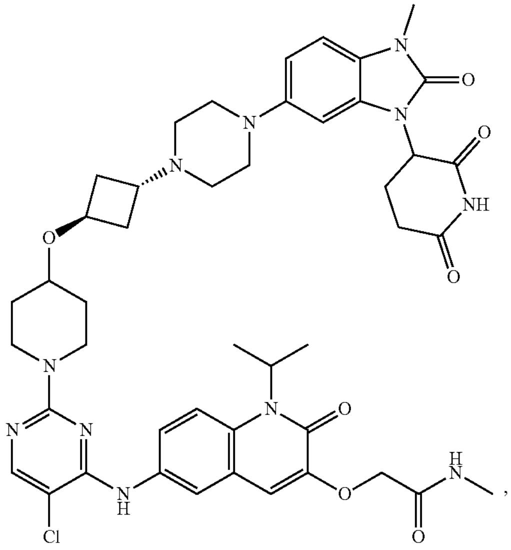
,
12
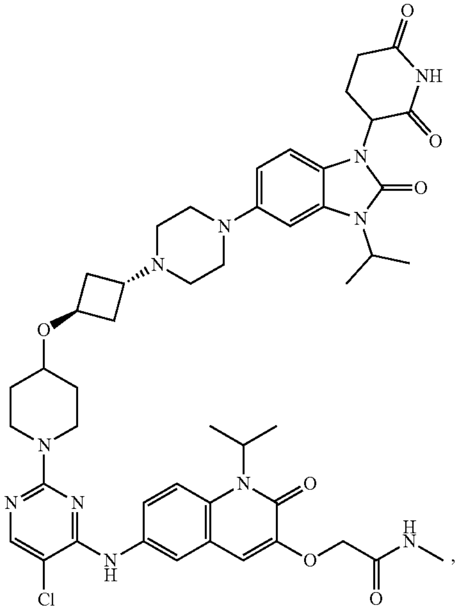
,

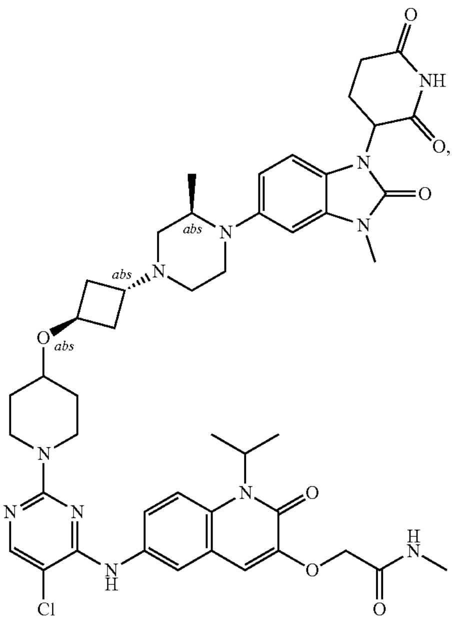
13
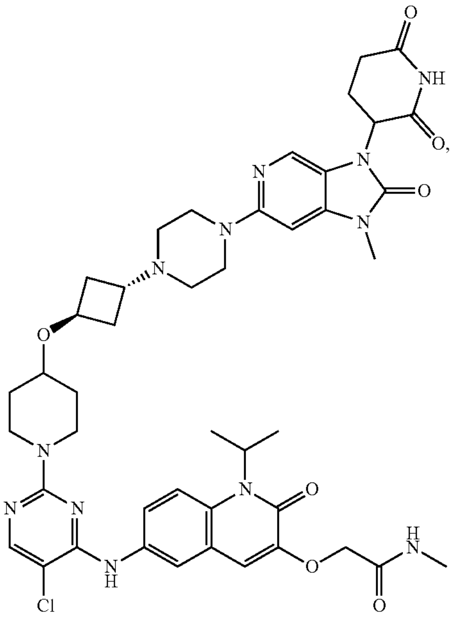
14
-continued
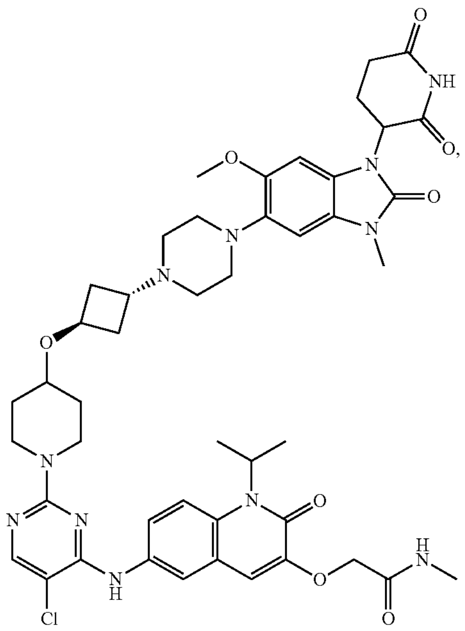
15
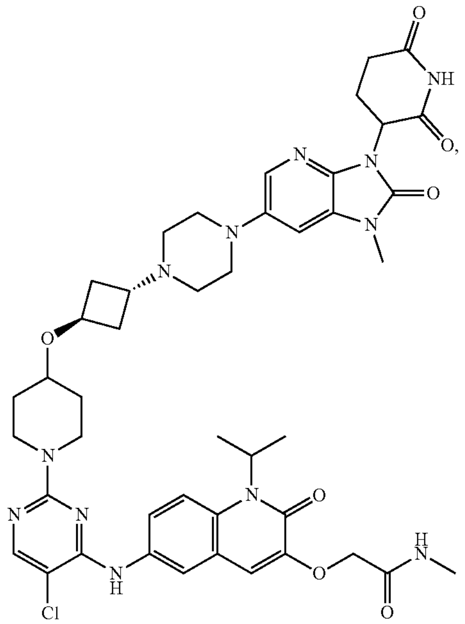
16

-continued
17
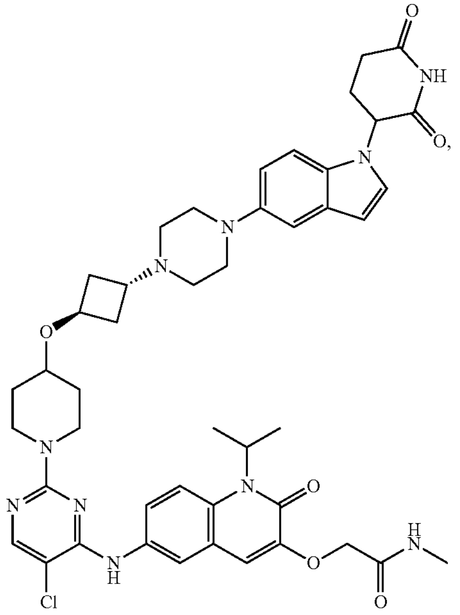
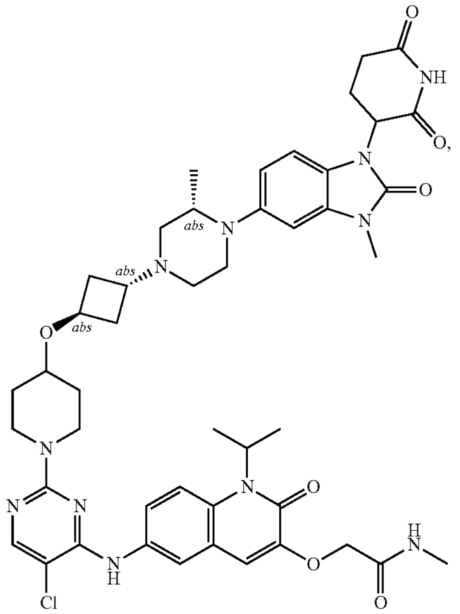
18
-continued
19
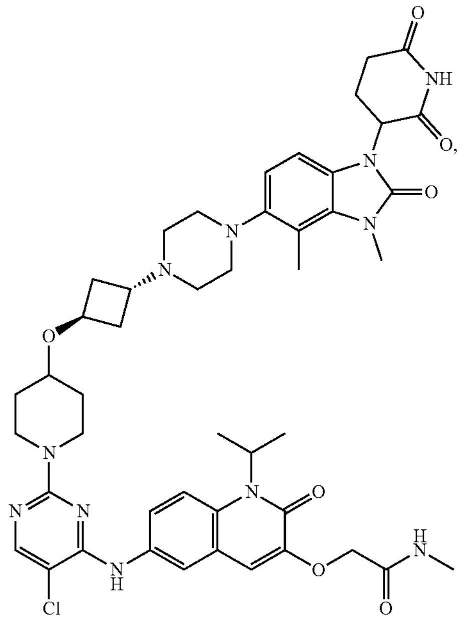
20
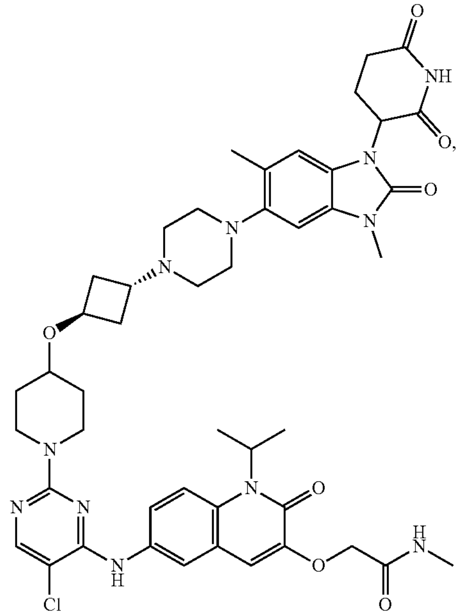

-continued
21
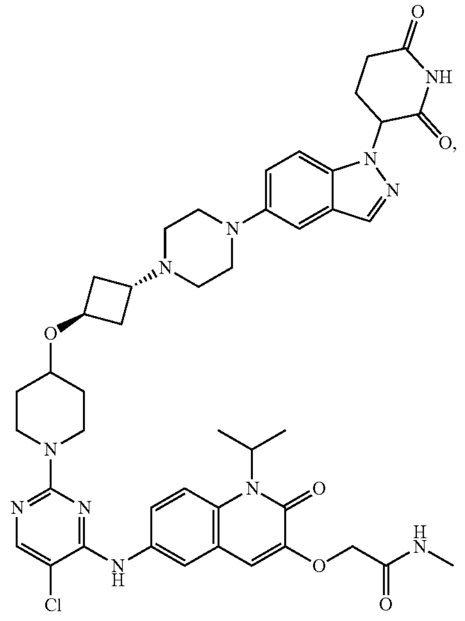
-continued
23
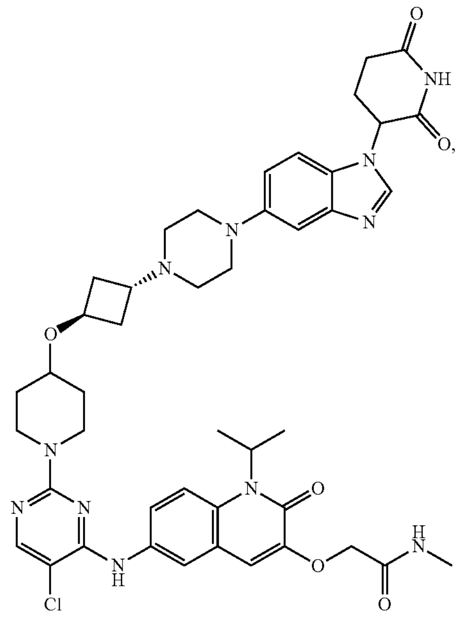
22
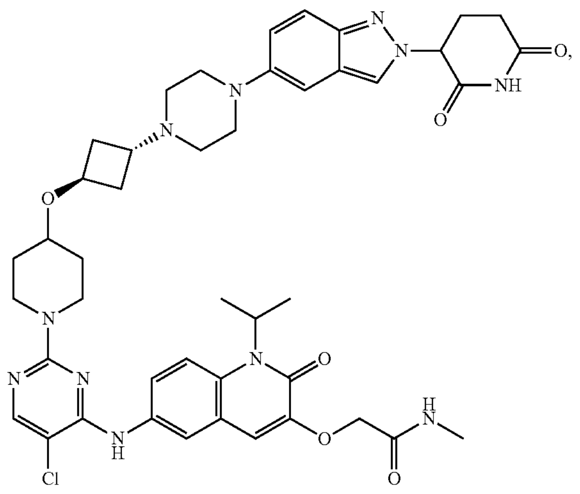
24
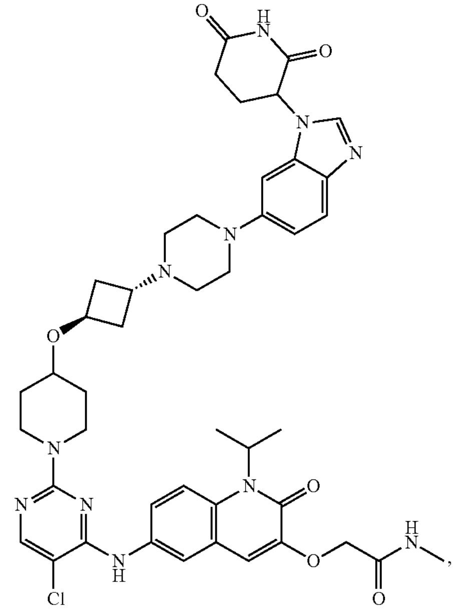

-continued
25
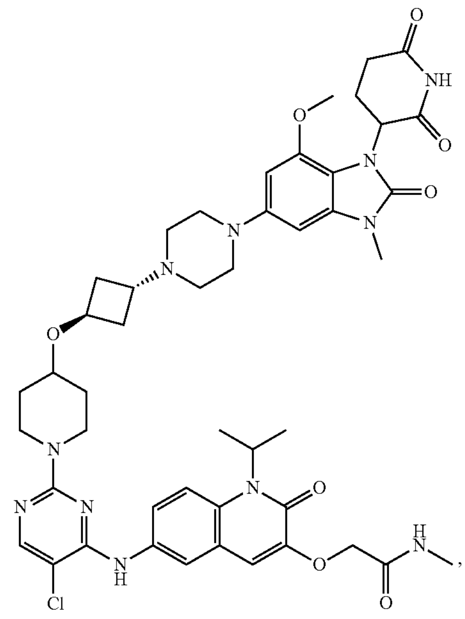
,
27
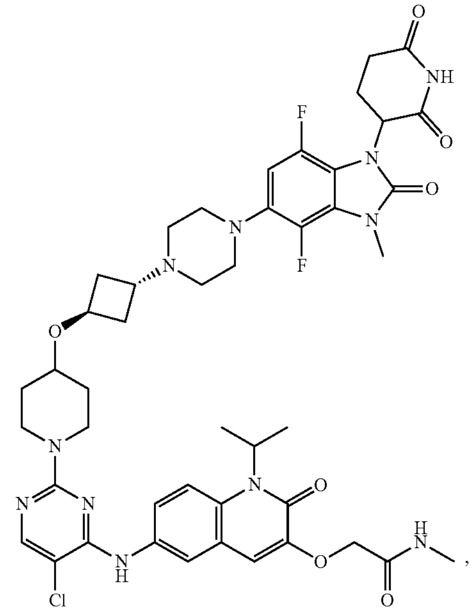
,
26
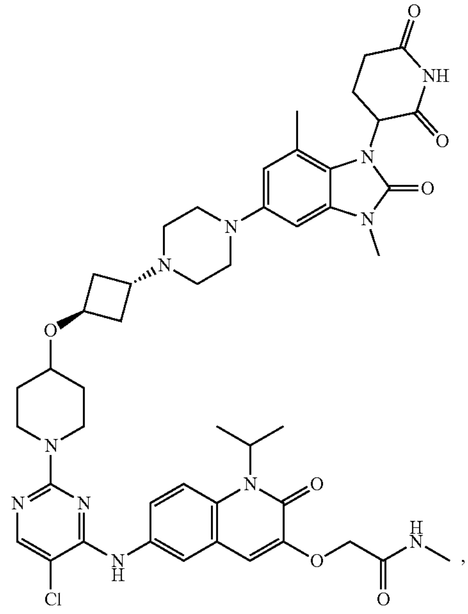
,
28
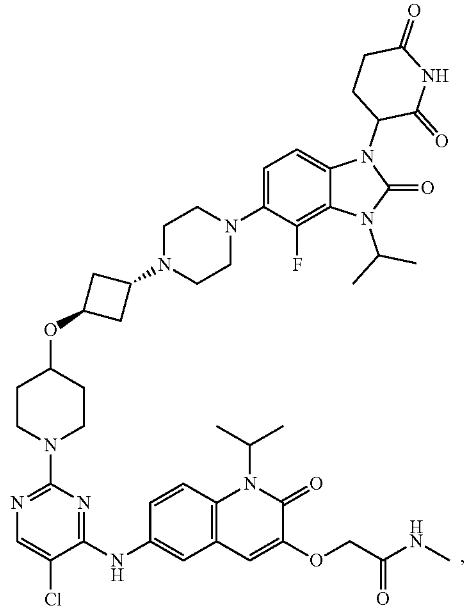
, and -continued

29

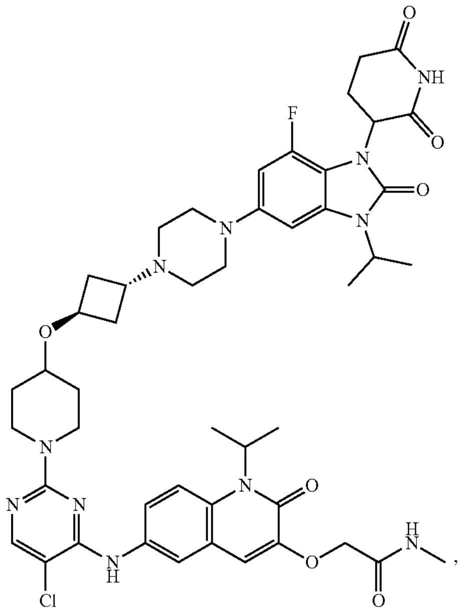

or a pharmaceutically acceptable salt thereof.

10. A pharmaceutical composition comprising the bifunctional compound of claim 1, or a pharmaceutically acceptable salt thereof, and one or more pharmaceutically acceptable excipients.

11. The pharmaceutical composition of claim 10, wherein the composition further comprises at least one additional anti-cancer agent.

* * * * *